(12) United States Patent
Gillespie et al.

(10) Patent No.: US 10,730,848 B2
(45) Date of Patent: Aug. 4, 2020

(54) PROTECTIVE MOLECULES AGAINST ANTHRAX TOXIN

(71) Applicant: The Regents of the University of California, Oakland, CA (US)

(72) Inventors: Eugene Gillespie, Los Angeles, CA (US); Robert Damoiseaux, Beverly Hills, CA (US); Chi-Lee Charlie Ho, Los Angeles, CA (US); Brian T. Chamberlain, Simi Valley, CA (US); Michael E. Jung, Los Angeles, CA (US); Kenneth A. Bradley, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 14/801,247

(22) Filed: Jul. 16, 2015

(65) Prior Publication Data

US 2016/0016930 A1 Jan. 21, 2016

Related U.S. Application Data

(63) Continuation of application No. PCT/US2014/011930, filed on Jan. 16, 2014.

(60) Provisional application No. 61/753,355, filed on Jan. 16, 2013.

(51) Int. Cl.
| | |
|---|---|
| C07D 333/28 | (2006.01) |
| C07C 281/14 | (2006.01) |
| C07C 335/26 | (2006.01) |
| C07D 213/53 | (2006.01) |
| C07D 307/56 | (2006.01) |
| C07C 281/18 | (2006.01) |
| C07C 337/08 | (2006.01) |
| C07D 231/12 | (2006.01) |
| C07C 243/22 | (2006.01) |
| C07C 311/08 | (2006.01) |

(Continued)

(52) U.S. Cl.
CPC .......... *C07D 333/28* (2013.01); *C07C 243/22* (2013.01); *C07C 281/14* (2013.01); *C07C 281/18* (2013.01); *C07C 311/08* (2013.01); *C07C 335/26* (2013.01); *C07C 337/08* (2013.01); *C07D 213/53* (2013.01); *C07D 231/12* (2013.01); *C07D 307/52* (2013.01); *C07D 307/56* (2013.01); *C07D 333/22* (2013.01)

(58) Field of Classification Search
None
See application file for complete search history.

(56) References Cited

FOREIGN PATENT DOCUMENTS

| EP | 2 100 602 A1 | 9/2009 |
|---|---|---|
| KR | 10-2011-0097576 A | 8/2011 |

(Continued)

OTHER PUBLICATIONS

Mock & Fouet. Anthrax. Annu. Rev. Microbiol. 2001. 55: 647-71.*

(Continued)

*Primary Examiner* — Anna Pagonakis
(74) *Attorney, Agent, or Firm* — Mintz, Levin, Cohn, Ferris, Glovsky and Popeo, P.C.

(57) ABSTRACT

Disclosed herein inter alia are compositions and methods useful in the treatment of infectious diseases and exposure to toxins.

11 Claims, 32 Drawing Sheets

(51) Int. Cl.
    C07D 307/52    (2006.01)
    C07D 333/22    (2006.01)

(56) References Cited

FOREIGN PATENT DOCUMENTS

KR        10-1207668 B1    12/2012
WO    WO-02/098420 A1      12/2002

OTHER PUBLICATIONS

Scobie & Young. Interactions between anthrax toxin receptors and protective antigen. Current Opinion in Microbiology, 2005, 8: 106-112.*

Li et al. (Expert Opin. Biol. Ther. 2007, 7(6): 843-854).*

Mayo Clinic. Infectious diseases. Electronic Resource: [https://www.mayoclinic.org/diseases-conditions/infectious-diseases/symptoms-causes/syc-20351173]. Retrieved on Aug. 7, 2019.*

Fauci & Morens. The Perpetual Challenge of Infectious Diseses. N. Engl. J. Med. 2012; 366: 454-61.*

Abrami, L. et al. (Aug. 30, 2004). "Membrane insertion of anthrax protective antigen and cytoplasmic delivery of lethal factor occur at different stages of the endocytic pathway," *J Cell Biol* 166(5):645-651.

Eshraghi, A. et al. (Jul. 31, 2014). "Cytolethal distending toxins require components of the ER-associated degradation pathway for host cell entry," *PLoS Pathog* 10(7):e1004295.

Friedlander, A.M. (Jun. 1986). "Macrophages are sensitive to anthrax lethal toxin through an acid-dependent process," *J Biol Chem* 261(16):7123-7126.

Gargi, A. et al. (Mar. 15, 2013, e-published Jan. 10, 2013). "Cellular interactions of the cytolethal distending toxins from *Escherichia coli* and Haemophilus ducreyi," *J Biol Chem* 288(11):7492-7505.

Gillespie, E.J. et al. (Dec. 10, 2013, e-published Nov. 4, 2013). "Selective inhibitor of endosomal trafficking pathways exploited by multiple toxins and viruses," *Proc Natl Acad Sci USA* 110(50):E4904-E4912.

International Search Report dated May 28, 2014, for PCT Application No. PCT/US2014/011930, filed Jan. 16, 2014, 4 pages.

Jung, M. et al. (Jan. 21, 2014). "Structure-Activity Relationship of Semicarbazone EGA Furnishes Photoaffinity Inhibitors of Anthrax Toxin Cellular Entry," *ACS Med Chem Lett* 5(4):363-367.

Jurgeit, A. et al. (2012, e-published Oct. 25, 2012). "Niclosamide is a proton carrier and targets acidic endosomes with broad antiviral effects," PLoS Pathog 8(10):e1002876, 14 pages.

Komiyama, T. et al. (Sep. 2005). "Protection from anthrax toxin-mediated killing of macrophages by the combined effects of furin inhibitors and chloroquine," *Antimicrob Agents Chemother* 49(9):3875-3882.

Lee, A.M. et al. (Jul. 4, 2008, e-publsihed May 18, 2008). "Unique small molecule entry inhibitors of hemorrhagic fever arenaviruses," *J Biol Chem* 283(27):18734-18742.

Packer, J. et al. (1952). "Mesitylurea and Mesitylsemicarbazide," *Journal of the Chemical Society* 2654-2656.

Saenz, J.B. et al. (Sep. 2007, e-published Jun. 18, 2007). "Identification and characterization of small molecules that inhibit intracellular toxin transport," *Infect Immun* 75(9):4552-4561.

Sanchez, A.M. et al. (Jul. 2007, e-published May 7, 2007). "Amiodarone and bepridil inhibit anthrax toxin entry into host cells," *Antimicrob Agents Chemother* 51(7):2403-2411.

Sanvig, K. et al. (Jun. 2005). "Delivery into cells: lessons learned from plant and bacterial toxins," *Gene Ther* 12(11):865-872.

Shalini, M. et al. (Mar. 2009). "Cyclization of the semicarbazone template of aryl semicarbazones: synthesis and anticonvulsant activity of 4,5-diphenyl-2H-1,2,4-triazol-3(4H)-one," *Biomed Pharmacother* 63(3):187-193.

Stechmann, B. et al. (Apr. 16, 2010). "Inhibition of retrograde transport protects mice from lethal ricin challenge," *Cell* 141(2):231-242.

Wahome, P.G. et al. (Sep. 1, 2010, e-published Mar. 27, 2010). "Identification of small-molecule inhibitors of ricin and shiga toxin using a cell-based high-throughput screen," *Toxicon* 56(3):313-323.

Written Opinion dated May 28, 2014, for PCT Application No. PCT/US2014/011930, filed Jan. 16, 2014, 8 pages.

Yogeeswari, P. et al. (Oct. 6, 2005). "Discovery of N-(2,6-dimethylphenyl)-substituted semicarbazones as anticonvulsants: hybrid pharmacophore-based design," *J Med Chem* 48(20):6202-6211.

Abrami, L. et al. (Feb. 3, 2003, e-published Jan. 27, 2003). "Anthrax toxin triggers endocytosis of its receptor via a lipid raft-mediated clathrin-dependent process," J Cell Biol 160(3):321-328.

Abrami, L. et al. (Jan. 16, 2006, e-published Jan. 9, 2006). Receptor palmitoylation and ubiquitination regulate anthrax toxin endocytosis, *J Cell Biol* 172(2):309-320.

Banks, D.J. et al. (Apr. 11, 2006). "New insights into the functions of anthrax toxin," *Expert Rev Mol Med* 8(7):1-18.

Bradley, K.A. et al. (Nov. 8, 2001). "Identification of the cellular receptor for anthrax toxin," *Nature* 414(6860): 225-229.

Goldman, D.L. et al. (Jun. 2008, e-published Apr. 30, 208). "Human serum contains a protease that protects against cytotoxic activity of Bacillus anthracis lethal toxin in vitro," *Clin Vaccine Immunol* 15(6): 970-973.

Klimpel, K.R. et al. (Nov. 1992). "Anthrax toxin protective antigen is activated by a cell surface protease with the sequence specificity and catalytic properties of furin," *Proc Natl Acad Sci U S A* 89(21):10277-10281.

Klimpel, K.R. et al. (Sep. 1994). "Anthrax toxin lethal factor contains a zinc metalloprotease consensus sequence which is required for lethal toxin activity," *Mol Microbiol* 13(6)1093-1100.

Krantz, B.A. et al. (Jul. 29, 2005) "A phenylalanine clamp catalyzes protein translocation through the anthrax toxin pore," *Science* 309(5735):777-781.

Leppla, S.H. (May 1982). "Anthrax toxin edema factor: a bacterial adenylate cyclase that increases cyclic AMP concentrations of eukaryotic cells," *Proc Natl Acad Sci U S A* 79(10): 3162-3166.

Miller, C.J. (Aug. 1999). "Anthrax protective antigen: prepore-to-pore conversion," *Biochemistry* 38(32):10432-10441.

Molloy, S.S. et al. (Aug. 15, 1992). "Human furin is a calcium-dependent serine endoprotease that recognizes the sequence Arg-X-X-Arg and efficiently cleaves anthrax toxin protective antigen," *J Biol Chem* 267(23):16396-16402.

Rainey, G.J. et al. (Sep. 13, 2005, e-published Sep. 1, 2005). "Receptor-specific requirements for anthrax toxin delivery into cells," *Proc Natl Acad Sci U S A* 102(37): 13278-13283.

Scobie, H.M. et al. (Apr. 29, 2003, e-published Apr. 16, 2003). "Human capillary morphogenesis protein 2 functions as an anthrax toxin receptor," *Proc Natl Acad Sci U S A* 100(9): 5170-5174.

Young, J.A. et al. (2007). "Anthrax toxin: receptor binding, internalization, pore formation, and translocation," *Annu Rev Biochem* 76:243-265.

W.L. Shoop et al., Anthrax Lethal Factor Inhibition, PNAS, May 31, 2005, vol. 102, No. 22 pp. 7958-7963.

S. Mazumdar, Raxibacumab, mAbs 1:6, 531-538; Nov./Dec. 2009; 2009 Landers Bioscience.

* cited by examiner

1 "EGA": X, Y= H, Z= Br;
$IC_{50}$= 1.4 μM
2: X= F, Y=H, Z= Br;
$IC_{50}$= 0.4 μM

Photoaffinity probes:
3: X= F, Y=H, Z= $N_3$; $IC_{50}$= 2.2 μM   NO PHOTOLABELING
4: X, Y= H, Z= $N_3$; $IC_{50}$= 2.8 μM   MODERATE PHOTOLABELING
5: X, Y= F, Z= $N_3$; $IC_{50}$= > 25 μM   BEST PHOTOLABELING

PROTECTIVE MOLECULES AGAINST ANTHRAX TOXIN

CROSS-REFERENCES TO RELATED APPLICATIONS

This application is a continuation of International Patent Application No. PCT/US2014/011930, filed Jan. 16, 2014, which claims the benefit of U.S. Provisional Patent Application No. 61/753,355, filed Jan. 16, 2013, each of which is incorporated herein by reference in its entirety and for all purposes.

STATEMENT AS TO RIGHTS TO INVENTIONS MADE UNDER FEDERALLY SPONSORED RESEARCH OR DEVELOPMENT

This invention was made with government support under Grant Nos. AI057870, AI077791, GM007185, GM098756, awarded by the National Institutes of Health. The government has certain rights in the invention.

BACKGROUND OF THE INVENTION

The success of a broad array of microbial pathogens, from viruses to bacteria to eukaryotic parasites, depends on the ability to gain entry into and/or transport proteins into the cytosol of host cells. Intracellular acting bacterial toxins have evolved to take advantage of numerous host-mediated entry mechanisms {Knodler, 2001}, and therefore, these toxins are ideal tools for studying endocytosis and vesicular trafficking. Indeed, the use of bacterial toxins has led to many key discoveries including, but not limited to, membrane recycling, clathrin-independent endocytosis, and retrograde transport {Sandvig, 2005}. Small molecules that disrupt toxin binding, entry, trafficking and host-response can not only serve as novel probes to dissect such eukaryotic cellular pathways, but are also possible therapies for infectious and genetic diseases. Several groups have identified compounds that inhibit entry of ricin, Shiga toxin, and *Pseudomonas aeruginosa* exotoxin A (ExoA) into host cells. (Saenz, 2007, Wahome, 2010, Stechmann, 2010). These small molecules exhibited varied mechanisms of action, including blockage of retrograde toxin trafficking at the early endosome-TGN junction, morphological disruption of the Golgi apparatus, and inhibition of the toxin active site.

*Bacillus anthracis*, the causative agent of the disease anthrax, secretes binary toxins that enter host cells and disrupt physiological processes. Lethal factor (LF) is a $Zn^{2+}$-dependent metalloprotease that cleaves mitogen activated protein kinase kinases (MKKs) 1-4, 6, and 7 {Duesbery, 1998; Vitale, 1999} and Nlrp1b and reproduces many pathologies of anthrax when injected into laboratory animals {Beall, 1962, Moayeri, 2009}. The cellular entry of LF is dependent on a cell-binding and translocation subunit known as protective antigen (PA). PA is an 83 kDa protein that is cleaved by host proteases into 63 and 20 kDa fragments, allowing oligomerization of the toxin into a prepore (Milne, 1994). The PA oligomer can then bind up to four monomers of LF, forming a holotoxin complex (Mogridge, 2002, Kintzer, 2009). Two cellular toxin receptors, TEM8 and CMG2, mediate toxin binding via a structural domain and interaction motif homologous to those seen in integrin binding {Bradley, 2001, Scobie, 2003, Bradley, 2003} and endocytic uptake. Also similar to integrins, PA binding to receptors is modulated by interactions between the cytosolic tail of the receptor and the actin cytoskeleton (Go, 2009, Garlick, 2010). Palmitoylation of cysteines in the cytosolic tail of the receptor is important to prevent premature clustering, internalization, and lysosomal degradation (Abrami, 2006). Upon toxin binding, oligomerized receptors migrate into detergent-resistant membrane fractions known as lipid rafts, promoting recruitment of the E3 ubiquitin ligase Cb1 by beta-arrestin and ubiquitination of the receptor (Abrami, 2003, Abrami et al. 2006). The receptor-toxin complex then recruits the adaptor protein AP-1 and clathrin. The newly formed clathrin-coated vesicle pinches off from the membrane in a manner dependent on actin and dynamin and transits to the early/sorting endosome (Abrami, 2010, Abrami, 2003). ARAP3 (ArfGAP and RhoGAP with ankyrin repeat and PH domains) also plays a role in toxin endocytosis, though its precise contribution is unclear (Lu, 2004). Acidification of the lumen of the late endosome drives a conformational change in the prepore resulting in insertion into the endosomal membrane and translocation of LF into the cytosol (Koehler, 1991; Milne, 1993; Miller, 1999). Alternatively, LF may be translocated to the interior of intraluminal vesicles and transported to the late endosome via multivesicular bodies in a process dependent on COPI and ALIX (Abrami, 2004). The vesicular membranes then fuse with the limiting endosomal membrane and thereby deliver LF to the cytosol (Abrami, 2004).

Small-molecules that interfere with acidification of cell transport vesicles called endosomes have been shown to have multiple effects in human health and disease. Lysosomotropic agents, which preferentially accumulate in cell-trafficking vesicles and raise pH, inhibit the effects of bacterial toxins such as anthrax toxin and *Diphtheria* toxin and limit the survival of viruses (Ooi, 2006, Perez 1994, Guinea, 1995). The compound chloroquine has been investigated as a potential therapeutic in HIV infection (Romanelli, 2004). Bafilomycin A1, a compound which specifically inhibits the vacuolar ATPase resulting in increased endosomal pH, has also been investigated for use in bone disorders involving excessive resorption (Sorensen, 2007, Niikura, 2005) and/or tumor treatment (McSheehy, 2003). It has been proved in principle that toxin inhibitors can partially protect animals from *B. anthracis* infection alone and can extend therapeutic window when used in conjunction with antibiotics (Shoop, 2005). Several small-molecules which disrupt anthrax toxin transport by raising endosomal pH have been discovered and shown to block intoxication both in cell-based in vitro systems and in vivo in animals. Anthrax toxin killing of cells is inhibited by compounds that inhibit acidification of the endosome such as ammonium chloride, chloroquine, and monensin (Friedlander, 1986). Chloroquine improves survival in a mouse intoxication model (Artenstein. 2004). Quinacrine, a molecule which accumulates in acidic endosomes and effectively raises endosomal pH, protects cells from LT, but was unable to protect animals in a spore infection model of disease (Comer, 2006). Several well-studied compounds with diverse known mechanisms of action have also been shown to inhibit intoxication by raising endosomal pH, rather than by the previously known action of the compound. The Ca2+ channel inhibitors amiodarone and bepridil, the P2X7 antagonist o-ATP, the natural product diphyllin, and the teniacide niclosamide all inhibit LT through disruption of proton gradients (Sanchez, 2007, Moayeri, 2006, Zhu, 2009).

The present invention addresses these and other problems in the prior art.

BRIEF SUMMARY OF THE INVENTION

In an aspect is provided a compound of the formula:

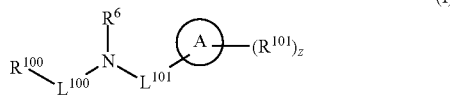

(I)

or pharmaceutically acceptable salt thereof. Ring A is a substituted or unsubstituted cycloalkylene, substituted or unsubstituted heterocycloalkylene, substituted or unsubstituted arylene or substituted or unsubstituted heteroarylene. $R^{100}$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^6$ is hydrogen, halogen, $C(X^1)_3$, $-OC(X^1)_3$, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{11A}R^{12A}$, $-OR^{13A}$, $-SR^{14A}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{101}$ is independently hydrogen, halogen, $-C(X^3)_3$, $-OC(X^3)_3$, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{11C}R^{12C}$, $-OR^{13C}$, $-SR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^{100}$ is $-NHC(=R^7)-$ or $-N=C(NH_2)-$. $L^{101}$ is $-NH-CH(R^{10})-$ or $-N=C(R^{10})-$. $R^7$ is O, S, or NH. $R^{10}$ is hydrogen, halogen, $-C(X^2)_3$, $-OC(X^2)_3$, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{11B}R^{12B}$, $-OR^{13B}$, $-SR^{14B}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{11A}$, $R^{12A}$, $R^{13A}$, $R^{14A}$, $R^{11B}$, $R^{12B}$, $R^{13B}$, $R^{14B}$, $R^{11C}$, $R^{12C}$, $R^{13C}$, and $R^{14C}$ are independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $X^1$, $X^2$ and $X^3$ are independently a halogen. The symbol z is an integer from 0 to 9.

In a second aspect is provided a pharmaceutical composition including a pharmaceutically acceptable excipient and a compound as described herein (including in embodiments), or pharmaceutically acceptable salt thereof.

In a third aspect is provided a method of treating a disease in a subject in need thereof, the method including administering an effective amount of a compound as described herein (including in embodiments), or pharmaceutically acceptable salt thereof, to a subject in need thereof.

In a fourth aspect is provided a method of treating a subject for contact with a toxic agent, the method including administering an effective amount of a compound as described herein (including in embodiments), or pharmaceutically acceptable salt thereof, to a subject in need thereof.

In a fifth aspect is provided a method of treating an infectious disease in a subject, the method including administering a therapeutically effective amount of a compound as described herein (including in embodiments), or pharmaceutically acceptable salt thereof, to a subject in need thereof.

In a sixth aspect is provided a method of modulating trafficking between early and late endosomes, the method including administering an effective amount of a compound as described herein (including in embodiments), or pharmaceutically acceptable salt thereof.

In a seventh aspect is provided a method of modulating maturation of an early endosome, the method including contacting a cellular component (e.g. protein or lipid) that regulates endosomal maturation with a compound as described herein, or pharmaceutically acceptable salt thereof, and allowing the compound to inhibit endosome maturation.

BRIEF DESCRIPTION OF THE DRAWINGS

(FIGS. 1A, 1B) Six hits from a high throughput screen of 30 k compounds were further characterized for their ability to protect RAW264.7 cells from LT. (FIG. 1A) $IC_{50}$ and, (FIG. 1B) maximal cell protection values were calculated from 3 independent experiments performed in triplicate; compound names and (ChemBridge ID) are: 1=EGA, 4-bromobenzaldehyde N-(2,6-dimethylphenyl)semicarbazone (5319257); 2=1-(2,6-dimethyl-1-piperidinyl)-3-[(2-isopropyl-5-methylcyclohexyl)oxy]-2-propanol hydrochloride (5807685); 3=1-(3,6-dichloro-9H-carbazol-9-yl)-3-(dimethylamino)-2-propanol (5236848); 4=4-fluoro-N'-[1-(2-pyridinyl)ethylidene]benzohydrazide (5325699); 5=17-{[(2-hydroxyethyl)amino]methyl}androstan-17-ol (5709157); 6=1,1'-(1,4-phenylene)bis[3-(2-pyridinyl)-2-propen-1-one] (5276688). (FIG. 1C) EGA was added to RAW264.7 cells at various times before or after the addition of LT; cell survival was measured at 24 h post toxin addition via ATPlite assay, with relative luminescence units (RLU) correlating with increased survival; data represent average values of triplicate samples +/−SD from a representative experiment. (FIG. 1D) BMDMs from two independent mice bearing LT-sensitive alleles of Nlrp1b were treated with a dose-titration of EGA followed by LT or media for 3 h, after which viability was measured as above; averages and standard deviations were calculated independently from technical triplicates for each mouse.

(FIG. 3A) EGA inhibits LT-mediated caspase-1 activation. BMDMs per well were seeded on clear-bottom 384-well plates, allowed to adhere overnight then incubated with 20 µM EGA or DMSO for 1 h before addition of PA and LF for 2 h. FLICA reagent was added for a further 1 hr then cells were stained with Hoechst 33342 and analyzed by automated fluorescence microscopy. Representative images are shown (left panel). DAPI, blue; FLICA, green. Percent overlap of DAPI-stained nuclei with active caspase-1, as measured by FLICA, was calculated from all cells in each well and averages of 3 well per condition are graphed with standard error (right panel). (FIG. 3B) EGA inhibits LT-mediated cleavage of MEK-2. RAW264.7 cells were incubated with 2.5 µM EGA or DMSO for 1 hr before addition of vehicle control or PA+LF for ~2.5 h. Cells were lysed with 1% NP-40 buffer and analyzed via immunoblotting with a MEK-2-specific antibody. Tubulin was used as a loading control. (FIG. 3C) EGA inhibits PA pore formation. RAW264.7 cells were incubated with EGA for 1 h before addition of 400 ng/mL PA for an additional 1 h. Cells were lysed with 1% NP-40 buffer and analyzed by immunoblotting with a PA-specific antibody. (FIG. 3D) EGA inhibits PA pore formation in a dose-dependent manner. RAW264.7 cells were incubated with a dose-titration of EGA for 1 h before addition of 400 ng/mL PA for an additional 1 h. Cells were lysed and analyzed as in (FIG. 3C).

(FIG. 4A) EGA Does Not Neutralize Acidic Compartments. HeLa cells were treated with compounds or vehicle control for 25 minutes before addition of Lysotracker Red and Hoechst for a further 10 minutes, all at 37° C. Cells were imaged with automated fluorescent microscopy and images were scored for number of Lysotracker Red-positive endosomes per cell. (FIG. 4B) EGA Does Not Block Texas Red-Dextran Trafficking to Phagosomes. Human THP-1 monocytic cells were incubated with 25 µM EGA or 250 nM bafilomycin A1 for a set time before addition of Texas Red-dextran. Co-localization of Texas Red dextran with polystyrene beads (phagosomal marker) was measured. (FIG. 4C) EGA Does Not Block Phagocytic Uptake of *F. tularensis*. Cells were incubated with compounds for a set time followed by addition of *F. tularensis* LVS strain for a set time. nuclei and internalized bacteria were counted and results are shown as bacteria/nuclei. (FIG. 4D) EGA Does Not Block *F. tularensis* Escape from the Phagosome. Cells were treated with compounds followed by addition of bacteria for three hours. Cells were digitonin-permeabilized and stained with antibody against *F. tularensis*. % bacteria accessible to antibody was calculated.

FIGS. 5A-5D: EGA does not block initial binding, endocytic uptake, or recycling at the plasma membrane, but does inhibit trafficking from early to late endosomes. (FIG. 5A) EGA, but not NH4Cl, stabilizes EGFR at 60 minutes. HeLa cells were treated with compounds or vehicle control and then stimulated with 100 ng/mL EGF. At 60 minutes post-stimulation, protein lysates were made and an EGFR antibody was used to detect protein levels by immunoblotting (left panel). EGFR signal was normalized to tubulin and the average values from at least 3 independent experiments are shown +/−SD. (FIG. 5B) EGA Slows EGFR-Degradation at 15 Minutes. HeLa cells were treated with EGA or vehicle and then stimulated with 100 ng/mL EGF. Protein lysates were made every 15 minutes for one hour, and EGFR levels were measured by immunoblotting (left panel). EGFR signal was quantified and normalized to tubulin loading control (right panel). (FIG. 5C) EGA Treatment Results in EGF Retention in EEA1+ Endosomes. HeLa cells were treated with EGA or vehicle and then stimulated with fluorescently-labeled EGF. Cells were then stained with fluorescently labeled antibody to EEA1, an early endosomal marker. Image is representative of several fields. (FIG. 5D) EGA Does Not Inhibit Transferrin Receptor Recycling to the Plasma Membrane. HeLa cells were incubated with transferrin receptor at 4° C. for binding, and then TfR was chased with fresh media at 37° C. The relative levels of transferrin recycling for EGA and vehicle treated cells was assessed at 10 and 25 minutes post-chase.

FIGS. 6A-6J: EGA Inhibits Entry of Multiple Toxins and Viruses. (FIG. 6A) EGA Inhibits Toxins That Transit Through Acidic Endosomes. Three fold dilutions of EGA, from 50 μM to xx μM, were added to HeLa cells at the indicated concentrations and incubated for 1 h at 37° C. Cells were then challenged with *Diphtheria* toxin at a concentration of 5 ng/mL, ExoA, and ricin. Cells were incubated for 2 d and viability was assessed using ATPlite. Average relative luminescence unit (RLU) values graphed with standard error. (FIG. 6B) EGA Inhibits cell cycle arrest induced by HdCDT. CHO-K1 cells were pretreated with 20 μM EGA for 1 h and then treated with 1 nM HdCDT or 100 nM EcCDT for 22 hours. Cells were stained with propidium iodide and fluorescence was measured by flow cytometry. Cell cycle distribution was calculated from propidium iodide staining intensity using Cell Quest software. Data represent analysis of $10^4$ cells per sample and are representative of at least 3 independent experiments; EGA Inhibits cytotoxicity induced by Hd-CDT but not Ec-CDT; CHO-pgsA745 cells were pretreated with 12.5 μM EGA (squares) or vehicle (circles) for 1 h and then treated with Hd-CDT or Ec-CDT; cell viability was measured 96 h later by ATPlite; data represent average values from three independent experiments performed in triplicate +/−SD. (FIG. 6C) EGA Traps HdCDT in Enlarged EEA-1-Positive Vesicles. HeLa cells were treated for 1 h with 20 μM EGA or vehicle control, the incubated with 200 nM HdCDT for an additional 1 h. Cells were then fixed and stained with Hoechst 33342 (blue), phaloidin (purple), α-EEA1 antibody (red) and α-HdCDT-B antibody (green). White scale bars indicate 5 μm. (FIG. 6D) Quantification of co-localization by Pearson's coefficient presented below. (FIG. 6E) EGA Does Not Inhibit Infection By pH-independent Nipah-pseudotyped lentivirus, (FIG. 6F) EGA Inhibits Infection by Low pH-dependent VSV-pseudotyped lentivirus. (FIGS. 6G-6H) VSV-pseudotyped, But Not MLV-A-pseudotyped Lentivirus Infection, is Inhibited by EGA, (FIG. 6I) EGA Reduces Acute LCMV Infection, (FIG. 6J) EGA Inhibits Entry of Influenza virus.

FIG. 7: Mechanism of photo-induced linking of aryl azides to enzymes; because the $N^1$-(4-azidobenzylidene)-$N^4$-(2,6-dimethyl-phenyl) semicarbazone inhibits anthrax induced cell death ($IC_{50}$~3.0 μM) proof of principle photolysis studies were conducted; cells that were incubated with the 4-$N_3$ analog of EGA and exposed to UV irradiation retained viability in the presence of anthrax lethal toxin even after the inhibitor was removed from the media by washing.

FIG. 8: The constituent portions of EGA, tested separately and together, do not protect cells from intoxication by LT.

FIG. 9: Photoaffinity labeling of RAW264.7 cells with aryl azide photoprobes. LT=Anthrax lethal toxin, UV=5 min ultraviolet (UVB) irradiation, 'washout' indicates replacing cell media with fresh media lacking 1, 3, 4, or 5 prior to intoxication with LT. Compounds 4 and 5 provided statistically significant protection (*=$p<0.05$, **=$p<0.01$) vs LT following photoirradiation and washout.

FIGS. 10A-10H: Compound protection of cells from intoxication by LT. (FIG. 10A) Compounds 100X and EGA. (FIG. 10B) Compounds 200X and EGA. (FIG. 10C) Compounds 300X and EGA. (FIG. 10D) Compounds 400X and EGA. (FIG. 10E) Compounds 500X and EGA. (FIG. 10F) Compounds 600X, 2004, and EGA. (FIG. 10G) Compounds 700X and EGA. (FIG. 10H) Compounds 800X and EGA.

FIG. 11: EGA Protects Cells from PA+LFnDTA; RAW264.7 cells and HeLa cells were pre-incubated with a titration of EGA for 1 h, followed by a 48 h intoxication with 500 ng/mL PA+1 ng/mL LFnDTA. Cell viability was measured via ATPlite.

DETAILED DESCRIPTION OF THE INVENTION

Figure 1A:
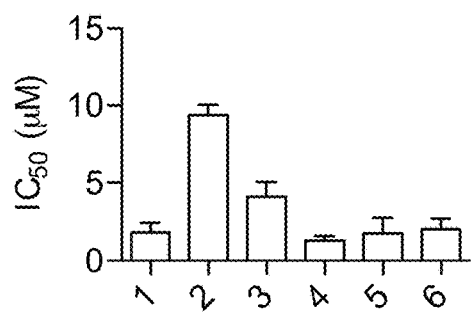
FIGS. 1A-1D: High-Throughput Screen Reveals Novel Inhibitor of LT.

Pathogenic microorganisms and toxins have evolved a variety of mechanisms to gain access to the host cell cytosol and thereby exert virulent effects upon the host. One common mechanism of cellular entry requires trafficking to an acidified endosome, which promotes translocation across the host membrane. In order to identify small-molecule inhibitors that block this process, a library of 30,000 small molecules was screened for inhibitors of anthrax lethal toxin (LT). $N^1$-(4-Bromobenzylidene)-$N^4$-(2,6-dimethylphenyl) semicarbazone (EGA) was discovered via high-throughput screening to be protective against anthrax lethal toxin. A series of novel semicarbazone derivatives have been synthesized in order to improve the potency of the hit as well as develop a strategy for identifying the unknown target. Disclosed herein is the synthesis and bioactivity of analogs of EGA that include the discovery of a compound more active than the original hit. EGA inhibits intoxication by LT and blocks the entry of multiple other acid-dependent bacterial toxins and viruses into mammalian cells. EGA also delays lysosomal targeting and degradation of the EGF receptor, but does not block endosomal recycling of transferrin, retrograde trafficking of ricin, phagolysosomal trafficking or phagosome permeabilization by *Franciscella tularensis*. Further, EGA does not neutralize acidic organelles, suggesting that its mechanism of action is distinct from pH-raising agents such as ammonium chloride and bafilomycin A1.

Despite substantial effort to define binding and entry mechanisms used by LT, there is still much that is unknown about how this, and indeed many other toxins and viruses, gain access to the host cytosol. Described herein is a high-throughput screen of 30,000 commercially available small-molecules for inhibitors of bacterial toxin internalization and/or trafficking using an LT-mediated macrophage cytotoxicity assay. Compounds were identified that display reproducible inhibition of LT. Using a series of biochemical and cell-based assays, one of the most potent compounds, EGA, was found to block trafficking of LT to an acidified endosome. Further, EGA was found to be an inhibitor of multiple other toxins and viruses that share a requirement for trafficking to acidified endosomes.

Many bacterial toxins and viruses require a low-pH step for entry into the host cell cytosol. Compounds that inhibit the entry of bacterial toxins and viruses by raising the pH of cellular vesicles have potential value as therapeutic agents for a host of infectious diseases. We have identified a novel small-molecule, which we call EGA, that interferes with this step in cellular entry.

One advantage of EGA over existing inhibitors of toxin entry is its low IC50 value and relatively low toxicity. EGA was initially calculated to be effective at low micromolar concentrations with an IC50 value of 1.4 micromolar in cell-based LT intoxication experiments, which is much lower than some previously reported toxin entry inhibitors such as quinacrine (40 micromolar), chloroquine (100 micromolar), and ammonium chloride (5 mM). Therefore, achieving a therapeutic concentration of EGA in an animal's bloodstream would require less drug and dosing well below a toxic level (i.e. good therapeutic window). Furthermore, we have found EGA to be stable in solution over several months at room temperature, indicating a favorable shelf life.

Described herein, inter alia, is the application of small-molecules as inhibitors of bacterial toxins and viruses that require endosome acidification. We have proven that such small-molecules are capable of protecting cells from killing by bacterial toxins that require endosome acidification including anthrax lethal toxin, *Diphtheria* toxin, and cytolethal distending toxin. In addition, compounds described herein (e.g. EGA or derivatives thereof) block infection by viruses that require acidified endosomes for entry, such as influenza A, lymphocytic choriomeningitis virus (LCMV), and viruses pseudotyped with vesicular stomatitis virus g-spike protein (VSV-G). A description of compound structures and methods for use are described herein.

I. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH₂—CH₂—O—CH₃, —CH₂—CH₂—NH—CH₃, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH=CH—O—CH₃, —Si(CH₃)₃, —CH₂—CH=N—OCH₃, —CH=CH—N(CH₃)—CH₃, —O—CH₃, —O—CH₂—CH₃, and —CN. Up to two or three heteroatoms may be consecutive, such as, for example, —CH₂—NH—OCH₃ and —CH₂—O—Si(CH₃)₃.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S(O₂)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—

OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol " $\sim\!\sim$ ' " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat exposure to a toxin (e.g. anthrax toxin) by preventing death caused by exposure to a toxin and/or causing recovery from one or more symptoms associated with exposure to a toxin. For example, the certain methods presented herein successfully treat infectious diseases (e.g. bacterial infections, *B. anthracis* infection, Influenza, influenza virus infection, viral infections) and/or causing recovery from one or more symptoms associated with an infectious disease. The term "treating" and conjugations thereof, include prevention of an injury, pathology, condition, or disease (e.g. preventing the development of one or more symptoms of exposure to a toxin or preventing death due to exposure to a toxin, preventing infection by an infectious agent such as a bacterium or virus, preventing a symptom of an infectious disease).

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme or protein relative to the absence of the antagonist. An "activity increasing amount," as used herein, refers to an amount of agonist (activator) required to increase the activity of an enzyme or protein relative to the absence of the agonist. A "function disrupting amount," as used herein, refers to the amount of antagonist (inhibitor) required to disrupt the function of an enzyme or protein relative to the absence of the antagonist. A "function increasing amount," as used herein, refers to the amount of agonist (activator) required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

The term "associated" or "associated with" in the context of a substance or substance activity or function associated with a disease (e.g. a protein associated disease, a symptom associated with toxin exposure or a symptom associated with an infection) means that the disease (e.g. toxin exposure or infection) is caused by (in whole or in part), or a symptom of the disease is caused by (in whole or in part) the substance or substance activity or function. For example, a symptom of a disease or condition associated with toxin exposure or infection may be a symptom that results (entirely or partially) from toxin exposure or infection (e.g. by an infectious agent producing a toxin). As used herein, what is described as being associated with a disease, if a causative agent, could be a target for treatment of the disease. For example, a disease associated with toxin exposure or an infectious agent, may be treated with an agent (e.g. compound as described herein) effective for reducing the effects of the toxin or for treating infection or preventing infection.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. a toxin, anthrax toxin, anthrax protective antigen, anthrax edema factor, anthrax lethal factor, or anthrax lethal toxin). In some embodiments contacting includes allowing a compound described herein to interact with a protein or enzyme that is involved in a signaling pathway.

As defined herein, the term "inhibition", "inhibit", "inhibiting" and the like in reference to a protein-inhibitor (e.g. antagonist) interaction means negatively affecting (e.g. decreasing) the activity or function of the protein (e.g. toxin, anthrax toxin, anthrax protective antigen, anthrax edema factor, anthrax lethal factor, or anthrax lethal toxin, protein associated with maturation of endosomes, or protein associated with acidification of endosomes) relative to the activity or function of the protein in the absence of the inhibitor (e.g. compound as described herein). In some embodiments inhibition refers to reduction of a disease or symptoms of disease. In some embodiments, inhibition refers to a reduction in the activity of a signal transduction pathway or signaling pathway (e.g. reduction of a pathway activated by a toxin, anthrax toxin, anthrax protective antigen, anthrax edema factor, anthrax lethal factor, or anthrax lethal toxin). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. a toxin, anthrax toxin, anthrax protective antigen, anthrax edema factor, anthrax lethal factor, or anthrax lethal toxin, or signal transduction activated by the toxin).

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator. In some embodiments, activation refers to an increase in the activity of a signal transduction pathway or signaling pathway. Thus, activation may include, at least in part, partially or totally increasing stimulation, increasing or enabling activation, or activating, sensitizing, or up-regulating signal transduction or enzymatic activity or the amount of a protein decreased in a disease (e.g. by a toxin, anthrax toxin, anthrax protective antigen, anthrax edema factor, anthrax lethal factor, or anthrax lethal toxin or an infectious agent).

The term "modulator" refers to a composition that increases or decreases the level of a target molecule or the function of a target molecule. In some embodiments, a modulator of toxin exposure or of an infectious disease is a compound that reduces the severity of one or more symptoms of a disease associated with toxin exposure (e.g. by a toxin, anthrax toxin, anthrax protective antigen, anthrax edema factor, anthrax lethal factor, or anthrax lethal toxin or an infectious agent) or an infectious agent.

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with a compound, pharmaceutical composition, or method provided herein. In some embodiments, the disease is a disease related to (e.g. caused by) exposure to a toxin (e.g. anthrax toxin, anthrax protective antigen, anthrax edema factor, anthrax lethal factor, or anthrax lethal toxin or an infectious agent). In some embodiments, the disease is a disease related to (e.g. caused by) an infectious agent (e.g. *Bacillus anthracis*). In some embodiments, the disease is anthrax. In some embodiments, the disease is related to (e.g. caused by) a bacterium. In some embodiments, the disease is related to (e.g. caused by) a virus. In some embodiments, the infectious agent is a virus and the disease is a viral infection. In some embodiments, the disease is influenza. In some embodiments, the infectious agent is the influenza virus. In some embodiments, the infectious agent uses acidified endosomes for entry into the cytoplasm (e.g. influenza A, lymphocytic choriomeningitis virus (LCMV), or viruses pseudotyped with vesicular stomatitis virus g-spike protein (VSV-G)).

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example anti-infectious agent therapies (e.g. raxibacumab) such as anti-virals or antibiotics (e.g. fluoroquinolones, doxycycline, erythromycin, vancomycin, penicillin, ciprofloxacin). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles. The compositions of the present invention can also be delivered as mesoporous silica nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. anthrax toxin, anthrax protective antigen, anthrax edema factor, anthrax lethal factor, or anthrax lethal toxin), and/or reducing, eliminating, or slowing the progression of disease symptoms (e.g. due to anthrax, infectious disease, bacterial infection, viral infection, *Bacillus anthracis* infection). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. toxin, amount of toxin, amount of bacteria, amount of *Bacillus anthracis* spores), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating a disease associated with toxin exposure (e.g. anthrax toxin, anthrax protective antigen, anthrax edema factor, anthrax lethal factor, or anthrax lethal toxin) or infectious agents (e.g. *Bacillus anthracis*), or with adjunctive agents that may not be effective alone, but may contribute to the efficacy of the active agent. The compounds described herein may be used in combination with an inhibitor of endosome acidification (e.g. ammonium chloride, chloroquine, or monensin). The compounds described herein may be used in combination with a compound that reduces acidification of an endosome (e.g. quinacrine). The compounds described herein may be used in combination with a compound that raises endosomal pH. The compounds described herein may be used in combination with a compound that disrupts proton gradients (e.g. amiodarone, bepridil, P2X7 antagonist o-ATP, diphyllin, or teniacide niclosamide.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

II. COMPOUNDS

In a first aspect is provided a compound, or pharmaceutically acceptable salt thereof, having the formula:

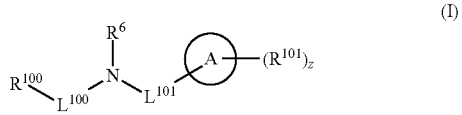

(I)

Ring A is a substituted or unsubstituted cycloalkylene, substituted or unsubstituted heterocycloalkylene, substituted or unsubstituted arylene or substituted or unsubstituted heteroarylene. $R^{100}$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^6$ is independently hydrogen, halogen, $-CX^1_3$, $-OCX^1_3$, $-OCHX^1_2$, $-CN$, $-NO_2$, $-SO_2C$, $-NHSO_2CH_3$, $-N_3$, $-NR^{11A}R^{12A}$, $-OR^{13A}$, $-SR^{14A}$, $-ONR^{11A}R^{12A}$, $-NHC=(O)NHNH_2$, $-NHC=(O)NR^{11A}R^{12A}$, $-C(O)R^{13A}$, $-C(O)-OR^{13A}$, $-C(O)NR^{11A}R^{12A}$, $-NR^{11A}SO_2R^{14A}$, $-NR^{11A}C=(O)R^{13A}$, $-NR^{11A}C(O)-OR^{13A}$, $-NR^{11A}OR^{13A}$, $-SOR^{14A}$, $-SO_2R^{14A}$, $-SO_3R^{14A}$, $-SO_4R^{14A}$, $-SONR^{11A}R^{12A}$, $-SO_2NR^{11A}R^{12A}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^{10}$ is independently hydrogen, halogen, $-CX^2_3$, $-OCX^2_3$, $-OCHX^2_2$, $-CN$, $-NO_2$, $-SO_2Cl$, $-NHSO_2CH_3$, $-N_3$, $-NR^{11B}R^{12B}$, $-OR^{13B}$, $-SR^{14B}$, $-ONR^{11B}R^{12B}$, $-NHC=(O)NHNH_2$, $-NHC=(O)NR^{11B}R^{12B}$, $-C(O)R^{13B}$, $-C(O)-OR^{13B}$, $-C(O)NR^{11B}R^{12B}$, $-NR^{11B}SO_2R^{14B}$, $-NR^{11B}C=(O)R^{13B}$, $-NR^{11B}C(O)-OR^{13B}$, $-NR^{11B}OR^{13B}$, $-SOR^{14B}$, $-SO_2R^{14B}$, $-SO_3R^{14B}$, $-SO_4R^{14B}$, $-SONR^{11B}R^{12B}$, $-SO_2NR^{11B}R^{12B}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. Each $R^{101}$ is independently hydrogen, halogen, $-CX^3_3$, $-OCX^3_3$, $-OCHX^3_2$, $-CN$, $-NO_2$, $-SO_2Cl$, $-NHSO_2CH_3$, $-N_3$, $-NR^{11C}R^{12C}$, $-OR^{13C}$, $-SR^{14C}$, $-ONR^{11C}R^{12C}$, $-NHC=(O)NHNH_2$, $-NHC=(O)NR^{11C}R^{12C}$, $-C(O)R^{13C}$, $-C(O)-OR^{13C}$, $-C(O)NR^{11C}R^{12C}$, $-NR^{11C}SO_2R^{14C}$, $-NR^{11C}C=(O)R^{13C}$, $-NR^{11C}(O)-OR^{13C}$, $-NR^{11C}OR^{13C}$, $-SOR^{14C}$, $-SO_2R^{14C}$, $-SO_3R^{14C}$, $-SO_4R^{14C}$, $-SONR^{11C}R^{12C}$, $-SO_2NR^{11C}R^{12C}$, Substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $L^{100}$ is $-NHC(=R^7)-$ or $-N=C(NH_2)-$. $L^{101}$ is $-NHCH(R^{10})-$, $-N=C(R^{10})-$, or $-C(O)-$. $R^7$ is O, S, or NH. Each $R^{11A}$, $R^{12A}$, $R^{13A}$, $R^{14A}$, $R^{11B}$, $R^{12B}$, $R^{13B}$, $R^{14B}$, $R^{11C}$, $R^{12C}$, $R^{13C}$, and $R^{14C}$ is independently a hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. Each $X^1$, $X^2$, and $X^3$ is independently a halogen. The symbol z is an integer from 0 to 9.

In embodiments, $R^6$ is independently hydrogen, halogen, $-CX^1_3$, $-OCX^1_3$, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{11A}R^{12A}$, $-OR^{13A}$, $-SR^{14A}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^{10}$ is independently hydrogen, halogen, $-CX^2_3$, $-OCX^2_3$, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{11B}R^{12B}$, $-OR^{13B}$, $-SR^{14B}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, each $R^{101}$ is independently hydrogen, halogen, $-CX^3_3$, $-OCX^3_3$, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{11C}R^{12C}$, $-OR^{13C}$, $-SR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, each $R^{11A}$, $R^{12A}$, $R^{13A}$, $R^{14A}$, $R^{11B}$, $R^{12B}$, $R^{13B}$, $R^{14B}$, $R^{11C}$, $R^{12C}$, $R^{13C}$, and $R^{14C}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^6$ is hydrogen. In embodiments, $R^6$ is $-CH_2CCH$. In embodiments, $R^6$ is Me. In embodiments, $R^6$ is Et. In embodiments, $R^6$ is iPr. In embodiments, $R^6$ is nPr. In embodiments, $R^6$ is nBu. In embodiments, $R^6$ is t-Bu.

In embodiments, $R^7$ is O. In embodiments, $R^7$ is S. In embodiments, $R^7$ is NH. In embodiments, $L^{100}$ is $-NHC(=R^7)-$. In embodiments, $L^{100}$ is $-N=C(NH_2)-$. In embodiments, $L^{101}$ is $-NHCH(R^{10})-$. In embodiments, $L^{101}$ is $-N=C(R^{10})-$. In embodiments, $L^{101}$ is $-C(O)-$. In embodiments, $L^{101}$ is $-NHCH(R^{10})-$ or $-N=C(R^{10})-$. In embodiments, $R^{10}$ is hydrogen. In embodiments, $R^{10}$ is Me. In embodiments, $R^{10}$ is Et. In embodiments, $R^{10}$ is Pr. In embodiments, $R^{10}$ is iPr. In embodiments, $R^{10}$ is Bu. In embodiments, $R^{10}$ is t-Bu.

In embodiments, ring A is a substituted or unsubstituted arylene or substituted or unsubstituted heteroarylene. In embodiments, ring A is an unsubstituted arylene or unsubstituted heteroarylene. In embodiments, ring A is an unsubstituted $C_6$-$C_{10}$ arylene or unsubstituted 5 to 10 membered heteroarylene. In embodiments, ring A is an unsubstituted $C_6$ arylene or unsubstituted 5 to 6 membered heteroarylene. In embodiments, ring A is an unsubstituted $C_6$ arylene. In embodiments, ring A is an unsubstituted thienylene. In embodiments, ring A is an unsubstituted furanylene. In embodiments, ring A is an unsubstituted pyridnylene.

In embodiments, $R^{100}$ is substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl or substituted or unsubstituted 5 to 10 membered heteroaryl. In embodiments, $R^{100}$ is substituted or unsubstituted $C_6$-$C_{10}$ aryl or substituted or unsubstituted 5 to 10 membered heteroaryl. In embodiments, $R^{100}$ is substituted $C_6$-$C_{10}$ aryl or substituted 5 to 10 membered heteroaryl. In embodiments, $R^{100}$ is substituted $C_6$ aryl or substituted 5 to 6 membered heteroaryl. In embodiments, $R^{100}$ is substituted phenyl. In embodiments, $R^{100}$ is substituted thienyl. In embodiments, $R^{100}$ is substituted furanyl. In embodiments, $R^{100}$ is substituted pyridinyl. In embodiments, $R^{100}$ is unsubstituted t-butyl. In embodiments, $R^{100}$ is substituted $C_1$-$C_4$ alkyl. In embodiments, $R^{100}$ is unsubstituted $C_1$-$C_4$ alkyl. In embodiments, $R^{100}$ is not 2, 4-Me$_2$ substituted phenyl. In embodiments, $R^{100}$ is not unsubstituted phenyl. In embodiments, $R^{100}$ is not unsubstituted biphenyl. In embodiments, $R^{100}$ is not t-Bu. In embodiments, $R^{100}$ is not unsubstituted t-butyl. In embodiments, $R^{100}$ is not substituted $C_1$-$C_4$ alkyl. In embodiments, $R^{100}$ is not unsubstituted $C_1$-$C_4$ alkyl.

In embodiments, each $R^{101}$ is independently halogen, —$CX^3_3$, —$OCX^3_3$, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{11C}R^{12C}$, —$OR^{13C}$, —$SR^{14C}$ substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, $R^{101}$ is hydrogen. In embodiments, $R^{101}$ is halogen. In embodiments, $R^{101}$ is —$CX^3_3$. In embodiments, $R^{101}$ is —$OCX^3_3$. In embodiments, $R^{101}$ is —CN. In embodiments, $R^{101}$ is —C(O)OH. In embodiments, $R^{101}$ is —$CONH_2$. In embodiments, $R^{101}$ is —$NO_2$. In embodiments, $R^{101}$ is —$SO_2Cl$. In embodiments, $R^{101}$ is —$SO_2NH_2$. In embodiments, $R^{101}$ is —$NHNH_2$. In embodiments, $R^{101}$ is —$NHSO_2CH_3$. In embodiments, $R^{101}$ is —$N_3$. In embodiments, $R^{101}$ is —$NR^{11C}R^{12C}$. In embodiments, $R^{101}$ is —$OR^{13C}$. In embodiments, $R^{101}$ is —$SR^{14C}$. In embodiments, $R^{101}$ is substituted or unsubstituted alkyl. In embodiments, $R^{101}$ is substituted or unsubstituted heteroalkyl. In embodiments, $R^{101}$ is substituted or unsubstituted cycloalkyl. In embodiments, $R^{101}$ is substituted or unsubstituted heterocycloalkyl. In embodiments, $R^{101}$ is substituted or unsubstituted aryl. In embodiments, $R^{101}$ is substituted or unsubstituted heteroaryl. In embodiments, $R^{101}$ is —F. In embodiments, $R^{101}$ is —Cl. In embodiments, $R^{101}$ is —Br. In embodiments, $R^{101}$ is —I. In embodiments, $R^{101}$ is —$CF_3$. In embodiments, $R^{101}$ is —$CH_3$. In embodiments, $R^{101}$ is —$OCH_3$. In embodiments, $R^{101}$ is Et. In embodiments, $R^{101}$ is iPr. In embodiments, $R^{101}$ is Pr. In embodiments, $R^{101}$ is Bu. In embodiments, $R^{101}$ is tBu. In embodiments, $R^{101}$ is —CCH. In embodiments, $R^{101}$ is —$NHSO_2Me$. In embodiments, $R^{101}$ is benzyl substituted triazolyl.

In embodiments, $X^1$ is —F. In embodiments, $X^1$ is —Cl. In embodiments, $X^1$ is —Br. In embodiments, $X^1$ is —I. In embodiments, $X^2$ is —F. In embodiments, $X^2$ is —Cl. In embodiments, $X^2$ is —Br. In embodiments, $X^2$ is —I. In embodiments, $X^3$ is —F. In embodiments, $X^3$ is —Cl. In embodiments, $X^3$ is —Br. In embodiments, $X^3$ is —I.

In embodiments, z is 0. In embodiments, z is 1. In embodiments, z is 2. In embodiments, z is 3. In embodiments, z is 4. In embodiments, z is 5. In embodiments, z is 6. In embodiments, z is 7. In embodiments, z is 8. In embodiments, z is 9.

In embodiments, the compound does not include the combination $L^{100}$ is —NHC(=O)—, $R^6$ is hydrogen, and $L^{101}$ is —$NHCH_2$—.

In embodiments, the compound has the formula:

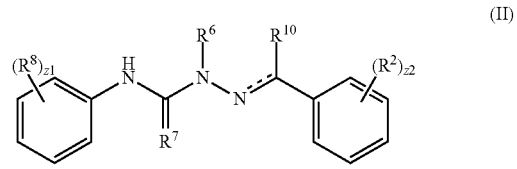

(II)

Each $R^6$, $R^7$, and $R^{10}$ is as described herein, including in embodiments.

Each $R^2$ is independently hydrogen, halogen, —$CX^3_3$, —$OCX^3_3$, —$OCHX^3_2$, —CN, —$NO_2$, —$SO_2Cl$, —$NHSO_2CH_3$, —$N_3$, —$NR^{11C}R^{12C}$, —$OR^{13C}$, —$SR^{14C}$, —$ONR^{11C}R^{12C}$, —NHC=(O)$NHNH_2$, —NHC=(O)$NR^{11C}R^{12C}$, —$C(O)R^{13C}$, —C(O)—$OR^{13C}$, —C(O)$NR^{11C}R^{12C}$, —$NR^{11C}SO_2R^{14C}$, —$NR^{11C}C$=(O)$R^{13C}$, —$NR^{11C}(O)$—$OR^{13C}$, —$NR^{11C}OR^{13C}$, —$SOR^{14C}$, —$SO_2R^{14C}$, —$SO_3R^{14C}$, —$SO_4R^{14C}$, —$SONR^{11C}R^{12C}$, —$SO_2NR^{11C}R^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. Each $R^8$ is independently hydrogen, halogen, —$CX_3$, —$OCX_3$, —$OCHX_2$, —CN, —$NO_2$, —$SO_2Cl$, —$NHSO_2CH_3$, —$N_3$, —$NR^{11}R^{12}$, —$OR^{13}$, —$SR^{14}$, —$ONR^{11}R^{12}$, —NHC=(O)$NHNH_2$, —NHC=(O)$NR^{11}R^{12}$, —$C(O)R^{13}$, —C(O)—$OR^{13}$, —C(O)$NR^{11}R^{12}$, —$NR^{11}SO_2R^{14}$, —$NR^{11}C$=(O)$R^{13}$, —$NR^{11}C(O)$—$OR^{13}$, —$NR^{11}OR^{13}$, —$SOR^{14}$, —$SO_2R^{14}$, —$SO_3R^{14}$, —$SO_4R^{14}$, —$SONR^{11}R^{12}$, —$SO_2NR^{11}R^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. The symbol $=====$ is a single or double bond, wherein if $=====$ is a single bond than —N$=====$C($R^{10}$)— is —NH—CH($R^{10}$)— and if $=====$ is a double bond than —N$=====$C($R^{10}$)— is —N=C($R^{10}$)—. The symbols z1 and z2 are independently an integer from 0 to 5. Each X is independently a halogen. Each $R^{11}$, $R^{12}$, $R^{13}$, and $R^{14}$ is independently a hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, each $R^2$ is independently hydrogen, halogen, —$CX^3_3$, —$OCX^3_3$, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{11C}R^{12C}$, —$OR^{13C}$, —$SR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, each $R^8$ is independently hydrogen, halogen, —$CX_3$, —$OCX_3$, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{11}R^{12}$, —$OR^{13}$, —$SR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, each $R^{11}$, $R^{12}$, $R^{13}$, and $R^{14}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^2$ is —Br. In embodiments, $R^2$ is —F. In embodiments, $R^2$ is —Cl. In embodiments, $R^2$ is —I. In embodiments, $R^2$ is Me. In embodiments, $R^2$ is Et. In embodiments, $R^2$ is iPr. In embodiments, $R^2$ is —CCH. In embodiments, $R^2$ is —OMe. In embodiments, $R^2$ is —CN. In embodiments, $R^2$ is —$N_3$. In embodiments, $R^2$ is —$NHSO_2Me$. In embodiments, $R^2$ is —$CF_3$. In embodiments, $R^2$ is pyridinyl. In embodiments, $R^2$ is substituted triazolyl. In embodiments, $R^2$ is benzyl substituted triazolyl.

In embodiments, $R^8$ is —Br. In embodiments, $R^8$ is —F. In embodiments, $R^8$ is —Cl. In embodiments, $R^8$ is —I. In embodiments, $R^8$ is Me. In embodiments, $R^8$ is Et. In embodiments, $R^8$ is iPr. In embodiments, $R^8$ is —CCH. In embodiments, $R^8$ is —OMe. In embodiments, $R^8$ is —CN. In embodiments, $R^8$ is —$N_3$. In embodiments, $R^8$ is —$NHSO_2Me$. In embodiments, $R^8$ is —$CF_3$. In embodiments, $R^8$ is pyridinyl. In embodiments, $R^8$ is substituted triazolyl. In embodiments, $R^8$ is benzyl substituted triazolyl. In embodiments, $R^8$ is not hydrogen.

In embodiments z1 is 0. In embodiments z1 is 1. In embodiments z1 is 2. In embodiments z1 is 3. In embodiments z1 is 4. In embodiments z1 is 5. In embodiments z2 is 0. In embodiments z2 is 1. In embodiments z2 is 2. In embodiments z2 is 3. In embodiments z2 is 4. In embodiments z2 is 5. In embodiments, X is —F. In embodiments, X is —Cl. In embodiments, X is —Br. In embodiments, X is —I.

In embodiments, z2 is not 1 when $R^2$ is 4-$NHSO_2Me$. In embodiments, z2 is not 3 when $R^2$ is 2,4,6-$OMe_3$. In embodiments, z2 is not 1 when $R^2$ is 2-Me. In embodiments, z2 is not 2 when $R^2$ is 2,3-$OMe_2$. In embodiments, z2 is not 2 when $R^2$ is 2-Cl and 3-$CF_3$. In embodiments, z2 is not 1 when $R^2$ is 4-pyridinyl. In embodiments, z2 is not 1 when $R^2$ is 4-pyridyl.

In embodiments, the compound has the formula:

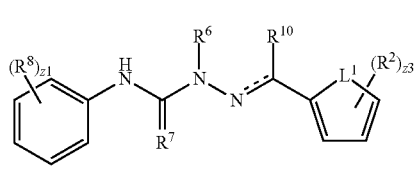

(III)

Each z1, $R^2$, $R^6$, $R^7$, $R^8$ and $R^{10}$ is as described herein, including in embodiments. $L^1$ is —O— or —S—. z3 is an integer from 0 to 3.

In embodiments, $L^1$ is —O—. In embodiments, $L^1$ is —S—. In embodiments, z3 is 0. In embodiments, z3 is 1. In embodiments, z3 is 2. In embodiments, z3 is 3.

In embodiments, z3 is not 0.

In embodiments is a compound, or pharmaceutically acceptable salt thereof, having the formula:

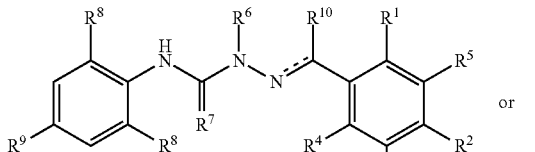

(IV)

or

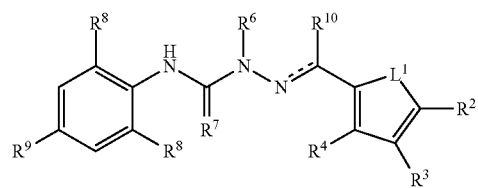

(V)

Each $L^1$, $R^2$, $R^6$, $R^7$, $R^8$, and $R^{10}$ is as described herein, including embodiments thereof.

$R^1$, $R^3$, $R^4$, and $R^5$, are independently hydrogen, halogen, —$CX^3_3$, —$OCX^3_3$, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{11C}R^{12C}$, —$OR^{13C}$, —$SR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. $R^9$ is independently hydrogen, halogen, —$CX_3$, —$OCX_3$, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{11}R^{12}$, —$OR^{13}$, —$SR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

The symbol ===== is a single or double bond, wherein if ===== is a single bond then —N===== $C(R^{10})$— is —NH—$CH(R^{10})$— and if ===== is a double bond then —N===== $C(R^{10})$— is —N=$C(R^{10})$—.

In embodiments, $R^1$ is —Br. In embodiments, $R^1$ is —F. In embodiments, $R^1$ is —Cl. In embodiments, $R^1$ is —I. In embodiments, $R^1$ is Me. In embodiments, $R^1$ is Et. In embodiments, $R^1$ is iPr. In embodiments, $R^1$ is —CCH. In embodiments, $R^1$ is —OMe. In embodiments, $R^1$ is —CN. In embodiments, $R^1$ is —$N_3$. In embodiments, $R^1$ is —$NHSO_2Me$. In embodiments, $R^1$ is —$CF_3$. In embodiments, $R^1$ is pyridinyl. In embodiments, $R^1$ is substituted triazolyl. In embodiments, $R^1$ is benzyl substituted triazolyl.

In embodiments, $R^3$ is —Br. In embodiments, $R^3$ is —F. In embodiments, $R^3$ is —Cl. In embodiments, $R^3$ is —I. In embodiments, $R^3$ is Me. In embodiments, $R^3$ is Et. In embodiments, $R^3$ is iPr. In embodiments, $R^3$ is —CCH. In embodiments, $R^3$ is —OMe. In embodiments, $R^3$ is —CN. In embodiments, $R^3$ is —$N_3$. In embodiments, $R^3$ is —$NHSO_2Me$. In embodiments, $R^3$ is —$CF_3$. In embodiments, $R^3$ is pyridinyl. In embodiments, $R^3$ is substituted triazolyl. In embodiments, $R^3$ is benzyl substituted triazolyl.

In embodiments, $R^4$ is —Br. In embodiments, $R^4$ is —F. In embodiments, $R^4$ is —Cl. In embodiments, $R^4$ is —I. In embodiments, $R^4$ is Me. In embodiments, $R^4$ is Et. In embodiments, $R^4$ is iPr. In embodiments, $R^4$ is —CCH. In embodiments, $R^4$ is —OMe. In embodiments, $R^4$ is —CN. In embodiments, $R^4$ is —$N_3$. In embodiments, $R^4$ is —$NHSO_2Me$. In embodiments, $R^4$ is —$CF_3$. In embodiments, $R^4$ is pyridinyl. In embodiments, $R^4$ is substituted triazolyl. In embodiments, $R^4$ is benzyl substituted triazolyl.

In embodiments, $R^5$ is —Br. In embodiments, $R^5$ is —F. In embodiments, $R^5$ is —Cl. In embodiments, $R^5$ is —I. In embodiments, $R^5$ is Me. In embodiments, $R^5$ is Et. In embodiments, $R^5$ is iPr. In embodiments, $R^5$ is —CCH. In embodiments, $R^5$ is —OMe. In embodiments, $R^5$ is —CN. In embodiments, $R^5$ is —$N_3$. In embodiments, $R^5$ is —$NHSO_2Me$. In embodiments, $R^5$ is —$CF_3$. In embodiments, $R^5$ is pyridinyl. In embodiments, $R^5$ is substituted triazolyl. In embodiments, $R^5$ is benzyl substituted triazolyl.

In embodiments, $R^9$ is —Br. In embodiments, $R^9$ is —F. In embodiments, $R^9$ is —Cl. In embodiments, $R^9$ is —I. In embodiments, $R^9$ is Me. In embodiments, $R^9$ is Et. In embodiments, $R^9$ is iPr. In embodiments, $R^9$ is —CCH. In embodiments, $R^9$ is —OMe. In embodiments, $R^9$ is —CN. In embodiments, $R^9$ is —$N_3$. In embodiments, $R^9$ is —$NHSO_2Me$. In embodiments, $R^9$ is —$CF_3$. In embodiments, $R^9$ is pyridinyl. In embodiments, $R^9$ is substituted triazolyl. In embodiments, $R^9$ is benzyl substituted triazolyl. In embodiments, $R^8$ and $R^9$ are not hydrogen.

In some embodiments of the compound, or a pharmaceutically acceptable salt thereof, $R^1$ is independently hydrogen, halogen, —$OR^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In some embodiments of the compound, or a pharmaceutically acceptable salt thereof, $R^1$ is independently hydrogen, halogen, or —$OR^{13C}$. In embodiments, $R^1$ is —$OR^{13C}$. In embodiments, $R^1$ is hydrogen. In embodiments, $R^1$ is substituted or unsubstituted $C_1$-$C_4$ alkyl. In embodiments, $R^1$ is unsubstituted $C_1$-$C_4$ alkyl. In embodiments, $R^1$ is substituted $C_1$-$C_4$ alkyl. In embodiments, $R^1$ is —$CX^3{}_3$. In embodiments, $R^1$ is a lower substituent. In embodiments, $R^1$ is a size limited substituent. In embodiments, $R^1$ is a halogen. In embodiments, $R^1$ is —$SR^{14C}$.

In some embodiments of the compound, or a pharmaceutically acceptable salt thereof, $R^2$ is independently hydrogen, halogen, —$CX^3{}_3$, —CN, —$NHSO_2CH_3$, —$N_3$, —$OR^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In some embodiments of the compound, or a pharmaceutically acceptable salt thereof, $R^2$ is independently hydrogen, halogen, —$CX^3{}_3$, —CN, —$NHSO_2CH_3$, —$N_3$, —$OR^{13C}$, or unsubstituted alkyl. In some embodiments of the compound, or a pharmaceutically acceptable salt thereof, $R^2$ is a halogen. In some embodiments of the compound, or a pharmaceutically acceptable salt thereof, $R^2$ is —Br. In embodiments, the compound of formula (V) does not include the combination $L^1$ is —O—, $R^2$ is —Br, $R^3$ is hydrogen, and $R^4$ is hydrogen. In embodiments, each $R^2$ is independently —$OR^{13C}$. In embodiments, each $R^2$ is independently hydrogen. In embodiments, each $R^2$ is independently substituted or unsubstituted $C_1$-$C_4$ alkyl. In embodiments, each $R^2$ is independently unsubstituted $C_1$-$C_4$ alkyl. In embodiments, each $R^2$ is independently substituted $C_1$-$C_4$ alkyl. In embodiments, each $R^2$ is independently —$CX^3{}_3$. In embodiments, each $R^2$ is independently a lower substituent. In embodiments, each $R^2$ is independently a size limited substituent. In embodiments, each $R^2$ is independently a halogen. In embodiments, each $R^2$ is independently —$SR^{14C}$.

In some embodiments of the compound, or a pharmaceutically acceptable salt thereof, $R^3$ is independently hydrogen, halogen, —$CX^3{}_3$, —$OR^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In some embodiments of the compound, or a pharmaceutically acceptable salt thereof, $R^3$ is independently hydrogen, halogen, —$CX^3{}_3$, —$OR^{13C}$, or unsubstituted alkyl. In embodiments, $R^3$ is —$OR^{13C}$. In embodiments, $R^3$ is hydrogen. In embodiments, $R^3$ is substituted or unsubstituted $C_1$-$C_4$ alkyl. In embodiments, $R^3$ is unsubstituted $C_1$-$C_4$ alkyl. In embodiments, $R^3$ is substituted $C_1$-$C_4$ alkyl. In embodiments, $R^3$ is —$CX^3{}_3$. In embodiments, $R^3$ is a lower substituent. In embodiments, $R^3$ is a size limited substituent. In embodiments, $R^3$ is a halogen. In embodiments, $R^3$ is —$SR^{14C}$.

In some embodiments of the compound, or a pharmaceutically acceptable salt thereof, $R^4$ is independently hydrogen, halogen, —$OR^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In some embodiments of the compound, or a pharmaceutically acceptable salt thereof, $R^4$ is independently hydrogen, halogen, —$OR^{13}C$, or unsubstituted alkyl. In some embodiments of the compound, or a pharmaceutically acceptable salt thereof, $R^4$ is independently hydrogen or —F. In embodiments, $R^4$ is —$OR^{13C}$. In embodiments, $R^4$ is hydrogen. In embodiments, $R^4$ is substituted or unsubstituted $C_1$-$C_4$ alkyl. In embodiments, $R^4$ is unsubstituted $C_1$-$C_4$ alkyl. In embodiments, $R^4$ is substituted $C_1$-$C_4$ alkyl. In embodiments, $R^4$ is —$CX^3{}_3$. In embodiments, $R^4$ is a lower substituent. In embodiments, $R^4$ is a size limited substituent. In embodiments, $R^4$ is a halogen. In embodiments, $R^4$ is —$SR^{14C}$.

In some embodiments of the compound, or a pharmaceutically acceptable salt thereof, each $R^6$, $R^8$, $R^9$, and $R^{10}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In some embodiments of the compound, or a pharmaceutically acceptable salt thereof, $R^6$ is independently hydrogen or unsubstituted alkyl. In embodiments, $R^6$ is hydrogen.

In embodiments, $R^6$ is substituted or unsubstituted $C_1$-$C_4$ alkyl. In embodiments, $R^6$ is unsubstituted $C_1$-$C_4$ alkyl. In embodiments, $R^6$ is substituted $C_1$-$C_4$ alkyl. In embodiments, $R^6$ is —$CX^3{}_3$. In embodiments, $R^6$ is a lower substituent. In embodiments, $R^6$ is a size limited substituent.

In some embodiments of the compound, or a pharmaceutically acceptable salt thereof, each $R^8$ is independently an unsubstituted alkyl. In embodiments, each $R^8$ is independently —$OR^{13}$. In embodiments, each $R^8$ is independently hydrogen. In embodiments, each $R^8$ is independently substituted or unsubstituted $C_1$-$C_4$ alkyl. In embodiments, each $R^8$ is independently unsubstituted $C_1$-$C_4$ alkyl. In embodiments, each $R^8$ is independently substituted $C_1$-$C_4$ alkyl. In embodiments, each $R^8$ is independently —$CX_3$. In embodiments, each $R^8$ is independently a lower substituent. In embodiments, each $R^8$ is independently a size limited substituent. In embodiments, each $R^8$ is independently a halogen. In embodiments, each $R^8$ is independently —$SR^{14}$.

In some embodiments of the compound, or a pharmaceutically acceptable salt thereof, $R^9$ is independently hydrogen or unsubstituted alkyl. In embodiments, $R^9$ is —$OR^{13}$. In embodiments, $R^9$ is hydrogen. In embodiments, $R^9$ is substituted or unsubstituted $C_1$-$C_4$ alkyl. In embodiments, $R^9$ is unsubstituted $C_1$-$C_4$ alkyl. In embodiments, $R^9$ is substituted $C_1$-$C_4$ alkyl. In embodiments, $R^9$ is —$CX_3$. In embodiments, $R^9$ is a lower substituent. In embodiments, $R^9$ is a size limited substituent. In embodiments, $R^9$ is a halogen. In embodiments, $R^9$ is —$SR^{14}$.

In some embodiments of the compound, or a pharmaceutically acceptable salt thereof, $R^{10}$ is independently hydrogen or unsubstituted alkyl. In embodiments, $R^{10}$ is —$OR^{13B}$. In embodiments, $R^{10}$ is hydrogen. In embodiments, $R^{10}$ is substituted or unsubstituted $C_1$-$C_4$ alkyl. In embodiments, $R^{10}$ is unsubstituted $C_1$-$C_4$ alkyl. In embodiments, $R^{10}$ is substituted $C_1$-$C_4$ alkyl. In embodiments, $R^{10}$ is —$CX^2_3$. In embodiments, $R^{10}$ is a lower substituent. In embodiments, $R^{10}$ is a size limited substituent. In embodiments, $R^{10}$ is a halogen. In embodiments, $R^{10}$ is —$SR^{14B}$.

In some embodiments of the compound, or a pharmaceutically acceptable salt thereof, each $R^{13C}$ is independently a hydrogen or a substituted or unsubstituted alkyl. In some embodiments of the compound, or a pharmaceutically acceptable salt thereof, each $R^{13C}$ is independently an unsubstituted alkyl. In embodiments, each $R^{13C}$ is independently hydrogen. In embodiments, each $R^{13C}$ is independently substituted or unsubstituted $C_1$-$C_4$ alkyl. In embodiments, each $R^{13C}$ is independently unsubstituted $C_1$-$C_4$ alkyl. In embodiments, each $R^{13C}$ is independently substituted $C_1$-$C_4$ alkyl. In embodiments, each $R^{13C}$ is independently —$CF_3$. In embodiments, each $R^{13C}$ is independently a lower substituent. In embodiments, each $R^{13C}$ is independently a size limited substituent.

In embodiments, $R^1$ is independently hydrogen, halogen, or —$OR^{13C}$; $R^2$ is independently hydrogen, halogen, —$CX^3_3$, —CN, —$NHSO_2CH_3$, —$N_3$, —$OR^{13C}$, unsubstituted alkyl; or substituted heteroaryl; $R^3$ is independently hydrogen, halogen, —$CX^3_3$, —$OR^{13C}$, or unsubstituted alkyl; $R^4$ is independently hydrogen, halogen, —$OR^{13C}$, or unsubstituted alkyl; $R^5$ is independently hydrogen, halogen, —$OR^{13C}$, or unsubstituted alkyl; $R^6$ is independently hydrogen or unsubstituted alkyl; each $R^8$ is independently an unsubstituted alkyl; $R^9$ is independently hydrogen or unsubstituted alkyl; $R^{10}$ is independently hydrogen or unsubstituted alkyl; each $R^{13C}$ is independently an unsubstituted alkyl; and $X^3$ is —F. In embodiments, $R^1$ is independently hydrogen, halogen, or —$OR^{13C}$; $R^2$ is independently hydrogen, halogen, —$CX^3_3$, —CN, —$NHSO_2CH_3$, —$N_3$, —$OR^{13C}$, or unsubstituted $C_1$-$C_4$ alkyl; $R^3$ is independently hydrogen, halogen, —$CX^3_3$, —$OR^{13C}$, or unsubstituted $C_1$-$C_4$ alkyl; $R^4$ is independently hydrogen, halogen, —$OR^{13C}$, or unsubstituted $C_1$-$C_4$ alkyl; $R^5$ is independently hydrogen, halogen, —$OR^{13C}$, or unsubstituted $C_1$-$C_4$ alkyl; $R^6$ is independently hydrogen or unsubstituted $C_1$-$C_4$ alkyl; each $R^8$ is independently an unsubstituted $C_1$-$C_4$ alkyl; $R^9$ is independently hydrogen or unsubstituted $C_1$-$C_4$ alkyl; $R^{10}$ is independently hydrogen or unsubstituted $C_1$-$C_4$ alkyl; each $R^{13C}$ is independently an unsubstituted $C_1$-$C_4$ alkyl; and $X^3$ is —F.

In embodiments the compound has the formula:

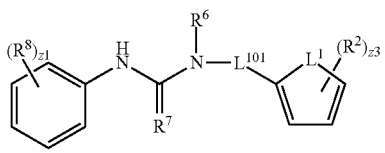

(IIa)

Each $R^2$, $R^6$, $R^7$, $R^8$, $L^{101}$, z1 and z2 is as described herein, including in embodiments.

In embodiments the compound has the formula:

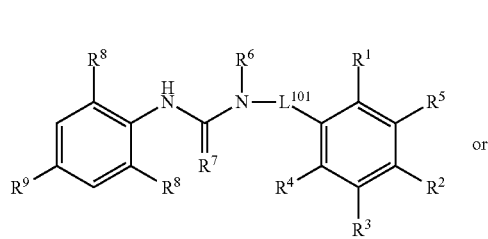

(IIIa)

Each $L^1$, $R^2$, $R^6$, $R^7$, $R^8$, $L^{101}$, z1 and z3 is as described herein, including in embodiments.

In embodiments the compound has the formula:

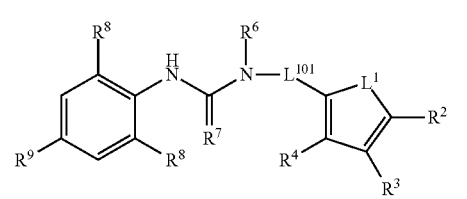

(IVa)

or

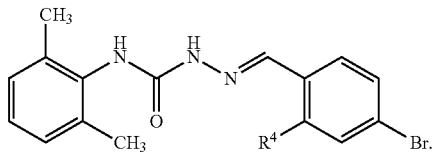

(Va)

Each $L^1$, $R^1$, $R^2$, $R^3$, $R^4$, $R^5$, $R^6$, $R^7$, $R^8$, $R^9$, $L^{101}$ is as described herein, including in embodiments.

In some embodiments of the compound, or a pharmaceutically acceptable salt thereof, the compound has the formula:

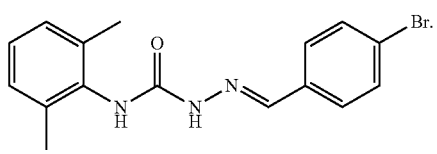

$R^4$ is as described herein, including in embodiments.

In embodiments the compound is

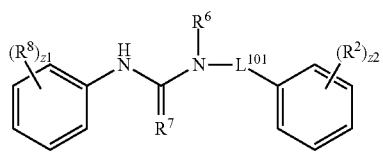

1

In embodiments the compound is

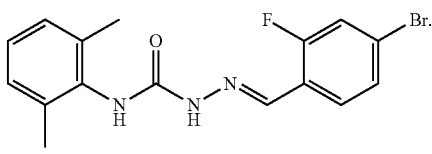

In embodiments the compound is

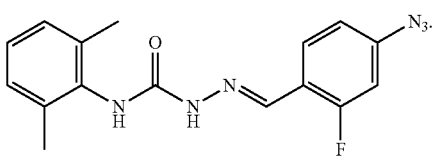

In embodiments the compound is

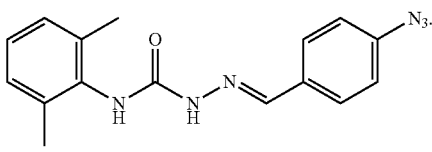

In embodiments the compound is

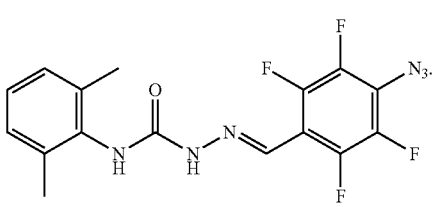

In embodiments the compound is

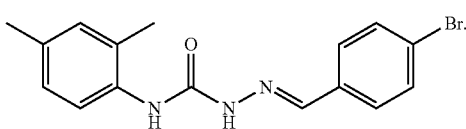

In embodiments the compound is

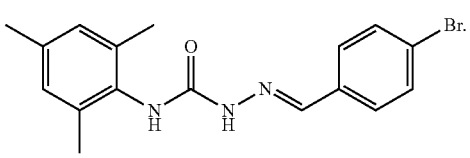

In embodiments the compound is

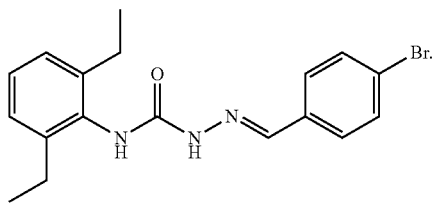

In embodiments the compound is

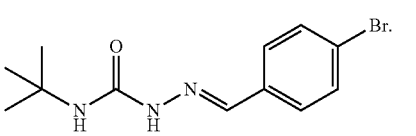

In embodiments the compound is

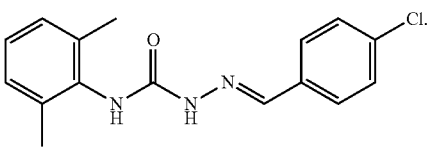

In embodiments the compound

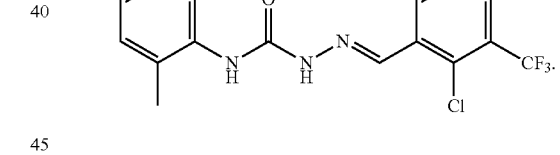

In embodiments the compound is

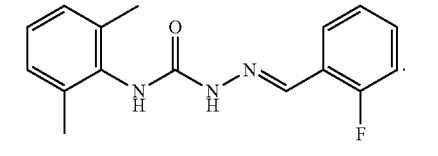

In embodiments the compound is

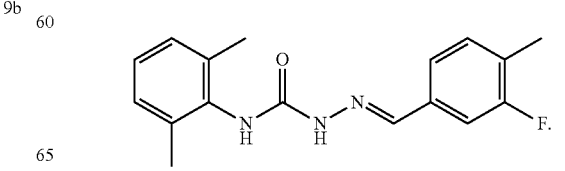

In embodiments the compound is

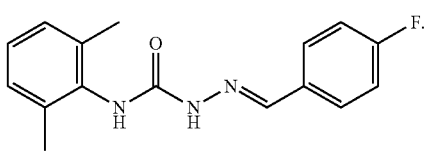
13e

In embodiments the compound is

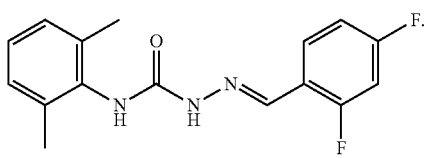
13f

In embodiments the compound is

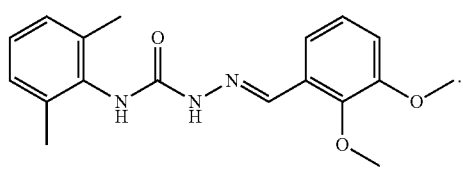
13g

In embodiments the compound is

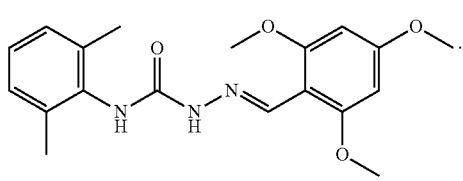
13h

In embodiments the compound is

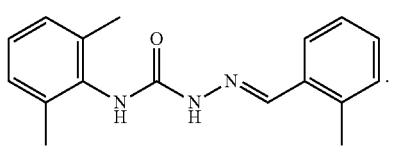
13i

In embodiments the compound is

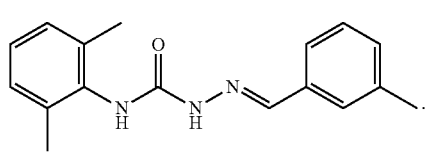
13j

In embodiments the compound is

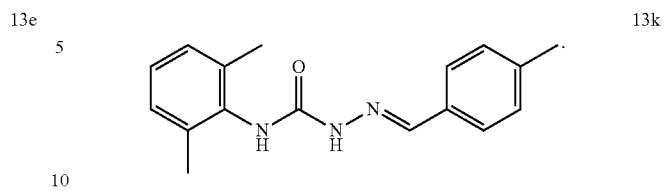
13k

In embodiments the compound is

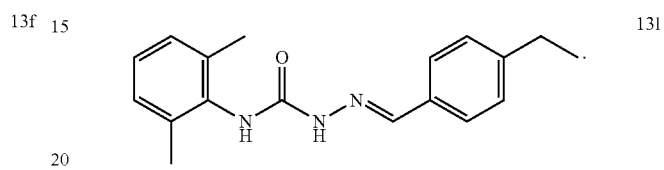
13l

In embodiments the compound is

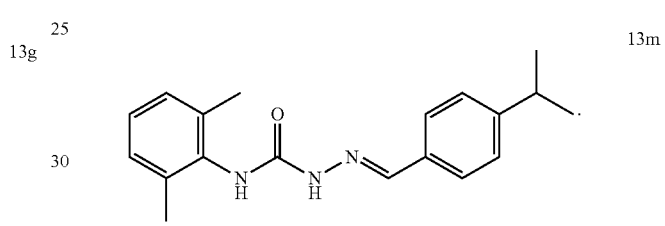
13m

In embodiments the compound is

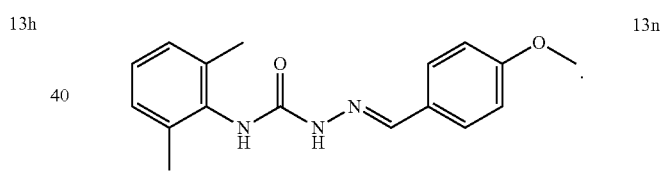
13n

In embodiments the compound is

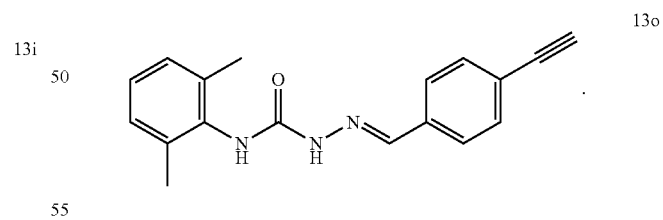
13o

In embodiments the compound is

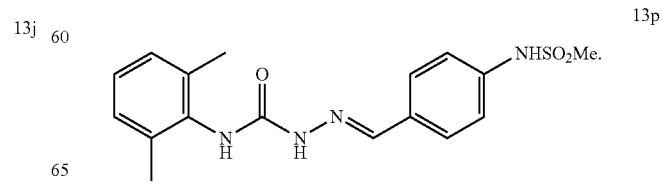
13p

In embodiments the compound is

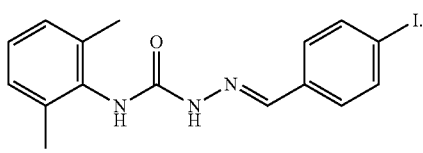
13q

In embodiments the compound is

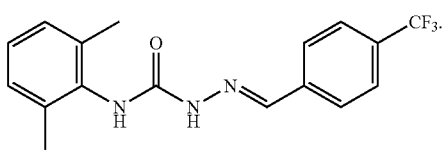
13r

In embodiments the compound is

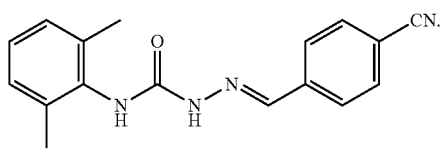
13s

In embodiments the compound is

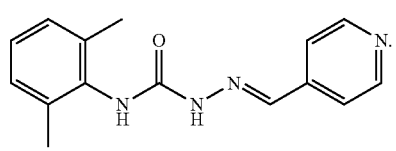
13t

In embodiments the compound is

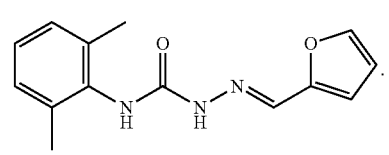
13u

In embodiments the compound is

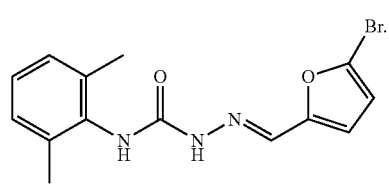
13v

In embodiments the compound is

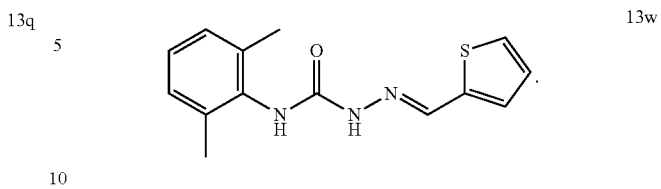
13w

In embodiments the compound is

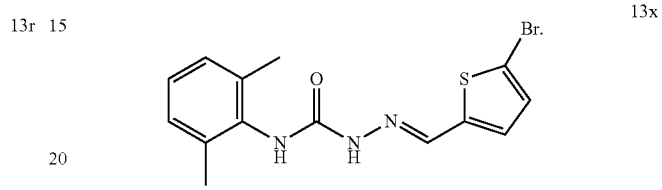
13x

In embodiments the compound is

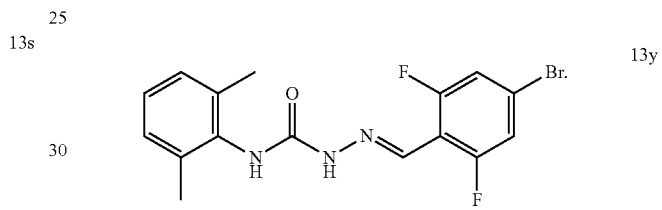
13y

In embodiments the compound is

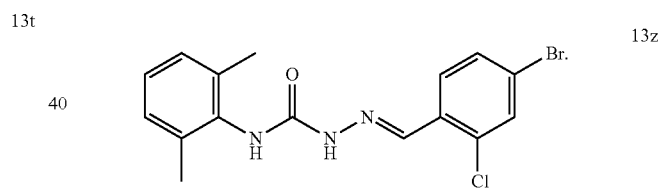
13z

In embodiments the compound is

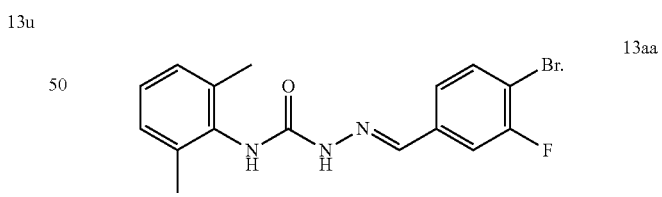
13aa

In embodiments the compound is

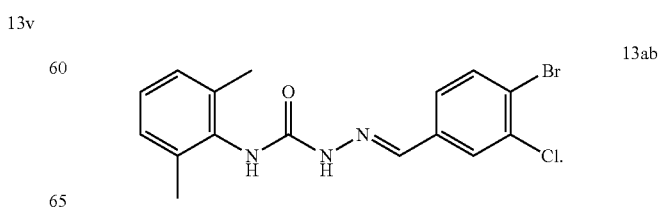
13ab

In embodiments the compound is

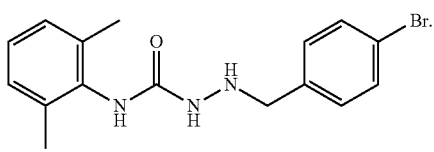

In embodiments the compound is

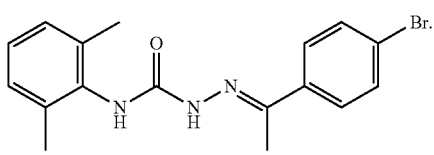

In embodiments the compound is

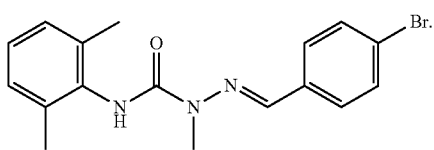

In embodiments the compound is

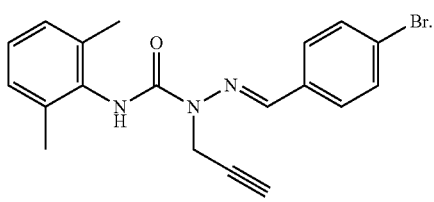

In embodiments the compound is

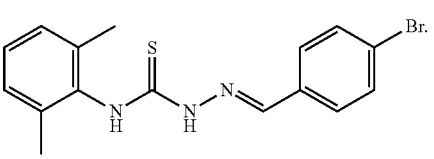

In embodiments the compound is

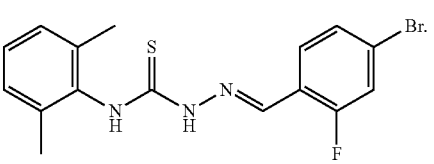

In embodiments the compound is

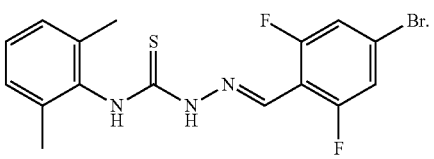

In embodiments the compound is.

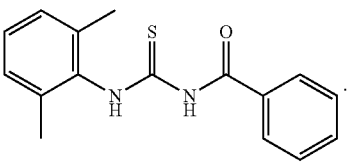 [SMILES: Cc1cccc(C)c1NC(=S)NC(=O)c1ccccc1]

In embodiments the compound is

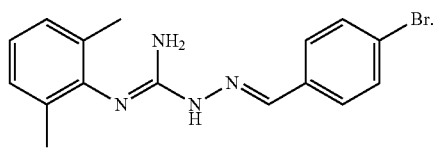

In embodiments the compound is

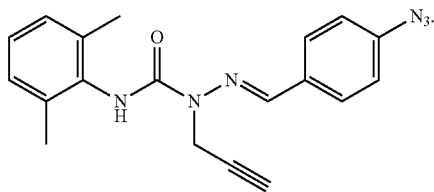

In embodiments the compound is

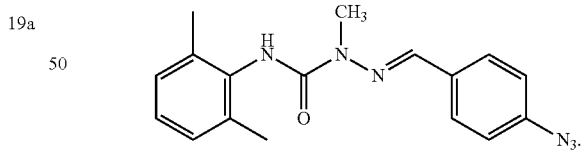

In embodiments the compound is

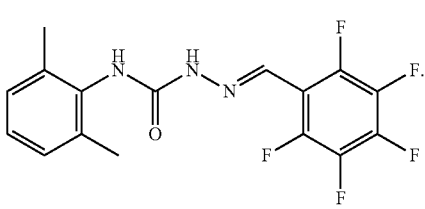 [SMILES: Cc1cccc(C)c1NC(=O)N/N=C/c1c(F)c(F)c(F)c(F)c1F]

In embodiments the compound is

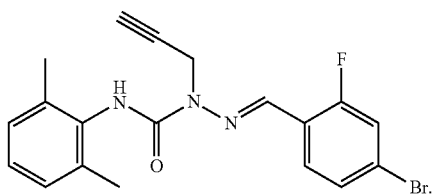 [SMILES: C#CCN(/N=C/c1ccc(Br)cc1F)C(=O)Nc1c(C)cccc1C]

In embodiments the compound is

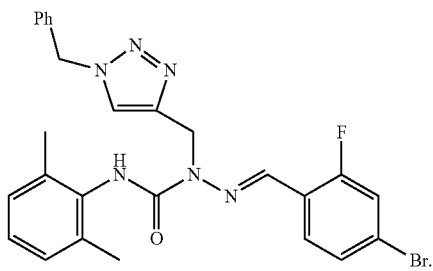

In embodiments the compound is

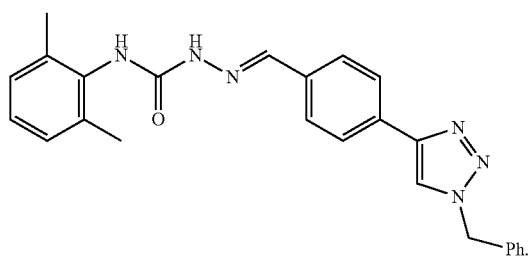 [SMILES: Cc1cccc(C)c1NC(=O)N/N=C/c1ccc(-c2cn(Cc3ccccc3)nn2)cc1]

In embodiments the compound is not

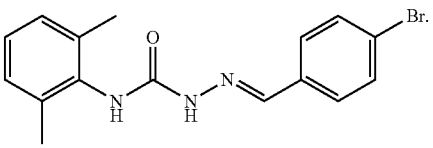

1

In embodiments the compound is not

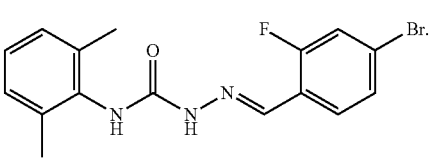

2

In embodiments the compound is not

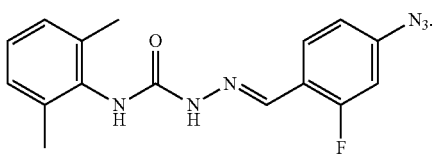

3

In embodiments the compound is not

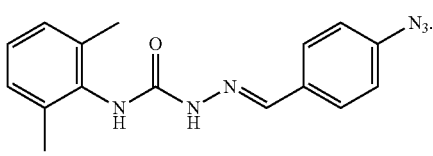

4

In embodiments the compound is not

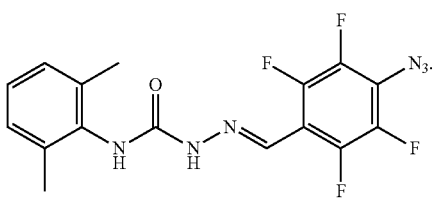

5

In embodiments the compound is not

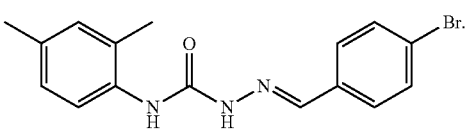

9a

In embodiments the compound is not

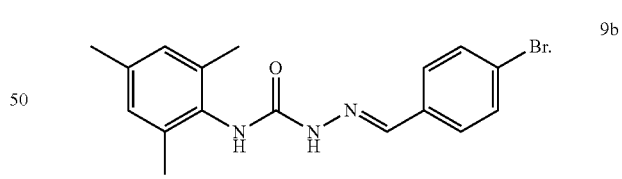

9b

In embodiments the compound is not

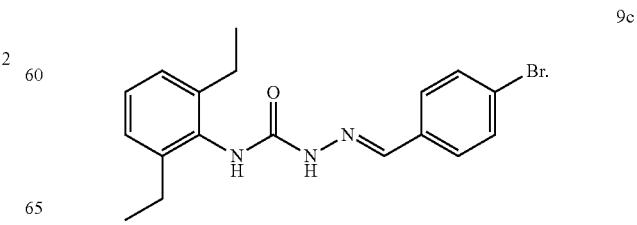

9c

In embodiments the compound is not

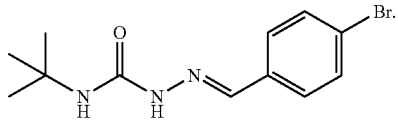

In embodiments the compound is not

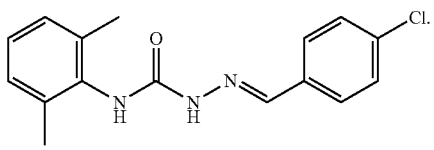

In embodiments the compound is not

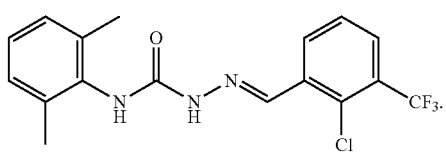

In embodiments the compound is not

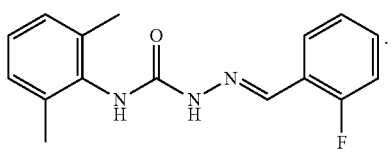

In embodiments the compound is not

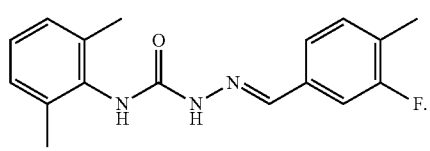

In embodiments the compound is not

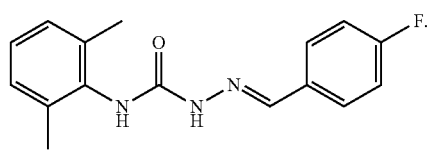

In embodiments the compound is not

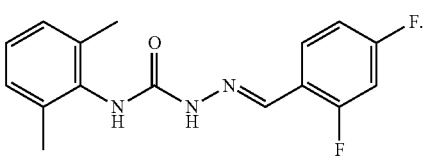

13f

In embodiments the compound is not

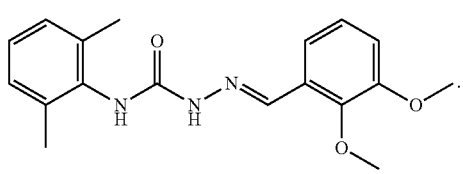

13g

In embodiments the compound is not

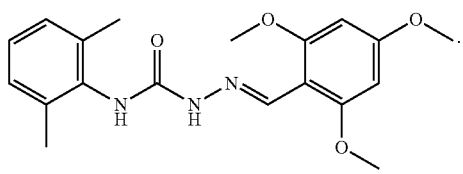

13h

In embodiments the compound is not

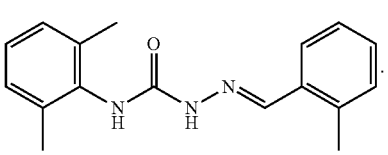

13i

In embodiments the compound is not

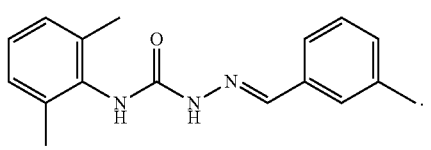

13j

In embodiments the compound is not

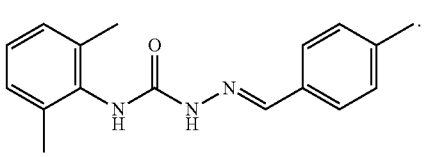

13k

In embodiments the compound is not

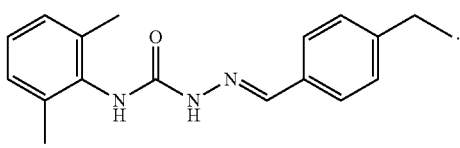
13l

In embodiments the compound is not

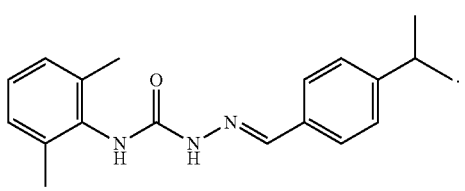
13m

In embodiments the compound is not

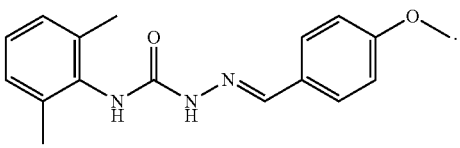
13n

In embodiments the compound is not

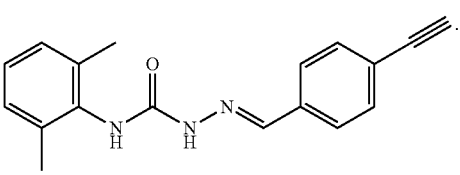
13o

In embodiments the compound is not

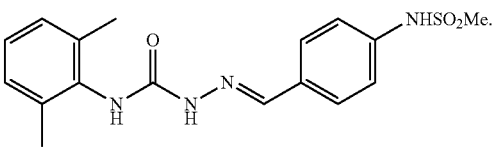
13p

In embodiments the compound is not

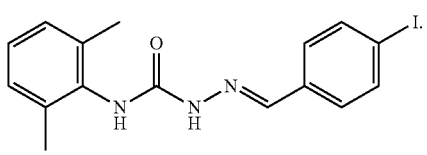
13q

In embodiments the compound is not

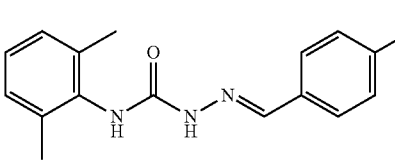
13r

In embodiments the compound is not

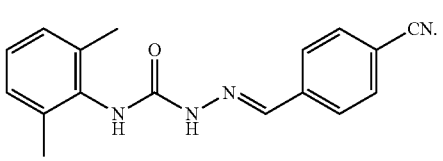
13s

In embodiments the compound is not

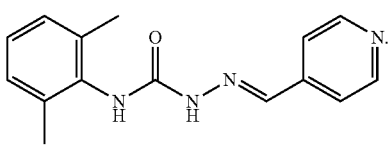
13t

In embodiments the compound is not

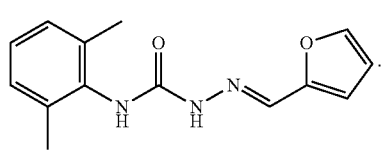
13u

In embodiments the compound is not

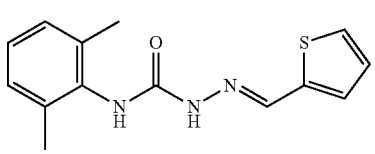
13v

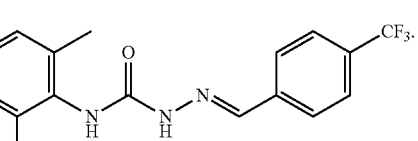
13w

In embodiments the compound is not

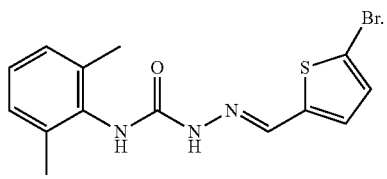

In embodiments the compound is not

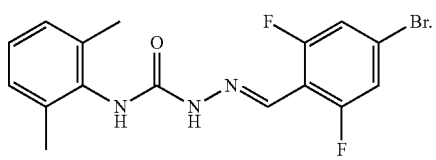

In embodiments the compound is not

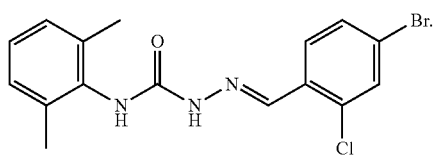

In embodiments the compound is not

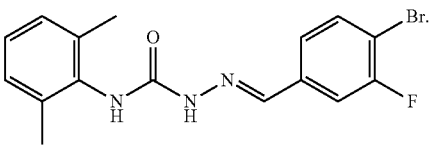

In embodiments the compound is not

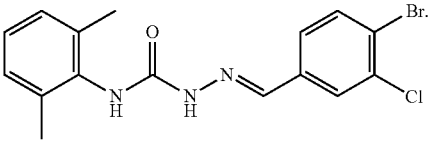

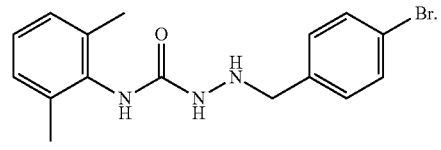

In embodiments the compound is not

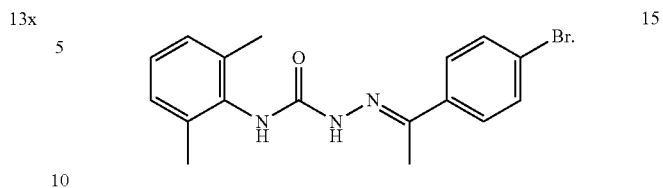

In embodiments the compound is not

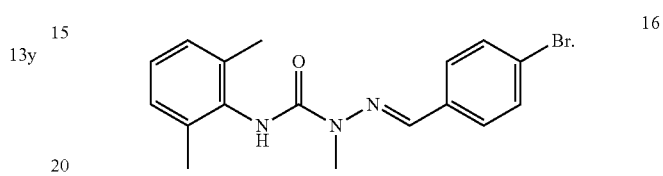

In embodiments the compound is not

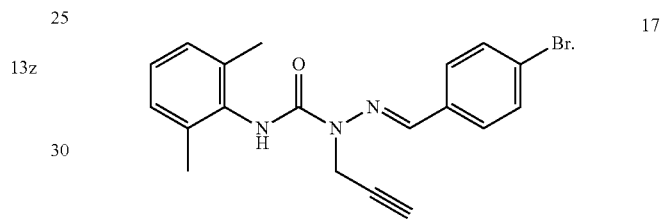

In embodiments the compound is not

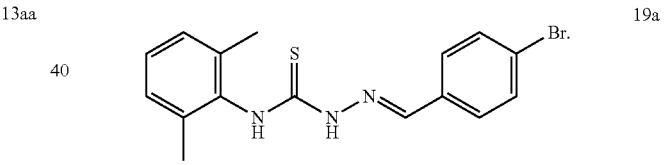

In embodiments the compound is not

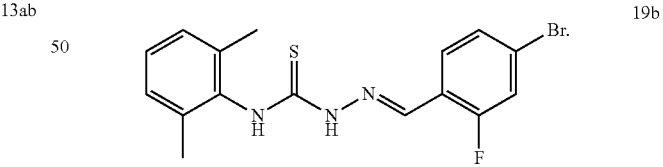

In embodiments the compound is not

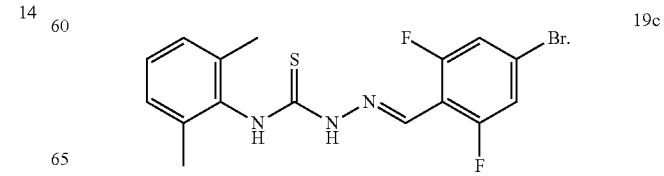

In embodiments the compound is not

In embodiments the compound is not

In embodiments the compound is not

In embodiments the compound is not

In embodiments the compound is not

In embodiments the compound is not

In embodiments the compound is not

In embodiments the compound is not

In some embodiments, the compound is a compound described herein. In some embodiments, the compound is EGA. In embodiments, the compound inhibits toxin entry mediated by protective antigen (PA). In embodiments, the compound does not inhibit assembly of anthrax lethal toxin (e.g. on cell surface). In embodiments, the compound is not a compound described as "not protective" in the Examples section below. In some embodiments, the compound is not EGA.

In some embodiments of the compounds provided herein, each $R^1$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

Each $R^{20}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

Each $R^{21}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

In some embodiments of the compounds provided herein, each $R^2$ is independently hydrogen, oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl. In embodiments, $R^2$ is $R^{23}$-substituted triazolyl.

Each $R^{23}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl. In embodiments, $R^{23}$ is $R^{24}$-substituted methyl.

Each $R^{24}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. In embodiments, $R^{24}$ is $R^{25}$-substituted phenyl. In embodiments, $R^{24}$ is unsubstituted phenyl.

In some embodiments of the compounds provided herein, each $R^3$ is independently hydrogen, oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

Each $R^{26}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

Each $R^{27}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In some embodiments of the compounds provided herein, each $R^4$ is independently hydrogen, oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl.

Each $R^{29}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{30}$-substituted or unsubstituted alkyl, $R^{30}$-substituted or unsubstituted heteroalkyl, $R^{30}$-substituted or unsubstituted cycloalkyl, $R^{30}$ substituted or unsubstituted heterocycloalkyl, $R^{30}$-substituted or unsubstituted aryl, or $R^{30}$-substituted or unsubstituted heteroaryl.

Each $R^{30}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$. $-OCHF_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In some embodiments of the compounds provided herein, each $R^5$ is independently hydrogen, oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

Each $R^{32}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{33}$-substituted or unsubstituted alkyl, $R^{33}$-substituted or unsubstituted heteroalkyl, $R^{33}$-substituted or unsubstituted cycloalkyl, $R^{33}$ substituted or unsubstituted heterocycloalkyl, $R^{33}$-substituted or unsubstituted aryl, or $R^{33}$-substituted or unsubstituted heteroaryl.

Each $R^{33}$ is independently oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

In some embodiments of the compounds provided herein, each $R^6$ is independently hydrogen, oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, —NHSO$_2$H, —NHC=(O)H, —NHC(O)—OH, —NHOH, —OCF$_3$, —OCHF$_2$, R$^{35}$-substituted or unsubstituted alkyl, R$^{35}$-substituted or unsubstituted heteroalkyl, R$^{35}$-substituted or unsubstituted cycloalkyl, R$^{35}$-substituted or unsubstituted heterocycloalkyl, R$^{35}$-substituted or unsubstituted aryl, or R$^{35}$-substituted or unsubstituted heteroaryl. In embodiments, R$^6$ is —CH$_2$CCH. In embodiments, R$^6$ is R$^{35}$-substituted methyl.

Each R$^{35}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{36}$-substituted or unsubstituted alkyl, R$^{36}$-substituted or unsubstituted heteroalkyl, R$^{36}$-substituted or unsubstituted cycloalkyl, R$^{36}$ substituted or unsubstituted heterocycloalkyl, R$^{36}$-substituted or unsubstituted aryl, or R$^{36}$-substituted or unsubstituted heteroaryl. In embodiments, R$^{35}$ is R$^{36}$-substituted triazolyl.

Each R$^{36}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{37}$-substituted or unsubstituted alkyl, R$^{37}$-substituted or unsubstituted heteroalkyl, R$^{37}$-substituted or unsubstituted cycloalkyl, R$^{37}$-substituted or unsubstituted heterocycloalkyl, R$^{37}$-substituted or unsubstituted aryl, or R$^{37}$-substituted or unsubstituted heteroaryl. In embodiments, R$^{36}$ is R$^{37}$-substituted methyl. In embodiments, R$^{37}$ is unsubstituted phenyl.

In some embodiments of the compounds provided herein, each R$^8$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{41}$-substituted or unsubstituted alkyl, R$^{41}$-substituted or unsubstituted heteroalkyl, R$^{41}$-substituted or unsubstituted cycloalkyl, R$^{41}$-substituted or unsubstituted heterocycloalkyl, R$^{41}$-substituted or unsubstituted aryl, or R$^{41}$-substituted or unsubstituted heteroaryl.

Each R$^{41}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —S(O)$_2$CHCH$_2$, —NHS(O)$_2$CHCH$_2$, R$^{42}$-substituted or unsubstituted alkyl, R$^{42}$-substituted or unsubstituted heteroalkyl, R$^{42}$-substituted or unsubstituted cycloalkyl, R$^{42}$ substituted or unsubstituted heterocycloalkyl, R$^{42}$-substituted or unsubstituted aryl, or R$^{42}$-substituted or unsubstituted heteroaryl.

Each R$^{42}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —S(O)$_2$CHCH$_2$, —NHS(O)$_2$CHCH$_2$, R$^{43}$-substituted or unsubstituted alkyl, R$^{43}$-substituted or unsubstituted heteroalkyl, R$^{43}$-substituted or unsubstituted cycloalkyl, R$^{43}$-substituted or unsubstituted heterocycloalkyl, R$^{43}$-substituted or unsubstituted aryl, or R$^{43}$-substituted or unsubstituted heteroaryl.

In some embodiments of the compounds provided herein, each R$^9$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{44}$-substituted or unsubstituted alkyl, R$^{44}$-substituted or unsubstituted heteroalkyl, R$^{44}$-substituted or unsubstituted cycloalkyl, R$^{44}$-substituted or unsubstituted heterocycloalkyl, R$^{44}$-substituted or unsubstituted aryl, or R$^{44}$-substituted or unsubstituted heteroaryl.

Each R$^{44}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{45}$-substituted or unsubstituted alkyl, R$^{45}$-substituted or unsubstituted heteroalkyl, R$^{45}$-substituted or unsubstituted cycloalkyl, R$^{45}$ substituted or unsubstituted heterocycloalkyl, R$^{45}$-substituted or unsubstituted aryl, or R$^{45}$-substituted or unsubstituted heteroaryl.

Each R$^{45}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{46}$-substituted or unsubstituted alkyl, R$^{46}$-substituted or unsubstituted heteroalkyl, R$^{46}$-substituted or unsubstituted cycloalkyl, R$^{46}$-substituted or unsubstituted heterocycloalkyl, R$^{46}$-substituted or unsubstituted aryl, or R$^{46}$-substituted or unsubstituted heteroaryl.

In some embodiments of the compounds provided herein, each R$^{1'}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl.

Each R$^{47}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{48}$-substituted or unsubstituted alkyl, R$^{48}$-substituted or unsubstituted heteroalkyl, R$^{48}$-substituted or unsubstituted cycloalkyl, R$^{48}$ substituted or unsubstituted heterocycloalkyl, R$^{48}$-substituted or unsubstituted aryl, or R$^{48}$-substituted or unsubstituted heteroaryl.

Each R$^{48}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{49}$-substituted or unsubstituted alkyl, R$^{49}$-substituted or unsubstituted heteroalkyl, R$^{49}$-substituted or unsubstituted cycloalkyl, R$^{49}$-substituted or unsubstituted heterocycloalkyl, R$^{49}$-substituted or unsubstituted aryl, or R$^{49}$-substituted or unsubstituted heteroaryl.

In some embodiments of the compounds provided herein, each R$^{t'}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, R$^{50}$-substituted or unsubstituted alkyl, R$^{50}$-substituted or unsubstituted heteroalkyl, R$^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl.

Each $R^{50}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{51}$-substituted or unsubstituted alkyl, $R^{51}$-substituted or unsubstituted heteroalkyl, $R^{51}$-substituted or unsubstituted cycloalkyl, $R^{51}$ substituted or unsubstituted heterocycloalkyl, $R^{51}$-substituted or unsubstituted aryl, or $R^{51}$-substituted or unsubstituted heteroaryl.

Each $R^{51}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{52}$-substituted or unsubstituted alkyl, $R^{52}$-substituted or unsubstituted heteroalkyl, $R^{52}$-substituted or unsubstituted cycloalkyl, $R^{52}$-substituted or unsubstituted heterocycloalkyl, $R^{52}$-substituted or unsubstituted aryl, or $R^{52}$-substituted or unsubstituted heteroaryl.

In some embodiments of the compounds provided herein, each $R^{12}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{53}$-substituted or unsubstituted alkyl, $R^{53}$-substituted or unsubstituted heteroalkyl, $R^{53}$-substituted or unsubstituted cycloalkyl, $R^{53}$-substituted or unsubstituted heterocycloalkyl, $R^{53}$-substituted or unsubstituted aryl, or $R^{53}$-substituted or unsubstituted heteroaryl.

Each $R^{53}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{54}$-substituted or unsubstituted alkyl, $R^{54}$-substituted or unsubstituted heteroalkyl, $R^{54}$-substituted or unsubstituted cycloalkyl, $R^{54}$ substituted or unsubstituted heterocycloalkyl, $R^{54}$-substituted or unsubstituted aryl, or $R^{54}$-substituted or unsubstituted heteroaryl.

Each $R^{54}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl.

In some embodiments of the compounds provided herein, each $R^{13}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl.

Each $R^{56}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{57}$-substituted or unsubstituted alkyl, $R^{57}$-substituted or unsubstituted heteroalkyl, $R^{57}$-substituted or unsubstituted cycloalkyl, $R^{57}$ substituted or unsubstituted heterocycloalkyl, $R^{57}$-substituted or unsubstituted aryl, or $R^{57}$-substituted or unsubstituted heteroaryl.

Each $R^{57}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$. —$OCHF_2$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl.

In embodiments of the compounds provided herein, each $R^{14}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl.

Each $R^{59}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

Each $R^{60}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

In some embodiments of the compounds provided herein, each $R^{11A}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{50A}$-substituted or unsubstituted alkyl, $R^{50A}$-substituted or unsubstituted heteroalkyl, $R^{50A}$-substituted or unsubstituted cycloalkyl, $R^{50A}$-substituted or unsubstituted heterocycloalkyl, $R^{50A}$-substituted or unsubstituted aryl, or $R^{50A}$-substituted or unsubstituted heteroaryl.

Each $R^{50A}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{51A}$-substituted or unsubstituted alkyl, $R^{51A}$-substituted or unsubstituted heteroalkyl, $R^{51A}$-substituted or unsubstituted cycloalkyl, $R^{51A}$-substituted or unsubstituted heterocycloalkyl, $R^{51A}$-substituted or unsubstituted aryl, or $R^{51A}$-substituted or unsubstituted heteroaryl.

Each $R^{51A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{52A}$-substituted or unsubstituted alkyl, $R^{52A}$-substituted or unsubstituted heteroalkyl, $R^{52A}$-substituted or unsubstituted cycloalkyl, $R^{52A}$-substituted or unsubstituted heterocycloalkyl, $R^{52A}$-substituted or unsubstituted aryl, or $R^{52A}$-substituted or unsubstituted heteroaryl.

In some embodiments of the compounds provided herein, each $R^{12A}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{53A}$-substituted or unsubstituted alkyl, $R^{53A}$-substituted or unsubstituted heteroalkyl, $R^{53A}$-substituted or unsubstituted cycloalkyl, $R^{53A}$-substituted or unsubstituted heterocycloalkyl, $R^{53A}$-substituted or unsubstituted aryl, or $R^{53A}$-substituted or unsubstituted heteroaryl.

Each $R^{53A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{54A}$-substituted or unsubstituted alkyl, $R^{54A}$-substituted or unsubstituted heteroalkyl, $R^{54A}$-substituted or unsubstituted cycloalkyl, $R^{54A}$-substituted or unsubstituted heterocycloalkyl, $R^{54A}$-substituted or unsubstituted aryl, or $R^{54A}$-substituted or unsubstituted heteroaryl.

Each $R^{54A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{55A}$-substituted or unsubstituted alkyl, $R^{55A}$-substituted or unsubstituted heteroalkyl, $R^{55A}$-substituted or unsubstituted cycloalkyl, $R^{55A}$-substituted or unsubstituted heterocycloalkyl, $R^{55A}$-substituted or unsubstituted aryl, or $R^{55A}$-substituted or unsubstituted heteroaryl.

In some embodiments of the compounds provided herein, each $R^{13A}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{56A}$-substituted or unsubstituted alkyl, $R^{56A}$-substituted or unsubstituted heteroalkyl, $R^{56A}$-substituted or unsubstituted cycloalkyl, $R^{56A}$-substituted or unsubstituted heterocycloalkyl, $R^{56A}$-substituted or unsubstituted aryl, or $R^{56A}$-substituted or unsubstituted heteroaryl.

Each $R^{56A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{57A}$-substituted or unsubstituted alkyl, $R^{57A}$-substituted or unsubstituted heteroalkyl, $R^{57A}$-substituted or unsubstituted cycloalkyl, $R^{57A}$-substituted or unsubstituted heterocycloalkyl, $R^{57A}$-substituted or unsubstituted aryl, or $R^{57A}$-substituted or unsubstituted heteroaryl.

Each $R^{57A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{58A}$-substituted or unsubstituted alkyl, $R^{58A}$-substituted or unsubstituted heteroalkyl, $R^{58A}$-substituted or unsubstituted cycloalkyl, $R^{58A}$-substituted or unsubstituted heterocycloalkyl, $R^{58A}$-substituted or unsubstituted aryl, or $R^{18A}$-substituted or unsubstituted heteroaryl.

In embodiments of the compounds provided herein, each $R^{14A}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{59A}$-substituted or unsubstituted alkyl, $R^{59A}$-substituted or unsubstituted heteroalkyl, $R^{59A}$-substituted or unsubstituted cycloalkyl, $R^{59A}$-substituted or unsubstituted heterocycloalkyl, $R^{59A}$-substituted or unsubstituted aryl, or $R^{59A}$-substituted or unsubstituted heteroaryl.

Each $R^{59A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{60A}$-substituted or unsubstituted alkyl, $R^{60A}$-substituted or unsubstituted heteroalkyl, $R^{60A}$-substituted or unsubstituted cycloalkyl, $R^{60A}$-substituted or unsubstituted heterocycloalkyl, $R^{60A}$-substituted or unsubstituted aryl, or $R^{60A}$-substituted or unsubstituted heteroaryl.

Each $R^{60A}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{61A}$-substituted or unsubstituted alkyl, $R^{61A}$-substituted or unsubstituted heteroalkyl, $R^{61A}$-substituted or unsubstituted cycloalkyl, $R^{61A}$-substituted or unsubstituted heterocycloalkyl, $R^{61A}$-substituted or unsubstituted aryl, or $R^{61A}$-substituted or unsubstituted heteroaryl.

In some embodiments of the compounds provided herein, each $R^{113}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{50B}$-substituted or unsubstituted alkyl, $R^{50B}$-substituted or unsubstituted heteroalkyl, $R^{50B}$-substituted or unsubstituted cycloalkyl, $R^{50B}$-substituted or unsubstituted heterocycloalkyl, $R^{50B}$-substituted or unsubstituted aryl, or $R^{50B}$-substituted or unsubstituted heteroaryl.

Each $R^{50B}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{51B}$-substituted or unsubstituted alkyl, $R^{51B}$-substituted or unsubstituted heteroalkyl, $R^{51B}$-substituted or unsubstituted cycloalkyl, $R^{51B}$-substituted or unsubstituted heterocycloalkyl, $R^{51B}$-substituted or unsubstituted aryl, or $R^{51B}$-substituted or unsubstituted heteroaryl.

Each $R^{51B}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{52B}$-substituted or unsubstituted alkyl, $R^{52B}$-substituted or unsubstituted heteroalkyl, $R^{52B}$-substituted or unsubstituted cycloalkyl, $R^{52B}$-substituted or unsubstituted heterocycloalkyl, $R^{52B}$-substituted or unsubstituted aryl, or $R^{52B}$-substituted or unsubstituted heteroaryl.

In some embodiments of the compounds provided herein, each $R^{12B}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{53B}$-substituted or unsubstituted alkyl, $R^{53B}$-substituted or unsubstituted heteroalkyl, $R^{53B}$-substituted or unsubstituted cycloalkyl, $R^{53B}$-substituted or unsubstituted heterocycloalkyl, $R^{53B}$-substituted or unsubstituted aryl, or $R^{53B}$-substituted or unsubstituted heteroaryl.

Each $R^{53B}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{54B}$-substituted or unsubstituted alkyl, $R^{54B}$-substituted or unsubstituted heteroalkyl, $R^{54B}$-substituted or unsubstituted cycloalkyl, $R^{54B}$-substituted or unsubstituted heterocycloalkyl, $R^{54B}$-substituted or unsubstituted aryl, or $R^{54B}$-substituted or unsubstituted heteroaryl.

Each $R^{54B}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{55B}$-substituted or unsubstituted alkyl, $R^{55B}$-substituted or unsubstituted heteroalkyl, $R^{55B}$-substituted or unsubstituted cycloalkyl, $R^{55B}$-substituted or unsubstituted heterocycloalkyl, $R^{55B}$-substituted or unsubstituted aryl, or $R^{55B}$-substituted or unsubstituted heteroaryl.

In some embodiments of the compounds provided herein, each $R^{13B}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{56B}$-substituted or unsubstituted alkyl, $R^{56B}$-substituted or unsubstituted heteroalkyl, $R^{56B}$-substituted or unsubstituted cycloalkyl, $R^{56B}$-substituted or unsubstituted heterocycloalkyl, $R^{56B}$-substituted or unsubstituted aryl, or $R^{56B}$-substituted or unsubstituted heteroaryl.

Each $R^{56B}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{57B}$-substituted or unsubstituted alkyl, $R^{57B}$-substituted or unsubstituted heteroalkyl, $R^{57B}$-substituted or unsubstituted cycloalkyl, $R^{57B}$-substituted or unsubstituted heterocycloalkyl, $R^{57B}$-substituted or unsubstituted aryl, or $R^{57B}$-substituted or unsubstituted heteroaryl.

Each $R^{57B}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{58B}$-substituted or unsubstituted alkyl, $R^{58B}$-substituted or unsubstituted heteroalkyl, $R^{58B}$-substituted or unsubstituted cycloalkyl, $R^{58B}$-substituted or unsubstituted heterocycloalkyl, $R^{58B}$-substituted or unsubstituted aryl, or $R^{58B}$-substituted or unsubstituted heteroaryl.

In embodiments of the compounds provided herein, each $R^{14B}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{59B}$-substituted or unsubstituted alkyl, $R^{59B}$-substituted or unsubstituted heteroalkyl, $R^{59B}$-substituted or unsubstituted cycloalkyl, $R^{59B}$-substituted or unsubstituted heterocycloalkyl, $R^{59B}$-substituted or unsubstituted aryl, or $R^{59B}$-substituted or unsubstituted heteroaryl.

Each $R^{59B}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{60B}$-substituted or unsubstituted alkyl, $R^{60B}$-substituted or unsubstituted heteroalkyl, $R^{60B}$-substituted or unsubstituted cycloalkyl, $R^{60B}$-substituted or unsubstituted heterocycloalkyl, $R^{60B}$-substituted or unsubstituted aryl, or $R^{60B}$-substituted or unsubstituted heteroaryl.

Each $R^{60B}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{61B}$-substituted or unsubstituted alkyl, $R^{61B}$-substituted or unsubstituted heteroalkyl, $R^{61B}$-substituted or unsubstituted cycloalkyl, $R^{61B}$-substituted or unsubstituted heterocycloalkyl, $R^{61B}$-substituted or unsubstituted aryl, or $R^{61B}$-substituted or unsubstituted heteroaryl.

In some embodiments of the compounds provided herein, each $R^{11C}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{50C}$-substituted or unsubstituted alkyl, $R^{50C}$-substituted or unsubstituted heteroalkyl, $R^{50C}$-substituted or unsubstituted cycloalkyl, $R^{50C}$-substituted or unsubstituted heterocycloalkyl, $R^{50C}$-substituted or unsubstituted aryl, or $R^{50C}$-substituted or unsubstituted heteroaryl.

Each $R^{50C}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{51C}$-substituted or unsubstituted alkyl, $R^{51C}$-substituted or unsubstituted heteroalkyl, $R^{51C}$-substituted or unsubstituted cycloalkyl, $R^{51C}$-substituted or unsubstituted heterocycloalkyl, $R^{51C}$-substituted or unsubstituted aryl, or $R^{51C}$-substituted or unsubstituted heteroaryl.

Each $R^{51C}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{52C}$-substituted or unsubstituted alkyl, $R^{52C}$-substituted or unsubstituted heteroalkyl, $R^{52C}$-substituted or unsubstituted cycloalkyl, $R^{52C}$-substituted or unsubstituted heterocycloalkyl, $R^{52C}$-substituted or unsubstituted aryl, or $R^{52C}$-substituted or unsubstituted heteroaryl.

In some embodiments of the compounds provided herein, each $R^{12C}$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{53C}$-substituted or unsubstituted alkyl, $R^{53C}$-substituted or unsubstituted heteroalkyl, $R^{53C}$-substituted or unsubstituted cycloalkyl, $R^{53C}$-substituted or unsubstituted heterocycloalkyl, $R^{53C}$-substituted or unsubstituted aryl, or $R^{53C}$-substituted or unsubstituted heteroaryl.

Each $R^{53C}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{54C}$-substituted or unsubstituted alkyl, $R^{54C}$-substituted or unsubstituted heteroalkyl, $R^{54C}$-substituted or unsubstituted cycloalkyl, $R^{54C}$-substituted or unsubstituted heterocycloalkyl, $R^{54C}$-substituted or unsubstituted aryl, or $R^{54C}$-substituted or unsubstituted heteroaryl.

Each $R^{54C}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{55C}$-substituted or unsubstituted alkyl, $R^{55C}$-substituted or unsubstituted heteroalkyl, $R^{55C}$-substituted or unsubstituted cycloalkyl, $R^{55C}$-substituted or unsubstituted heterocycloalkyl, $R^{55C}$-substituted or unsubstituted aryl, or $R^{55C}$-substituted or unsubstituted heteroaryl.

In some embodiments of the compounds provided herein, each $R^{13C}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{56C}$-substituted or unsubstituted alkyl, $R^{56C}$-substituted or unsubstituted heteroalkyl, $R^{56C}$-substituted or unsubstituted cycloalkyl, $R^{56C}$-substituted or unsubstituted heterocycloalkyl, $R^{56C}$-substituted or unsubstituted aryl, or $R^{56C}$-substituted or unsubstituted heteroaryl.

Each $R^{56C}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$. —OCHF$_2$, $R^{57C}$-substituted or unsubstituted alkyl, $R^{57C}$-substituted or unsubstituted heteroalkyl, $R^{57C}$-substituted or unsubstituted cycloalkyl, $R^{57C}$-substituted or unsubstituted heterocycloalkyl, $R^{57C}$-substituted or unsubstituted aryl, or $R^{57C}$-substituted or unsubstituted heteroaryl.

Each $R^{57C}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{58C}$-substituted or unsubstituted alkyl, $R^{58C}$-substituted or unsubstituted heteroalkyl, $R^{58C}$-substituted or unsubstituted cycloalkyl, $R^{58C}$-substituted or unsubstituted heterocycloalkyl, $R^{58C}$-substituted or unsubstituted aryl, or $R^{58C}$-substituted or unsubstituted heteroaryl.

In embodiments of the compounds provided herein, each $R^{14C}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{59C}$-substituted or unsubstituted alkyl, $R^{59C}$-substituted or unsubstituted heteroalkyl, $R^{59C}$-substituted or unsubstituted cycloalkyl, $R^{59C}$-substituted or unsubstituted heterocycloalkyl, $R^{59C}$-substituted or unsubstituted aryl, or $R^{59C}$-substituted or unsubstituted heteroaryl.

Each $R^{59C}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{60C}$-substituted or unsubstituted alkyl, $R^{60C}$-substituted or unsubstituted heteroalkyl, $R^{60C}$-substituted or unsubstituted cycloalkyl, $R^{60C}$-substituted or unsubstituted heterocycloalkyl, $R^{60C}$-substituted or unsubstituted aryl, or $R^{60C}$-substituted or unsubstituted heteroaryl.

Each $R^{60C}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{61C}$-substituted or unsubstituted alkyl, $R^{61C}$-substituted or unsubstituted heteroalkyl, $R^{61C}$-substituted or unsubstituted cycloalkyl, $R^{61C}$-substituted or unsubstituted heterocycloalkyl, $R^{61C}$-substituted or unsubstituted aryl, or $R^{61C}$-substituted or unsubstituted heteroaryl.

In embodiments of the compounds provided herein, each $R^{100}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl.

Each $R^{62}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl.

Each $R^{63}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl.

In embodiments, each $R^{101}$ is independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{65}$-substituted or unsubstituted alkyl, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl.

Each $R^{65}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF₃, —OCHF₂, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl.

Each $R^{66}$ is independently oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O)NHNH₂, —NHC═(O) NH₂, —NHSO₂H, —NHC═(O)H, —NHC(O)—OH, —NHOH, —OCF₃, —OCHF₂, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl.

Each $R^{22}$, $R^{25}$, $R^{28}$, $R^{31}$, $R^{34}$, $R^{37}$, $R^{40}$, $R^{43}$, $R^{46}$, $R^{49}$, $R^{52}$, $R^{55}$, $R^{58}$, $R^{61}$, $R^{52A}$, $R^{55A}$, $R^{58A}$, $R^{61A}$, $R^{52B}$, $R^{55B}$, $R^{58B}$, $R^{61B}$, $R^{52C}$, $R^{55C}$, $R^{58C}$, $R^{61C}$, $R^{64}$, and $R^{67}$, is independently hydrogen, oxo, halogen, —CF₃, —CN, —OH, —NH₂, —COOH, —CONH₂, —NO₂, —SH, —SO₂Cl, —SO₃H, —SO₄H, —SO₂NH₂, —NHNH₂, —ONH₂, —NHC═(O) NHNH₂, —NHC═(O) NH₂, —NHSO₂H, —NHC═(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, or unsubstituted heteroaryl.

In some embodiments, a compound as described herein may include multiple instances of $R^{101}$, $R^2$, $R^8$, $R^{11}$, $R^{12}$, $R^{13}$, $R^{14}$, $R^{11A}$, $R^{12A}$, $R^{13A}$, $R^{14A}$, $R^{11B}$, $R^{12B}$, $R^{13B}$, $R^{14B}$, $R^{11C}$, $R^{12C}$, $R^{13C}$, $R^{14C}$, X, $X^1$, $X^2$, $X^3$, and/or other variables. In such embodiments, each variable may optional be different and be appropriately labeled to distinguish each group for greater clarity. For example, where each $R^{101}$, $R^2$, $R^8$, $R^{11}$, $R^{12}$, $R^{13}$, $R^{14}$, $R^{11A}$, $R^{12A}$, $R^{13A}$, $R^{14A}$, $R^{11B}$, $R^{12B}$, $R^{13B}$, $R^{14B}$, $R^{11C}$, $R^{12C}$, $R^{13C}$, $R^{14C}$, X, $X^1$, $X^2$, and/or $X^3$ is different, they may be referred to, for example, as $R^{101.1}$, $R^{101.2}$, $R^{101.3}$, $R^{101.4}$, $R^{101.5}$, $R^{101.6}$, $R^{101.7}$, $R^{101.8}$, $R^{101.9}$, $R^{101.10}$, $R^{101.11}$, $R^{101.12}$, $R^{10113}$, $R^{101.14}$, $R^{101.15}$, $R^{101.16}$, $R^{101.17}$, $R^{101.18}$, $R^{101.19}$, $R^{101.20}$, $R^{101.21}$, $R^{101.22}$, $R^{101.23}$, $R^{101.24}$, $R^{101.25}$, $R^{101.26}$, $R^{101.27}$, $R^{101.28}$, $R^{101.29}$, $R^{101.30}$, $R^{101.31}$, $R^{101.32}$, $R^{101.33}$, $R^{101.34}$, $R^{101.35}$, $R^{101.36}$, $R^{101.37}$, $R^{101.38}$, $R^{101.39}$, $R^{101.40}$, $R^{101.41}$, $R^{101.42}$, $R^{2.1}$, $R^{2.2}$, $R^{2.3}$, $R^{2.4}$, $R^{2.5}$, $R^{2.6}$, $R^{2.7}$, $R^{2.8}$, $R^{2.9}$, $R^{2.10}$, $R^{2.11}$, $R^{2.12}$, $R^{2.13}$, $R^{2.14}$, $R^{2.15}$, $R^{2.16}$, $R^{2.17}$, $R^{2.18}$, $R^{2.19}$, $R^{2.20}$, $R^{2.21}$, $R^{2.22}$, $R^{2.23}$, $R^{2.24}$, $R^{2.25}$, $R^{2.26}$, $R^{2.27}$, $R^{2.28}$, $R^{2.29}$, $R^{2.30}$, $R^{2.31}$, $R^{2.32}$, $R^{2.33}$, $R^{2.34}$, $R^{2.35}$, $R^{2.36}$, $R^{2.37}$, $R^{2.38}$, $R^{2.39}$, $R^{2.40}$, $R^{2.41}$, $R^{2.42}$, $R^{8.1}$, $R^{8.2}$, $R^{8.3}$, $R^{8.4}$, $R^{8.5}$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{7.34}$, $R^{8.35}$, $R^{8.36}$, $R^{8.37}$, $R^{3.38}$, $R^{8.39}$, $R^{8.40}$, $R^{8.41}$, $R^{8.42}$, $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{10.11}$, $R^{11.12}$, $R^{10.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$, $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.20}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{1232}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$, $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$, $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{141.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{14.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{14.38}$, $R^{14.39}$, $R^{14.40}$, $R^{14.41}$, $R^{14.42}$, $R^{11A.1}$, $R^{11A.2}$, $R^{11A.3}$, $R^{11A.4}$, $R^{11A.5}$, $R^{11A.6}$, $R^{11A.7}$, $R^{11A.8}$, $R^{11A.9}$, $R^{11A.10}$, $R^{11A.11}$, $R^{11A.12}$, $R^{11A.13}$, $R^{11A.14}$, $R^{11A.15}$, $R^{11A.16}$, $R^{11A.17}$, $R^{11A.18}$, $R^{11A.19}$, $R^{11A.20}$, $R^{11A.21}$, $R^{11A.22}$, $R^{11A.23}$, $R^{11A.24}$, $R^{11A.25}$, $R^{11A.26}$, $R^{11A.27}$, $R^{11A.28}$, $R^{11A.29}$, $R^{11A.30}$, $R^{11A.31}$, $R^{11A.32}$, $R^{11A.33}$, $R^{11A.34}$, $R^{11A.35}$, $R^{11A.36}$, $R^{11A.37}$, $R^{11A.38}$, $R^{11A.39}$, $R^{11A.40}$, $R^{11A.41}$, $R^{11A.42}$, $R^{12A.1}$, $R^{12A.2}$, $R^{12A.3}$, $R^{12A.4}$, $R^{12A.5}$, $R^{12A.6}$, $R^{12A.7}$, $R^{12A.8}$, $R^{12A.9}$, $R^{12A.11}$, $R^{12A.12}$, $R^{12A.13}$, $R^{12A.14}$, $R^{12A.15}$, $R^{12A.16}$, $R^{12A.17}$, $R^{12A.18}$, $R^{12A.19}$, $R^{12A.20}$, $R^{12A.21}$, $R^{12A.22}$, $R^{12A.23}$, $R^{12A.24}$, $R^{12A.25}$, $R^{12A.26}$, $R^{12A.27}$, $R^{12A.28}$, $R^{12A.29}$, $R^{12A.30}$, $R^{12A.31}$, $R^{12A.32}$, $R^{12A.33}$, $R^{12A.34}$, $R^{12A.35}$, $R^{12A.36}$, $R^{12A.37}$, $R^{12A.38}$, $R^{12A.39}$, $R^{12A.40}$, $R^{12A.41}$, $R^{12A.42}$, $R^{13A.1}$, $R^{13A.2}$, $R^{13A.3}$, $R^{13A.4}$, $R^{13A.5}$, $R^{13A.6}$, $R^{13A.7}$, $R^{13A.8}$, $R^{13A.9}$, $R^{13A.10}$, $R^{13A.11}$, $R^{13A.12}$, $R^{13A.13}$, $R^{13A.14}$, $R^{13A.15}$, $R^{13A.16}$, $R^{13A.17}$, $R^{13A.18}$, $R^{13A.19}$, $R^{13A.20}$, $R^{13A.21}$, $R^{13A.22}$, $R^{13A.23}$, $R^{13A.24}$, $R^{13A.25}$, $R^{13A.26}$, $R^{13A.27}$, $R^{13A.28}$, $R^{13A.29}$, $R^{13A.30}$, $R^{13A.31}$, $R^{13A.32}$, $R^{13A.33}$, $R^{13A.34}$, $R^{13A.35}$, $R^{13A.36}$, $R^{13A.37}$, $R^{13A.38}$, $R^{13A.39}$, $R^{13A.40}$, $R^{13A.41}$, $R^{13A.42}$, $R^{14A.1}$, $R^{14A.2}$, $R^{14A.3}$, $R^{14A.4}$, $R^{14A.5}$, $R^{14A.6}$, $R^{14A.7}$, $R^{14A.8}$, $R^{14A.9}$, $R^{14A.10}$, $R^{14A.11}$, $R^{14A.12}$, $R^{14A.13}$, $R^{14A.14}$, $R^{14A.15}$, $R^{14A.16}$, $R^{14A.17}$, $R^{14A.18}$, $R^{14A.19}$, $R^{14A.20}$, $R^{14A.21}$, $R^{14A.22}$, $R^{14A.23}$, $R^{14A.24}$, $R^{14A.25}$, $R^{14A.26}$, $R^{14A.27}$, $R^{14A.28}$, $R^{14A.29}$, $R^{14A.30}$, $R^{14A.31}$, $R^{14A.32}$, $R^{14A.33}$, $R^{14A.34}$, $R^{14A.35}$, $R^{14A.36}$, $R^{14A.37}$, $R^{14A.38}$, $R^{14A.39}$, $R^{14A.40}$, $R^{14A.41}$, $R^{14A.42}$, $R^{11B.1}$, $R^{11B.2}$, $R^{11B.3}$, $R^{11B.4}$, $R^{11B.5}$, $R^{11B.6}$, $R^{11B.7}$, $R^{11B.8}$, $R^{11B.9}$, $R^{11B.10}$, $R^{11B.11}$, $R^{11B.12}$, $R^{11B.13}$, $R^{11B.14}$, $R^{11B.15}$, $R^{11B.16}$, $R^{11B.17}$, $R^{11B.18}$, $R^{11B.19}$, $R^{11B.20}$, $R^{11B.21}$, $R^{11B.22}$, $R^{11B.23}$, $R^{11B.24}$, $R^{11B.25}$, $R^{11B.26}$, $R^{11B.27}$, $R^{11B.28}$, $R^{11B.29}$, $R^{11B.30}$, $R^{11B.31}$, $R^{11B.32}$, $R^{11B.33}$, $R^{11B.34}$, $R^{11B.35}$, $R^{11B.36}$, $R^{11B.37}$, $R^{11B.38}$, $R^{11B.39}$, $R^{11B.40}$, $R^{11B.41}$, $R^{11A.42}$, $R^{12B.1}$, $R^{12B.2}$, $R^{12B.3}$, $R^{12B.4}$, $R^{12B.5}$, $R^{12B.6}$, $R^{12B.7}$, $R^{12B.8}$, $R^{12B.9}$, $R^{12B.10}$, $R^{12B.11}$, $R^{12B.12}$, $R^{12B.13}$, $R^{12B.14}$, $R^{12B.15}$, $R^{12B.16}$, $R^{12B.17}$, $R^{12B.18}$, $R^{12B.19}$, $R^{12B.20}$, $R^{12B.21}$, $R^{12B.22}$, $R^{12B.23}$, $R^{12B.24}$, $R^{12B.25}$, $R^{12B.26}$, $R^{12B.27}$, $R^{12B.28}$, $R^{12B.29}$, $R^{12B.30}$, $R^{12B.31}$, $R^{12B.32}$, $R^{12B.33}$, $R^{12B.34}$, $R^{12B.35}$, $R^{12B.36}$, $R^{12B.37}$, $R^{12B.38}$, $R^{12B.39}$, $R^{12B.40}$, $R^{12B.41}$, $R^{12B.42}$, $R^{13B.1}$, $R^{13B.2}$, $R^{13B.3}$, $R^{13B.4}$, $R^{13B.5}$, $R^{13B.6}$, $R^{13B.7}$, $R^{13B.8}$, $R^{13B.9}$, $R^{13B.10}$, $R^{13B.11}$, $R^{13B.12}$, $R^{13B.13}$, $R^{13B.14}$, $R^{13B.15}$, $R^{13B.16}$, $R^{13B.17}$, $R^{13B.18}$, $R^{13B.19}$, $R^{13B.20}$, $R^{13B.21}$, $R^{13B.22}$, $R^{13B.23}$, $R^{13B.24}$, $R^{13B.25}$, $R^{13B.26}$, $R^{13B.27}$, $R^{13B.28}$, $R^{13B.29}$, $R^{13B.30}$, $R^{13B.31}$, $R^{13B.32}$, $R^{13B.33}$, $R^{13B.34}$, $R^{13B.35}$, $R^{13B.36}$, $R^{13B.37}$, $R^{13B.38}$, $R^{13B.39}$, $R^{13B.40}$, $R^{13B.41}$, $R^{13B.42}$, $R^{14B.1}$, $R^{14B.2}$, $R^{14B.3}$, $R^{14B.4}$, $R^{14B.5}$, $R^{14B.6}$, $R^{14B.7}$, $R^{14B.8}$, $R^{14B.9}$, $R^{14B.10}$, $R^{14B.11}$, $R^{14B.12}$, $R^{14B.13}$, $R^{14B.14}$, $R^{14B.15}$, $R^{14B.16}$, $R^{14B.17}$, $R^{14B.18}$, $R^{14B.19}$, $R^{14B.20}$, $R^{14B.21}$, $R^{14B.22}$, $R^{14B.23}$, $R^{14B.24}$, $R^{14B.25}$, $R^{14B.26}$, $R^{14B.27}$, $R^{14B.28}$, $R^{14B.29}$, $R^{14B.30}$, $R^{14B.31}$, $R^{14B.32}$, $R^{14B.33}$, $R^{14B.34}$, $R^{14B.35}$, $R^{14B.36}$, $R^{14B.37}$, $R^{14B.38}$, $R^{14B.39}$, $R^{14B.40}$, $R^{14B.41}$, $R^{14B.42}$, $R^{11C.1}$, $R^{11C.2}$, $R^{11C.3}$, $R^{11C.4}$, $R^{11C.5}$, $R^{11C.6}$, $R^{11C.7}$, $R^{11C.8}$, $R^{11C.9}$, $R^{11C.10}$, $R^{11C.11}$, $R^{11C.12}$, $R^{11C.13}$, $R^{11C.14}$, $R^{11C.15}$, $R^{11C.16}$, $R^{11C.17}$, $R^{11C.18}$, $R^{11C.19}$, $R^{11C.20}$, $R^{11C.21}$, $R^{11C.22}$, $R^{11C.23}$, $R^{11C.24}$, $R^{11C.25}$, $R^{11C.26}$, $R^{11C.27}$, $R^{11C.28}$, $R^{11C.29}$, $R^{11C.30}$, $R^{11C.31}$, $R^{11C.32}$, $R^{11C.33}$, $R^{11C.34}$, $R^{11C.35}$, $R^{11C.36}$, $R^{11C.37}$, $R^{11C.38}$, $R^{11C.39}$, $R^{11C.40}$, $R^{11C.41}$, $R^{11C.42}$, $R^{12C.1}$, $R^{12C.2}$, $R^{12C.3}$, $R^{12C.4}$, $R^{12C.5}$, $R^{12C.6}$, $R^{12C.7}$, $R^{12C.8}$, $R^{12C.9}$, $R^{12C.10}$, $R^{12C.11}$, $R^{12C.12}$, $R^{12C.13}$, $R^{12C.14}$, $R^{12C.15}$, $R^{12C.16}$, $R^{12C.17}$, $R^{12C.18}$, $R^{12C.19}$, $R^{12C.20}$, $R^{12C.21}$, $R^{12C.22}$, $R^{12C.23}$, $R^{12C.24}$, $R^{12C.25}$, $R^{12C.26}$, $R^{12C.27}$, $R^{12C.28}$, $R^{12C.29}$, $R^{12C.30}$, $R^{12C.31}$, $R^{12C.32}$, $R^{12C.33}$, $R^{12C.34}$, $R^{12C.35}$, $R^{12C.36}$, $R^{12C.37}$, $R^{12C.38}$, $R^{12C.39}$, $R^{12C.40}$, $R^{12C.41}$, $R^{12C.42}$, $R^{13C.1}$, $R^{13C.2}$, $R^{13C.3}$, $R^{13C.4}$, $R^{13C.5}$, $R^{13C.6}$, $R^{13C.7}$, $R^{13C.8}$, $R^{13C.9}$, $R^{13C.10}$, $R^{13C.11}$, $R^{13C.12}$, $R^{13C.13}$, $R^{13C.14}$, $R^{13C.15}$, $R^{13C.16}$, $R^{13C.17}$, $R^{13C.18}$, $R^{13C.19}$, $R^{13C.20}$, $R^{13C.21}$, $R^{13C.22}$, $R^{13C.23}$, $R^{13C.24}$, $R^{13C.25}$, $R^{13C.26}$, $R^{13C.27}$, $R^{13C.28}$, $R^{13C.29}$, $R^{13C.30}$, $R^{13C.31}$, $R^{13C.32}$, $R^{13C.33}$, $R^{13C.34}$, $R^{13C.35}$, $R^{13C.36}$, $R^{13C.37}$, $R^{13C.38}$, $R^{13C.39}$, $R^{13C.40}$, $R^{13C.41}$, $R^{13C.42}$, $R^{14C.1}$, $R^{14C.2}$, $R^{14C.3}$, $R^{14C.4}$, $R^{14C.5}$, $R^{14C.6}$, $R^{14C.7}$, $R^{14C.8}$, $R^{14C.9}$, $R^{14C.10}$, $R^{14C.11}$, $R^{14C.12}$, $R^{14C.13}$, $R^{14C.14}$, $R^{14C.15}$, $R^{14C.16}$, $R^{14C.17}$, $R^{14C.18}$, $R^{14C.19}$, $R^{14C.20}$, $R^{14C.21}$, $R^{14C.22}$, $R^{14C.23}$, $R^{14C.24}$, $R^{14C.25}$, $R^{14C.26}$, $R^{14C.27}$, $R^{14C.28}$, $R^{14C.29}$, $R^{14C.30}$, $R^{14C.31}$, $R^{14C.32}$, $R^{14C.33}$, $R^{14C.34}$, $R^{14C.35}$, $R^{14C.36}$, $R^{14C.37}$, $R^{14C.38}$, $R^{14C.39}$, $R^{14C.40}$, $R^{14C.41}$, $R^{14C.42}$, $X^{0.1}$, $X^{0.2}$, $X^{0.3}$, $X^{0.4}$, $X^{0.5}$, $X^{0.6}$, $X^{0.7}$, $X^{0.8}$, $X^{0.9}$, $X^{0.10}$, $X^{0.11}$, $X^{00.12}$, $X^{00.13}$, $X^{00.14}$, $X^{00.15}$, $X^{00.16}$, $X^{00.17}$, $X^{00.18}$, $X^{00.19}$, $X^{0.20}$, $X^{0.21}$, $X^{0.22}$, $X^{0.23}$, $X^{0.24}$, $X^{0.25}$, $X^{0.26}$, $X^{0.27}$, $X^{0.28}$, $X^{0.29}$, $X^{0.30}$, $X^{0.31}$, $X^{0.32}$, $X^{0.33}$, $X^{0.34}$, $X^{0.35}$, $X^{0.36}$, $X^{03.7}$, $X^{03.8}$, $X^{0.39}$, $X^{0.40}$, $X^{0.41}$, $X^{0.42}$, $X^{1.1}$, $X^{1.2}$, $X^{1.3}$, $X^{1.4}$, $X^{1.5}$, $X^{1.6}$, $X^{1.7}$, $X^{1.8}$, $X^{1.9}$, $X^{1.10}$, $X^{1.11}$, $X^{1.12}$, $X^{1.13}$, $X^{1.14}$, $X^{1.15}$, $X^{1.16}$, $X^{1.17}$, $X^{1.18}$, $X^{1.19}$, $X^{1.20}$, $X^{1.21}$, $X^{1.22}$, $X^{1.23}$, $X^{1.24}$, $X^{1.25}$, $X^{1.26}$, $X^{1.27}$, $X^{1.28}$, $X^{1.29}$, $X^{1.30}$, $X^{1.31}$, $X^{1.32}$, $X^{1.33}$, $X^{1.34}$, $X^{1.35}$, $X^{1.36}$, $X^{1.37}$, $X^{1.38}$, $X^{1.39}$, $X^{1.40}$, $X^{1.41}$, $X^{1.42}$, $X^{2.1}$, $X^{2.2}$, $X^{2.3}$, $X^{2.4}$, $X^{2.5}$, $X^{2.6}$, $X^{2.7}$, $X^{2.8}$, $X^{2.9}$, $X^{2.10}$, $X^{2.11}$, $X^{2.12}$, $X^{2.13}$, $X^{2.14}$, $X^{2.15}$, $X^{2.16}$, $X^{2.17}$, $X^{2.18}$, $X^{2.19}$, $X^{2.20}$, $X^{2.21}$, $X^{2.22}$, $X^{2.23}$, $X^{2.24}$, $X^{2.25}$, $X^{2.26}$, $X^{2.27}$, $X^{2.28}$, $X^{2.29}$, $X^{2.30}$, $X^{2.31}$, $X^{2.32}$, $X^{2.33}$, $X^{2.34}$, $X^{2.35}$, $X^{2.36}$, $X^{2.37}$, $X^{2.38}$, $X^{2.39}$, $X^{2.40}$, $X^{2.41}$, $X^{2.42}$, $X^{3.1}$, $X^{3.2}$, $X^{3.3}$, $X^{3.4}$, $X^{3.5}$, $X^{3.6}$, $X^{3.7}$, $X^{3.8}$, $X^{3.9}$, $X^{3.10}$, $X^{3.11}$, $X^{3.12}$, $X^{3.13}$, $X^{3.14}$, $X^{3.15}$, $X^{3.16}$, $X^{3.17}$, $X^{3.18}$, $X^{3.19}$, $X^{3.20}$, $X^{3.21}$, $X^{3.22}$, $X^{3.23}$, $X^{3.24}$, $X^{3.25}$, $X^{3.26}$, $X^{3.27}$, $X^{3.28}$, $X^{3.29}$, $X^{3.30}$, $X^{3.31}$, $X^{3.32}$, $X^{3.33}$, $X^{3.34}$, $X^{3.35}$, $X^{1.36}$, $X^{3.37}$, $X^{3.38}$, $X^{3.39}$, $X^{3.40}$, $X^{3.41}$, $X^{3.42}$, respectively, wherein the definition of $R^{101}$ is assumed by $R^{101.1}$, $R^{101.2}$, $R^{101.3}$, $R^{101.4}$, $R^{101.5}$, $R^{101.6}$, $R^{101.7}$, $R^{101.8}$, $R^{101.9}$, $R^{101.10}$, $R^{101.11}$, $R^{101.12}$, $R^{101.13}$, $R^{101.14}$, $R^{101.15}$, $R^{101.16}$, $R^{101.17}$, $R^{101.18}$, $R^{101.19}$, $R^{101.20}$, $R^{101.21}$, $R^{101.22}$, $R^{101.23}$, $R^{101.24}$, $R^{101.25}$, $R^{101.26}$, $R^{101.27}$, $R^{101.28}$, $R^{101.29}$, $R^{101.30}$, $R^{101.31}$, $R^{101.32}$, $R^{101.33}$, $R^{101.34}$, $R^{101.35}$, $R^{101.36}$, $R^{101.37}$, $R^{101.38}$, $R^{101.39}$, $R^{101.40}$, $R^{101.41}$, $R^{101.42}$, the definition of $R^2$ is assumed by $R^{2.1}$, $R^{2.2}$, $R^{2.3}$, $R^{2.4}$, $R^{2.5}$, $R^{2.6}$, $R^{2.7}$, $R^{2.8}$, $R^{2.9}$, $R^{2.10}$, $R^{2.11}$, $R^{2.12}$, $R^{2.13}$, $R^{2.14}$, $R^{2.15}$, $R^{2.16}$, $R^{2.17}$, $R^{2.18}$, $R^{2.19}$, $R^{2.20}$, $R^{2.21}$, $R^{2.22}$, $R^{2.23}$, $R^{2.24}$, $R^{2.25}$, $R^{2.26}$, $R^{2.27}$, $R^{2.28}$, $R^{2.29}$, $R^{2.30}$, $R^{2.31}$, $R^{2.32}$, $R^{2.33}$, $R^{2.34}$, $R^{2.35}$, $R^{2.36}$, $R^{2.37}$, $R^{2.38}$, $R^{2.39}$, $R^{2.40}$, $R^{2.41}$, $R^{2.42}$, the definition of $R^8$ is assumed by $R^{8.1}$, $R^{8.2}$, $R^{8.3}$, $R^{8.4}$, $R^8$, $R^{8.6}$, $R^{8.7}$, $R^{8.8}$, $R^{8.9}$, $R^{8.10}$, $R^{8.11}$, $R^{8.12}$, $R^{8.13}$, $R^{8.14}$, $R^{8.15}$, $R^{8.16}$, $R^{8.17}$, $R^{8.18}$, $R^{8.19}$, $R^{8.20}$, $R^{8.21}$, $R^{8.22}$, $R^{8.23}$, $R^{8.24}$, $R^{8.25}$, $R^{8.26}$, $R^{8.27}$, $R^{8.28}$, $R^{8.29}$, $R^{8.30}$, $R^{8.31}$, $R^{8.32}$, $R^{8.33}$, $R^{8.34}$, $R^{8.35}$, $R^{8.36}$, $R^{8.37}$, $R^{8.38}$, $R^{8.39}$, $R^{8.40}$, $R^{8.41}$, $R^{8.42}$, the definition of $R^{11}$ is assumed by $R^{11.1}$, $R^{11.2}$, $R^{11.3}$, $R^{11.4}$, $R^{11.5}$, $R^{11.6}$, $R^{11.7}$, $R^{11.8}$, $R^{11.9}$, $R^{11.10}$, $R^{11.11}$, $R^{11.12}$, $R^{11.13}$, $R^{11.14}$, $R^{11.15}$, $R^{11.16}$, $R^{11.17}$, $R^{11.18}$, $R^{11.19}$, $R^{11.20}$, $R^{11.21}$, $R^{11.22}$, $R^{11.23}$, $R^{11.24}$, $R^{11.25}$, $R^{11.26}$, $R^{11.27}$, $R^{11.28}$, $R^{11.29}$, $R^{11.30}$, $R^{11.31}$, $R^{11.32}$, $R^{11.33}$, $R^{11.34}$, $R^{11.35}$, $R^{11.36}$, $R^{11.37}$, $R^{11.38}$, $R^{11.39}$, $R^{11.40}$, $R^{11.41}$, $R^{11.42}$ the definition of $R^{12}$ is assumed by $R^{12.1}$, $R^{12.2}$, $R^{12.3}$, $R^{12.4}$, $R^{12.5}$, $R^{12.6}$, $R^{12.7}$, $R^{12.8}$, $R^{12.9}$, $R^{12.10}$, $R^{12.11}$, $R^{12.12}$, $R^{12.13}$, $R^{12.14}$, $R^{12.15}$, $R^{12.16}$, $R^{12.17}$, $R^{12.18}$, $R^{12.19}$, $R^{12.20}$, $R^{12.21}$, $R^{12.22}$, $R^{12.23}$, $R^{12.24}$, $R^{12.25}$, $R^{12.26}$, $R^{12.27}$, $R^{12.28}$, $R^{12.29}$, $R^{12.30}$, $R^{12.31}$, $R^{12.32}$, $R^{12.33}$, $R^{12.34}$, $R^{12.35}$, $R^{12.36}$, $R^{12.37}$, $R^{12.38}$, $R^{12.39}$, $R^{12.40}$, $R^{12.41}$, $R^{12.42}$, the definition of $R^{13}$ is assumed by $R^{13.1}$, $R^{13.2}$, $R^{13.3}$, $R^{13.4}$, $R^{13.5}$, $R^{13.6}$, $R^{13.7}$, $R^{13.8}$, $R^{13.9}$, $R^{13.10}$, $R^{13.11}$, $R^{13.12}$, $R^{13.13}$, $R^{13.14}$, $R^{13.15}$, $R^{13.16}$, $R^{13.17}$, $R^{13.18}$, $R^{13.19}$, $R^{13.20}$, $R^{13.21}$, $R^{13.22}$, $R^{13.23}$, $R^{13.24}$, $R^{13.25}$, $R^{13.26}$, $R^{13.27}$, $R^{13.28}$, $R^{13.29}$, $R^{13.30}$, $R^{13.31}$, $R^{13.32}$, $R^{13.33}$, $R^{13.34}$, $R^{13.35}$, $R^{13.36}$, $R^{13.37}$, $R^{13.38}$, $R^{13.39}$, $R^{13.40}$, $R^{13.41}$, $R^{13.42}$, the definition of $R^{14}$ is assumed by $R^{14.1}$, $R^{14.2}$, $R^{14.3}$, $R^{14.4}$, $R^{14.5}$, $R^{14.6}$, $R^{14.7}$, $R^{14.8}$, $R^{14.9}$, $R^{14.10}$, $R^{14.11}$, $R^{14.12}$, $R^{14.13}$, $R^{14.14}$, $R^{14.15}$, $R^{14.16}$, $R^{14.17}$, $R^{14.18}$, $R^{14.19}$, $R^{14.20}$, $R^{14.21}$, $R^{14.22}$, $R^{14.23}$, $R^{14.24}$, $R^{4.25}$, $R^{14.26}$, $R^{14.27}$, $R^{14.28}$, $R^{14.29}$, $R^{14.30}$, $R^{14.31}$, $R^{14.32}$, $R^{14.33}$, $R^{14.34}$, $R^{14.35}$, $R^{14.36}$, $R^{14.37}$, $R^{1438}$, $R^{1439}$, $R^{14.40}$, $R^{14.41}$, $R^{14.42}$, the definition of $R^{11A}$ is assumed by $R^{11A.1}$, $R^{11A.2}$, $R^{11A.3}$, $R^{11A.4}$, $R^{11A.5}$, $R^{11A.6}$, $R^{11A.7}$, $R^{11A.8}$, $R^{11A.9}$, $R^{11A.10}$, $R^{11A.11}$, $R^{11A.12}$, $R^{11A.13}$, $R^{11A.14}$, $R^{11A.15}$, $R^{11A.16}$, $R^{11A.17}$, $R^{11A.18}$, $R^{11A.19}$, $R^{11A.20}$, $R^{11A.21}$, $R^{11A.22}$, $R^{11A.23}$, $R^{11A.24}$, $R^{11A.25}$, $R^{11A.26}$, $R^{11A.27}$, $R^{11A.28}$, $R^{11A.29}$, $R^{11A.30}$, $R^{11A.31}$, $R^{11A.32}$, $R^{11A.33}$, $R^{11A.34}$, $R^{11A.35}$, $R^{11A.36}$, $R^{11A.37}$, $R^{11A.38}$, $R^{11A.39}$, $R^{11A.40}$, $R^{11A.41}$, $R^{11A.42}$, the definition of $R^{12A}$ is assumed by $R^{12A.1}$, $R^{12A.2}$, $R^{12A.3}$, $R^{12A.4}$, $R^{12A.5}$, $R^{12A.6}$, $R^{12A.7}$, $R^{12A.8}$, $R^{12A.9}$, $R^{12A.10}$, $R^{12A.11}$, $R^{12A.12}$, $R^{12A.13}$, $R^{12A.14}$, $R^{12A.15}$, $R^{12A.16}$, $R^{12A.17}$, $R^{12A.18}$, $R^{12A.19}$, $R^{12A.20}$, $R^{12A.21}$, $R^{12A.22}$, $R^{12A.23}$, $R^{12A.24}$, $R^{12A.25}$, $R^{12A.26}$, $R^{12A.27}$, $R^{12A.28}$, $R^{12A.29}$, $R^{12A.30}$, $R^{12A.31}$, $R^{12A.32}$, $R^{12A.33}$, $R^{12A.34}$, $R^{12A.35}$, $R^{12A.36}$, $R^{12A.37}$, $R^{12A.38}$, $R^{12A.39}$, $R^{12A.40}$, $R^{12A.41}$, $R^{12A.42}$, the definition of $R^{13A}$ is assumed by $R^{13A.1}$, $R^{13A.2}$, $R^{13A.3}$, $R^{13A.4}$, $R^{13A.5}$, $R^{13A.6}$, $R^{13A.7}$, $R^{13A.8}$, $R^{13A.9}$, $R^{13A.10}$, $R^{13A.11}$, $R^{13A.12}$, $R^{13A.13}$, $R^{13A.14}$, $R^{13A.15}$, $R^{13A.16}$, $R^{13A.17}$, $R^{13A.18}$, $R^{13A.19}$, $R^{13A.20}$, $R^{13A.21}$, $R^{13A.22}$, $R^{13A.23}$, $R^{13A.24}$, $R^{13A.25}$, $R^{13A.26}$, $R^{13A.27}$, $R^{13A.28}$, $R^{13A.29}$, $R^{13A.30}$, $R^{13A.31}$, $R^{13A.32}$, $R^{13A.33}$, $R^{13A.34}$, $R^{13A.35}$, $R^{13A.36}$, $R^{13A.37}$, $R^{13A.38}$, $R^{13A.39}$, $R^{13A.40}$, $R^{13A.41}$, $R^{13A.42}$, the definition of $R^{14A}$ is assumed by $R^{14A.1}$, $R^{14A.2}$, $R^{14A.3}$, $R^{14A.4}$, $R^{14A.5}$, $R^{14A.6}$, $R^{14A.7}$, $R^{14A.8}$, $R^{14A.9}$, $R^{14A.10}$, $R^{14A.11}$, $R^{14A.12}$, $R^{14A.13}$, $R^{14A.14}$, $R^{14A.15}$, $R^{14A.16}$, $R^{14A.17}$, $R^{14A.18}$, $R^{14A.19}$, $R^{14A.20}$, $R^{14A.21}$, $R^{14A.22}$, $R^{14A.23}$, $R^{14A.24}$, $R^{14A.25}$, $R^{14A.26}$, $R^{14A.27}$, $R^{14A.28}$, $R^{14A.29}$, $R^{14A.30}$, $R^{14A.31}$, $R^{14A.32}$, $R^{14A.33}$, $R^{14A.34}$, $R^{14A.35}$, $R^{14A.36}$, $R^{14A.37}$, $R^{14A.38}$, $R^{14A.39}$, $R^{14A.40}$, $R^{14A.41}$, $R^{14A.42}$, the definition of $R^{11B}$ is assumed by $R^{11B.1}$, $R^{11B.2}$, $R^{11B.3}$, $R^{11B.4}$, $R^{11B.5}$, $R^{11B.6}$, $R^{11B.7}$, $R^{11B.8}$, $R^{11B.9}$, $R^{11B.10}$, $R^{11B.11}$, $R^{11B.12}$, $R^{11B.13}$, $R^{11B.14}$, $R^{11B.15}$, $R^{11B.16}$, $R^{11B.17}$, $R^{11B.18}$, $R^{11B.19}$, $R^{11B.20}$, $R^{11B.21}$, $R^{11B.22}$, $R^{11B.23}$, $R^{11B.24}$, $R^{11B.25}$, $R^{11B.26}$, $R^{11B.27}$, $R^{11B.28}$, $R^{11B.29}$, $R^{11B.30}$, $R^{11B.31}$, $R^{11B.32}$, $R^{11B.33}$, $R^{11B.34}$, $R^{11B.35}$, $R^{11B.36}$, $R^{11B.37}$, $R^{11B.38}$, $R^{11B.40}$, $R^{11B.41}$, $R^{11B.42}$, the definition of $R^{12B}$ is assumed by $R^{12B.1}$, $R^{12B.2}$, $R^{12B.3}$, $R^{12B.4}$, $R^{12B.5}$, $R^{12B.6}$, $R^{12B.7}$, $R^{12B.8}$, $R^{12B.9}$, $R^{12B.10}$, $R^{12B.11}$, $R^{12B.12}$, $R^{12B.13}$, $R^{12B.14}$, $R^{12B.15}$, $R^{12B.16}$, $R^{12B.17}$, $R^{12B.18}$, $R^{12B.19}$, $R^{12B.20}$, $R^{12B.21}$, $R^{12B.22}$, $R^{12B.23}$, $R^{12B.24}$, $R^{12B.25}$, $R^{12B.26}$, $R^{12B.27}$, $R^{12B.28}$, $R^{12B.29}$, $R^{12B.30}$, $R^{12B.31}$, $R^{12B.32}$, $R^{12B.33}$, $R^{12B.34}$, $R^{12B.35}$, $R^{12B.36}$, $R^{12B.37}$, $R^{12B.38}$, $R^{12B.39}$, $R^{12B.40}$, $R^{12B.41}$, $R^{12B.42}$ the definition of $R^{13B}$ is assumed by $R^{13B.1}$, $R^{13B.2}$, $R^{13B.3}$, $R^{13B.4}$, $R^{13B.5}$, $R^{13B.6}$, $R^{13B.7}$, $R^{13B.8}$, $R^{13B.9}$, $R^{13B.10}$, $R^{13B.11}$, $R^{13B.12}$, $R^{13B.13}$, $R^{13B.14}$, $R^{13B.15}$, $R^{13B.16}$, $R^{13B.17}$, $R^{13B.18}$, $R^{13B.19}$, $R^{13B.20}$, $R^{13B.21}$, $R^{13B.22}$, $R^{13B.23}$, $R^{13B.24}$, $R^{13B.25}$, $R^{13B.26}$, $R^{13B.27}$, $R^{13B.28}$, $R^{13B.29}$, $R^{13B.30}$, $R^{13B.31}$, $R^{13B.32}$, $R^{13B.33}$, $R^{13B.34}$, $R^{13B.35}$, $R^{13B.36}$, $R^{13B.37}$, $R^{13B.38}$, $R^{13B.39}$, $R^{13B.40}$, $R^{13B.41}$, $R^{13B.42}$, the definition of $R^{14B}$ is assumed by $R^{14B.1}$, $R^{14B.2}$, $R^{14B.3}$, $R^{14B.4}$, $R^{14B.5}$, $R^{14B.6}$, $R^{14B.7}$, $R^{14B.8}$, $R^{14B.9}$, $R^{14B.10}$, $R^{14B.11}$, $R^{14B.12}$, $R^{14B.13}$, $R^{14B.14}$, $R^{14B.15}$, $R^{14B.16}$, $R^{14B.17}$, $R^{14B.18}$, $R^{14B.19}$, $R^{14B.20}$, $R^{14B.21}$, $R^{14B.22}$, $R^{14B.23}$, $R^{14B.24}$, $R^{14B.25}$, $R^{14B.26}$, $R^{14B.27}$, $R^{14B.28}$, $R^{14B.29}$, $R^{14B.30}$, $R^{14B.31}$, $R^{14B.32}$, $R^{14B.33}$, $R^{14B.34}$, $R^{14B.35}$, $R^{14B.36}$, $R^{14B.37}$, $R^{14B.38}$, $R^{14B.39}$, $R^{14B.40}$, $R^{14B.41}$, $R^{14B.42}$, the definition of $R^{11C}$ is assumed by $R^{11C.1}$, $R^{11C.2}$, $R^{11C.3}$, $R^{11C.4}$, $R^{11C.5}$, $R^{11C.6}$, $R^{11C.7}$, $R^{11C.8}$, $R^{11C.9}$, $R^{11C.10}$, $R^{11C.11}$, $R^{11C.12}$, $R^{11C.13}$, $R^{11C.14}$, $R^{11C.15}$, $R^{11C.16}$, $R^{11C.17}$, $R^{11C.18}$, $R^{11C.19}$, $R^{11C.20}$, $R^{11C.21}$, $R^{11C.22}$, $R^{11C.23}$, $R^{11C.24}$, $R^{11C.25}$, $R^{11C.26}$, $R^{11C.27}$, $R^{11C.28}$, $R^{11C.29}$, $R^{11C.30}$, $R^{11C.31}$, $R^{11C.32}$, $R^{11C.33}$, $R^{11C.34}$, $R^{11C.35}$, $R^{11C.36}$, $R^{11C.37}$, $R^{11C.38}$, $R^{11C.39}$, $R^{11C.40}$, $R^{11C.41}$, $R^{11C.42}$, the definition of $R^{12C}$ is assumed by $R^{12C.1}$, $R^{12C.2}$, $R^{12C.3}$, $R^{12C.4}$, $R^{12C.5}$, $R^{12C.6}$, $R^{12C.7}$, $R^{12C.8}$, $R^{12C.9}$, $R^{12C.10}$, $R^{12C.11}$, $R^{12C.12}$, $R^{12C.13}$, $R^{12C.14}$, $R^{12C.15}$, $R^{12C.16}$, $R^{12C.17}$, $R^{12C.18}$, $R^{12C.19}$, $R^{12C.20}$, $R^{12C.21}$, $R^{12C.22}$, $R^{12C.23}$, $R^{12C.24}$, $R^{12C.25}$, $R^{12C.26}$, $R^{12C.27}$, $R^{12C.28}$, $R^{12C.29}$, $R^{12C.30}$, $R^{12C.31}$, $R^{12C.32}$, $R^{12C.33}$, $R^{12C.34}$, $R^{12C.35}$, $R^{12C.36}$, $R^{12C.37}$, $R^{12C.38}$, $R^{12C.39}$, $R^{12C.40}$, $R^{12C.41}$, $R^{12C.42}$, the definition of $R^{13C}$ is assumed by $R^{13C.1}$, $R^{13C.2}$, $R^{13C.3}$, $R^{13C.4}$, $R^{13C.5}$, $R^{13C.6}$, $R^{13C.7}$, $R^{13C.8}$, $R^{13C.9}$, $R^{13C.10}$, $R^{13C.11}$, $R^{13C.12}$, $R^{13C.13}$, $R^{13C.14}$, $R^{13C.15}$, $R^{13C.16}$, $R^{13C.17}$, $R^{13C.18}$, $R^{13C.19}$, $R^{13C.20}$, $R^{13C.21}$, $R^{13C.22}$, $R^{13C.23}$, $R^{13C.24}$, $R^{13C.25}$, $R^{13C.26}$, $R^{13C.27}$, $R^{13C.28}$, $R^{13C.29}$, $R^{13C.30}$, $R^{13C.31}$, $R^{13C.32}$, $R^{13C.33}$, $R^{13C.34}$, $R^{13C.35}$, $R^{13C.36}$, $R^{13C.37}$, $R^{13C.38}$, $R^{13C.39}$, $R^{13C.40}$, $R^{13C.41}$, $R^{13C.42}$, the definition of $R^{14C}$ is assumed by $R^{14C.1}$, $R^{14C.2}$, $R^{14C.3}$, $R^{14C.4}$, $R^{14C.5}$, $R^{14C.6}$, $R^{14C.7}$, $R^{14C.8}$, $R^{14C.9}$, $R^{14C.10}$, $R^{14C.11}$, $R^{14C.12}$, $R^{14C.13}$, $R^{14C.14}$, $R^{4C.15}$, $R^{14C.16}$, $R^{14C.17}$, $R^{14C.18}$, $R^{14C.19}$, $R^{14C.20}$, $R^{14C.21}$, $R^{14C.22}$, $R^{14C.23}$, $R^{14C.24}$, $R^{14C.25}$, $R^{14C.26}$, $R^{14C.27}$, $R^{14C.28}$, $R^{14C.29}$, $R^{14C.30}$, $R^{14C.31}$, $R^{14C.32}$, $R^{14C.33}$, $R^{14C.34}$, $R^{14C.35}$, $R^{14C.36}$, $R^{14C.37}$, $R^{14C.38}$, $R^{14C.39}$, $R^{14C.40}$, $R^{14C.41}$, $R^{14C.42}$, the definition of X is assumed by $X^{0.1}$, $X^{0.2}$, $X^{0.3}$, $X^{0.4}$, $X^{0.5}$, $X^{0.6}$, $X^{0.7}$, $X^{0.8}$, $X^{0.9}$, $X^{0.10}$, $X^{0.11}$, $X^{0.12}$, $X^{0.13}$, $X^{0.14}$, $X^{0.15}$, $X^{0.16}$, $X^{0.17}$, $X^{0.18}$, $X^{0.19}$, $X^{0.20}$, $X^{0.21}$, $X^{0.22}$, $X^{0.23}$, $X^{0.24}$, $X^{0.25}$, $X^{0.26}$, $X^{0.27}$, $X^{0.28}$, $X^{0.29}$, $X^{0.30}$, $X^{0.31}$, $X^{0.32}$, $X^{0.33}$, $X^{0.34}$, $X^{0.35}$, $X^{0.36}$, $X^{0.37}$, $X^{0.38}$, $X^{0.39}$, $X^{0.40}$, $X^{0.41}$, $X^{0.42}$, the definition of $X^1$ is assumed by $X^{1.1}$, $X^{1.2}$, $X^{1.3}$, $X^{1.4}$, $X^{1.5}$, $X^{1.6}$, $X^{1.7}$, $X^{1.8}$, $X^{1.9}$, $X^{1.10}$, $X^{1.11}$, $X^{1.12}$, $X^{1.13}$, $X^{1.14}$, $X^{1.15}$, $X^{1.16}$, $X^{1.17}$, $X^{1.18}$, $X^{1.19}$, $X^{1.20}$, $X^{1.21}$, $X^{1.22}$, $X^{1.23}$, $X^{1.24}$, $X^{1.25}$, $X^{1.26}$, $X^{1.27}$, $X^{1.28}$, $X^{1.29}$, $X^{1.30}$, $X^{1.31}$, $X^{1.32}$, $X^{1.33}$, $X^{1.34}$, $X^{1.35}$, $X^{1.36}$, $X^{1.37}$, $X^{1.38}$, $X^{1.39}$, $X^{1.40}$, $X^{1.41}$, $X^{1.42}$, the definition of $X^2$ is assumed by $X^{2.1}$, $X^{2.2}$, $X^{2.3}$, $X^{2.4}$, $X^{2.5}$, $X^{2.6}$, $X^{2.7}$, $X^{2.8}$, $X^{2.9}$, $X^{2.10}$, $X^{2.11}$, $X^{2.12}$, $X^{2.13}$, $X^{2.14}$, $X^{2.15}$, $X^{2.16}$, $X^{2.17}$, $X^{2.18}$, $X^{2.19}$, $X^{2.20}$, $X^{2.21}$, $X^{2.22}$, $X^{2.23}$, $X^{2.24}$, $X^{2.25}$, $X^{2.26}$, $X^{2.27}$, $X^{2.28}$, $X^{2.29}$, $X^{2.30}$, $X^{2.31}$, $X^{2.32}$, $X^{2.33}$, $X^{2.34}$, $X^{2.35}$, $X^{2.36}$, $X^{2.37}$, $X^{2.38}$, $X^{2.39}$, $X^{2.40}$, $X^{2.41}$, $X^{2.42}$, the definition of $X^3$ is assumed by $X^{3.1}$, $X^{3.2}$, $X^{3.3}$, $X^{3.4}$, $X^{3.5}$, $X^{3.6}$, $X^{3.7}$, $X^{3.8}$, $X^{3.9}$, $X^{3.10}$, $X^{3.11}$, $X^{3.12}$, $X^{3.13}$, $X^{3.14}$, $X^{3.15}$, $X^{3.16}$, $X^{3.17}$, $X^{3.18}$, $X^{3.19}$, $X^{3.20}$, $X^{3.21}$, $X^{3.22}$, $X^{3.23}$, $X^{3.24}$, $X^{3.25}$, $X^{3.26}$, $X^{3.27}$, $X^{3.28}$, $X^{3.29}$, $X^{3.30}$, $X^{3.31}$, $X^{3.32}$, $X^{3.33}$, $X^{3.34}$, $X^{3.35}$, $X^{3.36}$, $X^{3.37}$, $X^{3.38}$, $X^{3.39}$, $X^{3.40}$, $X^{3.41}$, $X^{3.42}$.

The variables used within a definition of $R^{101}$, $R^2$, $R^8$, $R^{11}$, $R^{12}$, $R^{13}$, $R^{14}$, $R^{11A}$, $R^{12A}$, $R^{13A}$, $R^{14A}$, $R^{11B}$, $R^{12B}$, $R^{13B}$, $R^{14B}$, $R^{11C}$, $R^{12C}$, $R^{13C}$, $R^{14C}$, X, $X^1$, $X^2$, $X^3$, and/or other variables that appear at multiple instances and are different may similarly be appropriately labeled to distinguish each group for greater clarity.

III. PHARMACEUTICAL COMPOSITIONS

In a second aspect is provided a pharmaceutical composition including a pharmaceutically acceptable excipient and a compound, or pharmaceutically acceptable salt thereof, as described herein (including embodiments).

In embodiments of the pharmaceutical compositions, the compound, or pharmaceutically acceptable salt thereof, as described herein, including embodiments, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating a subject for contact with a toxic agent. In embodiments of the pharmaceutical compositions, the second agent is an agent for treating an infectious disease. In embodiments of the pharmaceutical compositions, the second agent is an antibiotic. In embodiments of the pharmaceutical compositions, the second agent is an antiviral agent. In embodiments of the pharmaceutical compositions, the second agent is an agent for modulating trafficking between early and late endosomes. In embodiments of the pharmaceutical compositions, the second agent is an agent for treating contact with anthrax toxin, anthrax protective antigen, anthrax edema factor, anthrax lethal factor, or anthrax lethal toxin. In embodiments of the pharmaceutical compositions, the second agent is an agent for treating contact with *Bacillus anthracis*. In embodiments, the second agent is ciprofloxacin. In embodiments, the second agent is ciprofloxacin hydrochloride. In embodiments, the second agent is penicillin. In embodiments, the second agent is doxycycline. In embodiments, the second agent is raxibacumab. In embodiments, the second agent is a fluoroquinolone. In embodiments, the second agent is a tetracycline antibiotic. In embodiments, the second agent is a macrolide antibiotic. In embodiments, the second agent is a glycopeptide antibiotic (e.g. vancomycin). In embodiments, the second agent is a beta-lactam antibiotic. In embodiments, the second agent is an inhibitor of endosome maturation. In embodiments, the second agent is an inhibitor of endosome acidification. In embodiments, the second agent increases the pH of a vesicle (e.g. endosome, early endosome).

IV. METHODS OF TREATMENT

In a third aspect is provided a method of treating a disease in a subject in need thereof, the method including administering an effective amount of a compound, or pharmaceutically acceptable salt thereof, as described herein (including embodiments).

In a fourth aspect is provided a method of treating a subject for contact with a toxic agent, said method including administering an effective amount of a compound, or pharmaceutically acceptable salt thereof, as described herein (including embodiments).

In some embodiments of the method of treating a subject for contact with a toxic agent, the toxic agent is selected from the group consisting of anthrax toxin, anthrax protective antigen, anthrax edema factor, anthrax lethal factor, and anthrax lethal toxin.

In a fifth aspect is provided a method of modulating trafficking between early and late endosomes, the method including administering an effective amount of a compound, or pharmaceutically acceptable salt thereof, as described herein (including embodiments). The term "early endosome" is used in accordance with its ordinary meaning within the biological sciences. In embodiments, an early endosome is an endosome characterized by the presence of a tubular network, the presence of a tubular-vesicular network, the presence of RAB5A, the presence of RAB4, the presence of transferrin, the presence of transferrin receptor, and/or the presence of EEA1. The term "late endosome" is used in accordance with its ordinary meaning within the biological sciences. In embodiments, a late endosome is an endosome characterized by the absence of a tubular network or the presence of a minimal tubular network compared to an early endosome, the presence of close-packed luminal vesicles, the presence of RAB7, the presence of RAB9, and/or the presence of mannose 6-phosphate receptor. In embodiments, the administering is to a subject. In embodiments, the administering is in vitro. In embodiments, the administering is to a cell. In embodiments, the cell is in a subject. In embodiments, the method includes contacting an endosome (e.g. early endosome) with a compound as described herein. In embodiments, the endosome is in a cell. In embodiments, the cell is in a subject. In embodiments, the endosome is in vitro. In embodiments, the cell is in vitro. In embodiments, the subject is human. In embodiments, the method includes allowing the compound to interact with the endosome. In embodiments, the method includes inhibiting trafficking between early and late endosomes (e.g. slowing or reducing trafficking relative to the absence of the compound).

In a sixth aspect is provided a method of treating an infectious disease in a subject in need thereof, the method including administering an effective amount of a compound, or pharmaceutically acceptable salt thereof, as described herein (including embodiments).

In some embodiments of the method of treating an infectious disease, the infectious disease is caused by a bacterium. In some embodiments, the bacterium is *Bacillus anthracis*. In some embodiments of the method of treating an infectious disease, the infectious disease is caused by a virus. In some embodiments, the virus is an influenza virus (e.g. Influenzavirus A, Influenzavirus B, or Influenzavirus C, lymphocytic choriomeningitis virus (LCMV), or viruses pseudotyped with vesicular stomatitis virus g-spike protein (VSV-G)). In embodiments, the virus is an arenavirus (e.g. LCMV, GTOV, JUNV, LASV, LUJV, MACV, SABV). In embodiments the infectious agent enters the cell through an endosome. In embodiments the infectious agent uses an acidified endosome for entry into the cell (e.g. cytoplasm). In some embodiments, the infectious disease is influenza. In some embodiments, the method of treating is a method of preventing.

In a seventh aspect is provided a method of modulating maturation of an early endosome, the method including contacting a cellular component (e.g. protein or lipid) that regulates (e.g. modulates) endosomal maturation with a compound as described herein, or pharmaceutically acceptable salt thereof, and allowing the compound to inhibit endosome maturation. In embodiments, the method includes contacting the early endosome with a compound as described herein, or pharmaceutically acceptable salt thereof. In embodiments, the method includes contacting an early endosome with a compound as described herein. In embodiments, the endosome is in a cell. In embodiments, the cell is in a subject. In embodiments, the endosome is in vitro. In embodiments, the cell is in vitro. In embodiments, the subject is human. In embodiments, the compound is in an effective amount. In embodiments, the method includes allowing the compound to interact with the endosome. In embodiments, the compound inhibits the maturation of the early endosome (e.g. slows or reduces the maturation of the early endosome relative to the absence of the compound). In embodiments, the cellular component is a protein. In embodiments, the cellular component is a lipid. In embodiments, the cellular component is part of an endosome. In embodiments, the cellular component is part of an early endosome. In embodiments, inhibiting endosome maturation is reducing maturation relative to the absence of the compound. In embodiments, inhibiting endosome maturation is blocking maturation. In embodiments, inhibiting endosome maturation is stopping maturation. In embodiments, the cellular component (e.g. protein, lipid, receptor) is not part of an endosome. In embodiments, the cellular component (e.g. protein, lipid, receptor) is cytosolic.

In an aspect is provided a use of a compound described herein, or pharmaceutically acceptable salt thereof, in the manufacture of a medicament for the treatment of a disease in a subject in need thereof. In an aspect is provided a use of a compound described herein, or pharmaceutically acceptable salt thereof, in the manufacture of a medicament for treating a subject for contact with a toxic agent. In an aspect is provided a use of a compound described herein, or pharmaceutically acceptable salt thereof, in the manufacture of a medicament for modulating trafficking between early and late endosomes. In an aspect is provided a use of a compound described herein, or pharmaceutically acceptable salt thereof, in the manufacture of a medicament for treating an infectious disease in a subject in need thereof. In an aspect is provided a use of a compound described herein, or pharmaceutically acceptable salt thereof, in the manufacture of a medicament for treating a subject with an infectious. In an aspect is provided a use of a compound described herein, or pharmaceutically acceptable salt thereof, in the manufacture of a medicament for modulating maturation of an early endosome. In embodiments the uses of a compound described herein, or pharmaceutically acceptable salt thereof, in the manufacture of a medicament, described immediately above may include any of the embodiments described above for methods.

In an aspect is provided a method of treating a subject having an infectious disease in need thereof, the method including administering an effective amount of a compound, or pharmaceutically acceptable salt thereof, as described herein (including embodiments).

In some embodiments of the method of treating a subject having an infectious disease, the infectious disease is caused by a bacterium. In some embodiments, the bacterium is *Bacillus anthracis*. In some embodiments of the method of treating a subject having an infectious disease, the infectious disease is caused by a virus. In some embodiments, the virus is an influenza virus (e.g. Influenzavirus A, Influenzavirus B, Influenzavirus C, lymphocytic choriomeningitis virus (LCMV), or viruses pseudotyped with vesicular stomatitis virus g-spike protein (VSV-G)). In some embodiments, the infectious disease is influenza. In some embodiments, the method of treating is a method of preventing.

V. ADDITIONAL EMBODIMENTS

1. A compound of the formula:

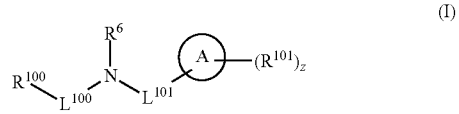

(I)

or pharmaceutically acceptable salt thereof, wherein ring A is a substituted or unsubstituted cycloalkylene, substituted or unsubstituted heterocycloalkylene, substituted or unsubstituted arylene or substituted or unsubstituted heteroarylene; $R^{100}$ is substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^6$ is hydrogen, halogen, $C(X^1)_3$, —OC$(X^1)_3$, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{11A}$R$^{12A}$, —OR$^{13A}$, —SR$^{14A}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^{101}$ is independently hydrogen, halogen, —C(X$^3$)$_3$, —OC(X$^3$)$_3$, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{11C}$R$^{12C}$, —OR$^{13C}$, —SR$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $L^{100}$ is —NHC(=$R^7$)— or —N=C(NH$_2$)—; $L^{101}$ is —NH—CH($R^{10}$)— or —N=C($R^{10}$)—; $R^7$ is O, S, or NH; $R^{10}$ is hydrogen, halogen, —C($X^2$)$_3$, —OC($X^2$)$_3$, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{11B}$R$^{112B}$, —OR$^{13B}$, —SR$^{14B}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^{11A}$, $R^{12A}$, $R^{13A}$, $R^{14A}$, $R^{11B}$, $R^{12B}$, $R^{13B}$, $R^{14B}$, $R^{11C}$, $R^{12C}$, $R^{13C}$, and $R^{14C}$ are independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $X^1$, $X^2$ and $X^3$ are independently a halogen; and z is an integer from 0 to 9.

2. The compound of embodiment 1, wherein ring A is a substituted or unsubstituted arylene or substituted or unsubstituted heteroarylene.

3. The compound of one of embodiments 1 to 2, wherein ring A is an unsubstituted arylene or unsubstituted heteroarylene.

4. The compound of one of embodiments 1 to 3, wherein ring A is an unsubstituted $C_6$-$C_{10}$ arylene or unsubstituted 5 to 10 membered heteroarylene.

5. The compound of one of embodiments 1 to 4, wherein ring A is an unsubstituted $C_6$ arylene or unsubstituted 5 to 6 membered heteroarylene.

6. The compound of one of embodiments 1 to 5, wherein $R^{100}$ is substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl or substituted or unsubstituted 5 to 10 membered heteroaryl.

7. The compound of one of embodiments 1 to 6, wherein $R^{100}$ is substituted or unsubstituted $C_6$-$C_{10}$ aryl or substituted or unsubstituted 5 to 10 membered heteroaryl.

8. The compound of one of embodiments 1 to 7, wherein $R^{100}$ is substituted $C_6$-$C_{10}$ aryl or substituted 5 to 10 membered heteroaryl.

9. The compound of one of embodiments 1 to 8, wherein $R^{100}$ is substituted $C_6$ aryl or substituted 5 to 6 membered heteroaryl.

10. The compound of one of embodiments 1 to 9, having the formula:

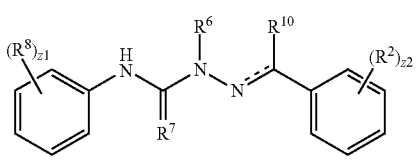

(II)

wherein each $R^2$ is independently hydrogen, halogen, —CX$^3_3$, —OCX$^3_3$, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{11C}$R$^{12C}$, —OR$^{13C}$, —SR$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; each $R^8$ is independently hydrogen, halogen, —CX$_3$, —OCX$_3$, —CN, —C(O)OH, —CONH$_2$, —NO$_2$, —SO$_2$C, —SO$_2$NH$_2$, —NHNH$_2$, —NHSO$_2$CH$_3$, —N$_3$, —NR$^{11}$R$^{12}$, —OR$^{13}$, —SR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; each $R^{11}$, $R^{12}$, $R^{13}$, and $R^{14}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; ----- is a single or double bond, wherein if ----- is a single bond than —N=====C($R^{10}$)— is —NH—CH($R^{10}$)— and if ----- is a double bond than —N=====C($R^{10}$)— is —N=C($R^{10}$)—; each X is independently a halogen; and z1 and z2 are independently an integer from 0 to 5.

11. The compound of one of embodiments 1 to 10, having the formula:

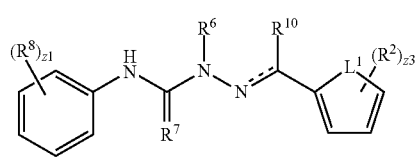

(III)

wherein each $R^2$ is independently hydrogen, halogen, —CX$^3_3$, —OCX$^3_3$, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{11C}$R$^{12C}$, —OR$^{13C}$, —SR$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; each $R^8$ is independently hydrogen, halogen, —CX$_3$, —OCX$_3$, —CN, —C(O)OH, —CONH$_2$, —NO$_2$, —SO$_2$Cl, —SO$_2$NH$_2$, —NHNH$_2$, —NHSO$_2$CH$_3$, —N$_3$, —NR$^{11}$R$^{12}$, —OR$^{13}$, —SR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; each $R^{11}$, $R^{12}$, $R^{13}$, and $R^{14}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; ----- is a single or double bond, wherein if ----- is a single bond than —N=====C($R^{10}$)— is —NH—CH($R^{10}$)— and if ----- is a double bond than —N=====C($R^{10}$)— is —N=C($R^{10}$)—; each X is independently a halogen; $L^1$ is —O— or —S—; z1 is an integer from 0 to 5; and z3 is an integer from 0 to 3.

12. The compound of one of embodiments 1 to 11 having the formula:

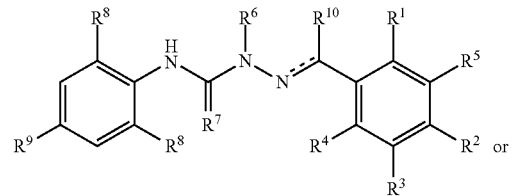

(IV)

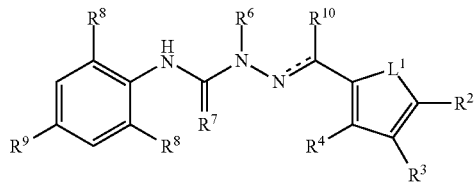

(V)

wherein each $R^1$, $R^2$, $R^3$, $R^4$, $R^5$ is independently hydrogen, halogen, —$CX^3{}_3$, —$OCX^3{}_3$, —CN, —C(O)OH, —$CONH_2$, —$NO_2$, —$SO_2C$, —$SO_2NH_2$, —$NHNH_2$, —$NHSO_2CH_3$, —$N_3$, —$NR^{11C}R^{12C}$, —$OR^{13C}$, —$SR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; each $R^8$ and $R^9$ is independently hydrogen, halogen, —$CX_3$, —$OCX_3$, —CN, —C(O)OH, —$CONH_2$, —$NO_2$, —$SO_2Cl$, —$SO_2NH_2$, —$NHNH_2$, —$NHSO_2CH_3$, —$N_3$, —$NR^{11}R^{12}$, —$OR^{13}$, —$SR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^7$ is O or S; $L^1$ is —O— or —S—; ----- is a single or double bond, wherein if ----- is a single bond, then —N=====C($R^{10}$)— is —NH—CH($R^{10}$)— and if ----- is a double bond then —N=====C($R^{10}$)— is —N=C($R^{10}$)—; each $R^{11}$, $R^{12}$, $R^{13}$, and $R^{14}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and each X is independently a halogen.

13. The compound of one of embodiments 1 to 12, wherein; $R^1$ and $R^4$ are independently hydrogen, halogen, —$OR^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^2$ is independently hydrogen, halogen, —$CX^3{}_3$, —CN, —$NHSO_2CH_3$, —$N_3$, —$OR^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^3$ and $R^5$ are independently hydrogen, halogen, —$CX^3{}_3$, —$OR^{13C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; each $R^6$, $R^8$, $R^9$, and $R^{10}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and each $R^{13C}$ is independently a hydrogen or a substituted or unsubstituted alkyl.

14. The compound, of one of embodiments 1 to 13, wherein; $R^1$ is independently hydrogen, halogen, or —$OR^{13C}$; $R^2$ is independently hydrogen, halogen, —$CX^3{}_3$, —CN, —$NHSO_2CH_3$, —$N_3$, —$OR^{13C}$, or unsubstituted alkyl; $R^3$ is independently hydrogen, halogen, —$CX^3{}_3$, —$OR^{13C}$, or unsubstituted alkyl; $R^4$ is independently hydrogen, halogen, —$OR^{13C}$, or unsubstituted alkyl; $R^5$ is independently hydrogen, halogen, —$OR^{13C}$, or unsubstituted alkyl; $R^6$ is independently hydrogen or unsubstituted alkyl; each $R^8$ is independently an unsubstituted alkyl; $R^9$ is independently hydrogen or unsubstituted alkyl; $R^{10}$ is independently hydrogen or unsubstituted alkyl; each $R^{13C}$ is independently an unsubstituted alkyl; and $X^3$ is —F.

15. The compound of one of embodiments 1 to 14 having the formula:

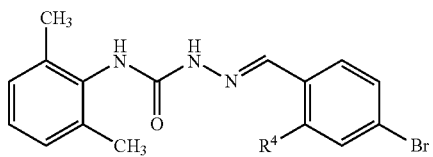

wherein $R^4$ is independently hydrogen or —F.

16. The compound of one of embodiments 1 to 16, having the formula:

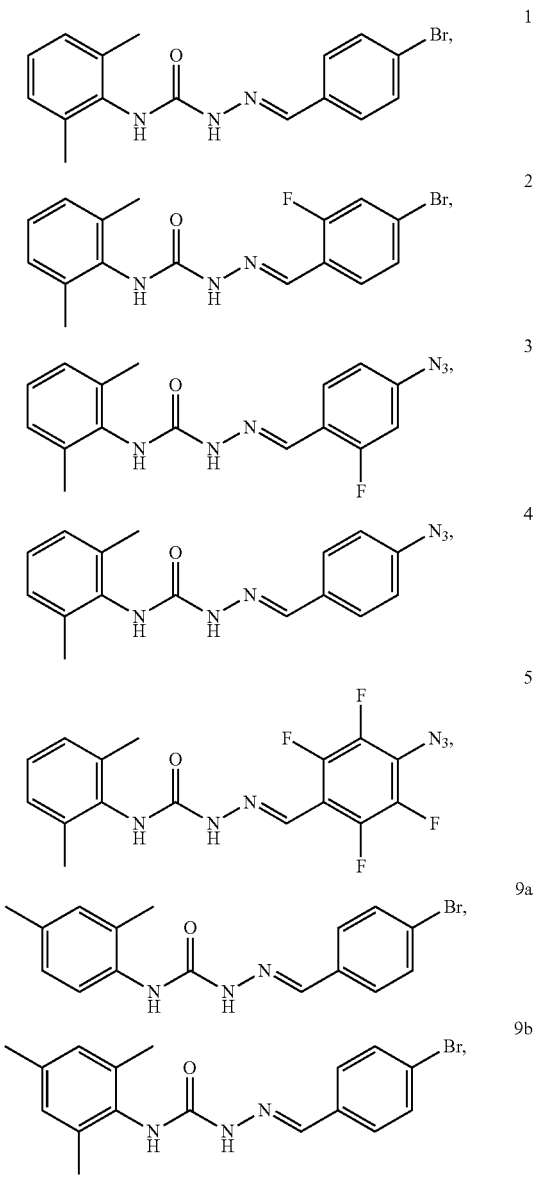

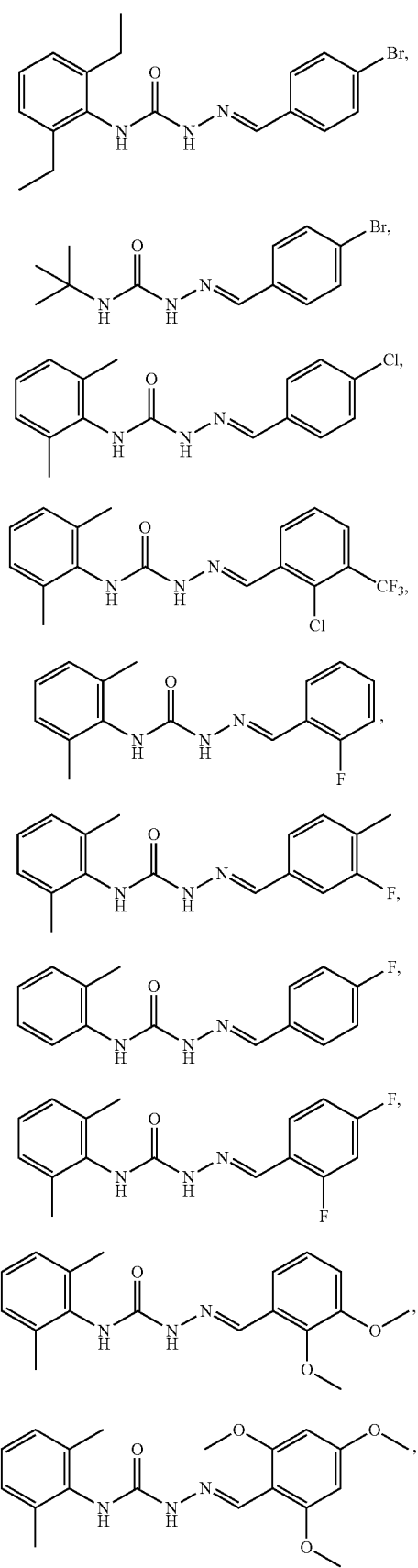
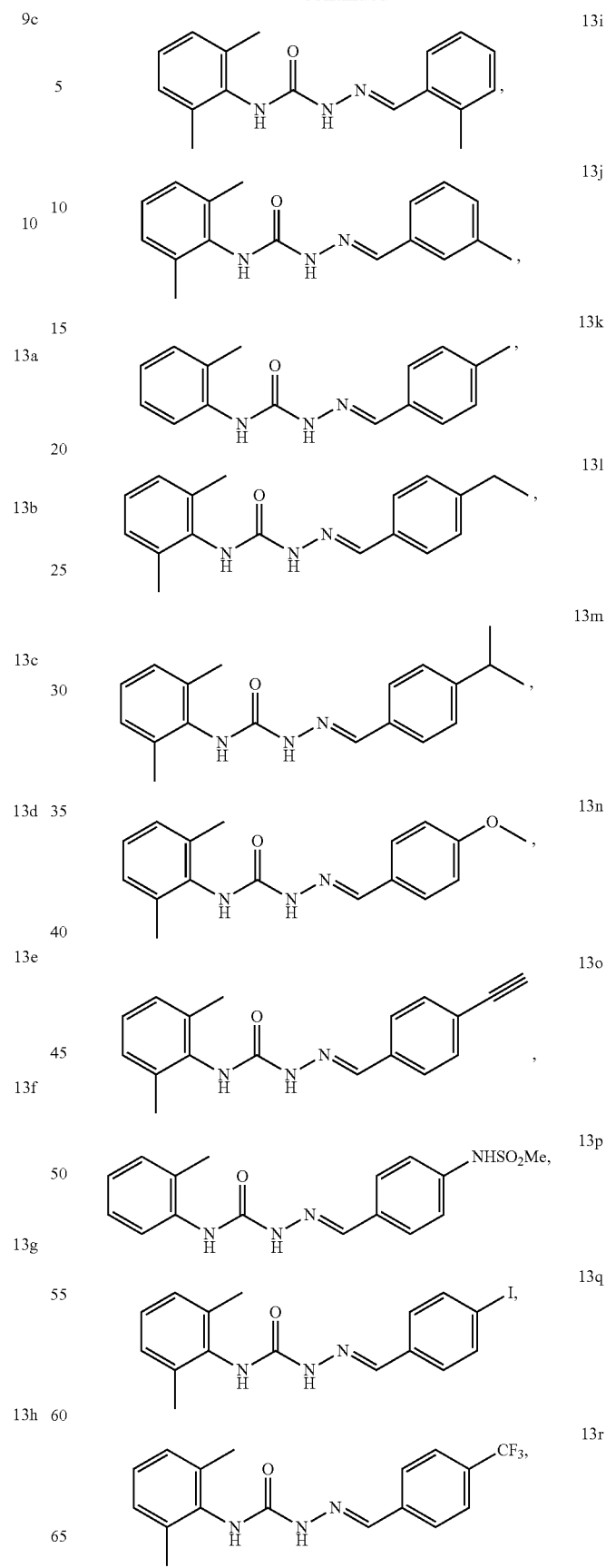

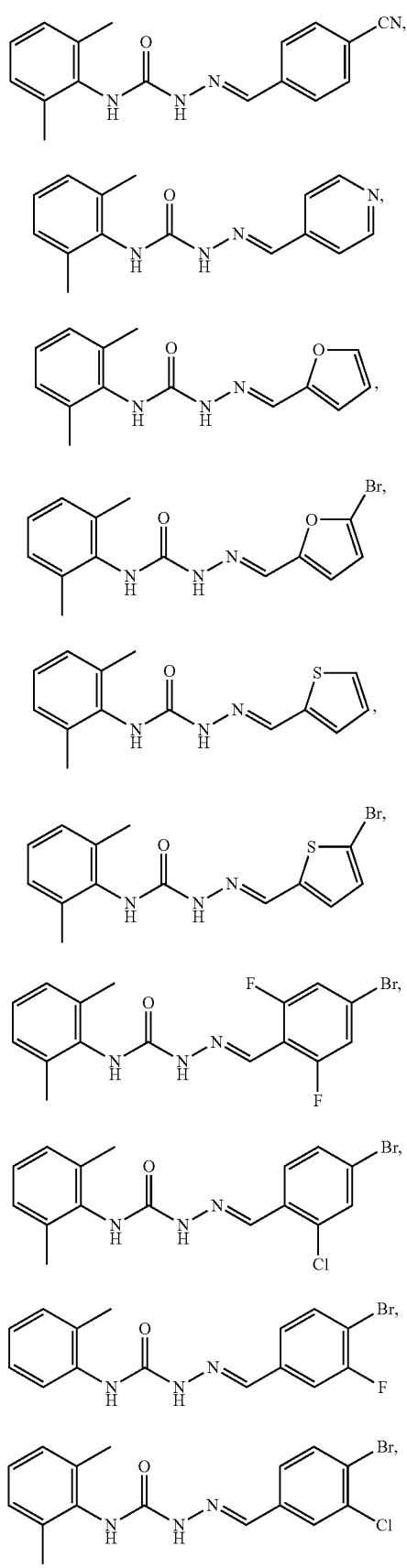
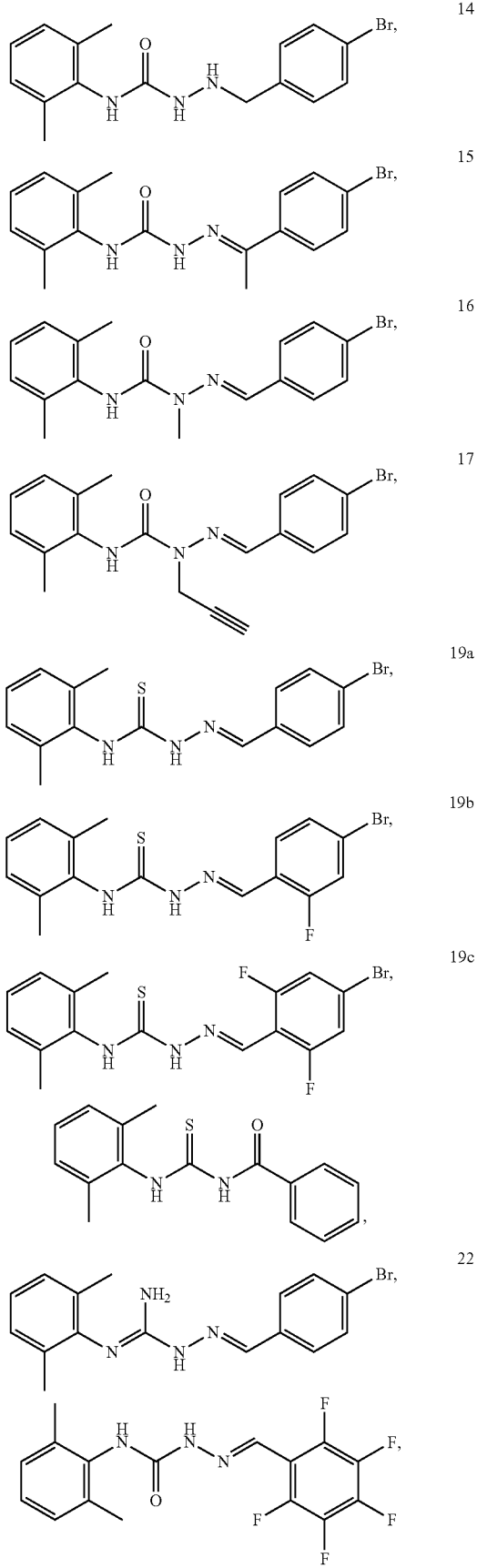

-continued

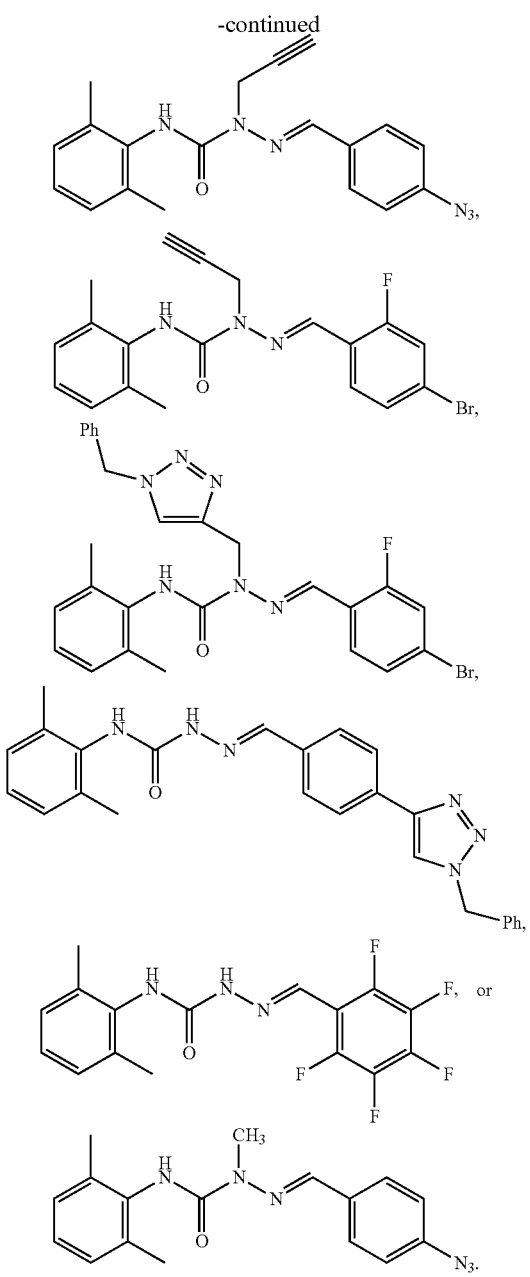

17. A pharmaceutical composition comprising a pharmaceutically acceptable excipient and a compound, or pharmaceutically acceptable salt thereof, of any one of embodiments 1 to 16.

18. A method of treating a disease in a subject in need thereof, said method comprising administering an effective amount of a compound, or pharmaceutically acceptable salt thereof, of any one of embodiments 1 to 16 to a subject in need thereof.

19. A method of treating a subject for contact with a toxic agent, said method comprising administering an effective amount of a compound, or pharmaceutically acceptable salt thereof, of one of embodiments 1 to 16 to a subject in need thereof.

20. The method of embodiment 19, wherein the toxic agent is selected from the group consisting of anthrax toxin, anthrax protective antigen, anthrax edema factor, anthrax lethal factor, and anthrax lethal toxin.

21. A method of treating an infectious disease in a subject, said method comprising administering a therapeutically effective amount of a compound, or pharmaceutically acceptable salt thereof, of any one of embodiments 1 to 16 to a subject in need thereof.

22. The method of embodiment 21, wherein the method of treating is a method of preventing.

23. The method of any one of embodiments 21 to 22, wherein the infectious disease is caused by an infectious agent selected from the group consisting of a virus and a bacterium.

24. The method of embodiment 23, wherein the virus is an influenza virus.

25. The method of embodiment 23, wherein the bacterium is *Bacillus anthracis*.

26. A method of modulating trafficking between early and late endosomes, said method comprising administering an effective amount of a compound, or pharmaceutically acceptable salt thereof, of any one of embodiments 1 to 16.

27. A method of modulating maturation of an early endosome, said method comprising contacting a cellular component (e.g. protein or lipid) that regulates endosomal maturation with a compound of any of embodiments 1 to 16, or pharmaceutically acceptable salt thereof, and allowing said compound to inhibit endosome maturation.

28. A compound, or pharmaceutically acceptable salt thereof, having the formula:

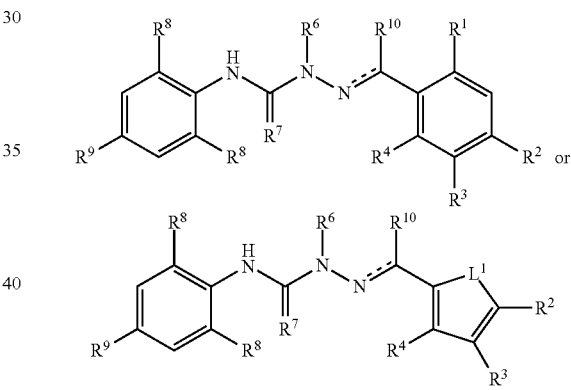

wherein $R^1$, $R^2$, $R^3$, $R^4$, $R^6$, $R^8$, $R^9$, and $R^{10}$ are independently hydrogen, halogen, $-CX_3$, $-OCX_3$, $-CN$, $-C(O)OH$, $-CONH_2$, $-NO_2$, $-SO_2Cl$, $-SO_2NH_2$, $-NHNH_2$, $-NHSO_2CH_3$, $-N_3$, $-NR^{11}R^{12}$, $-OR^{13}$, $-SR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^7$ is O or S; $L^1$ is $-O-$ or $-S-$; ----- is a single or double bond, wherein if ----- is a single bond than $-N$ ----- $C(R^{10})-$ is $-NH-CH(R^{10})-$ and if ----- is a double bond than $-N$ ----- $C(R^{10})-$ is $-N=C(R^{10})-$; each $R^{11}$, $R^{12}$, $R^{13}$, and $R^{14}$ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and each X is independently a halogen.

29. The compound, or pharmaceutically acceptable salt thereof, of embodiment 28, wherein; $R^1$ and $R^4$ are independently hydrogen, halogen, $-OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^2$ is independently hydrogen, halogen, —$CX_3$, —CN, —$NHSO_2CH_3$, —$N_3$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; $R^3$ is independently hydrogen, halogen, —$CX_3$, —$OR^{13}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; each $R^6$, $R^8$, $R^9$, and $R^{10}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and each $R^{13}$ is independently a hydrogen or a substituted or unsubstituted alkyl.

30. The compound, or pharmaceutically acceptable salt thereof, of any one of embodiments 28 to 29, wherein; $R^1$ is independently hydrogen, halogen, or —$OR^{13}$; $R^2$ is independently hydrogen, halogen, —$CX_3$, —CN, —$NHSO_2CH_3$, —$N_3$, —$OR^{13}$, or unsubstituted alkyl; $R^3$ is independently hydrogen, halogen, —$CX_3$, —$OR^{13}$, or unsubstituted alkyl; $R^4$ is independently hydrogen, halogen, —$OR^{13}$, or unsubstituted alkyl; $R^6$ is independently hydrogen or unsubstituted alkyl; each $R^8$ is independently an unsubstituted alkyl; $R^9$ is independently hydrogen or unsubstituted alkyl; $R^{10}$ is independently hydrogen or unsubstituted alkyl; each $R^{13}$ is independently an unsubstituted alkyl; and X is —F.

31. The compound, or pharmaceutically acceptable salt thereof, of any one of embodiments 28 to 30, having the formula

[Chemical structure: 2,6-dimethylphenyl semicarbazone of 4-bromobenzaldehyde with $R^4$ substituent]

wherein $R^4$ is independently hydrogen or —F.

32. A pharmaceutical composition comprising a pharmaceutically acceptable excipient and a compound, or pharmaceutically acceptable salt thereof, of any one of embodiments 28 to 31.

33. A method of treating a disease in a subject in need thereof, said method comprising administering an effective amount of a compound, or pharmaceutically acceptable salt thereof, of any one of embodiments 28 to 31.

34. A method of treating a subject for contact with a toxic agent, said method comprising administering an effective amount of a compound, or pharmaceutically acceptable salt thereof, of any one of embodiments 28 to 31.

35. The method of embodiment 34, wherein the toxic agent is selected from the group consisting of anthrax toxin, anthrax protective antigen, anthrax edema factor, anthrax lethal factor, and anthrax lethal toxin.

36. A method of treating an infectious disease in a patient in need of such treatment, said method comprising administering a therapeutically effective amount of a compound, or pharmaceutically acceptable salt thereof, of any one of embodiments 28 to 31 to the patient.

37. The method of embodiment 36, wherein the method of treating is a method of preventing.

38. The method of any one of embodiments 36 to 37, wherein the infectious disease is caused by an infectious agent selected from the group consisting of a virus and a bacterium.

39. The method of embodiment 38, wherein the virus is an influenza virus.

40. The method of embodiment 38, wherein the bacterium is *Bacillus anthracis*.

41. A method of modulating trafficking between early and late endosomes, said method comprising administering an effective amount of a compound, or pharmaceutically acceptable salt thereof, of any one of embodiments 28 to 31.

VI. EXAMPLES

A. Example 1: High-Throughput Screen Identifies Potent Anthrax Toxin Inhibitor In order to identify inhibitors of toxin entry, we employed a cellular intoxication assay using an immortalized macrophage cell line which undergoes a rapid cell death known as pyroptosis in response to anthrax LT. Pyroptosis is a pro-inflammatory, caspase-1 dependent cell death that occurs in response to LT in macrophages and dendritic cells encoding certain alleles of the inflammasome gene Nlrp1b {Boyden, 2006}. This rapid cytolytic response occurs within 2-3 hours of toxin addition and provides a convenient assay for toxin entry. A total of 30,000 small-molecules from a commercially available compound library, Chembridge DiverSet E, were screened for their ability to inhibit LT-mediated cytotoxicity. Hits were defined based on percent survival relative to untreated controls. All compounds that yielded survival greater than 7% (~0.1% hit rate) were selected for initial re-validation. 37 initial hits were picked from the source library, assembled onto a single master plate, and re-tested for protection in the LT macrophage cytotoxicity assay. Compounds that increased survival at least three standard deviations above controls treated with LT and vehicle were considered verified. Thirty-two compounds exhibited activity in validation assays, while five failed to reconfirm. Of the 32 confirmed hits, fresh powder stocks were ordered for eight compounds, including the five that displayed the highest level of protection from LT. Six of these yielded calculable $IC_{50}$ values in the macrophage cytotoxicity assay (FIG. 1A), while the other two compounds showed no activity.

Figure 1B:
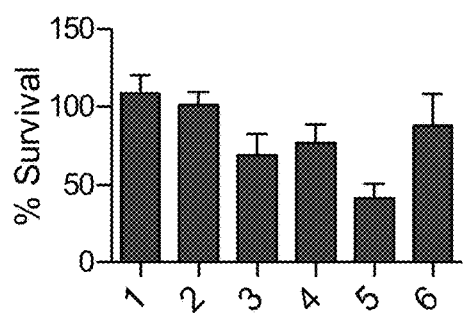
Figure 1C:
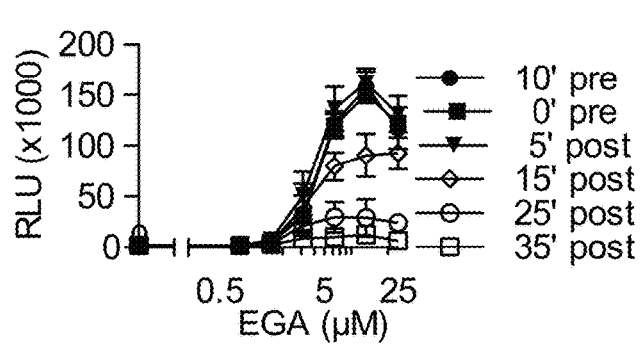
Figure 1D:
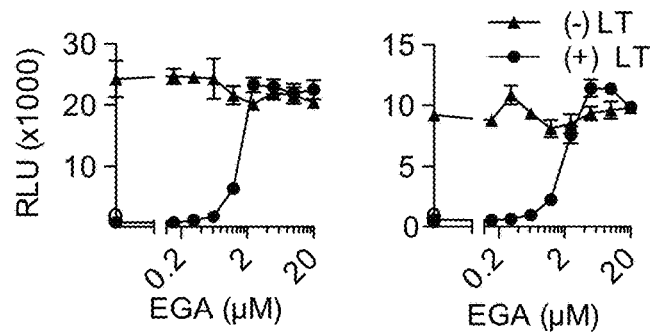
Figure 2A:
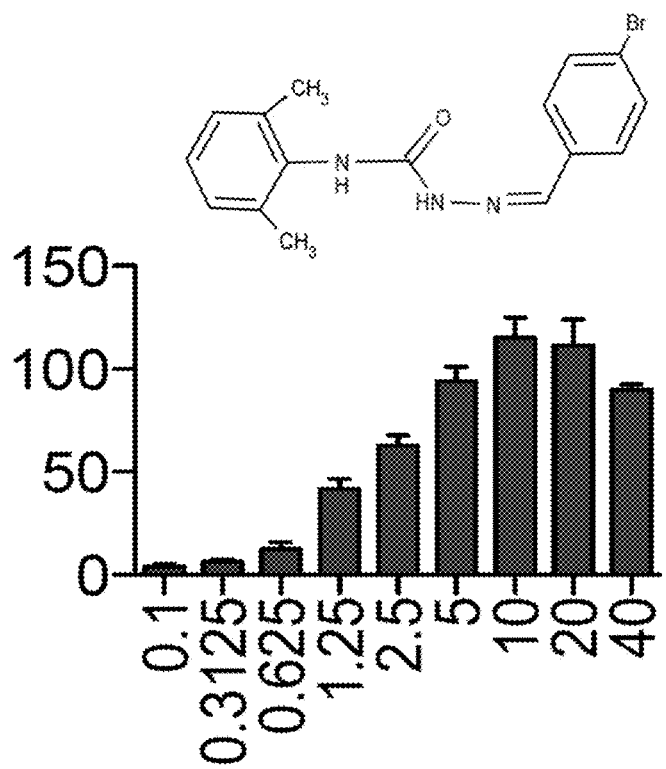
FIGS. 2A-2D: Structure Activity Relationship for EGA. EGA and commercially available structural analogues were tested for ability to inhibit LT-mediated cytotoxicity. RAW264.7 cells were seeded on 384-well plates, and the following day incubated with dose titrations of each compound for 1 h, followed by intoxication with PA and LF overnight. Cell viability was measured 24 later as in FIGS. 1A-1D.
Figure 2B:
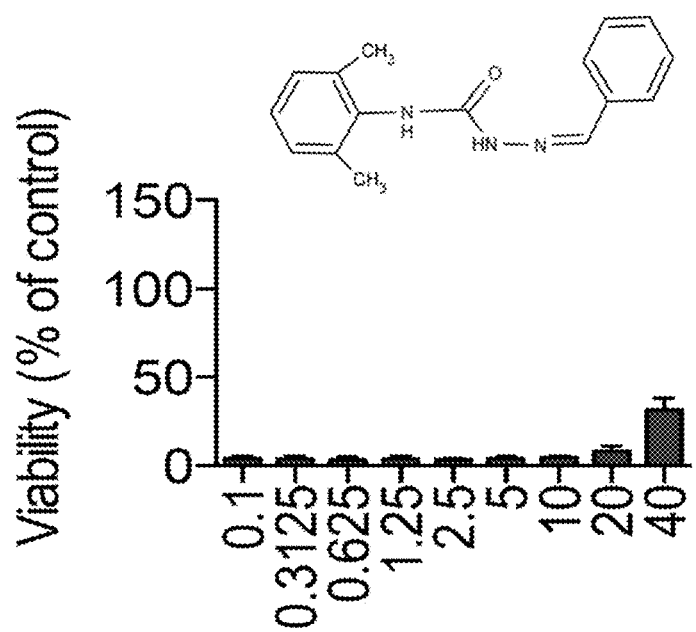
Figure 2C:
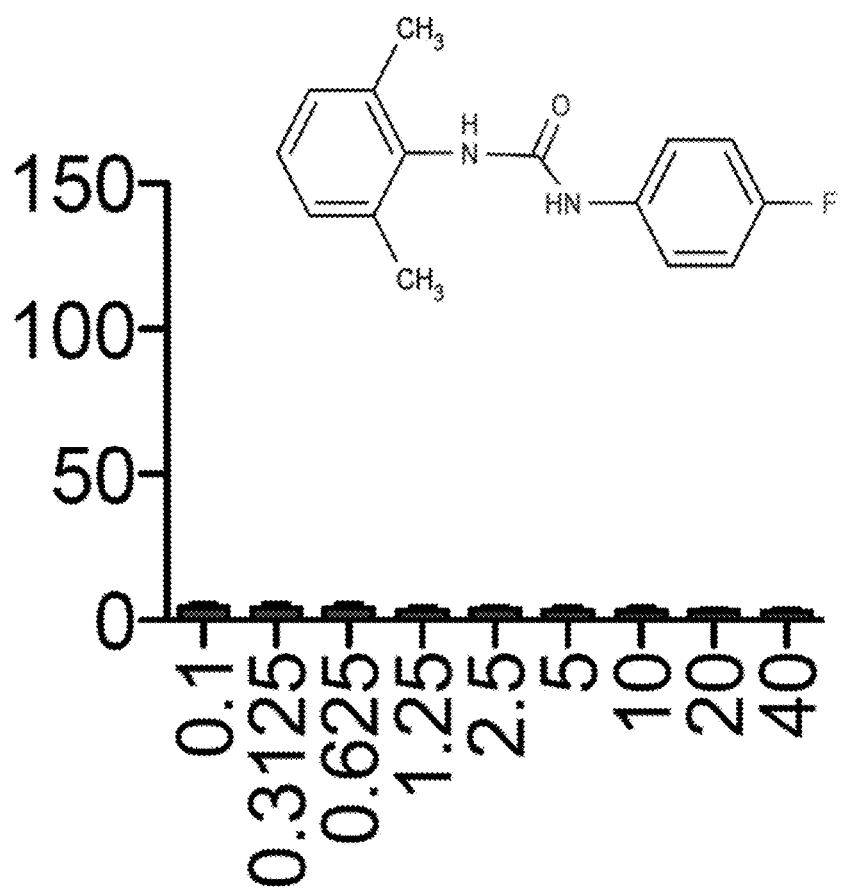
Figure 2D:
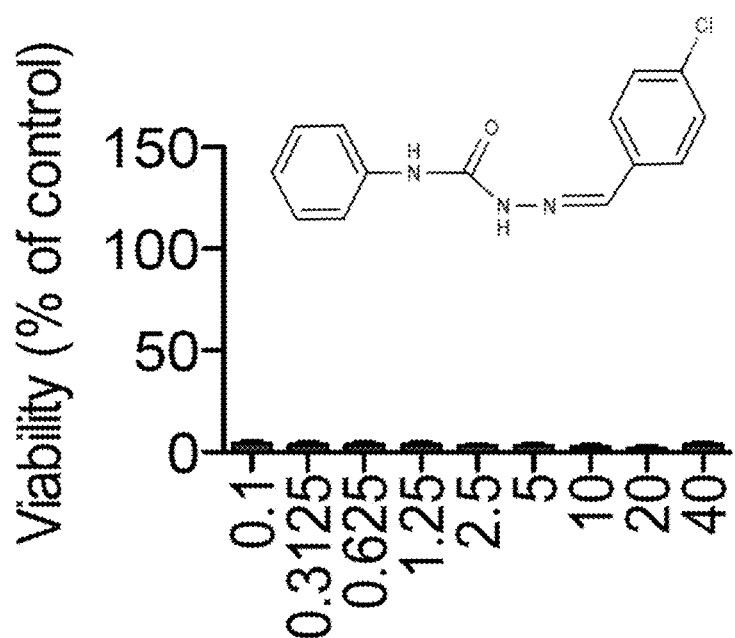

The most potent of the validated compounds, 4-bromobenzaldehyde N-(2,6-dimethylphenyl)semicarbazone, which we called EGA, rescued viability up to 100% of unintoxicated controls with an $IC_{50}$ of 1.4 μM (FIGS. 1A-1B). EGA could be added up to 15 minutes after LT and still completely protect cells from killing (FIG. 1C), suggesting EGA acts after toxin binding to host cells but at a step early in intoxication. In order to determine if the effect of EGA extended beyond established cell lines, primary bone-marrow derived macrophages (BMDMs) from mice with a toxin-sensitive Nlrp1b transgene were intoxicated in the presence or absence of EGA. While BMDMs treated with DMSO as a vehicle control were killed efficiently by LT, BMDMs treated with EGA were protected (FIG. 1D).

NMR and LC-MS analysis confirmed purity and structure of commercial EGA, reducing the possibility that the activity of EGA is due to a contaminant from its synthesis and/or from a breakdown product. Re-synthesis of EGA yielded similar activity as that obtained from the commercial source, further validating the identity of the compound. As an initial investigation of structure-activity relationship, a series of related compounds from Chembridge was assayed. Interestingly, none of the commercially available EGA analogues were active (FIGS. 2A-2D). These compounds revealed critical roles for 4-position substitution on the benzaldehyde, as well as 2,6 substitutions on the aniline ring. Further, the semicarbazone linker appeared to contribute to compound activity.

PA and LF were expressed and purified as described previously {Terra, 2011}. $LF_NDTA$ (a fusion of the amino terminus of LF with the *Diphtheria* toxin A chain) was a gift. *Diphtheria* toxin (DT) and *Pseudomonas* exotoxin A (ExoA) were purchased from List Biological Laboratories (Campbell, Calif.). Ricin, bafilomycin A1, and anti-β-tubulin antibody were purchased from Sigma Aldrich. Anti-PA rabbit serum was obtained. Anti-MEK-2 N-terminal antibody was purchased from Santa Cruz Biotechnology. Horseradish peroxidase (HRP)-conjugated anti-rabbit antibody was obtained from Invitrogen. HRP-conjugated anti-mouse antibody was purchased from AnaSpec (San Jose, Calif.). The compound library was from ChemBridge (DiverSet E) and made available through the Molecular Screening Shared Resource at UCLA. Working stock solutions of compounds were 1 mM compound in DMSO and were stored in sealed 384-well plates at room temperature in dessicated chambers.

RAW 264.7 macrophages were cultured in complete growth medium consisting of DMEM containing 10% FBS, 100 U/mL penicillin, 100 μg/mL streptomycin, 6.25 mM HEPES and 1× GlutaMAX-1 supplement (Invitrogen). Two thousand cells were added to each well of 384-well white polystyrene plates (Matrix) in a volume of 40 μL per well. The cells were allowed to grow overnight at 37° C., 5% $CO_2$. The following day 0.5 μL of 1 mM compound in DMSO was pin transferred onto cells with a Biomek FX (Beckman Coulter) and custom 500 nL pin transfer tool (V&P Scientific) to achieve a 12 μM final concentration of each compound per well. Cells were incubated with compound for 1 hour at 37° C., 5% $CO_2$ then challenged with LT by adding 15 μL of $1.4 \times 10^{-9}$ M LF and $1.0 \times 10^{-8}$ M PA dissolved in complete growth medium to achieve final concentrations of $3.7 \times 10^{-10}$ M LF and $2.8 \times 10^{-9}$ M PA. Assay plates were incubated at 37° C., 5% $CO_2$ for 20 hours then removed from the incubator, de-lidded and allowed to cool to room temperature for one hour. Twenty microliters of ATPlite reagent (Perkin Elmer) was added to each well. Luminescence values were measured with the Victor$^3$ V reader (Perkin Elmer).

B. Example 2: MEK2 Cleavage Assay

Figure 3A:
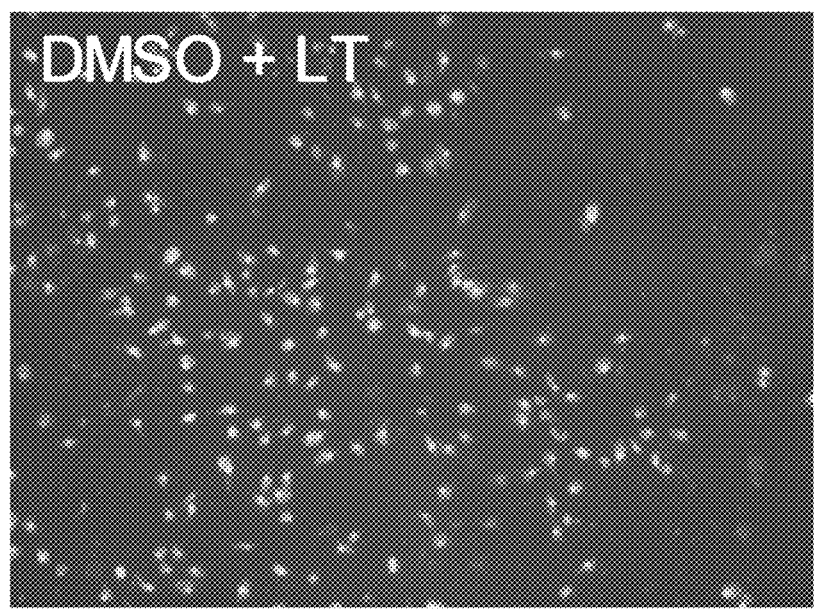
FIGS. 3A-3D: EGA Inhibits Cellular Entry of LF.
Figure 3A:
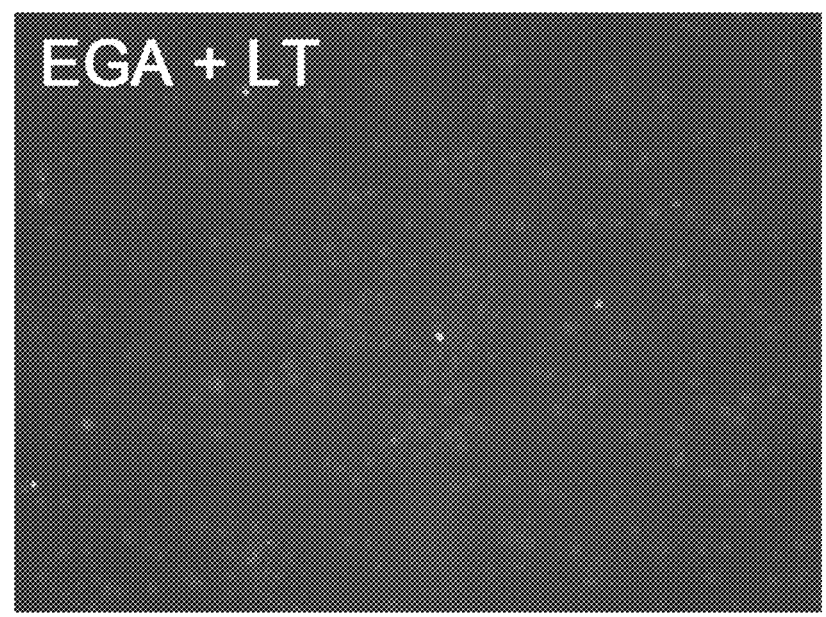
Figure 3A:
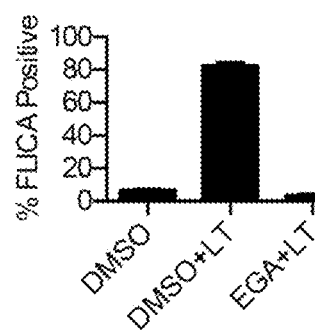
Figure 3A:
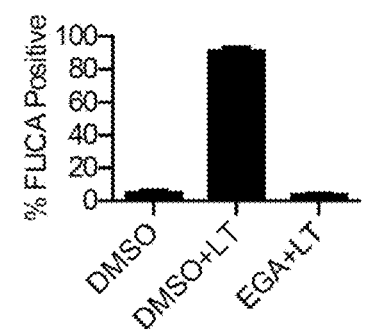
Figure 3B:
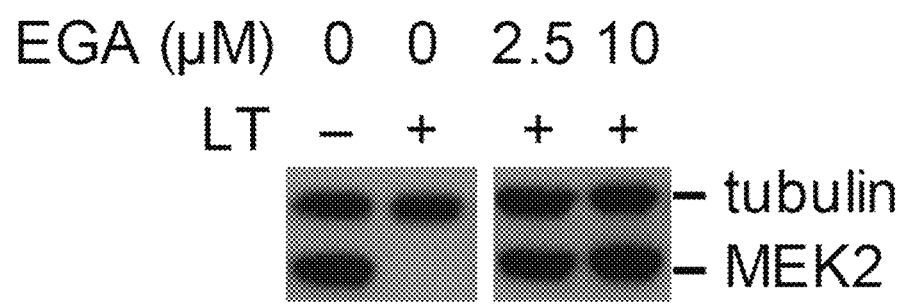

Activation of caspase-1 by LT is a late step in pyroptosis and depends on the activity of the proteasome, lysosomal membrane permeabilization and LF catalytic activity {Wickliffe, 2008; Squires, 2007; Averette, 2010}. In order to determine if EGA blocks a step upstream of LF proteolysis of MKKs, we assessed cleavage of MEK2 by western blot. While LT cleaved MEK2 in vehicle treated controls in both RAW264.7 cells and toxin-sensitive BMDMs, treatment with EGA completely abrogated this effect (FIG. 3B). EGA-treated cells were also found to be resistant to treatment with PA+LFnDTA, a chimeric protein that delivers the catalytic *Diphtheria* toxin A chain to the cytosol in a PA-dependent fashion. Because LF induces pyroptosis and *Diphtheria* toxin induces apoptosis due to inhibition of protein synthesis, inhibitors blocking both could affect some shared mechanism of internalization. These data, combined with the caspase-1 and MEK2 data, strongly suggest that EGA interferes with PA-mediated toxin entry.

Cell culture plates (2 cm) were seeded at $2 \times 10^6$ cells/plate and allowed to grow overnight at 37° C., 5% $CO_2$. The following day the media was removed and inhibitor-containing media or vehicle-containing control media were added to the plates and allowed to incubate for one hr at 37° C. Then, media was aspirated and $3.7 \times 10^{-10}$ M LF and $2.8 \times 10^{-9}$ M PA diluted in media was added to each plate. Inhibitors or vehicle were immediately added back at the same concentrations. Plates were returned to incubator for either 2.5 or 3 hours. Then, media was aspirated, cells were washed twice with PBS, and were scraped off in fresh PBS and centrifuged at 3000 g for two minutes. PBS was aspirated off and the cell pellet was re-suspended in 50 μL MCF-7 lysis buffer by incubating on ice for 10 minutes with periodic high speed vortexing. Debris was removed by centrifugation and protein concentration of supernatant liquid was measured (Bio-Rad Protein Assay). Reducing buffer was added to each sample and the samples were boiled for two minutes. Ten micrograms of each sample was run on a 10% SDS-PAGE gel for 80 minutes at 150 volts. Protein was transferred to PVDF membrane and membrane was incubated for 30 minutes in 5% milk to block non-specific interactions. Membrane was incubated with primary mouse anti-tubulin antibody (Sigma) followed by HRP-conjugated goat anti-mouse (Fisher). The membrane was the incubated with rabbit anti-MEK2 (Santa Cruz) for 1 hour followed by goat anti-rabbit (Invitrogen) for 1 hour. The membrane was treated using Immun-Star HRP Chemiluminescent Kit (Bio-Rad) and then exposed against film. Sanchez A M, et al. (2007) Amiodarone and bepridil inhibit anthrax toxin entry into host cells. *Antimicrob Agents Chemother* 51(7):2403-2411, incorporated herein by reference.

C. Example 3: Caspase-1 Activation

In order to identify the step at which EGA blocks LT-mediated cytotoxicity, processes involved in cellular entry and pyroptosis were assessed in the presence and absence of this compound. Caspase-1 activation, which occurs late in LT intoxication, can be monitored using a fluorescent probe, FLICA, that specifically binds to active caspase-1. While vehicle-treated controls showed high levels of caspase-1 activity upon LT treatment, active caspase-1 was not detected in EGA treated cells challenged with LT (FIG. 3A). This result indicates that EGA blocks intoxication upstream of caspase-1 activation.

BMDMs from Nlrp1b transgenic mice were isolated and cultured as previously described (Averette, 2009). Briefly, femur exudates from two C57BL/6 or two C57BL/6$^{Nlrp1b}$ (129S1) transgenic animals were cultured for 7 days in DMEM both supplemented with 10% fetal bovine serum (Atlanta, cat # S11550), 1% penicillin/streptomycin/glutamine (Gibco), 2% 14-22 conditioned media and incubated in a 5% $CO_2$ humidified incubator at 37° C. Twenty thousand BMDMs from each of the four animals were plated in DMEM (Cellgro, Mediatech, Inc. cat #15-018-CV) supplemented with 10% FBS and 1% PSG. The following day cells were treated with 20 μM EGA for one hour before addition of LT for a further two hours. FLICA reagent (Immunochemistry Technologies) was added for one hour. Nuclei were stained for counting using Hoechst 33342. Medium was either changed daily or on day 1 after compound addition. Plates were acquired on an Image-Xpress$^{micro}$ (Molecular Devices) equipped with laser autofocus. Images were processed using MetaXpress (Molecular Devices). Using this software allowed for counting the total number of cells by counting their nuclei. The number of active caspase-1 positive cells was counted by determining which of the previously counted nuclei was located in a cell that was stained positively with the FLICA suicide substrate. Four sites per well were acquired and averaged.

D. Example 4: PA Pore Formation

Figure 3C:
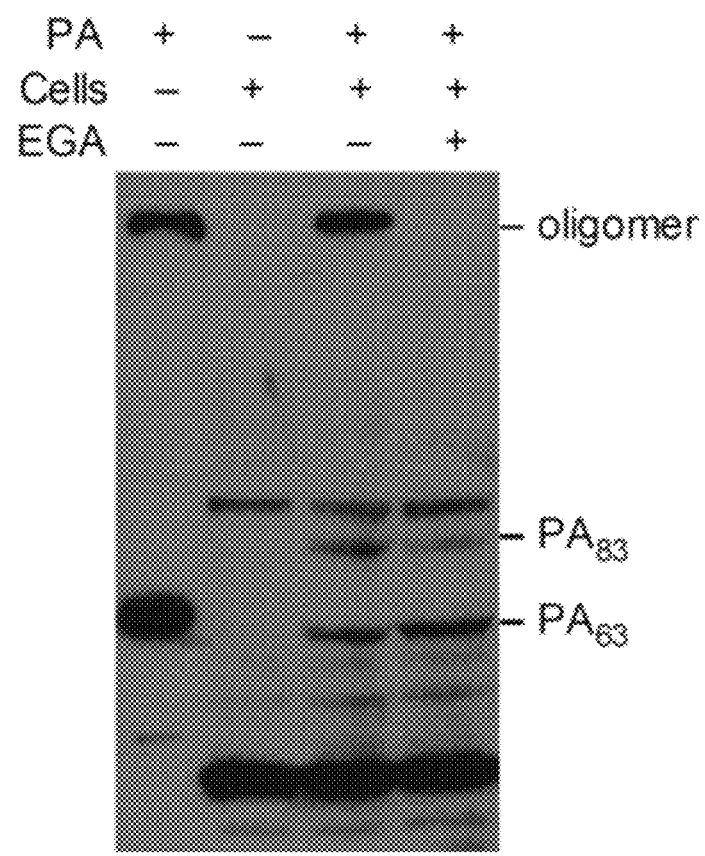
Figure 3D:
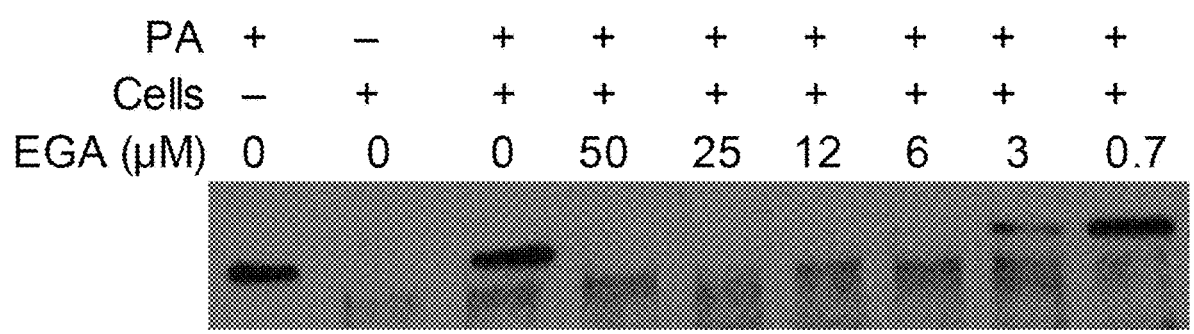

In order for LF to reach the cytosol, $PA_{83}$ must be proteolytically activated to $PA_{63}$, oligomerize into a pre-pore form, bind LF, and traffic to a low-pH endosome where it undergoes an acid-dependent conformational change from pre-pore to pore {Koehler, 1991, Milne, 1993, Miller, 1999}. Host cell binding, proteolytic processing and pore formation were monitored by western blot in the presence and absence of EGA. Specifically, the pore form of PA resulting from exposure to acidified endosomes is resistant to dissociation by SDS and runs as an oligomer on SDS-PAGE, while immature pre-pores formed by $PA_{63}$ are dissociated by SDS and run as monomers {Miller, 1999}. EGA completely inhibited formation of the SDS-resistant oligomer but did not block binding of $PA_{83}$ to cells or proteolytic processing to generate $PA_{63}$ (FIGS. 3C-3D). The effective dose range for EGA inhibition of oligomer formation closely mirrored the $IC_{50}$ in the toxicity assay (FIGS. 3C-3D, FIG. 1B), suggesting that this is the mechanism by which EGA protects cells from LT. These results indicate that EGA blocks intoxication at a step downstream of toxin assembly on the host cell surface but upstream of trafficking to acidified endosomes.

RAW264.7 cells were seeded at $1.8 \times 10^6$ cells/well on a 6-well plate one day prior to the experiment. The following day, cells were pre-incubated with compound (e.g. EGA) at indicated concentrations for one hour before incubation with PA at 400 ng/mL for one hour. Cells were then washed with PBS and lysed with 1% NP-40 lysis buffer. Protein lysates were collected, quantified, and separated by SDS-PAGE and proteins were transferred to a PVDF membrane. PA was detected using a 1:7500 dilution of rabbit anti-PA polyclonal sera (Covance) followed by a 1:7500 dilution of HRP-conjugated goat anti-rabbit. Protein levels were visualized as described above.

Figure 6A:
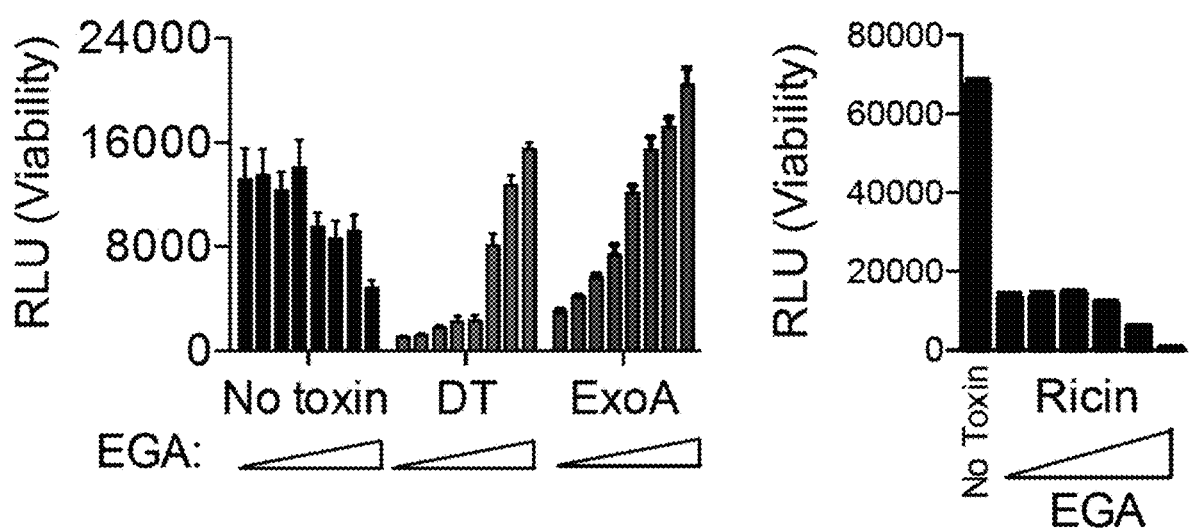

E. Example 5: Inhibition of Entry of Acid-Dependent Bacterial Toxins, Such as Lethal Toxin (Dose Response), *Diphtheria* Toxin, *Pseudomonas* Exotoxin A, and Ricin Several bacterial toxins and viruses are known to share similar entry requirements with LT, including trafficking to an acidified endosome. *Pseudomonas aeruginosa* exotoxin A (ExoA) and *Diphtheria* toxin affect cells by ADP-ribosylating EF-2, thereby halting protein synthesis (Collier, 2001, Iglewski and Kabat, 1975). While DT is transported to the cytosol from early endosomes, ExoA is transported in a retrograde fashion to the endoplasmic reticulum (ER) and then transported to the cytosol (Sandvig, 1984, Collier, 2001). However, despite these differences, efficient intoxication of the host cell by LT, DT and ExoA require a low pH step that is inhibited by agents that increase pH (Friedlander, 1986, Sandvig and Olsnes, 1980, 1981, Draper and Simon, 1980, FitzGerald, 1980, FitzGerald, 1983). The plant toxin ricin, like ExoA, is transported in a retrograde fashion to the ER and eventually to the cytosol. Ricin is an N-glycosylase that modifies the 28S rRNA of the eukaryotic ribosome and thereby inhibits translation. Unlike the three previously mentioned toxins, ricin does not require low pH to enter cells, and even seems to be more efficiently internalized when low pH compartments are neutralized (Sandvig, 1980) (Sandvig and Olsnes, 1982)(Melby, 1991). EGA effectively protected HeLa cells from DT and ExoA (FIG. 6A), though the protection from ExoA could be overcome by increasing toxin dose. The mechanism by which lysosomotropic agents block ExoA is unknown, but is thought to reflect preferential trafficking of this toxin to the Golgi from late endosomes. The ability of ExoA to overcome the EGA-mediated block may indicate that alternative trafficking pathways may be used when access to late endosomes is inhibited. Indeed, ricin traffics to the Golgi from early endosomes, and cytotoxicity mediated by ricin was not blocked by EGA. These data support the hypothesis that EGA inhibits the entry of toxins that require acidified endosomes, even those that gain access to the cytosol by two different endocytic routes.

Figure 6B:
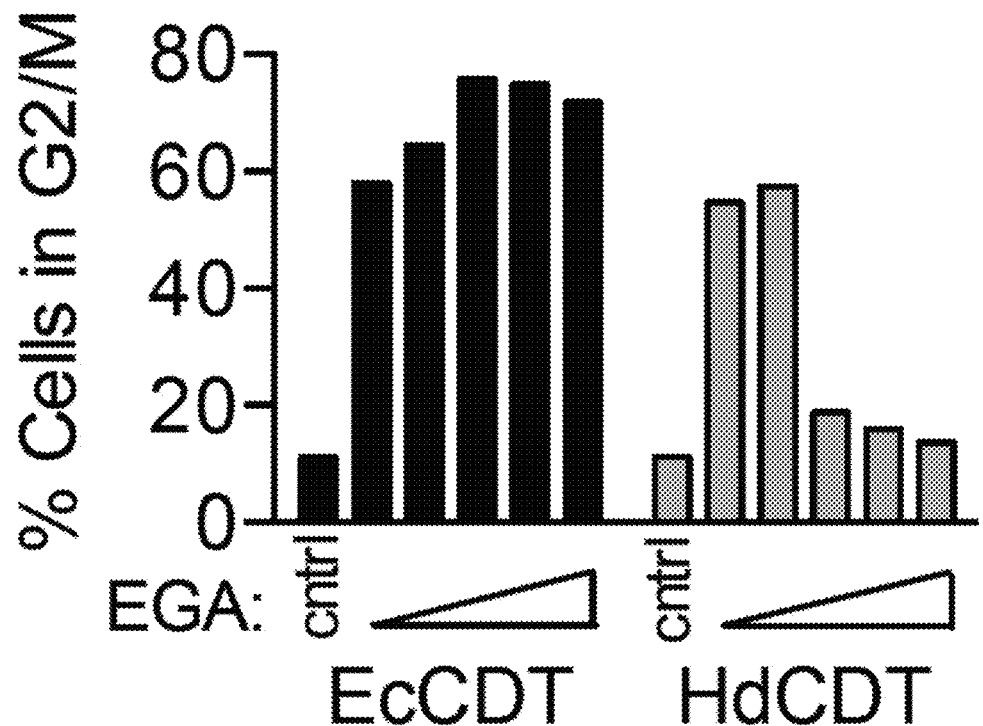
Figure 6B:
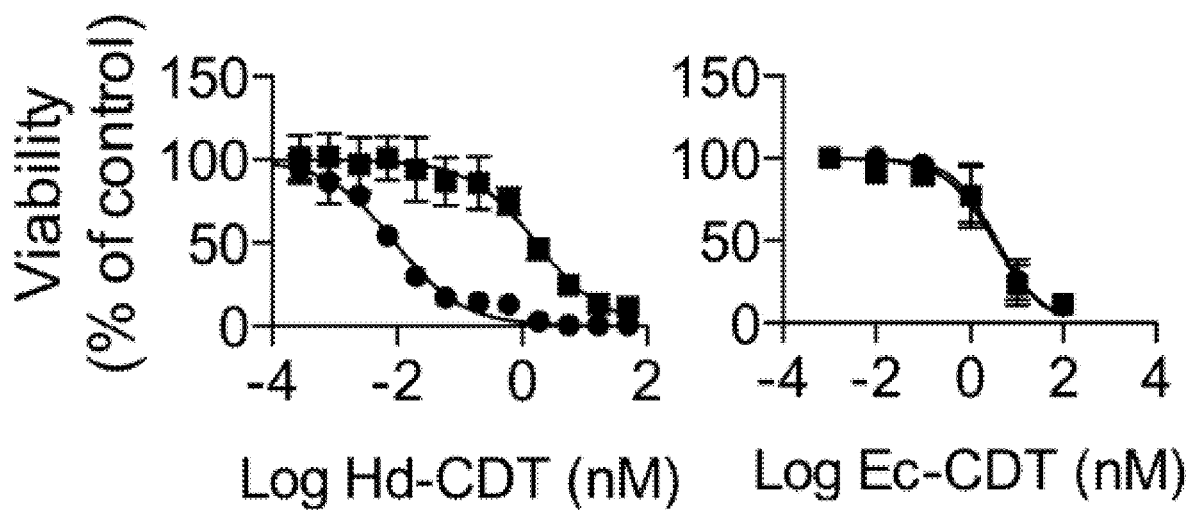
Figure 6C:
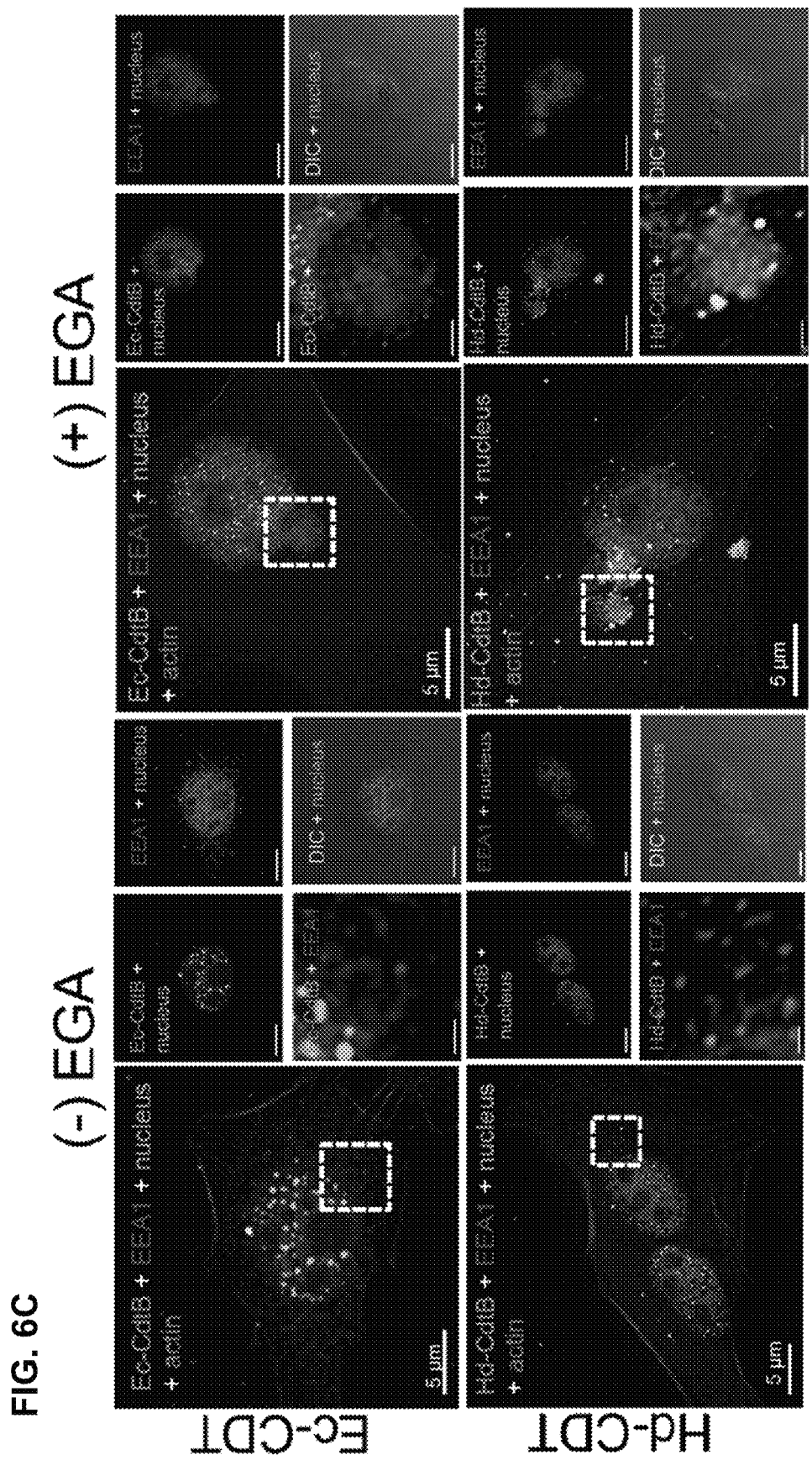
Figure 6D:
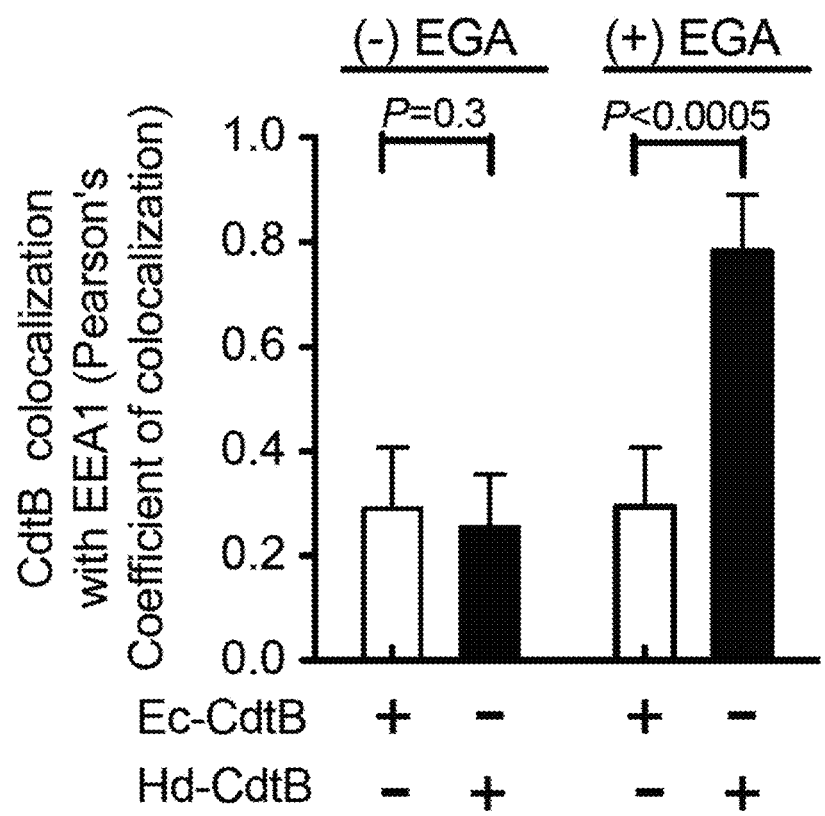

Based on the observation that EGA blocks entry of toxins that require trafficking to acidified endosomes, we next asked whether we could use this inhibitor to characterize entry pathways for toxins that are less well studied. Cytolethal distending toxins (CDTs) are produced by multiple human pathogens, where they promote invasiveness and/or persistence. CDTs are tripartite AB toxins consisting of a single catalytic domain CdtB, and two cell-binding domains, CdtA and CdtC. CdtB is ultimately trafficked to the host nucleus where it acts as a DNase, resulting in DNA damage response, cell cycle arrest and ultimately apoptosis. Studies on CDT from *Haemophilus ducreyi* (HdCDT or Hd-CDT) indicate that this toxin, unlike ricin, traffics through acidified endosomes in addition to retrograde trafficking through Golgi and ER {Guerra}. However, CDTs from other pathogens display distinct host factors for binding and entry {Eshraghi, 2010; Carette, 2011}, indicating that entry pathways utilized by various CDTs may be idiosyncratic to each. To test this, we determined the ability of EGA to inhibit intoxication by HdCDT as well as CDT derived from *E. coli* (EcCDT or Ec-CDT). As expected EGA inhibited cell cycle arrest induced by HdCDT (FIGS. 6B, 6C, 6D). Interestingly, EGA did not inhibit intoxication by EcCDT (FIGS. 6B, 6C, 6D), demonstrating that these two related toxins enter cells through distinct trafficking pathways. Consistent with the EGA-mediated accumulation of EGF in EEA-1 (EEA1) positive compartments, Hd-CDT, but not Ec-CDT, was found to accumulate in enlarged vesicles that were EEA-1 positive (FIGS. 6B, 6C, 6D). These data, along with the lack of inhibition of phagocytosis and recycling, support the model that EGA targets a specific subset of vesicular trafficking pathways.

RAW264.7 cells or BMDMs were pre-incubated with EGA or derivatives for one hour followed by intoxication with LT for three or 24 hours as indicated. ATPlite viability reagent (Perkin Elmer) was added and relative luminescence was measured as above HeLa cells were plated at $1 \times 10^3$ cells/well on each well of a 384-well plate (Greiner). The following day EGA (Chembridge), $NH_4Cl$ (Sigma-Aldrich), or Bafilomycin A1 (Calbiochem) were added to the indicated concentrations and incubated for 1 hr at 37° C. Then, *Diphtheria* toxin (List Laboratories) was added to a concentration of 5 ng/mL while exotoxin A from *Pseudomonas aeruginosa* (List Laboratories) and ricin were added at the indicated concentrations. Cells were incubated for 45-48 hrs and twenty L of ATPlite were added. Luminescence was measured using the Victor$^3$V (Perkin Elmer). Cell cycle arrest induced by CDT was measured by propidium iodide staining and flow cytometry as previously described. To monitor subcellular localization of Ec-CdtB or Hd-CdtB, cells were stained and imaged as described with the addition of mouse monoclonal anti-EEA1 antibody (1:50 dilution; Abcam). For each cell, images were collected from an average of 30 z-planes, each at a thickness of 0.2 µm. EEA1-localization analysis was conducted by using the DeltaVision SoftWoRx 3.5.1 software suite.

F. Example 6: Inhibition of Viral Infections

Upon learning that EGA protects cells from several bacterial toxins, it was hypothesized that EGA might also be able to inhibit viral entry. Influenza A virus, lymphocytic choriomeningitis virus (LCMV), vesicular stomatitis virus (VSV), among others, require low pH for membrane fusion and infection of host cells (White, 1981, JCB, White, 1983). Distinct from these, amphotropic murine leukemia virus (A-MLV or MLV-A) and Nipah virus (NiV) both enter the cell in a pH-independent fashion (McClure, 1990, Journal of General Virology, Beer, 2005, Journal of Virology, Smith, Popa et al., 2009, FEBS journal, Lamb et al., 2006, Virology).

Figure 6E:
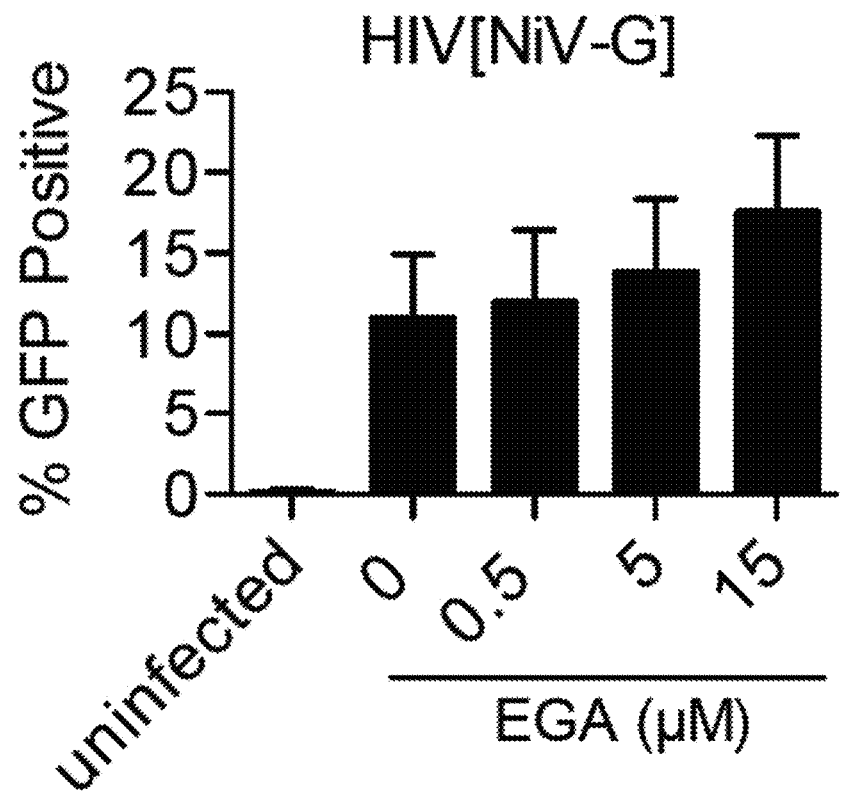
Figure 6F:
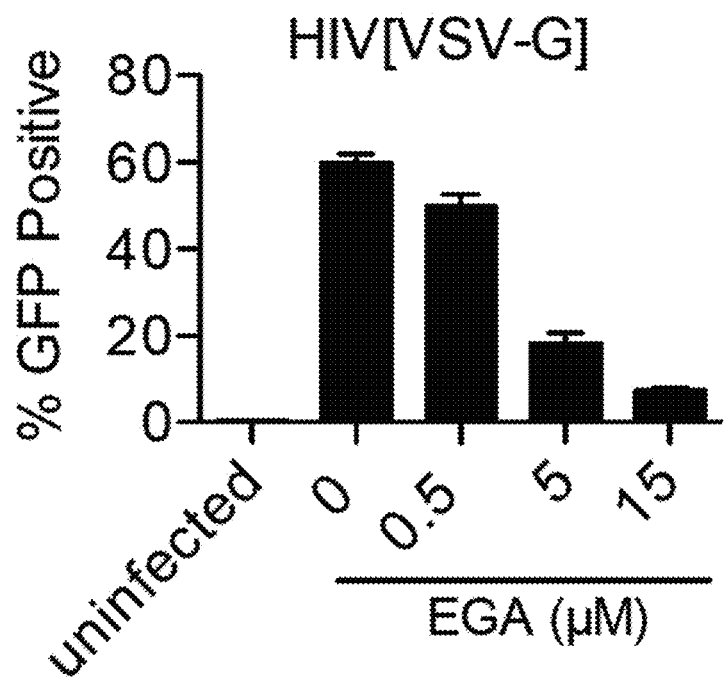

To test EGA-mediated inhibition of viral entry, we compared transduction by lentiviral vectors pseudotyped with Nipah virus- and VSV-envelope glycoproteins in a cell culture model. The lentiviral genome used encodes green fluorescent protein (GFP), and successful transduction of the host cell results in expression of GFP in the cytosol. EGA effectively inhibited infection of HeLa cells by the low pH-dependent VSV-pseudotyped lentivirus (FIG. 6F), but did not inhibit infection of cells by the pH-independent Nipah-pseudotyped lentivirus (FIG. 6E).

Figure 4A:
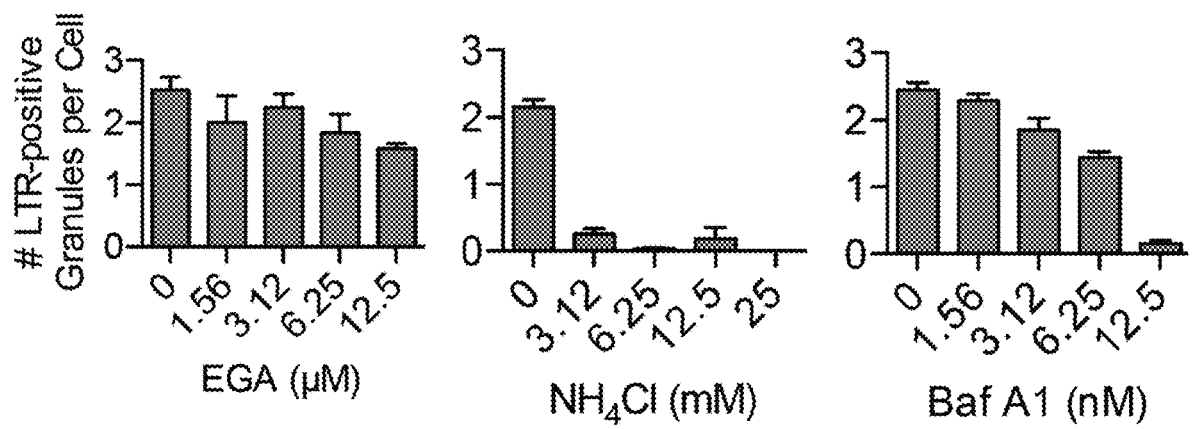
FIGS. 4A-4D: Disruption of Membrane Trafficking by EGA is Distinct from Other Endosome-Neutralizing Agents.
Figure 4B:
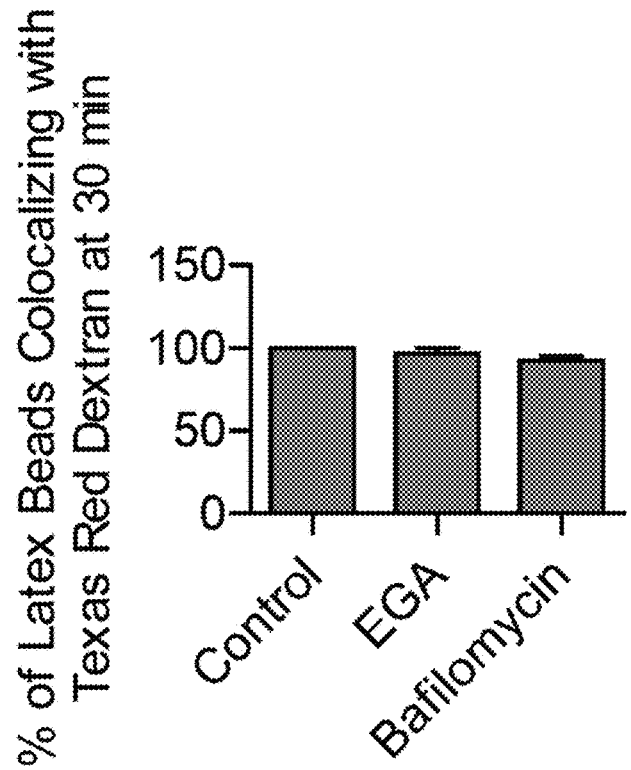
Figure 4C:
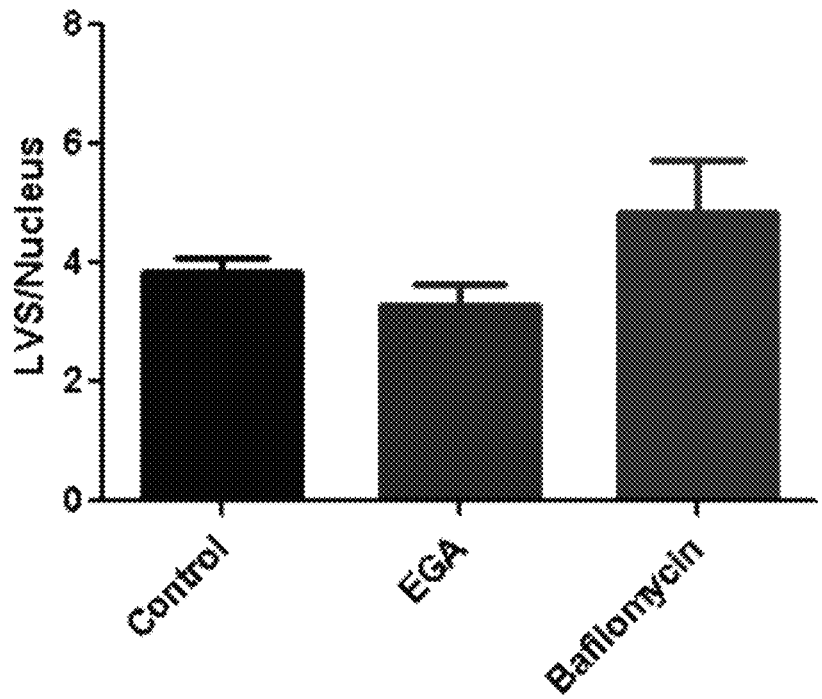
Figure 6G:
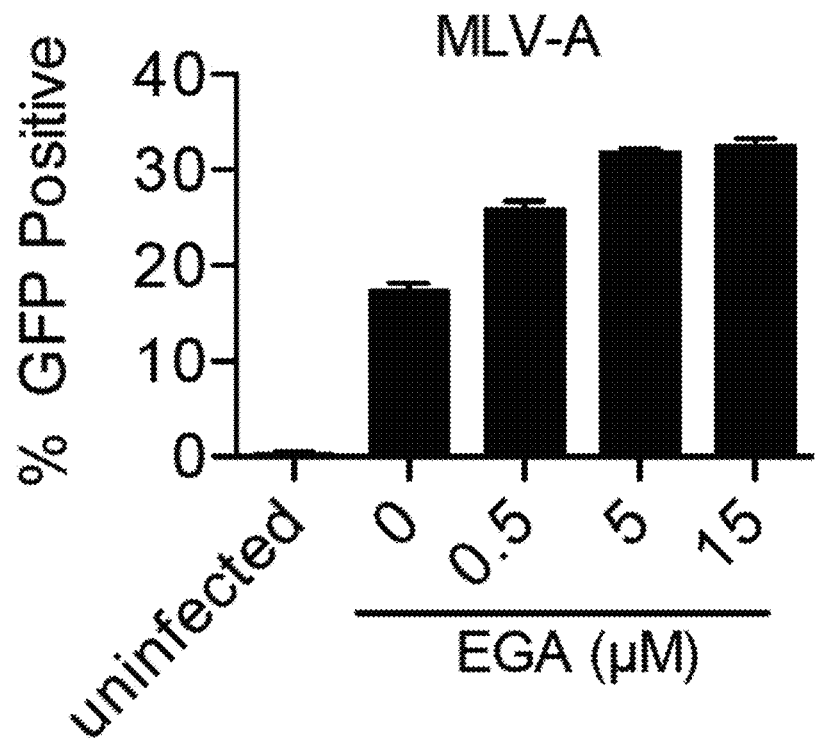
Figure 6H:
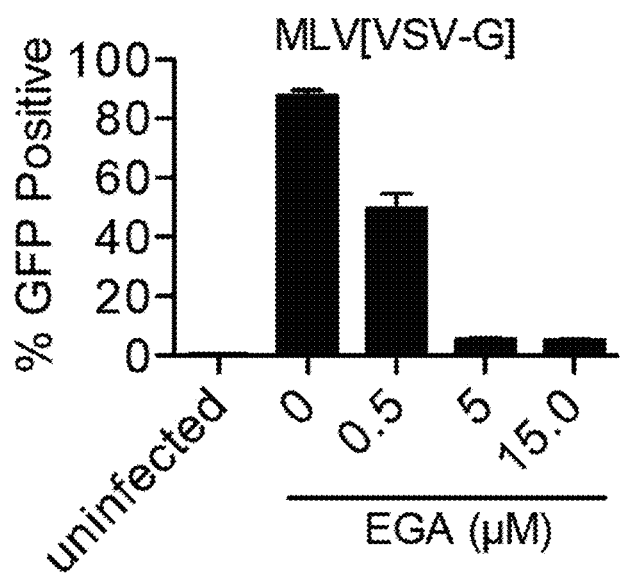
Figure 6I:
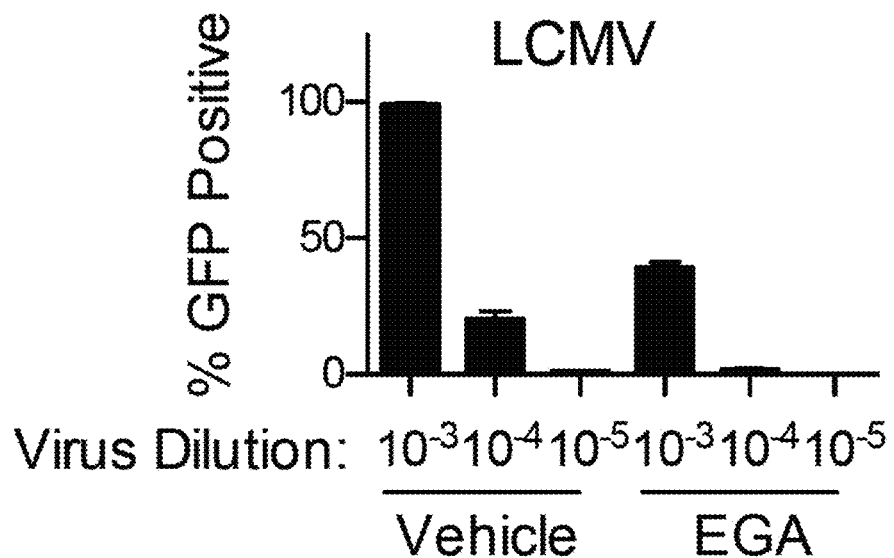
Figure 6J:
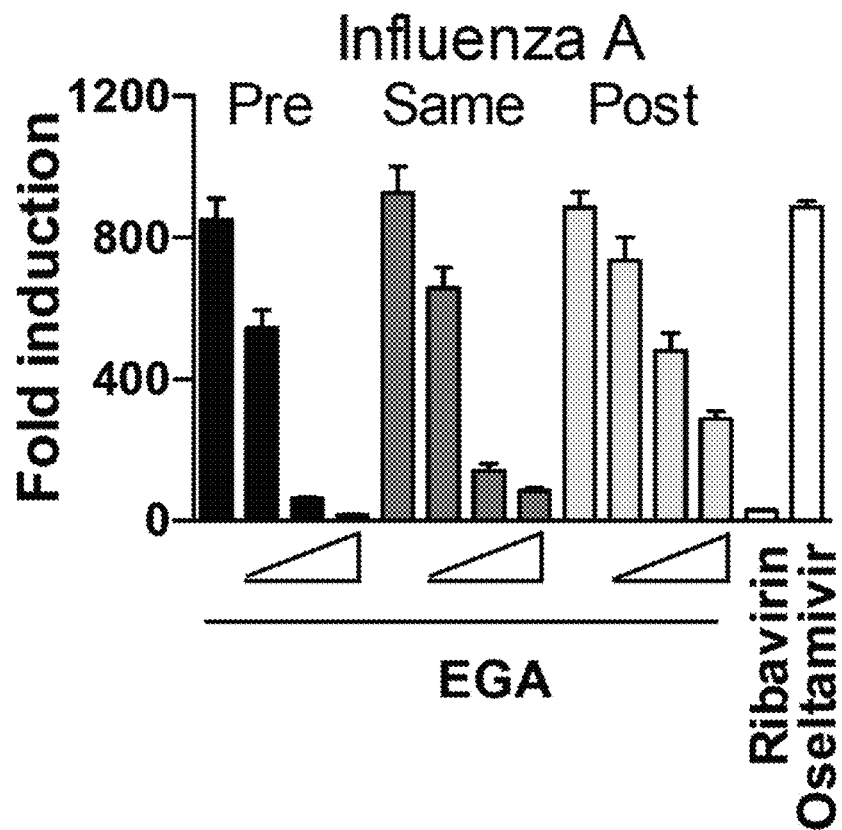
Figure 7:
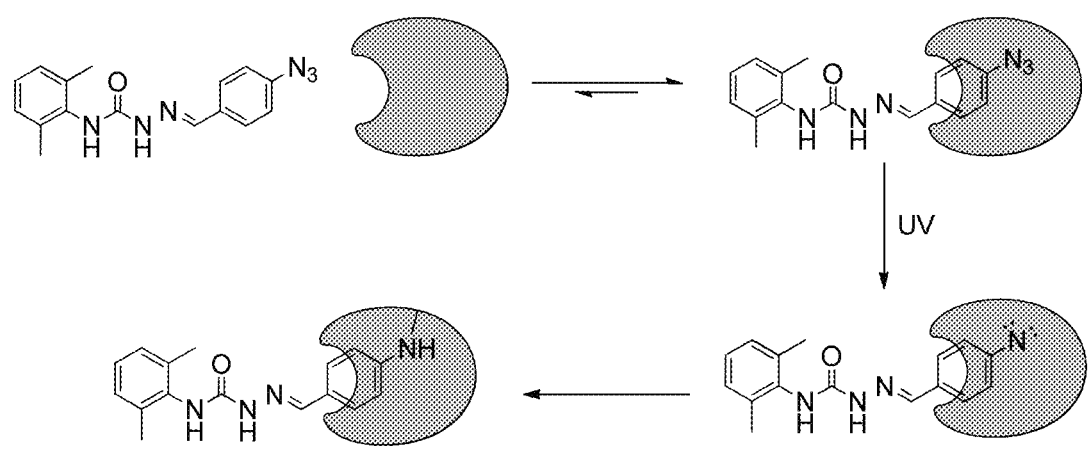

The finding that EGA inhibits infection by VSV-G pseudotyped lentiviruses encouraged us to assess its activity on infection by other viruses. We asked whether EGA could inhibit infection by MLV-A, as well as two human pathogens, LCMV and influenza. As expected, infection by MLV-A was not inhibited by EGA, as determined by GFP expression (FIGS. 6G, 6H). As a control, we found that the same MLV core was neutralized when pseudotyped with VSV-G. LCMV is a rodent-borne virus that causes meningitis and encephalitis in humans and the prototypical member of the arenaviridae, a family of viruses responsible for many severe hemorrhagic fevers. To determine if EGA affects acute LCMV infection, Vero cells were infected with serial dilutions of a GFP-expressing Armstrong variant of LCMV. EGA decreased the total number of cells infected and the amount of virus being produced by infected cells at one and two days after infection (FIG. 6I). Next, we investigated the effect of EGA on infection by the A/WSN/33 strain of influenza virus. Both LCMV and influenza virus are single-stranded, enveloped RNA viruses, but influenza virus belongs to the orthomyxoviridae family rather than the arenaviridae. To assess the effect of EGA on influenza virus infection, HeLa cells were transfected with a luciferase reporter responsive to the influenza polymerase complex, enabling measurement of early steps of viral infection (from viral entry until viral protein synthesis). This assay can determine if infection by influenza virus is inhibited at any step up to the translation of viral proteins. Ribavirin and oseltamivir were used as controls. Ribavirin, which is capable of blocking influenza, is an antiviral drug which blocks viral RNA synthesis, inhibits influenza and arenavirus infections, and is the only licensed drug for treatment of arenavirus infection, and oseltamivir, a neuraminidase inhibitor that blocks viral budding downstream of reporter activation, were used as controls (Lee et al., 2010 Virology). As expected, ribavirin effectively blocked reporter activation when added one hour post infection, while oseltamivir exhibited no protection. EGA completely inhibited infection when added one hour before or simultaneously with virus, and even exhibited partial protection when added one hour post infection (FIG. 4C). While EGA and ribavirin are active against both LCMV and influenza, their differential kinetics along with the known mechanism of action of ribavirin, suggest that EGA targets a different process. (McKee, 1988, Gessner et al., 1989.

In total, these data show that EGA inhibits cellular infection by multiple viruses, including two medically relevant human pathogens, influenza and LCMV. On the other hand, EGA did not block infection by Nipah virus or amphotropic-MLV, indicating that it is a specific inhibitor of a subset of viruses that traffic to acidified endosomes.

HeLa cells were transfected with a Flu gLuc reporter construct which expresses antisense transcripts of *Gaussia* luciferase flanked by the untranslated region of the influenza A/WSN/33 virus PA segment. Therefore, luciferase protein expression is dependent on the presence of influenza virus polymerase complex, thus allowing quantification of viral infection. At 12 hours post transfection of the reporter construct, cells were infected with influenza A/WSN/33 virus at an MOI=0.5. Cells were treated with EGA at indicated concentrations one hour before, simultaneous to, or one hour after infection with virus. Culture supernatants were collected 10 hours post infection. *Gaussia* luciferase activity was determined using the Renilla Luciferase Assay System (Promega) and luminescence was measured using the Infinite M1000 plate reader (TECAN). The graph represents an average of three independent experiments.

For lentiviral transductions with VSV-G and Nipah glycoprotein pseudotypes, $6.5 \times 10^4$ cells/mL were seeded the night before onto 24-well plates in DMEM. The following day the media was removed and fresh media containing EGA at indicated concentrations or DMSO only was added to cells. Nipah or VSV pseudotyped viral vectors encoding GFP were added 1 h later with 8 µg/mL polybrene. Cells were incubated for two days, fixed in formaldehyde, and analyzed by flow cytometry. For the VSV and MLV-A matched infections, $6.5 \times 10^4$ HeLa cells/well were seeded the night before. Cells were pre-incubated with 2× EGA for 1 hr and then dilutions of VSV or MLV-A pseudotyped, GFP-encoding retroviral vectors were added bringing EGA concentration to 1×. Polybrene was added to 8 µg/mL to increase transduction efficiency. Drug, virus, and cells were incubated overnight and media was changed the following day. Cells were fixed in PBS/formaldehyde and analyzed for fluorescence by flow cytometry the next day.

For LCMV infections, plates were seeded at $4 \times 10^5$ Vero cells/ml and incubated overnight at 37° C. The next day, drug and vehicle mixture were made, where drug mixture was 90 ml Vero media+45 µl EGA at 40 mM and vehicle mixture was 50 ml Vero media with 25 µl DMSO. Solutions were then filtered. Media was removed and cells were infected with 500 µl Armstrong GFP virus/media mixture per well in triplicate at $10^{-3}$, $10^{-4}$, $10^{-5}$ dilution (all steps from here on were done in tissue culture hood with light turned off to minimize bleaching of GFP signal). Cells and virus were incubated at 37 C for one hour, with shaking every 10 minutes. Virus media was removed and 3 mL new media was added. Cells were incubated at 37° C. overnight. The next day media was removed and cells were trypsinized and spun down by centrifugation. Resuspend cells in 400 µl of 1% PFA to fix for 15 minutes in the dark. Green fluorescence was measured by flow cytometry.

G. Example 7: Lysotracker Red DND-99

Neutralization of acidic compartments by lysosomotropic agents like ammonium chloride is a well-known mechanism of blocking anthrax toxin entry {Friedlander, 1989; Sanchez, 2007}. Similarly, endosome-neutralizing compounds block entry of certain viruses into the cell, such as in the case of niclosamide (Jurgeit et al.). The observed block to pore formation raised the possibility that EGA functions by neutralizing low-pH dependent steps in the endocytic pathway. In order to address this possibility, Lysotracker Red DND-99 was used to probe acidic compartments in the cell. Lysotracker is a red-fluorescent dye used for tracking acidic organelles in the cell and neutralization of these compartments can be visualized as a loss in punctuate, red-fluorescent structures. Ammonium chloride and bafilomycin A1, a specific inhibitor of vacuolar-type $H^+$-ATPases, markedly decreased cell-associated Lysotracker Red fluorescence (FIGS. 4A-4B). EGA, on the other hand, did not reduce Lysotracker Red signal at concentrations that fully protected cells from LT. These results suggest that EGA blocks the ability of PA to access acidified endosomes but does not function by neutralizing acidic compartments.

HeLa cells were treated with EGA, $NH_4Cl$ or DMSO for 25 minutes at 37° C. and then stained with Lysotracker Red and Hoechst for 10 minutes at 37° C. Cells were then washed, overlayed with PBS+2% FBS and imaged by automated fluorescence microscopy (ImageXpress Micro, Molecular Devices). Images were scored for number of LTR-positive endosomes per cell using the granularity calculation module in Meta Express software. An average of 175 cells per replicate were analyzed, and a minimum of three independent experiments each performed in triplicate were run.

H. Example 8: Impact of EGA on Endosomal Trafficking

Figure 5A:
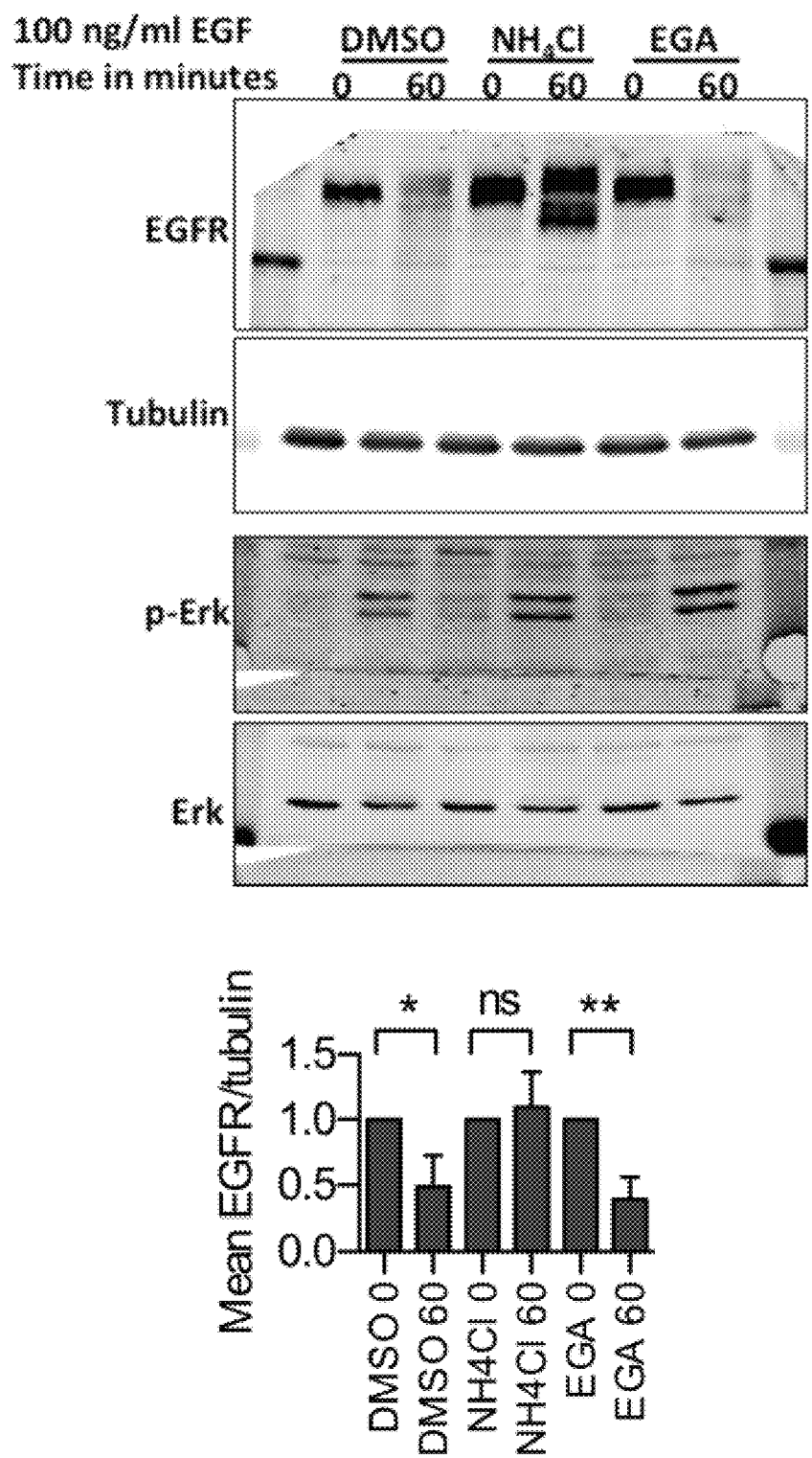
Figure 5B:
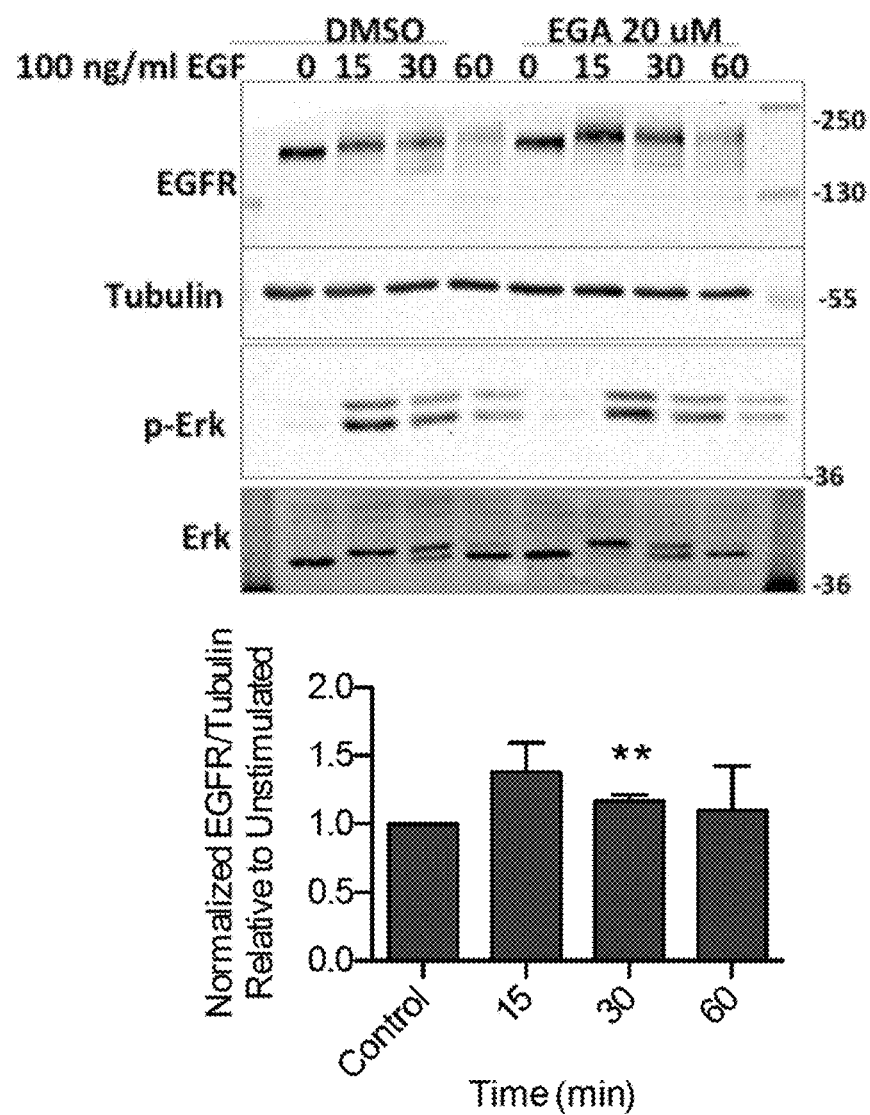
Figure 5C:
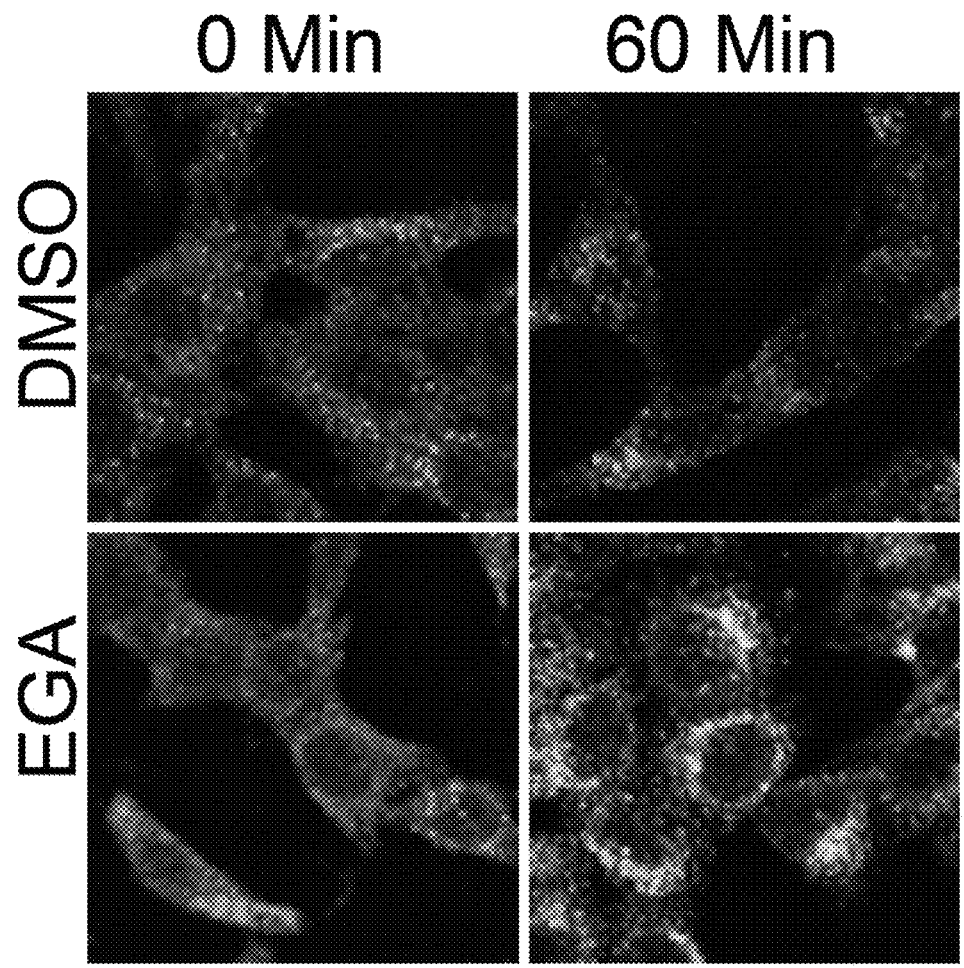

We next considered whether EGA-mediated inhibition of endosomal trafficking extended beyond anthrax toxin-receptor interactions by examining trafficking of the epidermal growth factor receptor (EGFR). HeLa cells were treated with epidermal growth factor (EGF) and the stability of EGFR was measured by immunoblotting. At the high dose of EGF used in these experiments (100 ng/mL), EGFR is trafficked to lysosomes and degraded (Sigismund, 2008). Lysosomal degradation of EGFR depends on the acidic lumenal pH and lysosomotropic agents such as $NH_4Cl$ inhibit EGF-induced receptor degradation (FIG. 5A){Carpenter, 1976; Stoscheck, 1974}. Unlike $NH_4Cl$, EGA treatment did not stabilize EGFR at 60 minutes. EGA treatment did slow degradation somewhat, however, with significantly less EGFR degraded at 30 min post EGF stimulation (p<0.05) (FIG. 5B). This suggested that EGA inhibits trafficking, but that this inhibition can be overcome by excess ligand stimulation over longer periods of time. To test this, we determined the ability of EGA to block lysosomal degradation induced by a lower dose of EGF (20 ng/mL). A microscopy assay using fluorescently labeled EGF was employed to directly visualize trafficking and degradation of EGF. Under these conditions, EGA stabilized EGF up to 60 min as compared to vehicle (DMSO)-treated controls (FIG. 5C). Notably, EGA treatment resulted in EGF being retained in enlarged endosomes that stained positive for the early endosome marker EEA1 (FIG. 5C). These findings indicated that EGA does not block initial binding or endocytic uptake from the plasma membrane, but does inhibit trafficking from early to late endosomes.

Figure 4D:
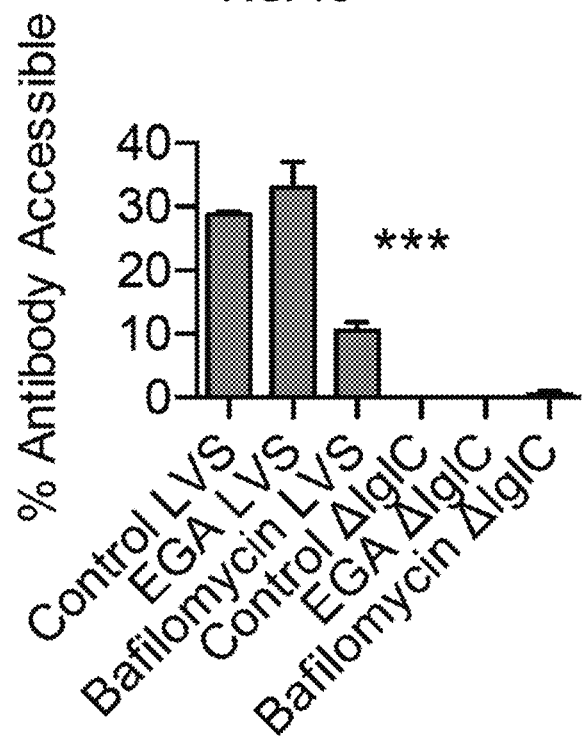

To determine whether other vesicular trafficking events were blocked by EGA, we tested the effect of this compound on phagocytosis and phagolysosomal trafficking. Neither EGA nor bafilomycin A1 inhibited endosomal trafficking of Texas-red dextran to phagosomes in human monocytic cells as determined by co-localization with polystyrene beads (FIG. 4C). To extend this experiment to bacterial pathogens, we asked whether EGA affects phagocytosis and trafficking of *F. tularensis*, a gram-negative pathogen that causes the potentially deadly disease tularemia in humans. Neither EGA nor bafilomycin A1 blocked phagocytic uptake of a live vaccine strain (LVS) of *F. tularensis* (FIG. 4D). Further, EGA had no effect on *F. tularensis* permeabilization of its phagosome as determined by accessibility of LVS to antibody staining in digitonin-treated cells. In contrast, escape was inhibited by bafilomycin A1 in the time frame of this assay. Therefore, although EGA blocks trafficking of PA to acidified endosomes, this compound does not inhibit phagocytic uptake, trafficking of endosomes to phagocytic compartments or phagosome maturation required for efficient escape of *F. tularensis*.

Figure 5D:
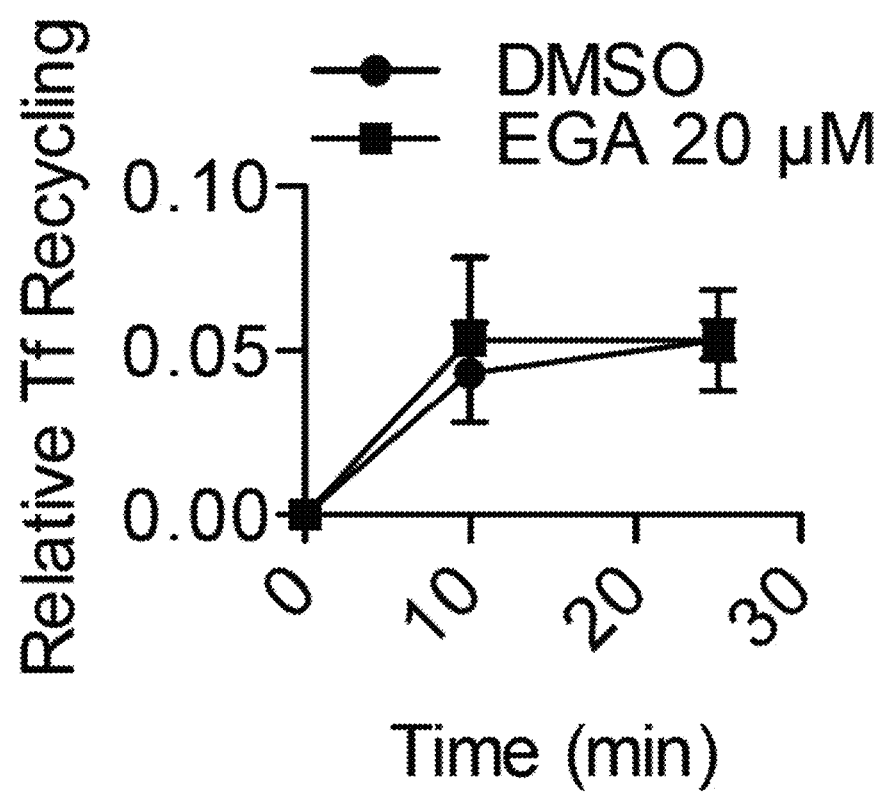

To further elucidate the specificity of EGA, we assessed the effect of this compound on endosome recycling using fluorescently labeled transferrin (Tf), which binds the Tf receptor (TFRC). Like ANTXR, TFRC is taken up by clathrin-mediated endocytosis upon binding its ligand. TFRC releases its iron cargo into the lumen of early endosomes, then the iron-free Tf-TFRC complex is recycled back to the cell surface through a Rab1 1 dependent process {Schlierf, 2000, Ullrich, 1996}. EGA had no affect on the amount of Tf recycled back to the surface of cells by 10 and 25 min post binding (FIG. 5D), indicated that this compound does not affect endosomal uptake or recycling.

For EGFR stability assays, HeLa cells were seeded at $4 \times 10^5$ cells per well in a 6-well plate, cultured overnight, serum starved for 18 h, treated with DMSO, 20 µM EGA or 10 mM $NH_4Cl$ for 15 minutes at 37° C., then stimulated with serum-free medium containing the compounds and 100 ng/ml EGF (Gibco) for the indicated time periods. Cells were then washed with cold PBS, lysed in NP-40 lysis buffer (150 mM NaCl, 50 mM Tris pH 8.0, 1% NP-40) and lysates were analyzed by immunoblotting with anti-EGFR 1:2000 (Santa Cruz, # SC-03), anti-Tubulin 1:5000 (Sigma Aldrich, # T6074-200 ul), anti-p-ERK1/2 pY204 1:1500 (Epitomics, #2219-1) and anti-ERK1/2 1:5000 (BD, #610123). Blots were imaged using a Li-Cor Odyssey scanner.

For immunofluorescence microscopy, EGF-Alexa Fluor 647 (Invitrogen, # E35351), anti-EEA1 (BD Transduction Laboratories, #610456) and goat-anti-mouse Alexa Fluor 647 (Invitrogen, # A21245) were used. Glass bottom 35 mm tissue culture plates (MatTek) were seeded with $4 \times 10^5$ cells. The cells were serum starved overnight and incubated in medium containing 20 ng/ml EGF-Alexa Flour-647 and 20 µM EGA or DMSO on ice for 2 h. They were then chased for 60 min at 37° C. in serum free medium containing only the compounds and were fixed in 4% paraformaldehyde, permeabilized in 0.1% Triton-X-100 detergent, quenched in 50 mM $NH_4Cl$ and blocked in 10% goat serum (Gibco). Images were acquired on a laser scanning confocal microscope (Axiovert 200M, Carl Zeiss LSM 5 Pascal) with a plan/neofluar 100× oil lens, NA 1.3. LSM 5 Pascal software (release version 4.2 sp1) was used to process the images.

For transferrin recycling assays, HeLa cells ($3\times10^5$ cells per well) were seeded in triplicate on 6-well plates. The cells were serum starved overnight. Following a 15 min pretreatment with 20 µM EGA or DMSO, cells were stimulated with Tf conjugated to Alexa Fluor-488 (Tf-488)(Invitrogen) at 20 ng/ml for 5 min, then washed with cold medium and stripped twice with 0.2 M sodium acetate buffer (pH 4.5). The cells were rinsed in cold serum-free medium and excess unlabeled Tf and chased at 37° C. for the indicated amounts of time. Following the chase, the cells were stripped twice in the sodium acetate buffer. Tf-488 fluorescence from acid washes and medium was measured on a Wallac 1420 multilabel counter (PerkinElmer) at 490/520 nm absorption/emission.

For phagocytosis studies, THP-1 cells were added ($1.5\times 10^5$ cells/cm$^2$) to poly-L-lysine (Sigma-Aldrich) coated glass coverslips in 2 cm$^2$ tissue culture wells and differentiated with phorbol 12-myristate 13-acetate (PMA, 100 nM) in RPMI-1640 with 10% heat inactivated FBS (HI-FBS) for 3 d at 37° C. in 5% $CO_2$, then pretreated for 1 h with 250 nm bafilomycin A, 20 µM EGA, or DMSO prior to addition of bacteria or latex beads. GFP-expressing *F. tularensis* LVS (LVS-GFP) and escape incompetent GFP-LVS-ΔIglC were prepared and cultured as previously described, and added to monolayers of THP-1 cells on glass coverslips in 24-well plates. The plates were centrifuged at 800 g for 30 min 4° C., incubated at 37° C. for 30 min, washed three times with HBSS to remove non-adherent bacteria, and incubated for 3 h at 37° C. in fresh RPMI-1640 with 10% HI-FBS containing 20 µM EGA, 250 nm bafilomycin, or DMSO vehicle. Phagosome integrity was assessed by a modification of the differential digitonin permeabilization method of Chercoun et. al. which permeabilizes the plasma membrane but not phagosomal membranes. Briefly, monolayers were fixed for exactly 1 min with HBSS+4% paraformaldehyde followed by permeabilization for exactly 1 min with 0.05 mg/ml digitonin in 110 mM potassium acetate, 20 mM HEPES, pH 7.3, 2 mM $MgCl_2$, 6% sucrose (KHM with 6% sucrose), washed twice with KHM containing 6% sucrose, and incubated with rabbit anti-*F. tularensis* antibody (1:1000 dilution, Becton Dickinson) in KHM buffer containing 6% sucrose and 0.1% BSA, washed three times with KHM containing 6% sucrose, fixed for 30 min in 4% paraformaldehyde in 75 mM sodium phosphate, pH 7.4, permeabilized in 0.1% saponin in PBS, washed with PBS, and incubated with Texas Red-X conjugated goat anti-rabbit IgG (Invitrogen) for 90 min at room temperature. Monolayers were washed, incubated with DAPI (1 µg/ml), mounted with Prolong Gold anti-fade mounting medium, and viewed by phase and fluorescence microscopy. Green fluorescent bacteria that stain red are scored as having permeabilzed their phagosomes. Escape incompetent GFP-LVS-ΔIglC are inaccessible to antibody after digitonin permeabilization of the plasma membrane and serve as negative controls. At least 400 cells were examined and enumerated in duplicate wells and the experiments were conducted twice with similar results. Numbers of GFP-bacteria per DAPI nucleus in each of the conditions was determined by particle analysis using ImageJ software.

To evaluate the impact of inhibitors on fusion of latex bead phagosomes with secondary lysosomes, we labeled the lysosomal compartments of PMA-differentiated THP-1 cells with lysine-fixable Texas Red-Dextran (70 kDa, 0.05 mg/ml, Invitrogen) for 12 h. Macrophages were treated with 250 nM bafilomycin A, 20 µM EGA, or DMSO vehicle control for 30 min prior to uptake of latex beads. Fluorescent blue 1 µm polystyrene microbeads (2.5% solids, Polysciences) were opsonized with human AB serum, diluted 50,000 fold ($10^6$ particles/ml) in RPMI-1640 with 10% HI-FBS, and added to the monolayers of differentiated THP-1 cells in 24-well plates. After incubation for 3 h at 37° C. with vehicle or inhibitors, the macrophages were fixed, stained with DAPI and mounted as described above. Colocalization of latex beads with Texas red dextran fluorescence was assessed by fluorescence and phase contrast microscopy. At least 40 particles were examined on duplicate coverslips and the experiments were repeated twice with similar results.

I. Example 9: Photochemistry

One strategy for target identification is to form a covalent linkage between the ligand and the protein, and then visualize the labeled protein via either a radiolabel or a fluorescent tag. Photolysis of aryl azides generates a highly reactive nitrene intermediate that will covalently attached to a protein if photolyzed while in the active site. Because the $N^1$-(4-azidobenzylidene)-$N^4$-(2,6-dimethyl-phenyl) semicarbazone inhibits anthrax induced cell death ($IC_{50}$~3.0 µM) photolysis studies were conducted. Cells that were incubated with the 4-$N_3$ analog of EGA and exposed to UV irradiation retained viability in the presence of anthrax lethal toxin even after the inhibitor was removed from the media by washing. UV photolysis experiments demonstrate that cells retain protection against anthrax lethal toxin after media is exchanged.

J. Example 10: Example Overview and Analysis

Here we report the use of high throughput screening to identify a novel small molecule, EGA, that blocks cellular entry of bacterial toxins and viruses that require trafficking to acidified endosomes. Remarkably, this compound is not cytotoxic. The high throughput screen used leveraged the rapid cytolysis caused by LT in a subset of monocyte-derived cells from certain inbred strains of rodents. However, Nlrplb-dependent cytolysis is a host-mediated protective response to LT rather than a mechanism of virulence {Terra, 2010}. As such, it is necessary to carefully define the utility of the macrophage cytotoxicity assay as a tool for screening LT inhibitors by clarifying the range of processes that could be affected. Inhibitors that act downstream of LF delivery to the cytosol would be most useful in investigating mechanisms of inflammasome activation, though they would not be predicted to be therapeutically relevant for anthrax. On the other hand, probing processes required for PA-mediated toxin entry is predicted to yield more broadly applicable therapeutic agents. A subset of the probes that block PA-mediated internalization are likely to interfere more generally with host endocytic processes, which, as described here, may expand their therapeutic relevance to other bacterial toxins and viruses and make them valuable chemical probes in host vessicular trafficking studies.

Indeed, despite the importance of endosomal trafficking in a myriad of cellular events, there is currently a dearth of chemical probes to study these processes. Dynamin and clathrin dependent events are blocked by dynasore and pitstop-1 and -2 respectively. Arf1-dependent trafficking between ER and Golgi is blocked by Brefeldin-A. Finally, high throughput screening for inhibitors of retrograde-trafficking toxins has resulted in identification of a small number of probes with unknown cellular targets {Stechmann, 2010; Saenz, 2007}. Currently, investigation into the role of numerous other trafficking events relies on inhibitors that target trafficking indirectly, such as lysosomotropic drugs (e.g. bafilomycin A1, NH$_4$Cl, chloroquine, ionomycin, nigericin, monensin), or compounds that target multiple cellular processes in addition to blocking trafficking such as kinase inhibitors (e.g. staurosporine, calphostin C, genistein), phosphatase inhibitors (e.g. okadaic acid, ortho-vanadate), actin and microtubule inhibitors (e.g. jasplakinolide, latrunculin A, nocodazole, taxol), the HSP90 inhibitor geldanamycin (PMID 23154999), and cholesterol depletion (e.g. MβCD, nystatin) {Engel PMID 21345959}. More specific inhibition of host proteins involved in trafficking is usually achieved by overexpression of dominant negative or constitutively active versions of host proteins, e.g. Rab GTPases, or RNAi-mediated knockdown. While powerful, these approaches are limited to cells that are readily transfectable, and are susceptible to compensatory mechanisms that may arise over the longer time course required to establish heterologous expression or knockdown.

The specific cellular target of EGA is currently unknown, but data presented here strongly suggest the mechanism of action is through inhibition of trafficking between early and late endosomes. The requirement for low pH found in late endosomes is a characteristic shared by toxins, viruses, and natural receptor/ligand pairs such as EGFR/EGF, which were blocked by EGA. Many of the known inhibitors of LT target this step by directly neutralizing endosomal pH (Zhu, 2009, Sanchez, 2007, Moayeri, 2006, Friedlander, 1986, etc). However, EGA does not block acidification of endosomes as determined by Lyso Tracker red staining (FIGS. 4A-4B). Further, EGA treatment caused an accumulation of EGF and Hd-CDT in enlarged endosomes that were positive for the early endosome marker EEA1 (FIGS. 5A-5D). Generation of enlarged EEA1-positive vesicles is also seen when overexpressing a constitutively active form of RabS {Stenmark, 1994}, consistent with maturation/trafficking between early and late endosomes as a target for EGA. Importantly, recycling endocytosis of TFRC, phagocytosis of polystyrene beads and live bacteria, and retrograde trafficking of ricin and EcCDT were all unaffected by EGA, indicating that this compound inhibits a specific trafficking event.

EGA is a biphenyl semicarabazone with structural similarity to compounds developed as anticonvulsive agents. The molecular target for anticonvulsive semicarbazones is unknown, but may involve sodium channel activity. Anticonvulsive semicarbazones are thought to function by altering levels of the neurotransmitter GABA. Like EGA, these compounds are well tolerated in rats. Similar to our predictions for EGA based on hydrophobicity, anticonvulsive semicarbazones appear to have a short serum half-life in vivo. The high degree of specificity observed in initial SAR studies suggest that EGA may have unique target(s) compared to previously described compounds (FIGS. 2A-2D). Studies will ascertain whether EGA displays anticonvulsive activity. Indeed, one of the most active anticonvulsive aryl semicarbazones, benzaldehyde N-(2,6-dimethylphenyl) semicarbazone, showed almost no activity against LT. Regardless, EGA is a potent new small molecule for studying vesicular trafficking with single-digit micromolar potency and in vivo efficacy against LT.

LT and ET are important targets for therapeutics aimed at treating anthrax. Smith and Keppie predicted nearly 60 years ago that inhibition of these toxins would extend the therapeutic window in which patients infected with *B. anthracis* could be treated with antibiotics. Indeed, a small molecule inhibitor of LF increases efficacy and therapeutic window of ciprofloxacin {Schoop, 2005}. Based on this prediction, the majority of HTS for inhibitors of anthrax toxin have focused on enzymatic assays using purified LF as a molecular target {Turk et al., 2004, Panchal et al., 2004, Lee et al., 2004, Schepetkin, 2006, Shoop et al., 2005, Min et al., 2004, Dell'Aica 2004, Turk et al., 2012}. This strategy takes advantage of the fact that LT can recapitulate many elements of human disease and is thus a good target for therapy. Additional targeted strategies focusing on receptor binding, furin cleavage, or oligomerization of PA, as well as subsequent binding and/or translocation of catalytic subunits have also yielded successful cell-based inhibitors (Scobie, 2005, Basha et al., 2006, Kacprzak, 2004, Sarac, 2004, Opal, 2005, Komiyama, 2005, Jiao, 2006, Shiryaev, 2007, Komiyama, 2009, Sellman, 2001, Joshi et al., 2011, Backer, 2007). In contrast to such target-based approaches, the phenotypic screen described here identified a novel inhibitor of a host process that is broadly applicable to a variety of bacterial and viral diseases as both a research tool and therapeutic treatments and development. Influenza virus causes over 100,000 hospitalizations and 20,000 deaths per year in the United States alone (NIAID). Significant resources have been allotted to specifically discover agents that inhibit influenza (Severson, 2008, Bottini et al, 2012, Ortigoza, 2012). LCMV, which is also inhibited by EGA, is a prototypical arenavirus and a neglected human pathogen. The arenaviridae family is of particular therapeutic interest because several members of it cause severe hemorrhagic fevers, such as Lassa virus and Machupo virus (Lee, Kunz et al., 2011). Furthermore, new arenaviruses emerge every three years on average (Lee, Kunz et al., 2011), and many, like LCMV display dependence on low pH.

K. Example 11: Example Compound Synthesis and Characterization

Chemicals were used as received except for aniline derivatives which were distilled under reduced pressure prior to use. Unless noted, aryl aldehydes were obtained commercially (Sigma-Aldrich, Oakwood Chemical). 4-Ethynylbenzaldehyde, N-(4-formylphenyl)methanesulfonamide, 4-azido-2,3,5,6-pentafluorobenzaldehyde were prepared according to literature procedure while 4-azidobenzaldehyde and 4-azido-2-fluorobenzaldehyde were prepared as described herein. $^1$H-NMR and $^{13}$C-NMR spectra were referenced internal solvent resonances (CHCl$_3$: δ 7.26 and δ 77.2 ppm; DMSO: δ 2.50 and δ 39.5 ppm). $^{19}$F-NMR were referenced to external Freon-113 in benzene (−73.75 ppm). Infrared spectra were recorded using a Jasco ATR-FTIR spectrometer. Melting points were obtained using Buchi B-545 melting point apparatus and are uncorrected. cLogP calculations were performed with ChemBio3D Ultra 13.0 cLogP driver. Cellular intoxication assays were performed as described.[4] Briefly, RAW 264.7 murine macrophages were seeded into 384-well plates at 2×10$^3$ cells/well, incubated overnight, treated with 2-fold dilution series of compounds for 1 h then challenged with LT (500 ng/mL PA; 500 ng/mL LF) for 4 h. Cell viability was assessed using ATPlite reagent (Perkin Elmer). IC$_{50}$ values were calculated using PrismS (Graphpad) and are based on at least 3 independent experiments each performed in triplicate. Compounds giving incomplete dose-response curves up to 25 μM are characterized by an activity limit (i.e. IC$_{50}$>12.5 μM or IC$_{50}$>25 μM) or as 'not protective' if no bioactivity was observed at 25 μM. For photolabeling experiments, 2×10$^6$ RAW264.7 cells were seeded per well on 6-well plates the day prior to treatment with 12.5 μM 1 or 3, or 25 μM 4 or 5 for 1 h. Cells were then exposed to UVB source (LAX-Cute, Asahi Spectra) for 5 min. In 'washout' samples, media was removed and replaced with fresh media lacking compounds. All cells were then treated with LT (500 ng/mL PA; 500 ng/mL LF) for 4 h and viability measured by ATPlite. Data represent average values from 3 independent experiments +/−SD.

Representative Procedure for Synthesis of Aryl Semicarbazides.

N-(2,6-DIMETHYLPHENYL) SEMICARBAZIDE, 6

2,6-dimethylaniline (1.0 g, 8 mmol, 1 eq) was dissolved with triethylamine (0.89 g, 8.8 mmol, 1.1 eq) in 15 mL of DCM and cooled on ice-bath. Phenyl chloroformate (1.25 g, 8 mmol, 1 eq) was added dropwise. After addition the flask was brought to rt and stirred for 2 h. The reaction mixture was concentrated and then diluted with 50 mL of EtOAc and washed with 1N HCl (50 mL, 2×), sat. NaHCO$_3$ (50 ml, 2×), H$_2$O (50 mL, 1×), and brine (50 mL, 1×). The organic layer was dried with MgSO$_4$, filtered and concentrated to give approximately 1.4 g of a crude white solid that was used without further purification. This white solid was dissolved in 40 mL DCM and mixed with hydrazine monohydrate (0.80 g, 16 mmol, 2 eq) at room temperature and stirred vigorously overnight. Solvent was removed under reduced pressure and the crude solid was purified by column chromatography on silica gel (reaction mixture adsorbed to silica in EtOH; mobile phase, 5-10% MeOH: DCM) to yield 0.75 g (48%) of target compound upon concentration. $^1$H-NMR (CDCl$_3$; 300 MHz): δ 7.09 (s, 3H), 5.92 (bs, 1H), 3.84 (bs, 2H), 2.28 (s, 6H) ppm.

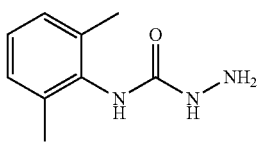

6

N-(2,4-DIMETHYLPHENYL) SEMICARBAZIDE, 7A $^1$H-NMR (CDCl$_3$; 300 MHz): δ 7.82 (bs, 1H), 7.69 (d, J=7.8 Hz, 1H), 7.01 (d, J=7.8 Hz, 1H), 6.99 (s, 1H), 5.97 (bs, 1H), 3.85 (bs, 2H), 2.28 (s, 3H), 2.25 (s, 3H) ppm.

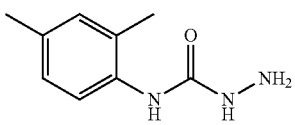

7a

N-(2,4,6-TRIMETHYLPHENYL) SEMICARBAZIDE, 7B $^1$H-NMR (CDCl$_3$; 300 MHz): δ 6.90 (s, 2H), 5.92 (bs, 1H), 3.82 (bs, 2H), 2.26 (s, 3H), 2.23 (s, 6H) ppm.

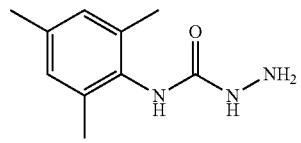

7b

N-(2,6-DIETHYLPHENYL) SEMICARBAZIDE, 7C $^1$H-NMR (CDCl$_3$; 300 MHz): δ 7.24-7.19 (m, 1H), 7.14-7.11 (m, 2H), 5.86 (bs, 1H), 3.84 (bs, 2H), 2.65 (q, J=7.6 Hz, 4H), 1.20 (t, J=7.6 Hz, 6H) ppm.

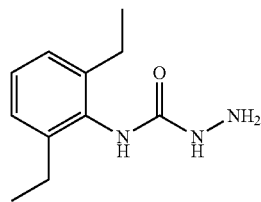

7c

N-(TERT-BUTYL) SEMICARBAZIDE, 8 tert-Butyl isocyanate (0.50 g, 5.1 mmol, 1 eq) was dissolved in 10 mL of DCM and stirred vigorously at rt. Hydrazine monohydrate (0.28 g, 5.6 mmol, 1.1 eq) was added to the solution and stirring was continued overnight. Volatiles were removed to give 425 mg (63%) of a white solid that did not require further purification. $^1$H-NMR (CDCl$_3$; 300 MHz): δ 5.96 (bs, 1H), 5.26 (bs, 1H), 3.62 (bs, 1.5H), 1.63 (bs, 0.5H), 1.36-1.35 (m, 9H) ppm.

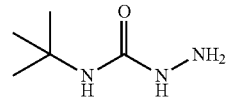

8

Representative Procedure for Synthesis of Biaryl Semicarbazones.

N$^1$-(4-BROMOBENZYLIDENE)-N$^4$-(2,6-DIMETHYLPHENYL)SEMICARBAZONE, 1

N-(2,6-Dimethylphenyl) semicarbazide, 2, (40 mg, 0.22 mmol, 1 eq) was suspended in 4 mL of absolute ethanol which was brought to reflux and 0.25 mL glacial HOAc was added. When 2 had dissolved, 4-bromobenzaldehyde (42 mg, 0.22 mmol, 1 eq) dissolved in 1 mL of absolute ethanol was added. The reaction mixture was refluxed for 10 min and a white precipitate formed. TLC displayed complete consumption of starting materials with the formation of a single spot detectable by UV with intermediate rf. The reaction mixture was cooled, concentrated, and recrystallized from 95% ethanol to give 44 mg (57%) of pure 1. $^1$H-NMR (DMSO-d$_6$; 400 MHz): δ 10.64 (s, 1H), 8.57 (s, 1H), 7.88 (s, 1H), 7.81 (d, J=8.5 Hz, 2H), 7.57 (d, J=8.5 Hz, 2H), 7.09 (s, 3H), 2.20 (s, 6H) ppm. HRMS [M+H]$^+$: calc for C$_{16}$H$_{16}$BrN$_3$OH: 346.0555; found: 346.0544 m/z.

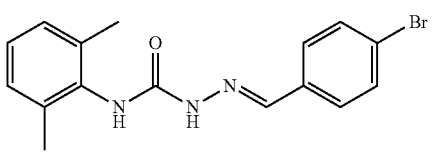

1

N¹-(4-BROMO-2-FLUOROBENZYLIDENE)-N⁴-(2,6-DIMETHYLPHENYL)SEMICARBAZONE, 2

¹H-NMR (DMSO-$d_6$; 400 MHz): δ 10.79 (s, 1H), 8.64 (s, 1H), 8.30 (dd, J=8.5 Hz, J=8.0 Hz, 1H), 8.07 (s, 1H), 7.61 (dd, J=10.3 Hz, J=1.8 Hz, 1H), 7.43 (dd, J=8.5 Hz, J=1.5 Hz, 1H), 7.09 (s, 3H), 2.20 (s, 6H) ppm. ¹³C-NMR (DMSO-$d_6$; 126 MHz): δ 160.0 (d, J=253.1 Hz), 153.5, 136.2, 135.4, 131.2 (d, J=4.8 Hz), 128.2 (d, J=3.2 Hz), 127.8 (d, J=3.1 Hz), 127.5, 126.3, 122.3 (d, J=9.9 Hz), 121.8 (d, J=9.7 Hz), 119.1 (d, J=24.4 Hz), 18.2 ppm. ¹⁹F-NMR (DMSO-$d_6$; 282 MHz): δ −120.1 (dd, J=10.3 Hz, J=8.1 Hz) ppm. FTIR (neat): 3250, 1642, 1554, 1487, 1219, 1081, 764 cm⁻¹. Melting point: 234-235° C. HRMS [M+H]⁺: calc for $C_{16}H_{15}BrFN_3OH$: 364.0461; found: 364.0458 m/z.

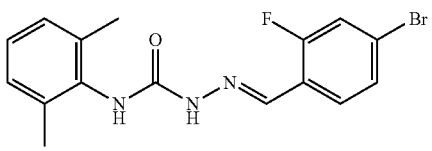

2

N¹-(4-AZIDO-2-FLUOROBENZYLIDENE)-N⁴-(2,6-DIMETHYLPHENYL)SEMICARBAZONE, 3

¹H-NMR (DMSO-$d_6$; 400 MHz): δ 10.71 (s, 1H), 8.60 (s, 1H), 8.35 (t, J=8.4 Hz, 1H), 8.07 (s, 1H), ~7.11 (dd, J=~11.5 Hz, J=2.1 Hz, 1H), 7.09 (s, 3H), 6.99 (dd, J=8.6 Hz, J=2.1 Hz, 1H), 2.20 (s, 6H) ppm. ¹³C-NMR (DMSO-$d_6$; 126 MHz): δ 160.7 (d, J=249.9 Hz), 153.6, 141.7 (d, J=10.6 Hz), 136.2, 135.5, 131.6 (d, J=4.4 Hz), 128.0 (d, J=4.1 Hz), 127.5, 126.2, 119.1 (d, J=10.2 Hz), 115.8 (d, J=2.8 Hz), 106.8 (d, J=25.0 Hz), 18.2 ppm. ¹⁹F-NMR (DMSO-$d_6$; 282 MHz): δ −120.7 (dd, J=11.5 Hz, J=8.5 Hz) ppm. FTIR (neat): 2947, 2115, 1677, 1598, 1497, 1292, 1213, 1146, 1085, 767 cm⁻¹. HRMS [M+H]⁺: calcd for $C_{16}H_{15}FN_6OH$: 327.1370; found: 327.1357 m/z.

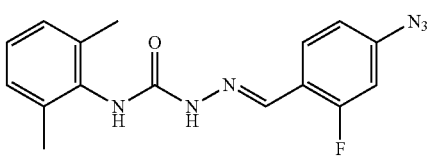

3

N¹-(4-AZIDOBENZYLIDENE)-N⁴-(2,6-DIMETHYLPHENYL)SEMICARBAZONE, 4

¹H-NMR (DMSO-$d_6$; 400 MHz): δ 10.57 (s, 1H), 8.53 (s, 1H), 7.89-7.87 (m, 3H), 7.13 (d, J=8.6 Hz, 2H), 7.08 (s, 3H), 2.20 (s, 6H) ppm. ¹³C-NMR (DMSO-$d_6$; 126 MHz): δ 153.7, 139.8, 138.9, 136.2, 135.6, 131.8, 128.5, 127.5, 126.1, 119.3, 18.2 ppm. FTIR (neat):2922, 2850, 2119, 2084, 1674, 1602, 1501, 1281, 1143, 830 cm⁻¹. HRMS [M+H]⁺: calc for $C_{16}H_{16}N_6OH$: 309.1464; found: 309.1464 m/z.

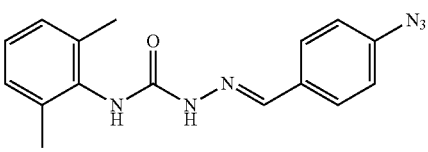

4

N¹-(4-AZIDO-2,3,5,6-TETRAFLUOROBENZYLIDENE)-N⁴-(2,6-DIMETHYLPHENYL)SEMICARBAZONE, 5

¹H-NMR (DMSO-$d_6$; 400 MHz): δ 11.03 (s, 1H), 8.00 (s, 2H), 7.08 (s, 3H), 2.18 (s, 6H) ppm. ¹⁹F-NMR (DMSO-$d_6$; 376 MHz): δ −144.4 (dd, J=9 Hz, 21 Hz), −153.5 (dd, J=9 Hz, J=21 Hz) ppm. FTIR (neat): 3379, 3094, 2930, 2116, 1700, 1648, 1609, 1476, 1239, 1154, 981, 770 cm⁻¹. HRMS [M+H]⁺: calc for $C_{16}H_{19}F_4N_6OH$: 381.1087; found: 381.1078 m/z.

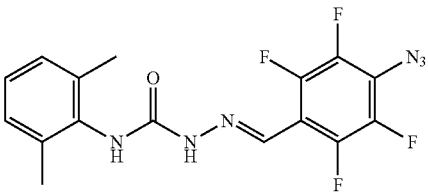

5

N¹-(4-BROMOBENZYLIDENE)-N⁴-(2,4-DIMETHYLPHENYL)SEMICARBAZONE, 9A

¹H-NMR (DMSO-$d_6$; 400 MHz): δ 10.76 (s, 1H), 8.50 (s, 1H), 7.91 (s, 1H), 7.75 (d, J=8.5 Hz, 2H), 7.61 (d, J=8.5 Hz, 2H), 7.42 (d, J=8.0 Hz, 1H), 7.04 (s, 1H), 6.98 (d, J=8.0 Hz, 1H), 2.26 (s, 3H), 2.22 (s, 3H) ppm. HRMS [M+H]⁺: calc for $C_{16}H_{16}BrN_3OH$: 346.0555; found: 346.0566 m/z.

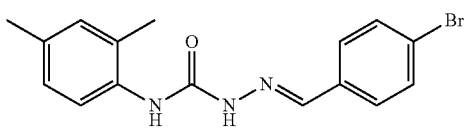

9a

$N^1$-(4-BROMOBENZYLIDENE)-$N^4$-(2,4,6-DIMETHYLPHENYL)SEMICARBAZONE, 9B $^1$H-NMR (DMSO-$d_6$; 400 MHz): δ 10.60 (s, 1H), 8.47 (s, 1H), 7.87 (s, 1H), 7.80 (d, J=8.5 Hz, 2H), 7.58 (d, J=8.5 Hz, 2H), 6.89 (s, 2H), 2.24 (s, 3H), 2.15 (s, 6H) ppm. HRMS [M+H]$^+$: calc for $C_{17}H_{18}BrN_3OH$: 360.0711; found: 360.0696 m/z.

(3005)

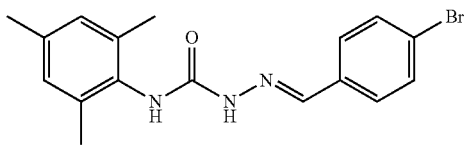

$N^1$-(4-BROMOBENZYLIDENE)-$N^4$-(2,6-DIETHYLPHENYL)SEMICARBAZONE, 9C $^1$H-NMR (DMSO-$d_6$; 400 MHz): δ 10.64 (s, 1H), 8.55 (s, 1H), 7.88 (s, 1H), 7.81 (d, J=8.5 Hz, 1H), 7.58 (d, J=8.5 Hz, 1H), 7.19 (m, 1H), 7.12-7.10 (m, 2H), 2.57 (q, J=7.6 Hz, 4H), 1.13 (t, J=7.6 Hz, 6H) ppm. HRMS [M+H]$^+$: calc for $C_{18}H_{20}BrN_3OH$: 374.0868; found: 374.0873 m/z.

(4007)

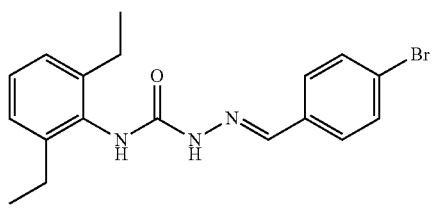

$N^1$-(4-BROMOBENZYLIDENE)-$N^4$-(TERT-BUTYL)SEMICARBAZONE, 10

$^1$H-NMR (DMSO-$d_6$; 400 MHz): δ 10.28 (s, 1H), 7.81 (s, 1H), 7.61 (d, J=8.8 Hz, 2H), 7.58 (d, J=8.8 Hz, 2H), 6.20 (s, 1H), 1.34 (s, 9H) ppm. HRMS [M+H]$^+$: calcd for $C_{12}H_{16}BrN_3OH$: 298.0555; found: 298.0553 m/z.

(6005)

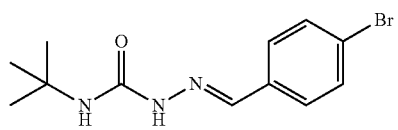

$N^1$-(4-CHLOROBENZYLIDENE)-$N^4$-(2,6-DIMETHYLPHENYL)SEMICARBAZONE, 13A $^1$H-NMR (DMSO-$d_6$; 400 MHz; assignments supported by HMBC): δ 10.64 (s, 1H, CONHN), 8.57 (s, 1H, Ar—NHCO), 7.90 (s, 1H, CHNNH), 7.88 (d, 8.5 Hz, 2H, ortho-H), 7.44 (d, 8.5 Hz, 2H, meta-H), 7.09 (s, 3H, ArH), 2.20 (s, 6H, CH$_3$) ppm. $^{13}$C-NMR (DMSO-$d_6$; 126 MHz): δ 153.7 (NCON), 138.4 (CHNN), 136.3 (ArC—NHCO), 135.6, 133.8, 133.5, 128.6, 128.5, 127.5, 126.2, 18.2 (CH$_3$) ppm. HRMS [M+H]$^+$: calc for $C_{16}H_{16}ClN_3OH$: 302.1060; found: 301.1060 m/z.

(1001)

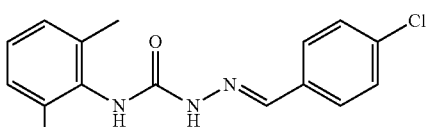

$N^1$-(2-CHLORO-3-TRIFLUOROMETHYLBENZYLIDENE)-$N^4$-(2,6-DIMETHYLPHENYL)SEMICARBAZONE, 13B $^1$H-NMR (DMSO-$d_6$; 400 MHz): δ 10.97 (s, 1H), 8.71 (bs, 2H), 8.42 (s, 1H), 7.84 (d, J=7.4 Hz, 1H), 7.55 (dd, J=8.0 Hz, J=8.0 Hz, 1H), 7.10 (s, 3H), 2.20 (s, 6H) ppm. $^{19}$F-NMR (DMSO-$d_6$; 282 MHz): δ −59.3 (s) ppm. HRMS [M+H]$^+$: calc for $C_{17}H_{15}ClF_3N_3OH$: 370.0934; found: 370.0926 m/z.

(1005)

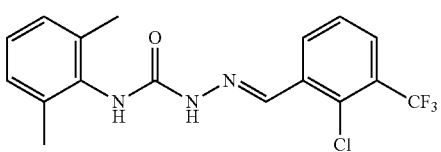

$N^1$-(2-FLUOROBENZYLIDENE)-$N^4$-(2,6-DIMETHYLPHENYL)SEMICARBAZONE, 13C $^1$H-NMR (DMSO-$d_6$; 300 MHz): δ 10.74 (s, 1H), 8.58 (s, 1H), 8.32 (m, 1H), 8.14 (s, 1H), 7.41 (m, 1H), 7.24 (m, 2H), 7.09 (s, 3H), 2.20 (s, 6H) ppm. $^{19}$F-NMR (DMSO-$d_6$; 282 MHz; $^1$H-dc): δ −120.8 ppm. HRMS [M+H]$^+$: calc for $C_{16}H_{16}FN_3OH$: 286.1356; found: 286.1354 m/z.

(1006)

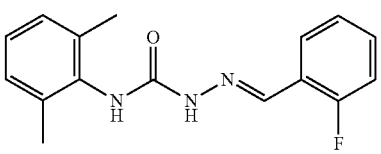

$N^1$-(3-FLUORO-4-METHYLBENZYLIDENE)-$N^4$-(2,6-DIMETHYLPHENYL)SEMICARBAZONE, 13D $^1$H-NMR (DMSO-$d_6$; 400 MHz): δ 10.60 (s, 1H), 8.60 (s, 1H), 7.86 (s, 1H), 7.83 (d, J=11.2 Hz, 1H), 7.42 (d, J=7.8 Hz, 1H), 7.29 (dd, J=7.8 Hz, J=7.8 Hz, 1H), 7.09 (s, 3H), 2.24 (s, 3H), 2.20 (s, 6H) ppm. $^{19}$F-NMR (DMSO-$d_6$; 282 MHz;

$^1$H-dc): δ −116.0 ppm. HRMS [M+H]$^+$: calc for C$_{17}$H$_{18}$FN$_3$OH: 300.1512; found: 300.1512 m/z.

(1008)

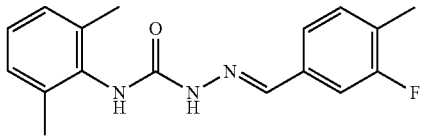

13d

N$^1$-(4-FLUOROBENZYLIDENE)-N$^4$-(2,6-DIMETHYLPHENYL)SEMICARBAZONE, 13E $^1$H-NMR (DMSO-d$_6$; 400 MHz): δ 10.57 (s, 1H), 8.54 (s, 1H), 7.92-7.88 (m, 3H), 7.22 (dd, J=8.8 Hz, J=8.8 Hz, 2H), 7.08 (s, 3H), 2.20 (s, 6H) ppm. $^{19}$F-NMR (DMSO-d$_6$; 282 MHz; $^1$H-dc): δ −110.4 ppm. HRMS [M+H]$^+$: calc for C$_{16}$H$_{16}$FN$_3$OH: 286.1356; found: 286.1367 m/z.

(1003)

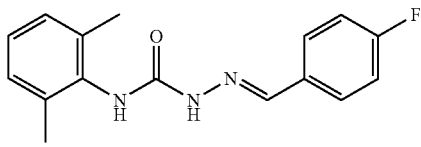

13e

N$^1$-(2,4-DIFLUOROBENZYLIDENE)-N$^4$-(2,6-DIMETHYLPHENYL)SEMICARBAZONE, 13F $^1$H-NMR (DMSO-d$_6$; 400 MHz): δ 10.72 (s, 1H), 8.61 (s, 1H), 8.40 (m, 1H), 8.08 (s, 1H), 7.30 (m, 1H), 7.14, (m, 1H), 7.09 (s, 3H), 2.20 (s, 6H) ppm. $^{19}$F-NMR (DMSO-d$_6$; 282 MHz; $^1$H-dc): δ −106.8 (d, J=7.3 Hz), −116.8 (d, J=7.3 Hz) ppm. HRMS [M+H]$^+$: calc for C$_{16}$H$_{15}$F$_2$N$_3$OH: 304.1261; found: 304.1265 m/z.

(1004)

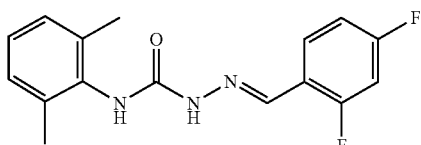

13f

N$^1$-(2,3-DIMETHOXYBENZYLIDENE)-N$^4$-(2,6-DIMETHYLPHENYL)SEMICARBAZONE, 13G $^1$H-NMR (DMSO-d$_6$; 400 MHz): δ 10.57 (s, 1H), 8.46 (s, 1H), 8.21 (s, 1H), 7.79 (dd, 2.2 Hz, 7.1 Hz, 1H), 7.08 (s, 3H), 7.06-7.02 (m, 2H), 3.82 (s, 3H), 3.76 (s, 3H), 2.20 (s, 6H) ppm. HRMS [M+H]$^+$: calc for C$_{18}$H$_{21}$N$_3$O$_3$H: 328.1661; found: 328.1609 m/z.

(1009)

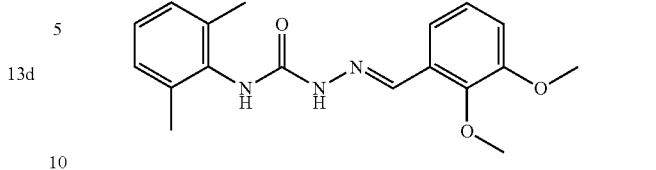

13g

N$^1$-(2,4,6-TRIMETHOXYBENZYLIDENE)-N$^4$-(2,6-DIMETHYLPHENYL)SEMICARBAZONE, 13H $^1$H-NMR (DMSO-d$_6$; 400 MHz): δ 10.32 (s, 1H), 8.10 (s, 1H), 7.82 (1H), 7.07 (m, 3H), 6.28 (s, 2H), 3.82 (s, 3H), 3.80 (s, 6H), 2.21 (s, 6H) ppm. HRMS [M+H]$^+$: calc for C$_{19}$H$_{23}$N$_3$O$_4$H: 358.1767; found: 358.1769 m/z.

(4004)

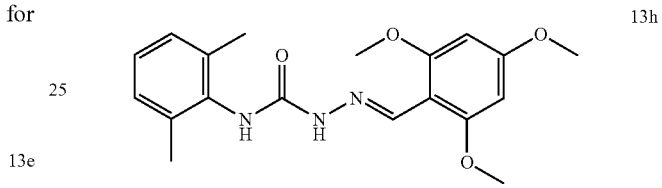

13h

N$^1$-(2-METHYLBENZYLIDENE)-N$^4$-(2,6-DIMETHYLPHENYL)SEMICARBAZONE, 13I $^1$H-NMR (DMSO-d$_6$; 300 MHz): δ 10.51 (s, 1H), 8.41 (s, 1H), 8.22 (s, 1H), 8.10 (d, J=7.6 Hz, 1H), 7.28-7.17 (m, 3H), 7.08 (s, 3H), 2.40 (s, 3H), 2.20 (s, 6H) ppm. HRMS [M+H]$^+$: calc for C$_{17}$H$_{19}$N$_3$OH: 282.1606; found, 282.1602 m/z.

(1007)

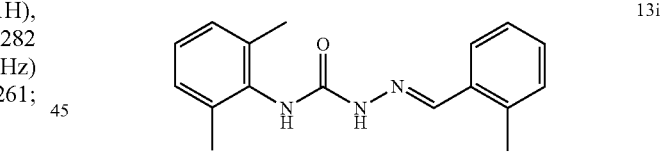

13i

N$^1$-(3-METHYLBENZYLIDENE)-N$^4$-(2,6-DIMETHYLPHENYL)SEMICARBAZONE, 13J $^1$H-NMR (DMSO-d$_6$; 400 MHz): δ 10.54 (s, 1H), 8.48 (s, 1H), 7.88 (s, 1H), 7.70 (s, 1H), 7.56 (d, J=7.6 Hz. 1H), 7.27 (dd, J=7.6 Hz, J=7.7 Hz, 1H), 7.17 (d, J=7.7 Hz, 1H), 7.09 (s, 3H), 2.33 (s, 3H), 2.21 (s, 6H) ppm. HRMS [M+H]$^+$: calc for C$_{17}$H$_{19}$N$_3$OH: 282.1606; found: 282.1609 m/z.

(1010)

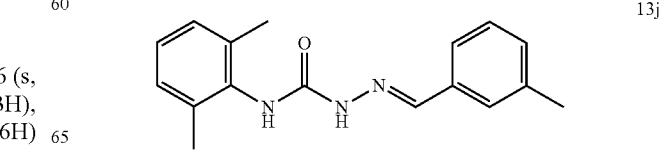

13j

N¹-(4-METHYLBENZYLIDENE)-N⁴-(2,6-DIMETHYLPHENYL)SEMICARBAZONE, 13K

¹H-NMR (DMSO-d₆; 400 MHz): δ 10.49 (s, 1H), 8.46 (s, 1H), 7.88 (s, 1H), 7.72 (d, J=8.1, 2H), 7.20 (d, J=8.1 Hz, 2H), 7.08 (s, 3H), 2.32 (s, 3H), 2.20 (s, 6H) ppm. Lit[5]: (DMSO-d₆, 300 MHz): δ 9.42 (s, 1H), 8.34 (s, 1H), 8.02 (s, 1H), 7.25 (d, J=7.6 Hz, 2H), 7.04 (s, 3H), 6.57 (d, J=7.6 Hz, 2H), 2.32 (s, 3H), 2.14 (s, 6H) ppm. HRMS [M+H]⁺: calc for $C_{17}H_{19}N_3OH$: 282.1606; found: 282.1611 m/z.

(4002)

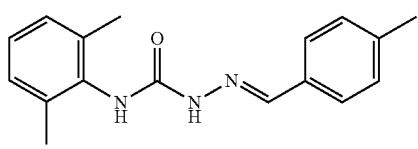

13k

N¹-(4-ETHYLBENZYLIDENE)-N⁴-(2,6-DIMETHYLPHENYL)SEMICARBAZONE, 13L

¹H-NMR (DMSO-d₆; 400 MHz): δ 10.50 (s, 1H), 8.45 (s, 1H), 7.89 (s, 1H), 7.73 (d, J=8.2 Hz, 2H), 7.23 (d, J=8.2 Hz, 2H), 7.08 (s, 3H), 2.62 (q, J=7.6 Hz, 2H), 2.20 (s, 6H), 1.19 (t, J=7.6 Hz, 3H) ppm. HRMS [M+H]⁺: calc for $C_{18}H_{21}N_3OH$: 296.1763; found: 296.1772 m/z.

(2001)

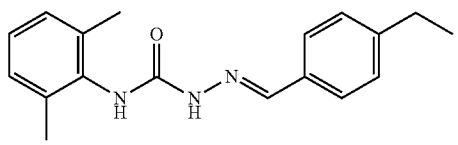

13l

N¹-(4-I-PROPYLBENZYLIDENE)-N⁴-(2,6-DIMETHYLPHENYL)SEMICARBAZONE, 13M

¹H-NMR (DMSO-d₆; 400 MHz): δ 10.50 (s, 1H), 8.44 (s, 1H), 7.89 (s, 1H), 7.73 (d, J=8.3 Hz, 2H), 7.26 (d, J=8.3 Hz, 2H), 7.08 (s, 3H), 2.91 (septet, J=6.9 Hz, 1H), 2.20 (s, 6H), 1.21 (t, J=6.9 Hz, 6H) ppm. HRMS [M+H]⁺: calc for $C_{19}H_{23}N_3OH$: 310.1919; found: 310.1918 m/z.

(2002)

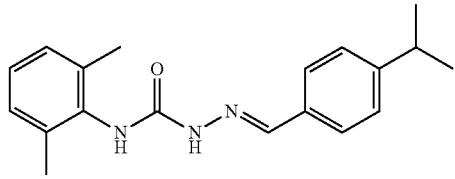

13m

N¹-(4-METHOXYBENZYLIDENE)-N⁴-(2,6-DIMETHYLPHENYL)SEMICARBAZONE, 13N

¹H-NMR (DMSO-d₆; 400 MHz): δ 10.41 (s, 1H), 8.43 (s, 1H), 7.86 (s, 1H), 7.76 (d, J=8.7 Hz, 2H), 7.08 (s, 3H), 6.95 (d, J=8.7 Hz, 2H), 3.79 (s, 3H), 2.20 (s, 6H) ppm. HRMS [M+H]⁺: calc for $C_{17}H_{19}N_3O_2H$: 298.1556; found: 298.1562 m/z.

(4001)

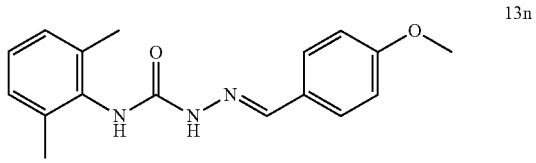 [SMILES: COc1ccc(/C=N/NC(=O)Nc2c(C)cccc2C)cc1]

13n

N¹-(4-ETHYNYLBENZYLIDENE)-N⁴-(2,6-DIMETHYLPHENYL)SEMICARBAZONE, 13O

¹H-NMR (DMSO-d₆; 400 MHz): δ 10.67 (s, 1H), 8.57 (s, 1H), 7.91 (s, 1H), 7.85 (d, J=8.2 Hz, 2H), 7.48 (d, J=8.2 Hz, 2H), 7.09 (s, 3H), 4.29 (s, 1H), 2.20 (s, 6H) ppm. HRMS [M+H]⁺: calc for $C_{18}H_{17}N_3OH$: 292.1450; found: 292.1455 m/z.

(2003)

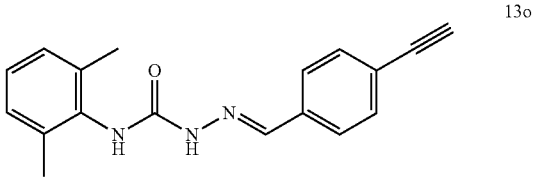 [SMILES: C#Cc1ccc(/C=N/NC(=O)Nc2c(C)cccc2C)cc1]

13o

N¹-(4-(N-(4-FORMYLPHENYL)METHANESULFONAMIDE)BENZYLIDENE-N⁴-(2,6-DIMETHYLPHENYL)SEMICARBAZONE, 13P

¹H-NMR (DMSO-d₆; 400 MHz): δ 10.52 (s, 1H), 9.89 (s, 1H), 8.45 (s, 1H), 7.86 (s, 1H), 7.79 (d, J=8.7 Hz, 2H), 7.21 (d, J=8.7 Hz, 2H), 7.08 (s, 3H), 3.02 (s, 3H), 2.20 (s, 6H) ppm. HRMS [M+H]⁺: calc for $C_{17}H_{20}N_4O_3SH$: 361.1334; found: 361.1337 m/z.

(2005)

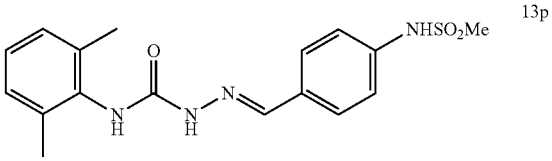

13p

N¹-(4-IODOBENZYLIDENE)-N⁴-(2,6-DIMETHYLPHENYL)SEMICARBAZONE, 13Q

¹H-NMR (DMSO-d₆; 400 MHz): δ 10.63 (s, 1H), 8.55 (s, 1H), 7.86 (s, 1H), 7.75 (d, J=8.4 Hz, 2H), 7.64 (d, J=8.4 Hz, 2H), 7.08 (s, 3H), 2.20 (s, 6H) ppm. HRMS [M+H]⁺: calc for $C_{16}H_{16}IN_3OH$: 394.0416; found: 394.0427 m/z.

(2006)

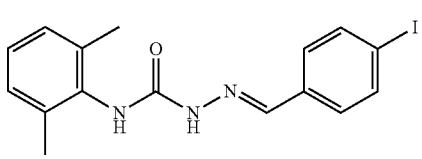

13q

N¹-(4-TRIFLUOROMETHYLBENZYLIDENE)-N⁴-(2,6-DIMETHYLPHENYL)SEMICARBAZONE, 13R

¹H-NMR (DMSO-d$_6$; 400 MHz): δ 10.80 (s, 1H), 8.65 (s, 1H), 8.07 (d, J=8.0 Hz, 2H), 7.98 (s, 1H), 7.73 (d, J=8.0 Hz, 2H), 7.09 (s, 3H), 2.21 (s, 6H) ppm. ¹⁹F-NMR (DMSO-d$_6$; 282 MHz): δ −61.3 (s) ppm. HRMS [M+H]⁺: calc for C$_{17}$H$_{16}$F$_3$N$_3$OH: 336.1324; found: 336.1317 m/z.

(3002)

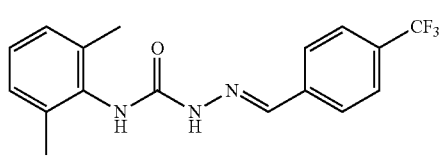

13r

N¹-(4-CYANOMETHYLBENZYLIDENE)-N⁴-(2,6-DIMETHYLPHENYL)SEMICARBAZONE, 13S

¹H-NMR (DMSO-d$_6$; 400 MHz): δ 10.86 (s, 1H), 8.69 (s, 1H), 8.05 (d, J=8.4 Hz, 2H), 7.95 (s, 1H), 7.84 (d, J=8.4 Hz, 2H), 7.09 (s, 3H), δ 2.20 (s, 6H) ppm. HRMS [M+H]⁺: calc for C$_{17}$H$_{16}$N$_4$OH: 293.1402; found: 293.1398 m/z.

(4003)

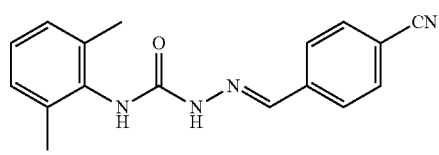

13s

N¹-(PYRIDIN-4-YLMETHYLENE)-N⁴-(2,6-DIMETHYLPHENYL)SEMICARBAZONE, 13T

¹H-NMR (DMSO-d$_6$; 400 MHz): δ 10.92 (s, 1H), 8.68 (s, 1H), 8.57 (m, 2H), 7.88 (s, 1H), 7.82 (m, 2H), 7.10 (s, 3H), 2.20 (s, 6H) ppm. HRMS [M+H]⁺: calc for C$_{15}$H$_{16}$N$_4$OH: 269.1402; found: 269.1397 m/z.

(5007)

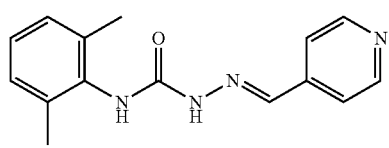

13t

N¹-(FURAN-2-YLMETHYLENE)-N⁴-(2,6-DIMETHYLPHENYL)SEMICARBAZONE, 13U

¹H-NMR (DMSO-d$_6$; 400 MHz): δ 10.56 (s, 1H), 8.17 (s, 1H), 7.85 (s, 1H), 7.77 (d, J=1.7 Hz, 1H), 7.07 (s, 3H), 6.92 (d, J=3.4 Hz, 1H), 6.60 (dd, J=3.4 Hz, J=1.7 Hz, 1H), 2.18 (s, 6H) ppm. HRMS [M+H]⁺: calc for C$_{14}$H$_{15}$N$_3$O$_2$H: 258.1243; found: 258.1242 m/z.

(5003)

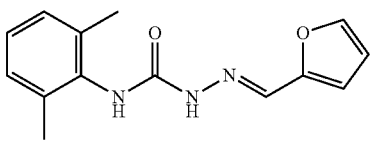

13u

N¹-(5-BROMOFURAN-2-YLMETHYLENE)-N⁴-(2,6-DIMETHYLPHENYL)SEMICARBAZONE, 13V

¹H-NMR (DMSO-d$_6$; 400 MHz): δ 10.63 (s, 1H), 8.23 (s, 1H), 7.77 (s, 1H), 7.07 (s, 3H), 6.95 (d, J=3.5 Hz, 1H), 6.72 (d, J=3.5 Hz, 1H), 2.18 (s, 6H) ppm. HRMS [M+H]⁺: calc for C$_{14}$H$_{14}$BrN$_3$O$_2$H: 336.0348; found: 336.0345 m/z.

(5004)

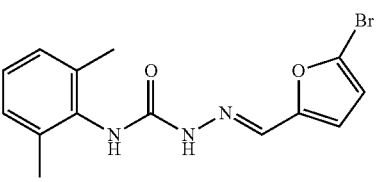

13v

N¹-(THIOPHENE-2-YLMETHYLENE)-N⁴-(2,6-DIMETHYLPHENYL)SEMICARBAZONE, 13W

¹H-NMR (DMSO-d$_6$; 400 MHz): δ 10.56 (s, 1H), 8.13 (s, 1H), 8.10 (s, 1H), 7.59 (d, J=5.0 Hz, 1H), 7.40 (d, J=3.6 Hz, 1H), 7.10 (dd, J=5.0 Hz, J=3.6 Hz, 1H), 7.08 (s, 3H), 2.19 (s, 6H) ppm. HRMS [M+H]⁺: calc for C$_{14}$H$_{15}$N$_3$OSH: 274.1014; found: 274.1005 m/z.

(5005)

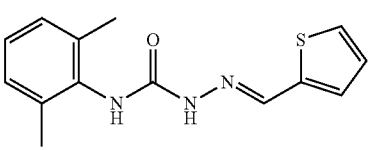

13w

N¹-(5-BROMOTHIOPHENE-2-YLMETHYLENE)-N⁴-(2,6-DIMETHYLPHENYL)SEMICARBAZONE, 13X

¹H-NMR (DMSO-d$_6$; 400 MHz): δ 10.64 (s, 1H), 8.18 (s, 1H), 8.03 (s, 1H), 7.22 (d, J=3.9 Hz, 1H), 7.21 (d, J=3.9 Hz, 1H), 7.08 (s, 3H), 2.18 (s, 6H) ppm. $^{13}$C-NMR (DMSO-d$_6$; 126 MHz): δ 153.3, 141.4, 136.0, 135.3, 134.5, 130.9, 129.4, 127.5, 126.2, 113.4, 18.2 ppm. FTIR (neat): 3237, 1694, 1641, 1559, 1205, 765, 675 cm$^{-1}$. Melting point: 221-222° C. HRMS [M+H]$^+$: calc for C$_{14}$H$_{14}$BrN$_3$OSH: 352.0119; found: 352.0345 m/z.

(5006)

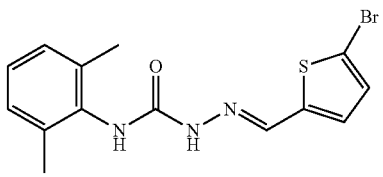

13x

N$^1$-(4-BROMO-2,6-DIFLUOROBENZYLIDENE)-N$^4$-(2,6-DIMETHYLPHENYL)SEMICARBAZONE, 13Y $^1$H-NMR (DMSO-d$_6$; 300 MHz): δ 10.94 (s, 1H), 8.00 (s, 1H), 7.95 (s, 1H), 7.58 (d, J=8.3 Hz, 2H), 7.08 (s, 3H), 2.18 (s, 6H) ppm. $^{19}$F-NMR (DMSO-d$_6$; 282 MHz; $^1$H-dc): δ −111.6 (s) ppm. HRMS [M+H]$^+$: calc for 382.0367; found: 382.0371 m/z.

(4006)

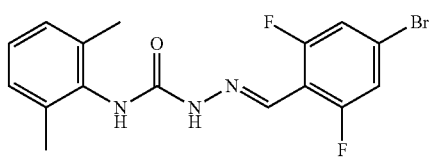

13y

N$^1$-(4-BROMO-2-CHLOROBENZYLIDENE)-N$^4$-(2,6-DIMETHYLPHENYL)SEMICARBAZONE, 13Z $^1$H-NMR (DMSO-d$_6$; 400 MHz): δ 10.87 (s, 1H), 8.67 (s, 1H), 8.36 (d, J=8.6 Hz, 1H), 8.25 (s, 1H), 7.77 (d, J=2.0 Hz, 1H), 7.55 (dd, J=8.6 Hz, J=2.0 Hz, 1H), 7.09 (s, 3H), 2.19 (s, 6H) ppm. HRMS [M+H]$^+$: calc for C$_{16}$H$_{15}$BrClN$_3$OH: 380.0165; found: 380.0155 m/z.

(4005)

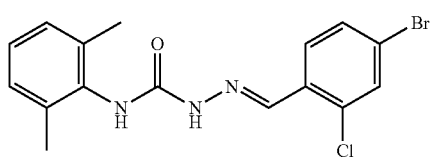

13z

N$^1$-(4-BROMO-3-FLUOROBENZYLIDENE)-N$^4$-(2,6-DIMETHYLPHENYL)SEMICARBAZONE, 13AA $^1$H-NMR (DMSO-d$_6$; 400 MHz): δ 10.76 (s, 1H), 8.70 (s, 1H), 8.08 (d, J=11.0 Hz, 1H), 7.88 (s, 1H), 7.71 (dd, J=8.1 Hz, J=7.6 Hz, 1H), 7.51 (d, J=8.1 Hz, 1H), 7.09 (s, 3H), 2.20 (s, 6H) ppm. $^{19}$F-NMR (DMSO-d$_6$; 282 MHz): δ −108.8 (dd, J=11.0 Hz, J=7.6 Hz) ppm. HRMS [M+H]$^+$: calc for C$_{16}$H$_{15}$BrFN$_3$OH: 364.0461; found: 364.0460 m/z.

(5001)

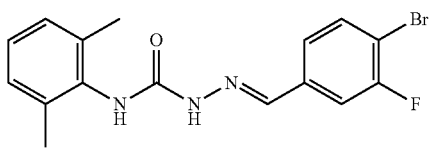

13aa

N$^1$-(4-BROMO-3-CHLOROBENZYLIDENE)-N$^4$-(2,6-DIMETHYLPHENYL)SEMICARBAZONE, 13AB $^1$H-NMR (DMSO-d$_6$; 400 MHz): δ 10.76 (s, 1H), 8.87 (s, 1H), 8.27 (d, J=1.9 Hz, 1H), 7.86 (s, 1H), 7.77 (d, J=8.3 Hz, 1H), 7.65 (dd, J=8.3 Hz, J=1.9 Hz, 1H), 7.09 (s, 3H), 2.20 (s, 6H) ppm. HRMS [M+H]$^+$: calc for C$_{16}$H$_{15}$BrClN$_3$OH: 380.0165; found: 380.0169 m/z.

(5002)

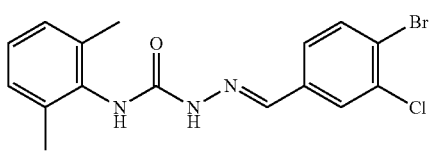

13ab

2-(4-BROMOBENZYL)-N-(2,6-DIMETHYLPHENYL)HYDRAZINECARBOXAMIDE, 14

N$^1$-4-Bromobenzylidene-N$^4$-(2,6-dimethylphenyl) semicarbazone, 1, (40 mg, 0.12 mmol) was placed into a flask under Ar atmosphere and BH$_3$THF (1 M soln, 0.58 mL, 5 eq) was added by syringe and the reaction mixture was heated to 50° C. for 3 h. Reaction mixture was cooled to rt and quenched with 2 mL 1N HCl. pH was adjusted to basic by litmus by addition of 2M NaOH. The precipitate was collected by filtration and purified by silica gel chromatography (35% EtOAc: DCM) which yielded 31 mg (77%) target compound as a white solid upon concentration. $^1$H-NMR (DMSO-d$_6$; 400 MHz): δ 7.75 (bs, 1H), 7.50 (d, J=8.3 Hz, 2H), 7.41 (d, J=8.3 Hz, 2H), 7.35 (s, 1H), 6.99 (s, 3H), 5.33 (bs, 1H), 3.84 (d, J=4.5 Hz, 2H), 2.01 (s, 6H) ppm. $^{13}$C-NMR (DMSO-d$_6$; 126 MHz): δ 156.8, 137.9, 135.81, 135.75, 131.4, 130.9, 127.4, 125.6, 120.1, 54.6, 18.0 ppm. HRMS [M+H]$^+$: calc for C$_{16}$H$_{18}$BrN$_3$OH: 348.0711; found: 348.0717 m/z.

(3004)

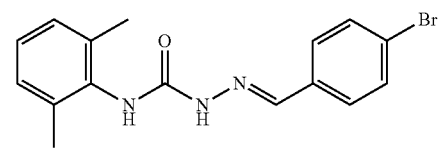

14

$N^1$-(4-BROMOPHENYLETHYLIDENE)-$N^4$-(2,6-DIMETHYLPHENYL)SEMICARBAZONE, 15

$^1$H-NMR (DMSO-$d_6$; 400 MHz): δ 9.74 (s, 1H), 8.52 (s, 1H), 7.93 (d, J=8.6, 2H), 7.54 (d, J=8.6 Hz, 2H), 7.09 (s, 3H), 2.32 (s, 3H), 2.20 (s, 6H) ppm. $^{13}$C-NMR (DMSO-$d_6$; 101 MHz): δ 154.2, 143.5, 137.3, 136.2, 135.6, 131.0, 128.3, 127.5, 126.1, 121.9, 18.2, 13.2 ppm. HRMS [M+H]$^+$: calc for $C_{17}H_{18}BrN_3OH$: 360.0711; found: 360.0709 m/z.

(3003)

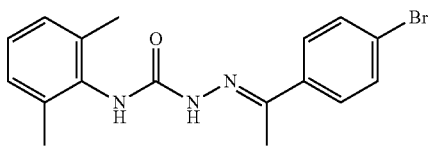

$N^1$-2-(4-BROMOBENZYLIDENE)-$N^4$-(2,6-DIMETHYLPHENYL)1-METHYLHYDRAZINECARBOXAMIDE, 16

$N^1$-2-(4-bromobenzylidene)-$N^4$-(2,6-dimethylphenyl) semicarbazone, 1, (50 mg, 0.14 mmol, 1 eq) was dissolved in 1 mL anhyd DMF. To this soln was added $K_2CO_3$ (44 mg, 0.32 mmol, 2.2 eq) and methyl iodide (44 mg, 0.32 mmol, 2.2 eq) and the mixture was stirred at rt overnight. The reaction mixture was then diluted with $H_2O$ (5 mL) and the precipitate collected as a pellet following centrifugation. Flash chromatography on silica gel (35% EtOAc: $C_6$) provided 47 mg (91%) of target compound upon concentration. $^1$H-NMR (DMSO-$d_6$; 400 MHz): δ 8.92 (s, 1H), 7.95 (d, J=8.5 Hz, 2H), 7.79 (s, 1H), 7.59 (d, J=8.5 Hz, 2H), 7.09 (s, 3H), 3.33 (s, 3H), 2.18 (s, 6H) ppm. $^1$H-NMR (CDCl$_3$; 500 MHz): δ 8.05 (s, 1H), 7.55-7.52 (m, 5H), 7.10 (s, 3H), 3.45 (s, 3H), 2.30 (s, 6H) ppm. $^{13}$C-NMR (CDCl$_3$; 126 MHz): δ 153.7, 136.1, 135.5, 134.6, 133.9, 132.3, 128.4, 128.2, 127.1, 123.6, 28.7, 18.8 ppm. HRMS [M+H]$^+$: calc for $C_{17}H_{18}BrN_3OH$: 360.0711; found: 360.0705 m/z.

(4008)

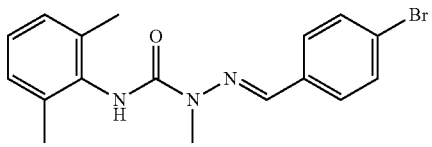

2-(4-BROMOBENZYLIDENE)-N-(2,6-DIMETHYLPHENYL)-1-(PROP-2-YN-1-YL)HYDRAZINECARBOXAMIDE, 17

$N^1$-2-(4-bromobenzylidene)-$N^4$-(2,6-dimethylphenyl) semicarbazone, 1, (25 mg, 72 μmol, 1 eq) was dissolved in 0.5 mL anhyd DMF and to this soln was added $K_2CO_3$ (30 mg, 0.22 mmol, 3 eq) and propargyl bromide (80% wt. soln in PhCH$_3$, 27 mg, 2.5 eq) and the mixture was stirred for 5 h at rt. The reaction mixture was then diluted with $H_2O$ (5 mL) and the precipitate collected as a pellet following centrifugation. Flash chromatography on silica gel (20% EtOAc: $C_6$) provided 24 mg (86%) of target compound upon concentration. $^1$H-NMR (DMSO-$d_6$; 400 MHz): δ 8.98 (s, 1H), 7.97 (d, J=8.6 Hz, 2H), 7.90 (s, 1H), 7.61 (d, J=8.6 Hz, 2H), 7.11 (s, 3H), 4.83 (d, J=2.3 Hz, 2H), 3.27 (t, J=2.3 Hz, 1H), 2.17 (s, 6H) ppm. $^{13}$C-NMR (DMSO-$d_6$; 126 MHz): δ 153.1, 138.0, 136.7, 136.2, 134.5, 132.0, 129.8, 128.1, 126.9, 123.1, 78.4, 75.4, 30.8, 18.6 ppm. HRMS [M+H]$^+$: calc for $C_{19}H_{18}BrN_3OH$: 384.0711; found: 384.0727 m/z.

(5008)

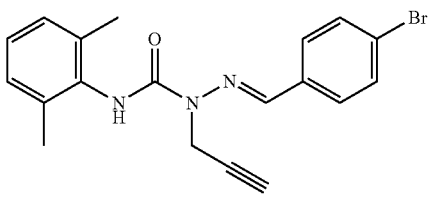

N-(2,6-DIMETHYLPHENYL)THIOSEMICARBAZIDE, 18

2,6-dimethylaniline (0.50 g, 4.1 mmol, 1 eq) was dissolved in 5 mL anhydrous DMF with NaOH (0.16 g, 1.2 eq). Carbon disulfide (0.31 g, 1 eq) was added and the mixture was stirred at rt for 1 h. Hydrazine monohydrate (0.62 g, 3 eq) was added and the reaction mixture was heated to 60° C. for 1 h. Upon cooling, the target compound was precipitated from the reaction mixture by the addition of 100 mL $H_2O$. The precipitate was collected by filtration, washed with water, and dried to give 409 mg (51%) of the target compound as a white solid. $^1$H-NMR (DMSO-$d_6$; 300 MHz): δ 9.16-8.88 (m, 2H), 7.04 (s, 3H), 4.69 (bs, 2H), 2.14 (s, 6H) ppm.

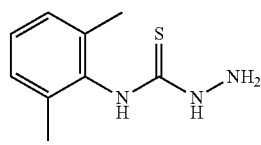

Representative Procedure for Synthesis of Biaryl Thiosemicarbazones.

$N^1$-(4-BROMOBENZYLIDENE)-$N^4$-(2,6-DIMETHYLPHENYL)THIOSEMICARBAZONE, 19A

N-(2,6-Dimethylphenyl) thiosemicarbazide, 18, (40 mg, 0.21 mmol, 1 eq) was suspended in 15 mL of absolute ethanol. 4-Bromobenzaldehyde (38 mg, 0.21 mmol, 1 eq) and 1 mL of glacial acetic acid were added and the mixture was refluxed for 1 hr. Upon cooling, solvent was removed under reduced pressure and the remaining solid was recrystallized from absolute ethanol to give 52 mg (70%) target compound (first crop). $^1$H-NMR (DMSO-$d_6$; 500 MHz): δ 11.80 (s, 1H), 9.94 (s, 1H), 8.09 (s, 1H), 7.87 (d, J=8.6 Hz, 2H), 7.60 (d, J=8.6 Hz, 1H), 7.15-7.09 (m, 3H), 2.18 (s, 6H) ppm. $^{13}$C-NMR (DMSO-$d_6$; 126 MHz): δ 176.8, 140.8, 137.1, 136.4, 133.6, 131.5, 129.4, 127.6, 126.9, 123.0, 18.0 ppm. HRMS [M+H]$^+$: calc for $C_{16}H_{16}BrN_3SH$: 362.0327; found: 362.0330 m/z.

(4009)

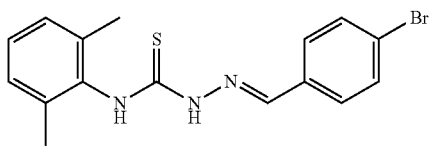

N¹-(4-BROMO-2-FLUOROBENZYLIDENE)-N⁴-(2,6-DIMETHYLPHENYL)THIOSEMICARBAZONE, 19B

¹H-NMR (DMSO-d₆; 400 MHz): δ 11.91 (s, 1H), 10.01 (s, 1H), 8.39 (dd, J=8.3 Hz, J=8.3 Hz, 1H), 8.29 (s, 1H), 7.64 (dd, J=10.3 Hz, J=1.8 Hz, 1H), 7.45 (dd, J=8.5 Hz, J=1.8 Hz, 1H), 7.12 (m, 3H), 2.18 (s, 6H). ¹⁹F-NMR: (DMSO-d₆; 282 MHz): δ −119.4 (dd, J=10.3 Hz, 8.3 Hz) ppm. HRMS [M+H]⁺: calcd for C₁₆H₁₅BrFN₃SH: 380.0232; found: 380.0244 m/z.

(6003)

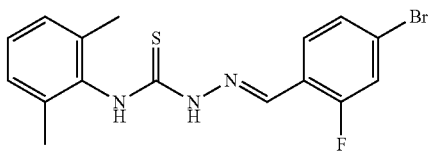

N¹-(4-BROMO-2,6-DIFLUOROBENZYLIDENE)-N⁴-(2,6-DIMETHYLPHENYL)THIOSEMICARBAZONE, 19C

¹H-NMR (DMSO-d₆; 400 MHz): δ 12.00 (s, 1H), 9.37 (s, 1H), 8.22 (s, 1H), 7.59 (d, J=8.2 Hz, 2H), 7.09 (m, 3H), 2.16 (s, 6H) ppm. ¹⁹F-NMR: (DMSO-d₆; 282 MHz): δ −110.7 (d, J=8.4 Hz) ppm. HRMS [M+H]⁺: calcd for C₁₆H₁₄BrF₂N₃SH: 398.0138; found: 398.0121 m/z.

(6004)

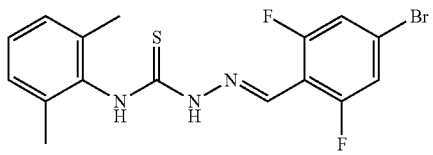

Procedures for Synthesis of Other Compounds

N-((2,6-DIMETHYLPHENYL)CARBAMOTHIOYL)BENZAMIDE

According to the literature synthesis of similar thioureas,⁶ ammonium thiocyanate (0.41 g, 5.3 mmol, 1.3 eq) was dissolved in 10 mL of acetone and benzoyl chloride (0.69 g, 4.9 mmol, 1.2 eq) was added dropwise over 5 min. The soln was brought to reflux and after 15 min, 2,6-dimethylaniline (0.50 g, 4.1 mmol, 1 eq) was added in one portion. The mixture was refluxed for an additional 30 min and then poured over ice. The yellow solid was collected by filtration and washed with H₂O and dried to give 1.10 g (95%) of N-((2,6-dimethylphenyl)carbamothioyl)benzamide.
¹H-NMR (CDCl₃; 300 MHz): δ 11.84 (s, 1H), 9.18 (s, 1H), 7.92 (m, 2H), 7.70-7.64 (m, 1H), 7.59-7.54 (m, 2H), 7.24-7.19 (m, 1H), 7.16-7.13 (m, 2H), 2.33 (s, 6H) ppm.

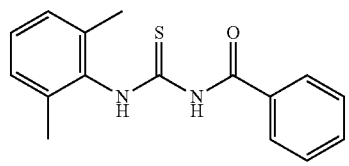

(2,6-DIMETHYLPHENYL)THIOUREA, 20

Solid N-((2,6-dimethylphenyl)carbamothioyl)benzamide (0.50 g, 1.8 mmol) was added in one portion to a 5 mL soln of 5% NaOH heated to 80° C. After 15 min of vigorous stirring the mixture is poured into ice-cold 2N HCl. The pH was then adjusted to apprx. 8.5 with Na₂CO₃ and the resulting white solid was collected by filtration, washed with H₂O, and dried to give 0.24 g (75%) of (2,6-dimethylphenyl)thiourea. ¹H-NMR (CDCl₃; 300 MHz): δ 7.51 (bs, 1H), 7.24-7.19 (m, 1H), 7.16-7.14 (m, 2H), 6.04 (bs, 1H), 5.32 (bs, 1H), 2.31 (s, 6H) ppm.

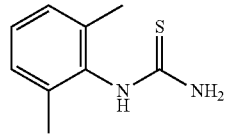

METHYL N'-(2,6-DIMETHYLPHENYL)CARBAMIMIDOTHIOATE, 21

(2,6-dimethylphenyl)thiourea (0.81 g, 4.5 mmol, 1 eq) was mixed with methyl iodide (0.77 g, 5.4 mmol, 1.2 eq) and refluxed in EtOH for 1 h. Reaction mixture was concentrated under reduced pressure, diluted with Na₂CO₃ soln and extract into Et₂O which was dried and removed give 0.89 g of methyl N'-(2,6-dimethylphenyl)carbamimidothioate (85%) as a yellow solid. ¹H-NMR (CDCl₃; 400 MHz): δ 7.02 (d, J=7.4 Hz, 2H), 6.87 (t, J=7.4 Hz, 1H), 4.27 (bs, 2H), 2.53 (bs, 3H), 2.11 (s, 6H) ppm.

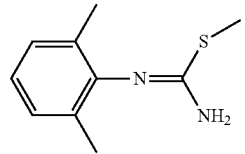

2-(4-BROMOBENZYLIDENE)-N'-(2,6-DIMETHYLPHENYL)HYDRAZINECARBOXIMIDAMIDE, 22

Methyl N'-(2,6-dimethylphenyl)carbamimidothioate (25 mg, 0.13 mmol, 1 eq) was dissolved in 2 mL of absolute ethanol which was brought to reflux and 0.1 mL glacial HOAc was added. Hydrazine monohydrate (10 mg, 0.20 mmol, 1.5 eq) was added and heating was continued for 1 h. MS analysis confirmed conversion to hydrazinecarboximidamide. The reaction mixture was concentrated under reduced pressure and then dissolved in 2 mL of absolute ethanol with 0.1 mL glacial acetic acid. 4-bromobenzaldehyde was dissolved in ethanol and added to the reaction mixture which was stirred at rt overnight. Solvent was removed and the resulting solid was purified by silica gel column chromatography (5% MeOH: DCM) which gave 22 mg (49%) of desired product. $^1$H-NMR (DMSO-$d_6$; 400 MHz): δ 8.13 (s, 1H), 7.80 (d, J=7.1 Hz, 2H), 7.60 (d, J=8.4 Hz, 2H), 7.18 (s, 3H), 2.21 (s, 6H) ppm. HRMS [M+H]$^+$: calcd for $C_{16}H_{18}BrN_4H$: 345.0715; found: 345.0703 m/z.

(6002)

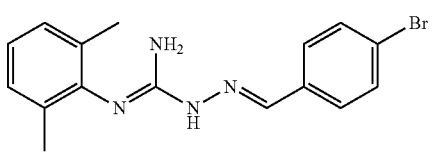

4-AZIDOBENZALDEHYDE, 25

4-azidobenzyl alcohol was prepared according to published procedure[7] from 4-iodobenzyl alcohol. $^1$H-NMR analysis demonstrated 83% conversion to 4-azidobenzyl alcohol. The crude mixture was dissolved in 4 mL of DCM to which pyridinium chlorochromate (0.285 g, 1.3 mmol, 1.2 eq) was added and stirred at rt for 1 h. The reaction mixture was filtered through a plug of silica gel, and concentrated. Purification by silica gel chromatography (3% EtOAc: $C_6$) gave 91 mg (56% overall) of 4-azidobenzaldehyde. Spectral data are in agreement with literature[8]: $^1$H-NMR (CDCl$_3$; 500 MHz): δ 9.95 (s, 1H), 7.89 (d, J=8.5 Hz, 2H), 7.17 (d, J=8.5 Hz, 2H) ppm. $^{13}$C-NMR (CDCl$_3$; 126 MHz): δ 190.7, 146.4, 133.3, 131.7, 119.6 ppm.

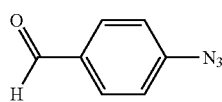

4-AZIDO-2-FLUOROBENZALDEHYDE, 26

4-Bromo-2-fluorobenzyl alcohol (0.90 g, 4.4 mmol) was combined with sodium azide (572 mg, 8.8 mmol, 2 eq), copper iodide (84 mg, 0.44 mmol, 0.1 eq) and sodium ascorbate (44 mg, 0.22 mmol, 0.05 eq). This flask was evacuated and back-filled with Ar several times. 2 mL DMSO:H$_2$O (5:1; degassed with Ar) with N,N'-dimethylethylenediamine (116 mg, 0.66 mmol, 0.15 eq) was added and the solution was stirred at 600 under Ar overnight. The solution was diluted in 10 mL of brine and extracted with EtOAc which was dried, passed through a plug of silica, and concentrated. $^1$H-NMR analysis indicated 28% conversion to 4-azido-2-fluorobenzylalcohol. Oxidation with PCC followed by silica gel chromatography gave 142 mg (20%) of 4-azido-2-fluorobenzaldehye as a white solid. $^1$H-NMR (CDCl$_3$; 400 MHz): δ 10.26 (s, 1H), 7.89 (dd, J=8.4 Hz, J=7.6 Hz, 1H), 6.94 (dd, J=8.4 Hz, J=2.1 Hz, 1H), 6.82 (dd, J=11.0 Hz, J=2.1 Hz) ppm. $^{19}$F-NMR (CDCl$_3$; 377 MHz): δ −119.8 (dd, J=11.0 Hz, J=7.6 Hz) ppm.

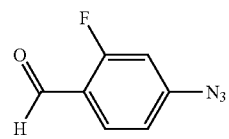

2-(4-Azidobenzylidene)-N-(2,6-dimethylphenyl)-1-(prop-2-yn-1-yl)hydrazinecarboxamide 28

Prepared from 4 following the procedure for the synthesis of 17 (28% yield). $^1$H-NMR (DMSO-$d_6$; 400 MHz): δ 8.95 (s, 1H), 8.05 (d, J=8.7 Hz, 2H), 7.92 (s, 1H), 7.15 (d, J=8.7 Hz, 2H), 7.11 (s, 3H), 4.83 (d, J=2.2 Hz, 2H), 3.26 (t, J=2.3 Hz, 1H), 2.18 (s, 6H) ppm. $^{13}$C-NMR (DMSO-$d_6$; 126 MHz): δ 152.9, 140.1, 137.9, 136.2, 135.8, 131.7, 129.1, 127.6, 126.4, 119.3, 78.1, 74.9, 30.2, 18.2 ppm. FTIR (neat): 3389, 3301, 2920, 2252, 2119, 1682, 1603, 1488, 1280, 1143, 945, 907, 730 cm$^{-1}$. HRMS [M+H]$^+$: calc for $C_{19}H_{18}N_6OH$: 347.1620; found: 347.1623 m/z.

(7003)

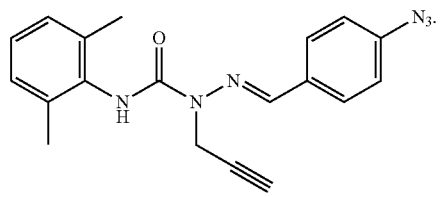

Additional examples of synthesized compounds:

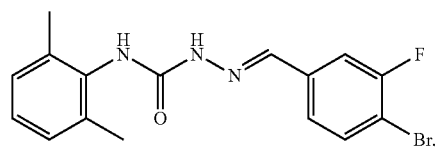

(5001)

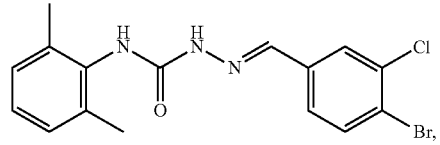

(5002)

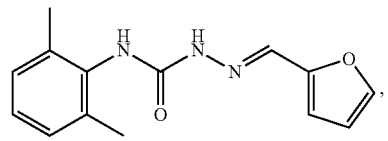

(5003)

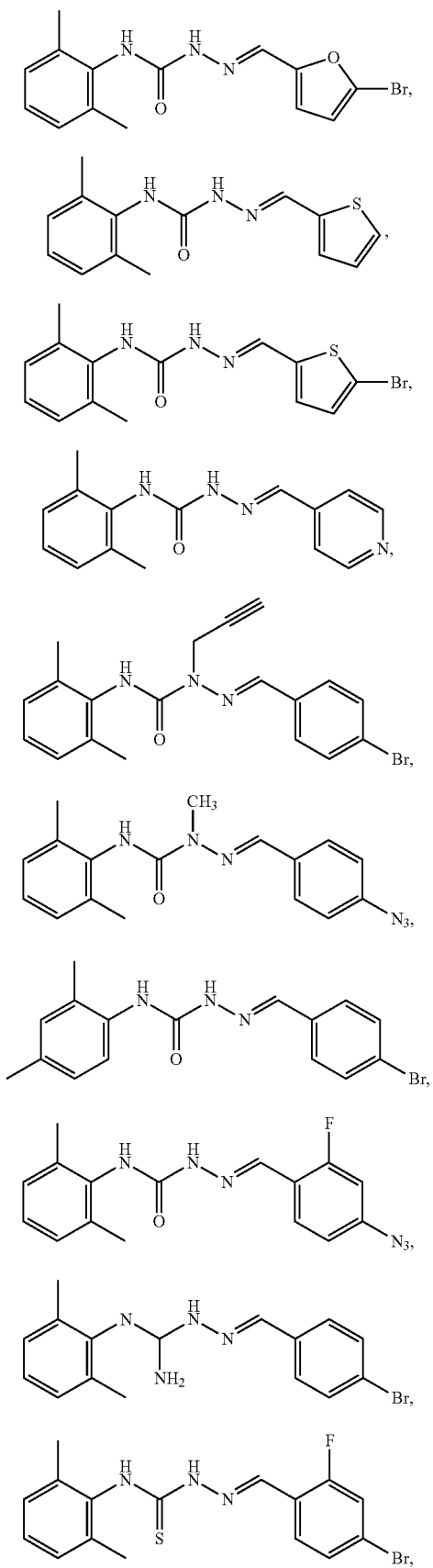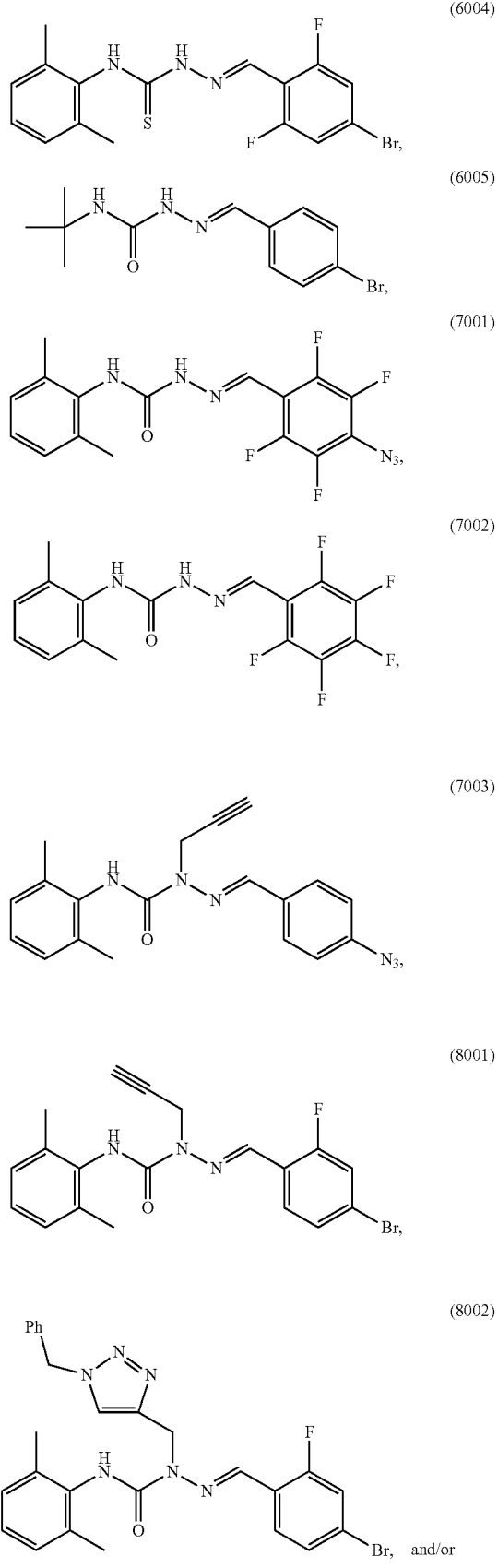

-continued
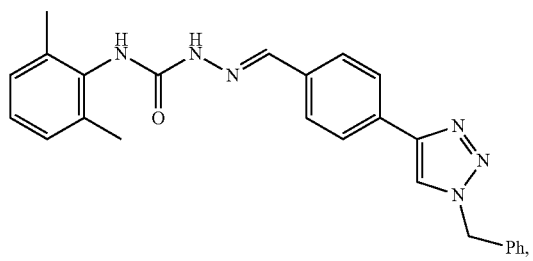 [SMILES: Cc1cccc(C)c1NC(=O)N/N=C/c1ccc(-c2cn(Cc3ccccc3)nn2)cc1]
(8003)
Example Syntheses
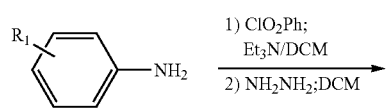
R₁ = 2,6-Me₂; 2,4-Me₂;
2,4,6-Me₃; 2,6-Et₂
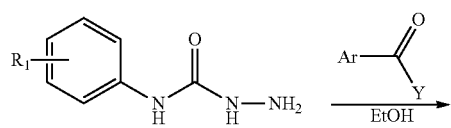
38% – 45%
-continued
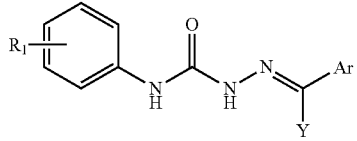
~ 70% from recryst.
Y = H, Me
35 examples
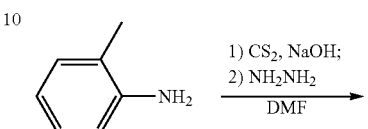
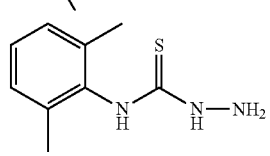
51%
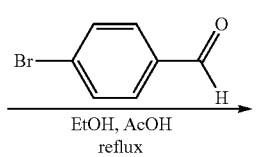
71%
Novel Semicarbazone Transformations
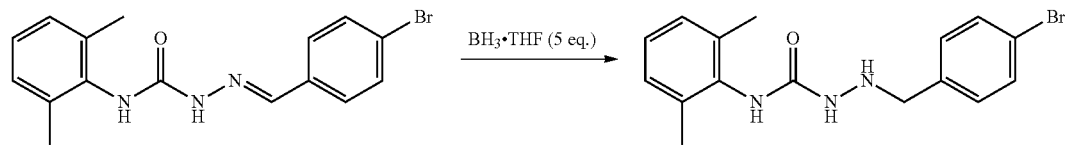
> 95% conversion
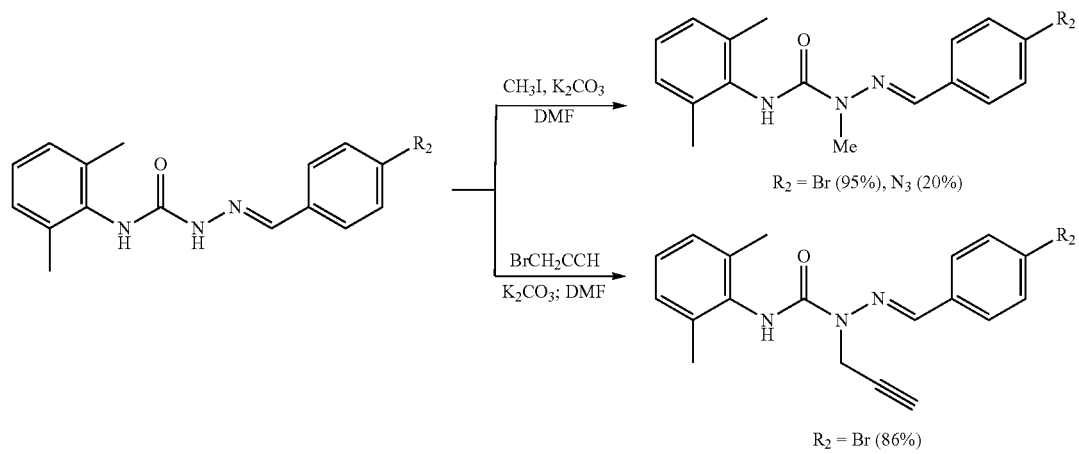
R₂ = Br (95%), N₃ (20%)
R₂ = Br (86%)

Regiochemistry confirmed via alternate synthetic route that can only provide the $N^2$-alk compound.

TABLE 1

Figure 12A:
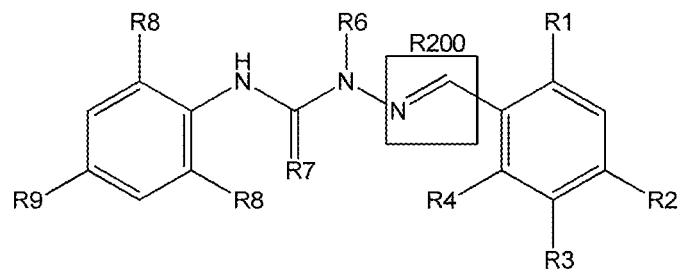
FIGS. 12A-12E: Chemical structures in accordance with some embodiments.

Blank cells in table below indicate that the R group is identical to the corresponding R group in the first row of the table below the heading row. Compounds in accordance with Table 1 are represented by the structure illustrated in FIG. 12A. (i.e. wherein Compound (=X) is EGA).

| $IC_{50}$ (In uM) | Compound (=X) | R1 | R2 | R3 | R4 | R200 | R6 | R7 | R8 | R9 |
|---|---|---|---|---|---|---|---|---|---|---|
| | 1.4 | EGA | H | Br | H | H | No Change | H | O | $CH_3$ | H |
| 100X | 1.65 | 1 (13a) | | Cl | | | | | | | |
| | 1.27 | 2 (EGA) | | | | | | | | | |
| | 7.00 | 3 (13e) | | F | | | | | | | |
| | 2.14 | 4 (13f) | | F | | F | | | | | |
| | NP | 5 (13b) | | H | $CF_3$ | Cl | | | | | |
| | 8.23 | 6 (13c) | | H | | F | | | | | |
| | NP | 7 (13i) | | H | | $CH_3$ | | | | | |
| | 1.81 | 8 (13d) | | $CH_3$ | F | | | | | | |
| | NP | 9 (13g) | | H | MeO | MeO | | | | | |
| | 13.38 | 10 (13j) | | H | $CH_3$ | | | | | | |
| 200X | 3.02 | 1 (13l) | | Et | | | | | | | |
| | 6.48 | 2 (13m) | | iPr | | | | | | | |
| | 1.69 | 3 (13o) | | C≡C—H | | | | | | | |
| | 2.82 | 4 (4) | | $N_3$ | | | | | | | |
| | NP | 5 (13p) | | NH—$SO_2$—$CH_3$ | | | | | | | |
| | 1.77 | 6 (13q) | | I | | | | | | | |
| 300X | 0.40 | 1 (2) | | Br | | F | | | | | |
| | 2.59 | 2 (13r) | | $CF_3$ | | | | | | | |
| | 2.50 | 3 (15) | | | | | ![N=C(CH3)2] | | | | |
| | NP | 4 (14) | | | | | ![NH-Et] | | | | |
| | 12.6 | 5 (9b) | | | | | | | | | $CH_3$ |
| 400X | >12.5 | 1 (13n) | | MeO | | | | | | | |
| | 2.90 | 2 (13k) | | $CH_3$ | | | | | | | |
| | 2.45 | 3 (13s) | | CN | | | | | | | |
| | NP | 4 (13h) | MeO | MeO | | MeO | | | | | |
| | 3.24 | 5 (13z) | | Br | | Cl | | | | | |
| | 3.95 | 6 (13y) | F | Br | | F | | | | | |
| | >12.5 | 7 (9c) | | | | | | | | Et | |
| | 1.96 | 8 (16) | | | | | | $CH_3$ | | | |
| | 1.52 | 9 (19a) | | | | | | | S | | |

*NP = not protective. No activity measured against anthrax lethal toxin in this assay.

TABLE 2

Structures and ATPlite data for select Chembridge analogues (in assays used to test the compounds at this time), including active and in-active compounds.

| Compound structure | ChemBridge No. | Compound name |
|---|---|---|
| benzaldehyde phenylsemicarbazone structure | 5104684 | benzaldehyde N-phenylsemicarbazone |
| 1-(2-hydroxyphenyl)-1-ethanone phenylsemicarbazone structure | 5105387 | 1-(2-hydroxyphenyl)-1-ethanone N-phenylsemicarbazone |

TABLE 2-continued

Structures and ATPlite data for select Chembridge analogues (in assays used to test the compounds at this time), including active and in-active compounds.

| Compound structure | ChemBridge No. | Compound name |
|---|---|---|
| 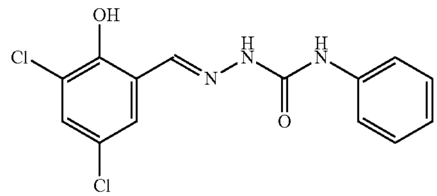 [SMILES: O=C(N/N=C/c1cc(Cl)cc(Cl)c1O)Nc1ccccc1] | 5105404 | 3,5-dichloro-2-hydroxybenzaldehyde N-phenylsemicarbazone |
| 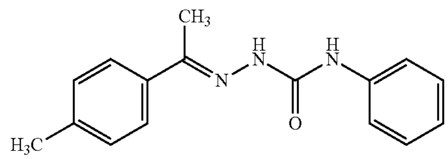 [SMILES: C/C(=N\NC(=O)Nc1ccccc1)c1ccc(C)cc1] | 5105429 | 1-(4-methylphenyl)-1-ethanone N-phenylsemicarbazone |
| 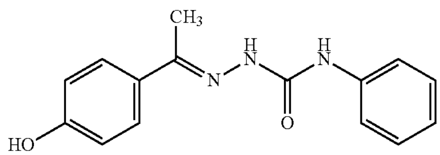 [SMILES: C/C(=N\NC(=O)Nc1ccccc1)c1ccc(O)cc1] | 5105446 | 1-(4-hydroxyphenyl)-1-ethanone N-phenylsemicarbazone |
| 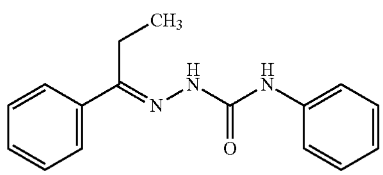 [SMILES: CC/C(=N\NC(=O)Nc1ccccc1)c1ccccc1] | 5105447 | 1-phenyl-1-propanone N-phenylsemicarbazone |
| 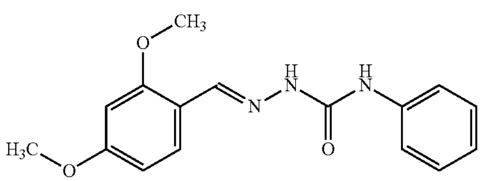 [SMILES: COc1ccc(/C=N/NC(=O)Nc2ccccc2)c(OC)c1] | 5105470 | 2,4-dimethoxybenzaldehyde N-phenylsemicarbazone |
| 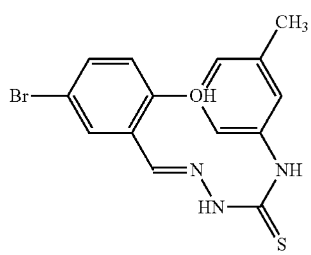 | 5257201 | 5-bromo-2-hydroxybenzaldehyde N-(3-methylphenyl)thiosemicarbazone |
| 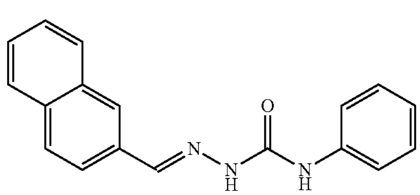 [SMILES: O=C(N/N=C/c1ccc2ccccc2c1)Nc1ccccc1] | 5284933 | 2-naphthaldehyde N-phenylsemicarbazone |
| 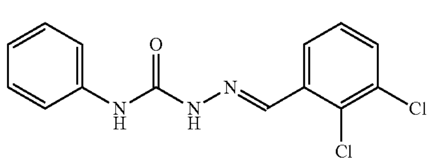 [SMILES: O=C(N/N=C/c1cccc(Cl)c1Cl)Nc1ccccc1] | 5315465 | 2,3-dichlorobenzaldehyde N-phenylsemicarbazone |

TABLE 2-continued

Structures and ATPlite data for select Chembridge analogues (in assays used to test the compounds at this time), including active and in-active compounds.

| Compound structure | ChemBridge No. | Compound name |
|---|---|---|
| 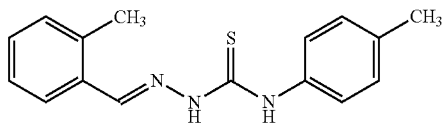 [SMILES: Cc1ccc(NC(=S)N/N=C/c2ccccc2C)cc1] | 5317779 | 2-methylbenzaldehyde N-(4-methylphenyl)thiosemicarbazone |
| 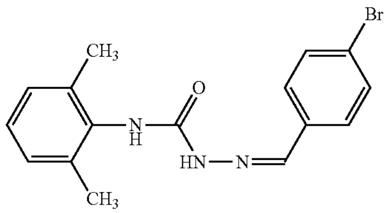 [SMILES: Cc1cccc(C)c1NC(=O)NN=Cc1ccc(Br)cc1] | 5319257 | 4-bromobenzaldehyde N-(2,6-dimethylphenyl)semicarbazone |
| 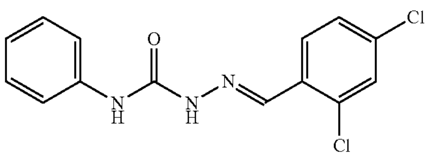 [SMILES: O=C(N/N=C/c1ccc(Cl)cc1Cl)Nc1ccccc1] | 5321252 | 2,4-dichlorobenzaldehyde N-phenylsemicarbazone |
| 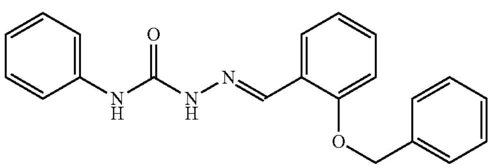 [SMILES: O=C(N/N=C/c1ccccc1OCc1ccccc1)Nc1ccccc1] | 5321767 | 2-(benzyloxy)benzaldehyde N-phenylsemicarbazone |
| 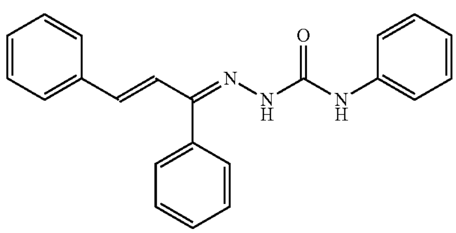 [SMILES: O=C(N/N=C(/C=C/c1ccccc1)c1ccccc1)Nc1ccccc1] | 5105364 | 1,3-diphenyl-2-propen-1-one N-phenylsemicarbazone |
| 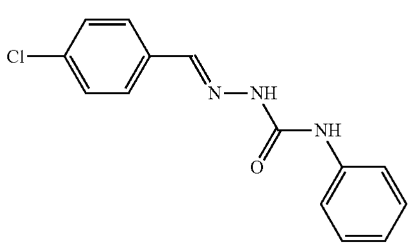 [SMILES: O=C(N/N=C/c1ccc(Cl)cc1)Nc1ccccc1] | 5191420 | 4-chlorobenzaldehyde N-phenylsemicarbazone |
| 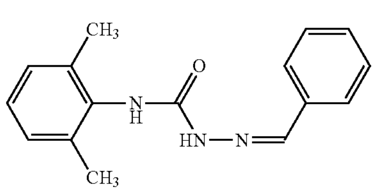 [SMILES: Cc1cccc(C)c1NC(=O)NN=Cc1ccccc1] | 5319438 | benzaldehyde N-(2,6-dimethylphenyl)semicarbazone |

TABLE 2-continued

Structures and ATPlite data for select Chembridge analogues (in assays used to test the compounds at this time), including active and in-active compounds.

| Compound structure | ChemBridge No. | Compound name |
|---|---|---|
| (structure) | 5523252 | 5-(hydroxymethyl)-2,4-dimethylbenzaldehyde semicarbazone |
| (structure) | 5529342 | N'',N'''-bis(5-bromo-2-hydroxybenzylidene)carbonohydrazide |
| (structure) | 7982104 | 2-(4-fluorophenyl)-N-(2-methylphenyl)hydrazinecarboxamide |
| (structure) | 9062150 | N-(2,6-dimethylphenyl)-N'-(4-fluorophenyl)urea |

TABLE 3

Figure 12B:
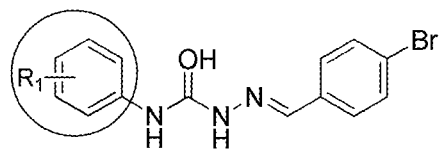

Structure-Activity Relationship of $N^4$-phenyl substituents
Compounds in accordance with Table 3 are represented by the structure illustrated in FIG. 12B.

| $R^1$ | IC$_{50}$ (µM) |
|---|---|
| 2,6-Me$_2$ (EGA) | 1.4 |
| Phenyl | Not protective |
| 2,4-Me$_2$ | Not protective |
| 2,6-Et$_2$ | 16.7 |
| 2,4,6-Me$_3$ | 12.6 |

Not protective: IC$_{50}$ > 25 µM for all tables in this Appendix

TABLE 4

Figure 12C:
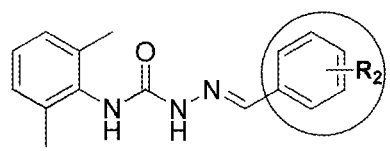

Structure-Activity Relationship of $N^1$-benzylidene substituents
Compounds in accordance with Table 4 are represented by the structure illustrated in FIG. 12C.

| R$_2$ | IC$_{50}$ (µM) | R$_2$ | IC$_{50}$ (µM) |
|---|---|---|---|
| 4-F | 7.00 | 2,4-F$_2$ | 2.1 |
| 4-Cl | 1.65 | 2-F, 4-Br | 0.4 |
| 4-Br (EGA) | 1.4 | 2-Cl, 4-Br | 3.2 |
| 4-I | 1.77 | 2,6-F$_2$, 4-Br | 3.9 |
| 4-Me | 2.9 | 2-F | 8.2 |
| 4-Et | 3.0 | 2-Me | Not protective |
| 4-iPr | 6.5 | 2,3-OMe$_2$ | Not protective |
| 4-CCH | 1.7 | 2-Cl, 3-CF$_3$ | Not protective |
| 4-OMe | >12.5 | 3-Me | 13.4 |
| 4-CN | 2.45 | 3-F, 4-Me | 1.8 |
| 4-N$_3$ | 2.8 | 3-F, 4-Br | 1.5 |
| 4-NHSO$_2$Me | Not protective | 3-Cl, 4-Br | 3.4 |
| 2,4,6-OMe$_3$ | Not protective | 4-pyr | Not protective |

TABLE 5

Figure 12D:
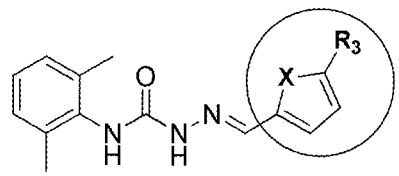

Structure-Activity Relationship of $N^1$-heterocyclic substituents
Compounds in accordance with Table 5 are represented by the structure illustrated in FIG. 12D.

| X; R$_3$ | IC$_{50}$ (µM) |
|---|---|
| O; H | Not protective |
| O; Br | Not protective |

TABLE 5-continued

Structure-Activity Relationship of $N^1$-heterocyclic substituents
Compounds in accordance with Table 5 are
represented by the structure illustrated in FIG. 12D.

| X; $R_3$ | $IC_{50}$ (µM) |
|---|---|
| S; H | Not protective |
| S; Br | 1.67 |

TABLE 6

Figure 12E:
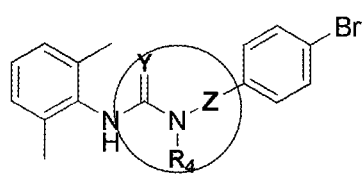

Structure-Activity Relationship of Semicarbazone Core
Compounds in accordance with Table 6 are
represented by the structure illustrated in FIG. 12E.

| Y; $R_4$; Z | $IC_{50}$ (µM) |
|---|---|
| S; H; —N=CH— | 1.52 |
| O; H; —N=CMe— | 2.5 |
| O; Me; —N=CH— | 1.96 |
| O; $CH_2CCH$; —N=CH— | >12.5 |
| O; H; —NH—$CH_2$— | Not protective |
| O; Me; —N=CH—; 4-Br replaced with 4-$N_3$ | some protection |

Summary of Structure-Activity Relationships.

Incorporation of 2,6-$Me_2$ in the $N^4$-position is important for activity. Substitution in the 4-position of the $N^1$-benzylidene is important for potency. Potency can be augmented by including a fluorine in the 2-position; however, 2,6-$F_2$, 4-Br; 2-Cl, 4-Br; and 3-F, 4-Br are less potent in compounds tested. 2-Br thiophene is a viable replacement for 4-Br phenyl in the $N^1$-position. Modifications to the semicarbazone core appear well tolerated.

L. Compound SAR

A series of derivatives of 1 were synthesized and tested, revealing precise requirements for activity in a tight and relatively flat structure-activity landscape. The 2,6-dimethyl substitution in the $N^4$-ring as well as an unaltered semicarbazone core were shown to be optimal for activity while certain modifications to the $N^1$-phenyl ring were tolerated. From the SAR, a compound more potent than the original hit was generated, namely the $N^1$-2-fluoro-4-bromophenyl analogue ($IC_{50}$=0.4 µM), 2. In addition, three photoaffinity probes, 3-5, two of which possess low micromolar activity, were designed and synthesized. One key finding is that the expected photochemistry of the phenyl azide moiety is a more important factor than the $IC_{50}$ of the photoprobe in achieving successful photolabeling. While 3 was the most potent inhibitor of intoxication by LT in the standard assay, it did not provide protection to the cells upon UV photolysis. Conversely 5, which possesses two fluorine atoms ortho to the azido function, was a poor inhibitor in the standard assay yet provided cells with the most effective irreversible protection against LT upon UV irradiation. These results highlight useful considerations for photoaffinity labeling studies in general.

Figure 8:
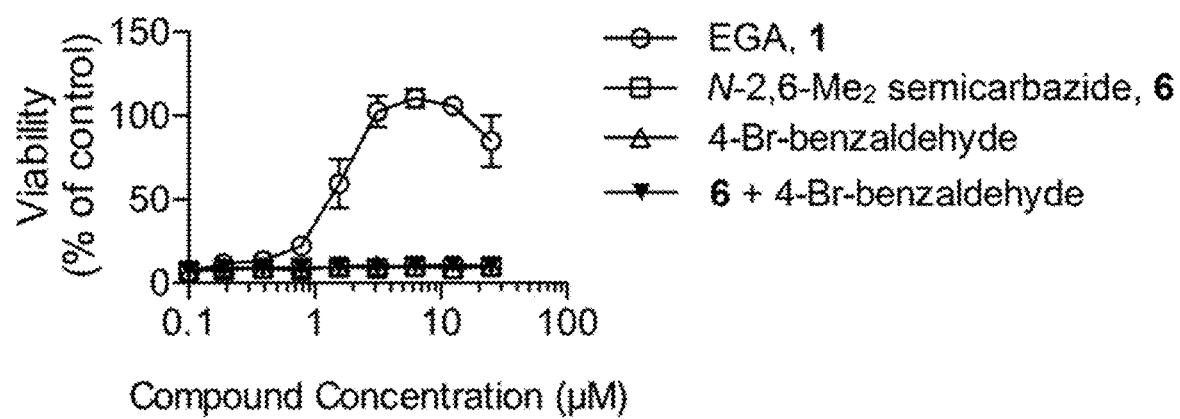
Figure 9:
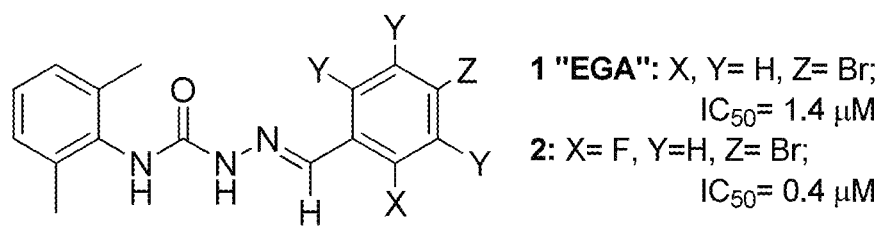
Figure 9:
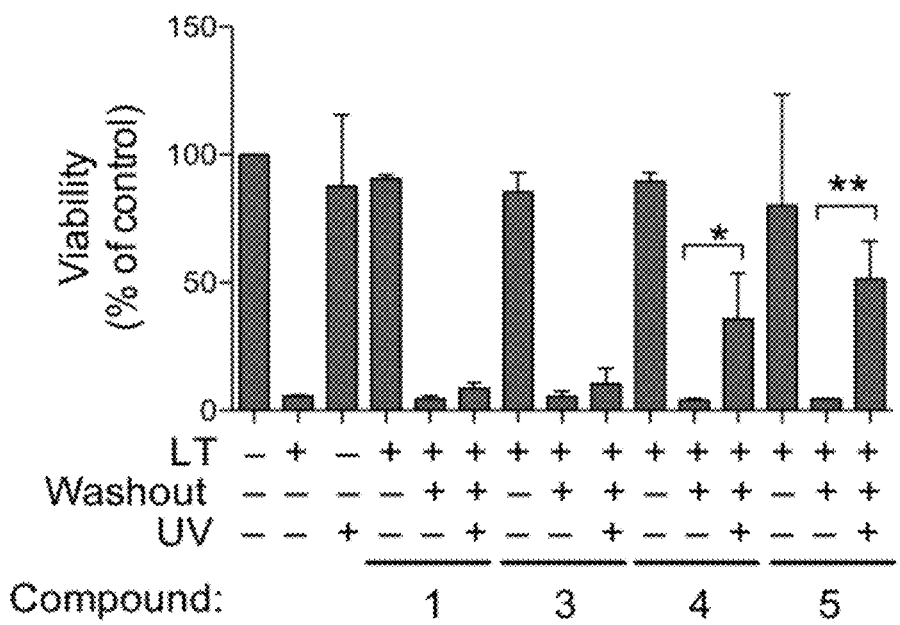
Figure 10A:
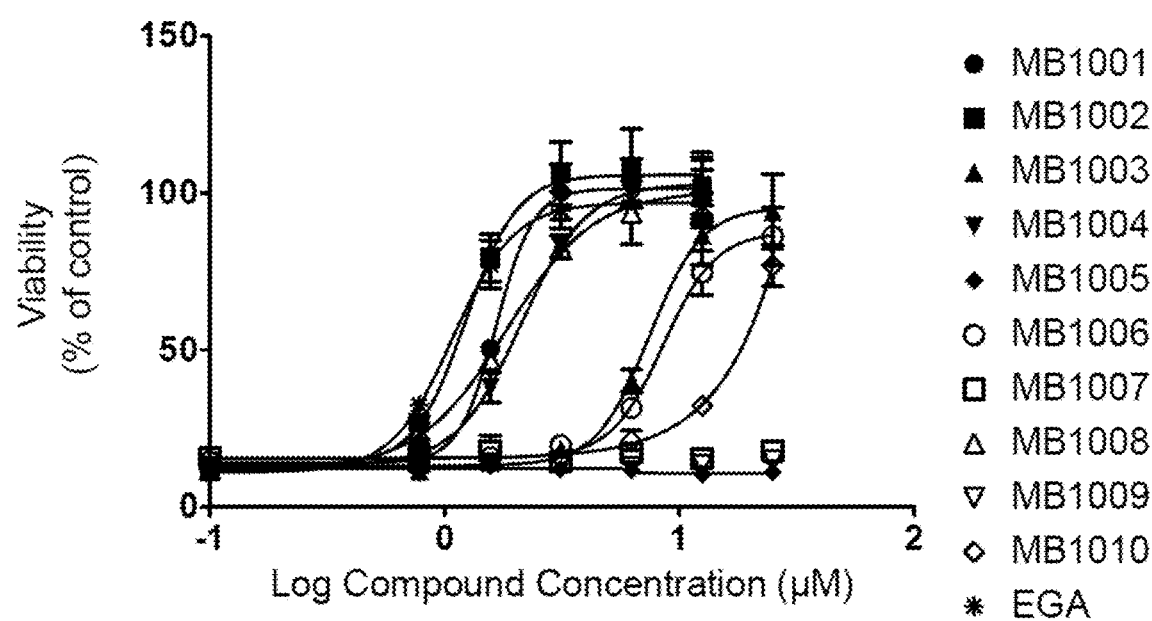
Figure 10B:
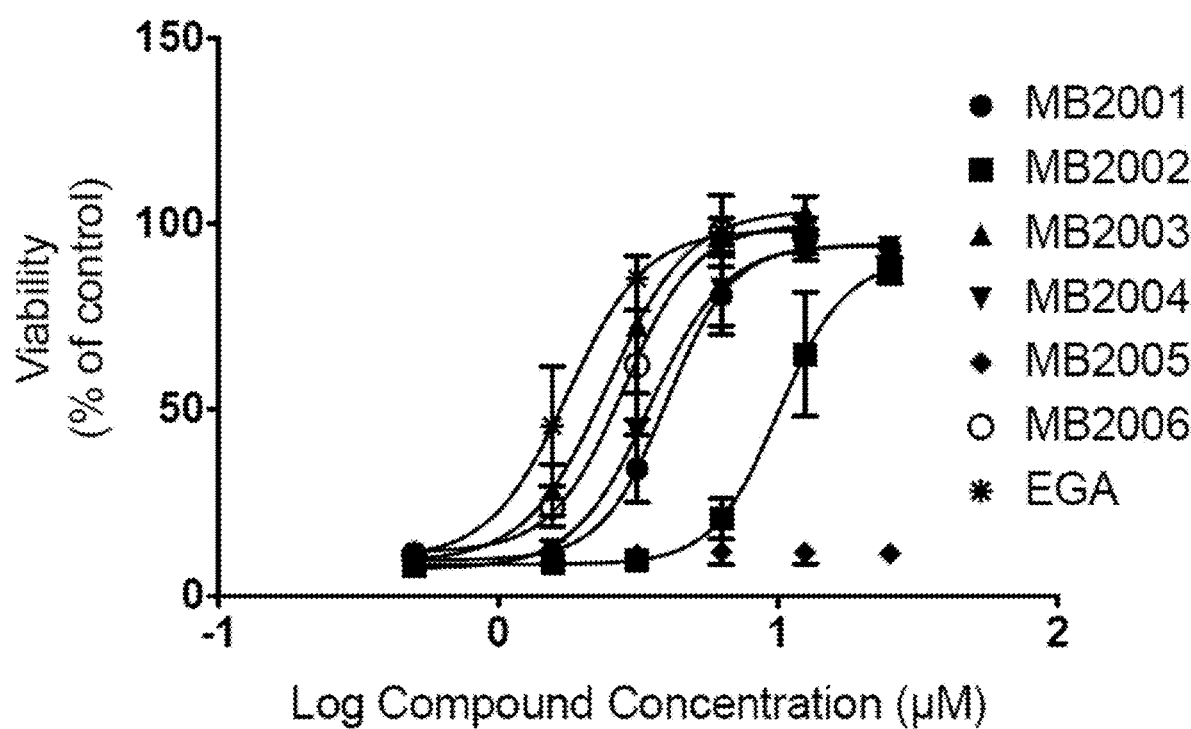
Figure 10C:
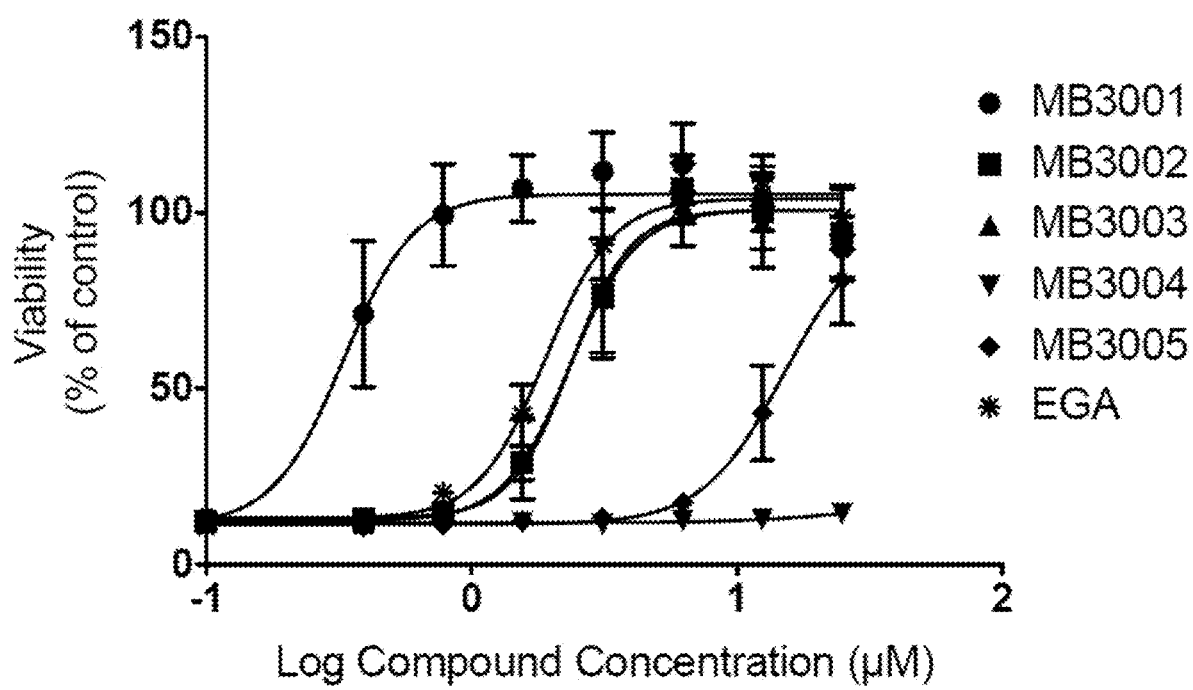
Figure 10D:
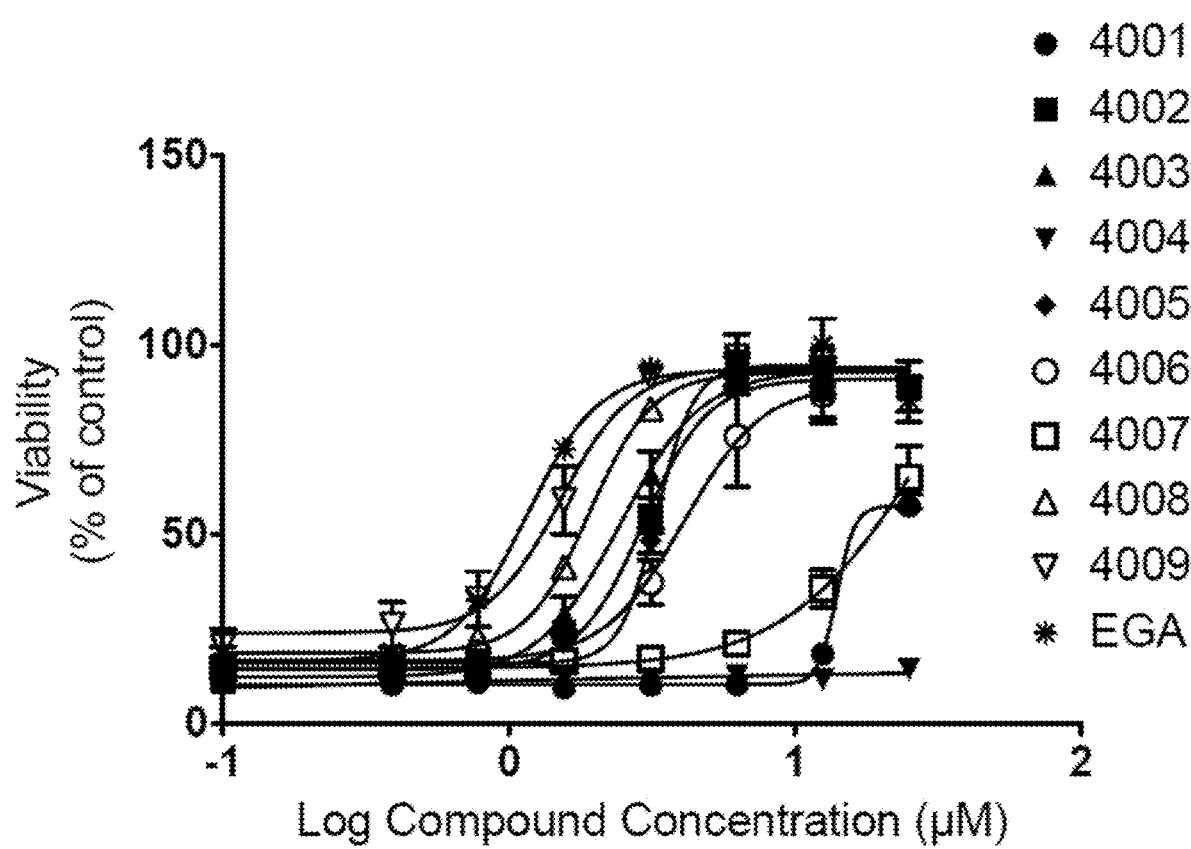
Figure 10E:
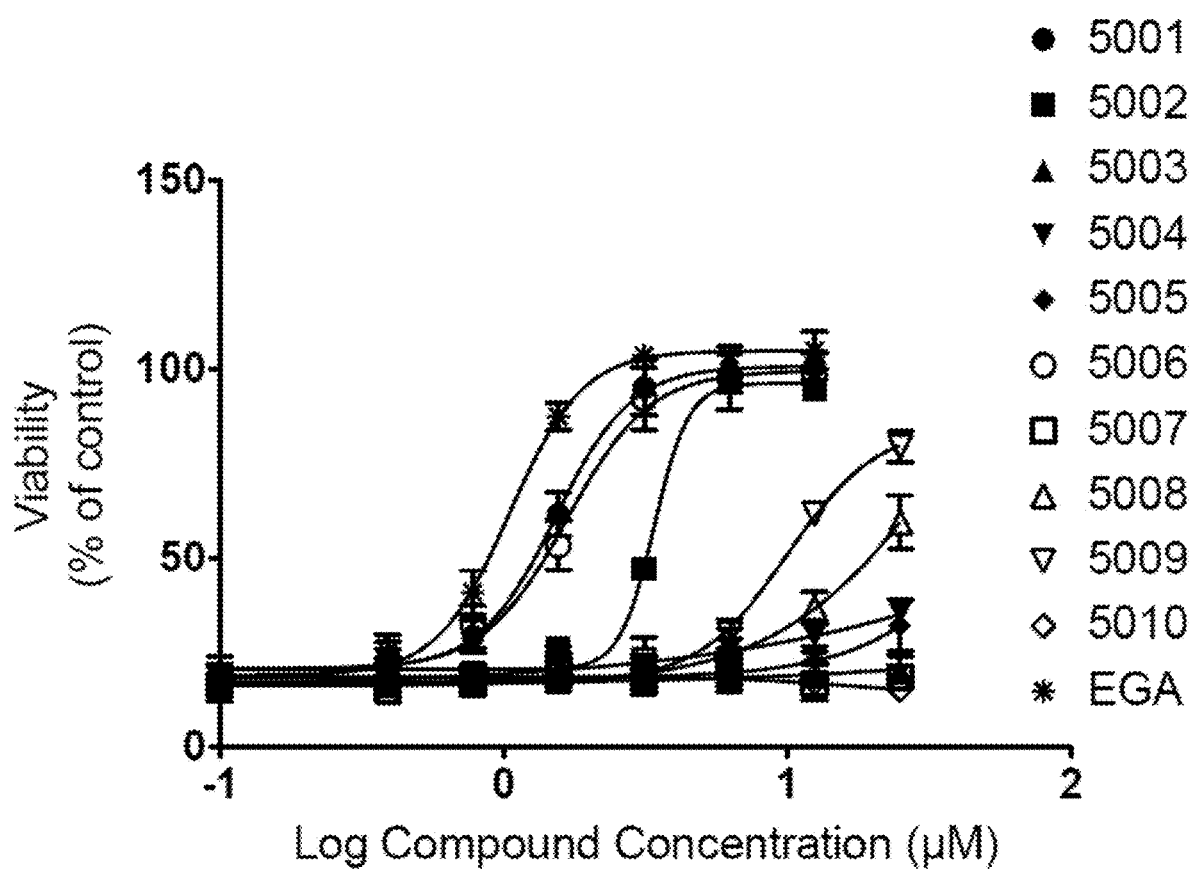
Figure 10F:
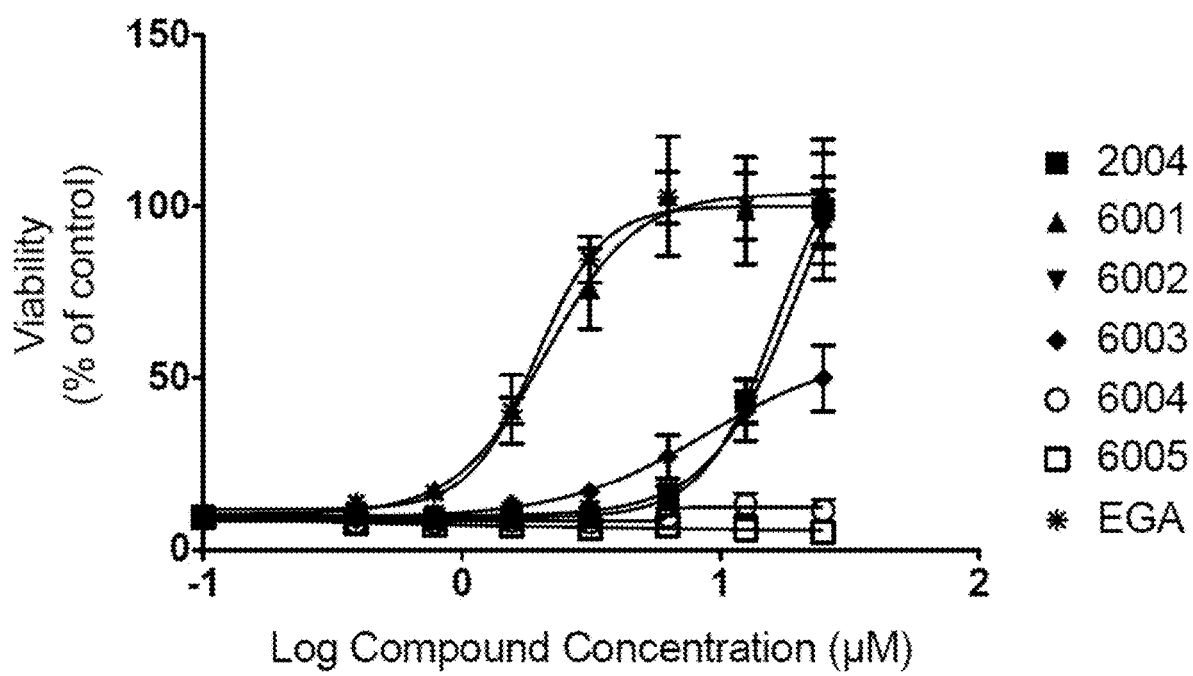
Figure 10G:
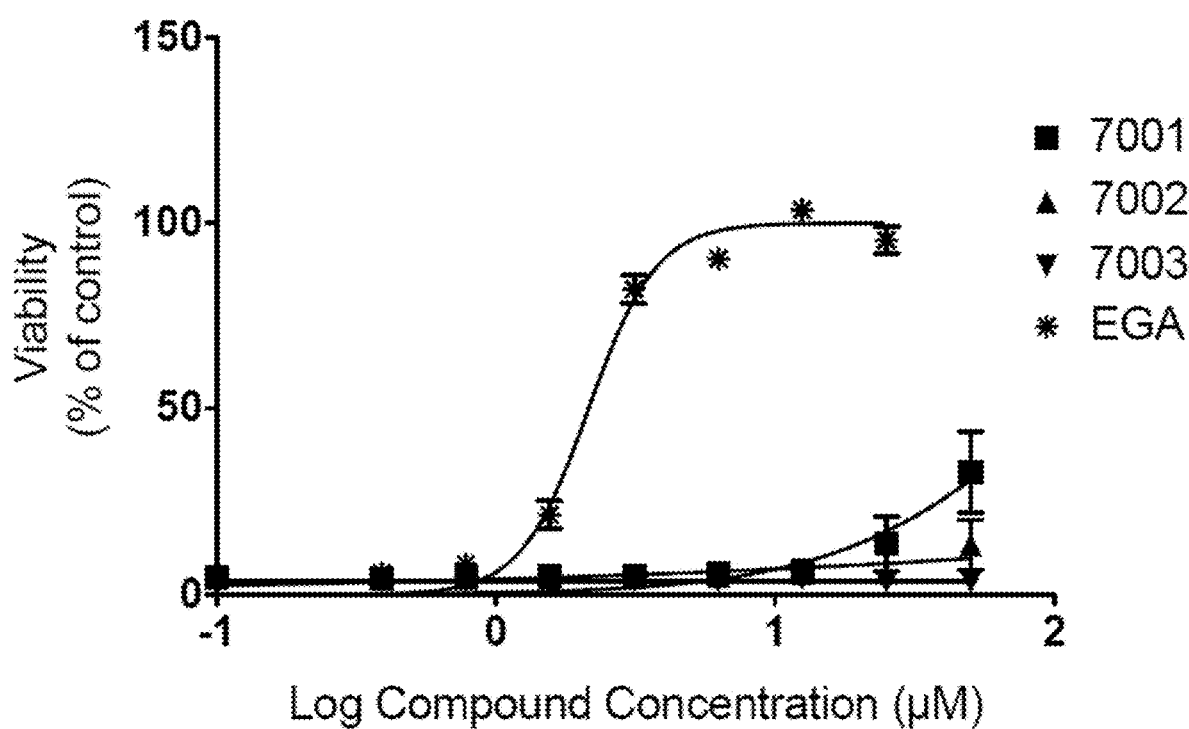
Figure 10H:
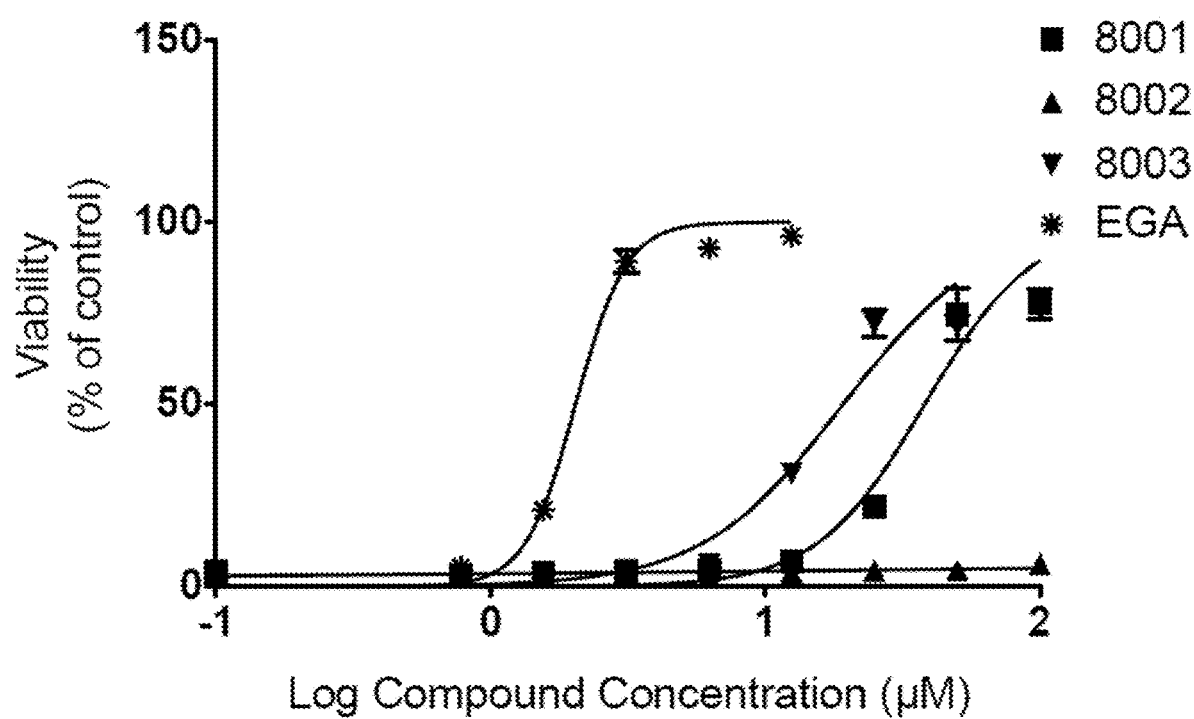
Figure 11:
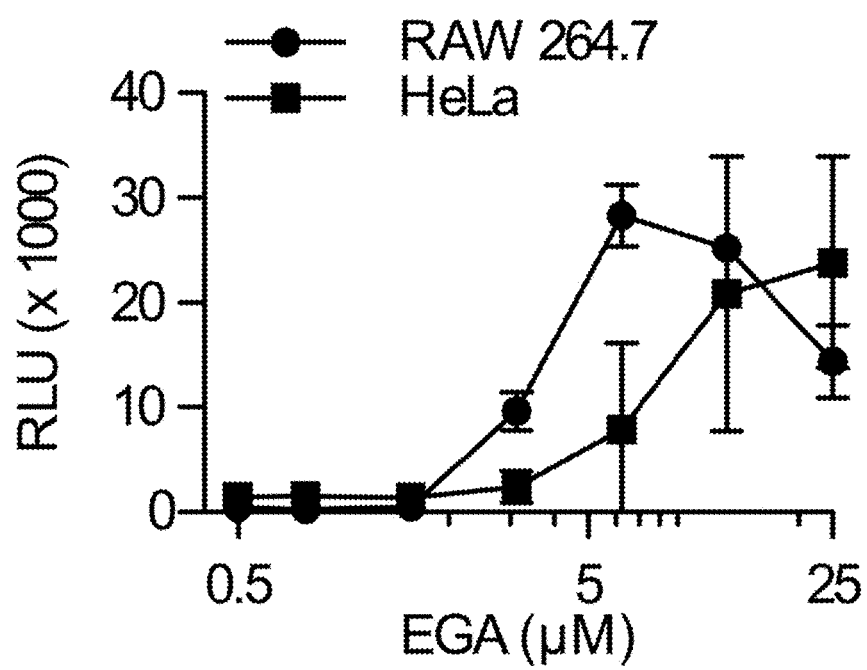

Prior to launching the structure-activity relationship study, it was confirmed that the intact semicarbazone structure of 1 was the entity responsible for the inhibition of membrane trafficking. In a previous study, semicarbazones derived from aldehyde-based Cathepsin K inhibitors were shown to have poor C=N bond stability which, along with other evidence, led researchers to conclude that the semicarbazones were functioning as prodrugs delivering a bioactive aldehyde. On the other hand, structurally distinct peptide-semicarbazones were shown to be stable in acidic media, requiring reflux to induce decomposition. In the present case, incubating RAW 264.7 macrophages with the semicarbazide (6) and the benzaldehyde component of 1 (both individually and in combination) prior to addition of LT did not prevent toxin-induced cell death, which indicates that the complete semicarbazone structure is required for bioactivity (FIG. 8).

The structure-activity relationship study began by evaluating the importance of the $N^4$-2,6-dimethylphenyl moiety for the bioactivity of 1. Several N-substituted semicarbazides (6, 7a-c) were synthesized by reaction of hydrazine with an intermediate phenyl carbamate, or via direct addition of hydrazine with tert-butyl isocyanate (8). Condensation of these semicarbazides with 4-bromobenzaldehyde proceeded well in all examples and the desired products (1, 9a-c, and 10) were obtained pure by recrystallization (Scheme 1). The stereochemistry of the semicarbazone double-bond is assigned as E based on analogy with known benzaldehyde semicarbazone structures.

Scheme 1. Synthesis of 1, 9a-c, 10.

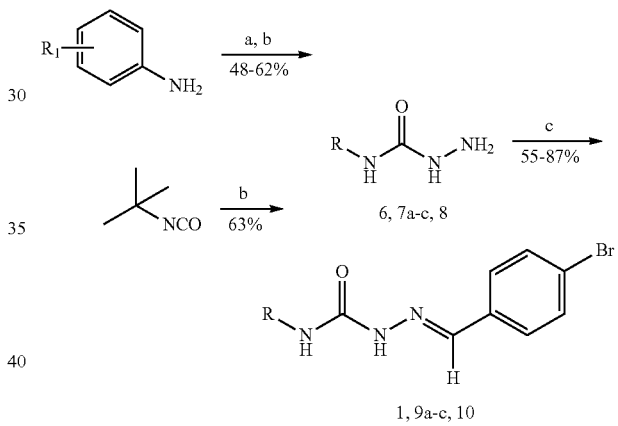

Reagents and conditions: (a) $ClCO_2Ph$, $Et_3N$, DCM, rt; (b) $NH_2NH_2\cdot H_2O$, DCM, rt; (c) 4-Br$C_6H_4$CHO, EtOH, HOAc, reflux. 6 = 2,6-dimethylphenyl semicarbazide, 7a = 2,4-dimethylphenyl semicarbazide, 7b = 2,4,6-trimethylphenyl semicabazide, 7c = 2,6-diethylphenyl semicabazide, 8 = tert-butyl.

Cell viability data demonstrated the critical importance of the 2,6-dimethylphenyl moiety for the inhibition of membrane trafficking (Table 7). For the less active analogues, precise $IC_{50}$ values were not determined due to poor solubility above 25 µM. These compounds are characterized by an activity limit (i.e. >12.5 µM, >25 µM) or as 'not protective' if no bioactivity was observed up to 25 µM. Thus compounds lacking this motif (9a, 10, and 11) were not protective, and a 2,6-diethylphenyl moiety (9c) displayed significantly diminished bioactivity ($IC_{50}$>12.5 µM). Additionally, the $N^4$-2,4,6-trimethylphenyl analogue 9b was approximately 10-fold less active than 1.

Examination of the $N^1$-position began with the synthesis and testing of ten compounds prepared from a variety of benzaldehydes (13a-j) (Table 8). The bioactivity supported the hypothesis from preliminary SAR work (i.e., 12) that substitution in the 4-position was important for potency. Next, nine compounds prepared from 4-substituted benzaldehydes were examined in order to give more detailed characterization of that important position (13k-s). Substitution in this position was found to be generally well tolerated with 9 of the 13 compounds featuring a benzylidene motif substituted only in the 4-position registering an $IC_{50}$ between 1 and 4 µM. Five analogues consisting of heterocyclic rings were also synthesized. While 13t-13w did not offer protection to cells challenged with LT, the 5-bromothiophen-2-ylmethylene example (13x) possessed bioactivity similar to 1 ($IC_{50}$ 1.7 µM and 1.4 µM, respectively).

TABLE 7

Inhibition of LT-induced cell death by 1, 9a-c, 10, 11.

| Entry | | $IC_{50}$ (µM) |
|---|---|---|
| 1 | 2,6-(Me)$_2$C$_6$H$_3$ | 1.4 ± 0.2 |
| 9a | 2,4-(Me)$_2$C$_6$H$_3$ | NP |
| 9b | 2,4,6-(Me)$_3$C$_6$H$_2$ | 12.6 ± 2.2 |
| 9c | 2,6-(Et)$_2$C$_6$H$_3$ | >12.5 |
| 10 | t-Bu | NP |
| 11* | Ph | NP |

*$N^1$-(4-Cl-benzylidene)-$N^4$-phenylsemicarbazone was obtained commercially and tested previously. Note that bioactivity of 13a is similar to 1.
NP = not protective.

The fact that the $N^1$-2,4-difluoro analogue (13f) was notably more potent than the analogue from 4-fluorobenzaldehyde (13e) ($IC_{50}$=2.1 µM vs. $IC_{50}$=7.0 µM) led to examination of whether including a fluorine in the 2-position of the $N^1$-ring would similarly augment the potency of 1. Indeed, compound 2 displayed a significant increase in activity ($IC_{50}$=0.4 µM). Encouraged by this result compounds 13y-13ab were synthesized and tested, which gave $IC_{50}$ values that were all larger than the original lead compound 1.

The effects of modifications made to the semicarbazone core are compiled in Scheme 2. The imine bond of 1 could be effectively reduced to the disubstituted hydrazine derivative (14) using an excess of borane in THF with heating. The compound was not protective at the concentrations tested. The 1-(4-bromophenyl)-ethylidene analogue (15) was synthesized by the condensation of the semicarbazide 6 with 4'-bromoacetophenone. This change caused a minor reduction in potency with 15 showing an $IC_{50}$ of 2.5 µM. The semicarbazone core of 1 could be methylated with high regioselectivity by treatment with iodomethane and K$_2$CO$_3$ in DMF to give 16. Synthesis of 16 via addition of methyl hydrazine to 4-bromobenzaldehyde followed by reaction with phenyl (2,6-dimethylphenyl)carbamate gave a product with identical $^1$H-NMR and $^{13}$C-NMR spectra and thus confirmed the regiochemistry of methylation at the $N^2$-position. The bioactivity of 16 was not significantly affected compared to 1 ($IC_{50}$=2.0 µM and 1.4 µM respectively). Incorporating a propargyl group into this position by alkylation with propargyl bromide generated 17, which had somewhat impaired bioactivity ($IC_{50}$>12.5 µM).

Scheme 2. Synthesis and bioactivity of 14, 16, and 17.

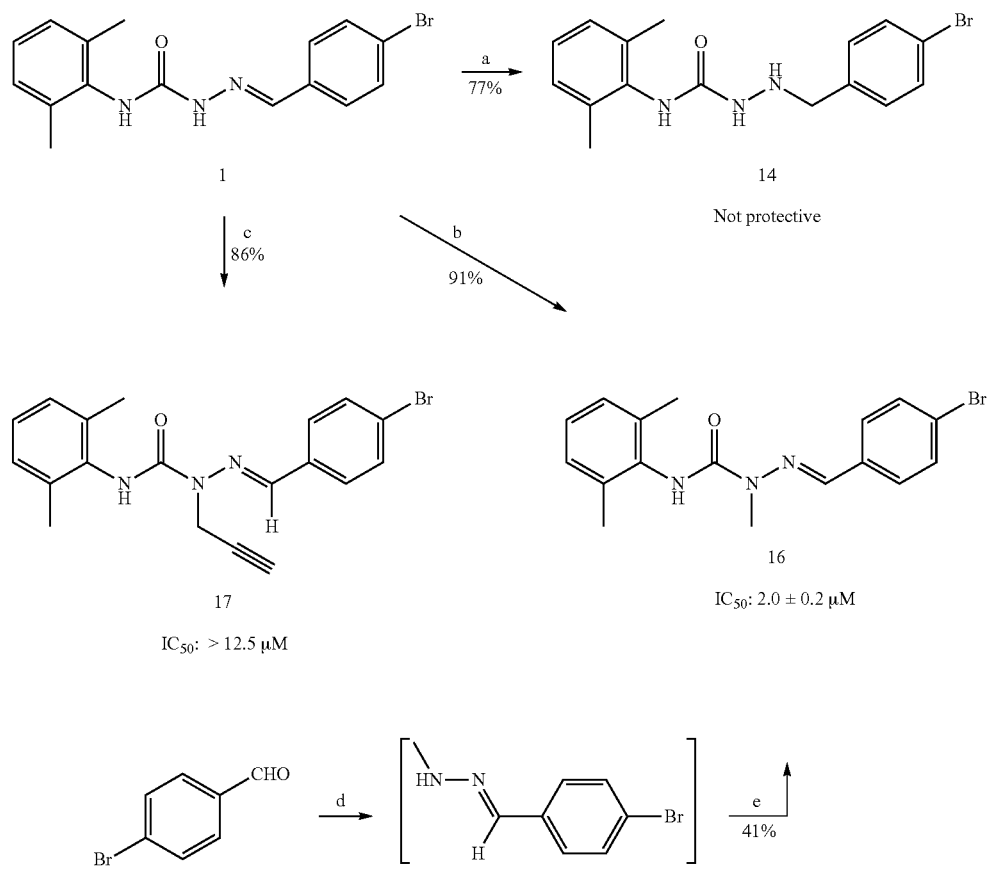

Reagents and conditions: (a) BH$_3$•THF, 50° C.; (b) MeI,K$_2$CO$_3$, DMF, rt; (c) BrCH$_2$CCH, K$_2$CO$_3$, DMF, rt; (d) NH$_2$NH$_2$•H$_2$O,EtOH, reflux; (e) Ph 2,6-Me$_2$phenyl carbamate, EtOH.

TABLE 8

Inhibition of LT-induced cell death by 1, 2, 12-13ab, 15, and 28.

Structure

| Entry | 12-13ab | IC$_{50}$ (μM) |
|---|---|---|
| 1 | Ar= 4-BrC$_6$H$_4$ | 1.4 ± 0.2 |
| 2 | 4-Br-2-FC$_6$H$_3$ | 0.4 ± 0.2 |
| 12* | Ph | NP |
| 13a | 4-ClC$_6$H$_4$ | 1.7 ± 0.2 |
| 13b | (2-Cl-3-CF$_3$)C$_6$H$_3$ | NP |
| 13c | 2-FC$_6$H$_4$ | 8.2 ± 1.6 |
| 13d | (3-F-4-Me)C$_6$H$_3$ | 1.8 ± 0.4 |
| 13e | 4-FC$_6$H$_4$ | 7.0 ± 1.3 |
| 13f | 2,4-F$_2$C$_6$H$_3$ | 2.1 ± 0.4 |
| 13g | 2,3-(OMe)$_2$C$_6$H$_3$ | NP |
| 13h | 2,4,6-(OMe)$_3$C$_6$H$_3$ | NP |
| 13i | 2-MeC$_6$H$_4$ | NP |
| 13j | 3-MeC$_6$H$_4$ | 13.4 ± 1.3 |
| 13k | 4-MeC$_6$H$_4$ | 2.9 ± 0.1 |
| 13l | 4-EtC$_6$H$_4$ | 3.0 ± 0.5 |
| 13m | 4-iPrC$_6$H$_4$ | 6.5 ± 0.6 |
| 13n | 4-(OMe)C$_6$H$_4$ | >12.5 |
| 13o | 4-(CCH)C$_6$H$_4$ | 1.7 ± 0.6 |
| 13p | 4-(NHSO$_2$Me)C$_6$H$_4$ | NP |
| 13q | 4-IC$_6$H$_4$ | 1.8 ± 0.3 |
| 13r | 4-(CF$_3$)C$_6$H$_4$ | 2.6 ± 0.5 |
| 13s | 4-CNC$_6$H$_4$ | 2.5 ± 0.3 |
| 13t | 4-Pyridyl | NP |
| 13u | 2-Furyl | NP |
| 13v | (5-Br-2-Furyl) | >25 |
| 13w | 2-Thiophenyl | >25 |
| 13x | (5-Br-2-Thiophenyl) | 1.7 ± 0.3 |
| 13y | 4-Br-2,6-F$_2$C$_6$H$_2$ | 4.0 ± 0.8 |
| 13z | 4-Br-2-ClC$_6$H$_3$ | 3.2 ± 0.1 |
| 13aa | 4-Br-3-FC$_6$H$_3$ | 1.5 ± 0.1 |
| 13ab | 4-Br-3-ClC$_6$H$_3$ | 3.4 ± 0.1 |
| 15 | | 2.5 ± 0.6 |
| 28 | | NP |

*Compound was obtained commercially and tested previously. NP = not protective.

The thiosemicarbazones (19a-c) were synthesized from N-2,6-dimethylphenyl thiosemicarbazide, 18, and the corresponding benzaldehyde in refluxing ethanol and acetic acid-(Scheme 3). Substituting the carbonyl of 1 with a thiocarbonyl 19a had little effect on the potency of the compound (IC$_{50}$=1.5 μM) while exacerbating an already problematic solubility profile. For example, compounds 19b and 19c were poorly soluble at assay concentrations (cLogP: 19a, 5.8; 19b, 6.0; 19c, 6.1; 1, 5.2) and did not return meaningful dose-response curves. A significantly more soluble C=NH compound (22) (cLogP: 3.9-4.0) was elaborated from the S-methylation of (2,6-dimethylphenyl)thiourea, 20, to give 21, followed by displacement with hydrazine and condensation with 4-bromobenzaldehyde to give the hydrazinecarboximidamide, 22. Unfortunately, the bioactivity of this compound was diminished (IC$_{50}$=13.8 μM).

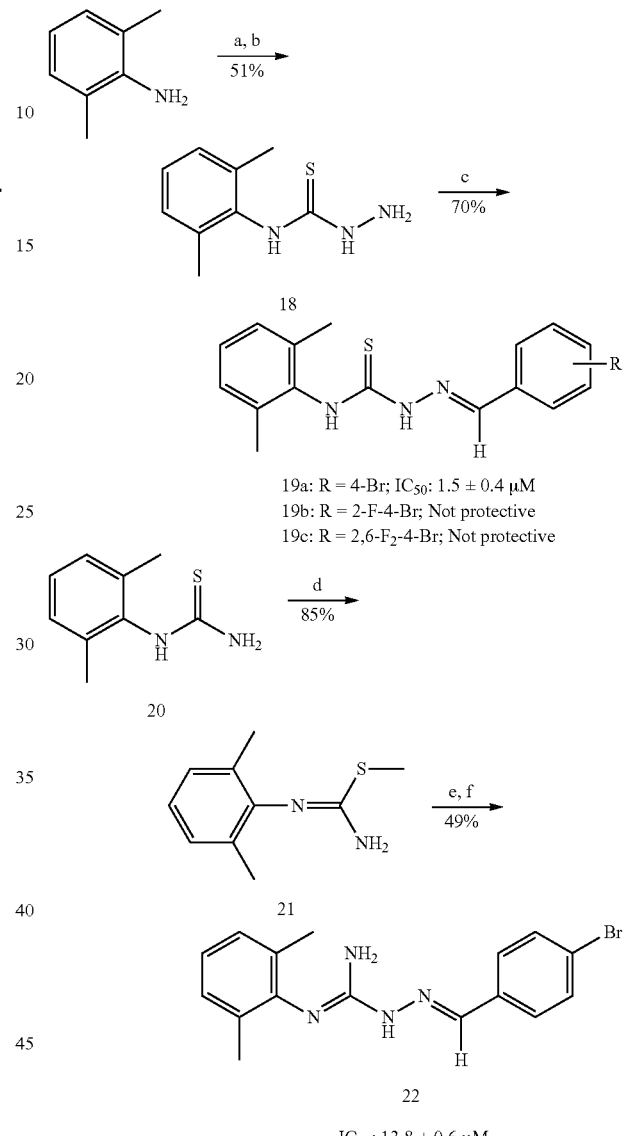

Scheme 3. Synthesis and bioactivity of 19a-c and 22.

19a: R = 4-Br; IC$_{50}$: 1.5 ± 0.4 μM
19b: R = 2-F-4-Br; Not protective
19c: R = 2,6-F$_2$-4-Br; Not protective

IC$_{50}$: 13.8 ± 0.6 μM

Reagents and conditions: (a) CS$_2$, NaOH, DMF; (b) NH$_2$NH$_2$·H$_2$O,DMF; (c) 4-BrC$_6$H$_4$CHO,, EtOH, HOAc, reflux; (d) MeI, EtOH, reflux, Na$_2$CO$_3$; (e) NH$_3$NH$_2$·H$_2$O, EtOH, HOAc, reflux; (f) 4-BrC$_6$H$_4$CHO,, EtOH, HOAc, reflux.

From the structure-activity relationship data, it was evident that the most effective photoaffinity probe would contain an N$^4$-2,6-dimethylphenyl unit, an unmodified semicarbazone core, and a 4-substituted benzylidene motif at the N$^1$-position. As the course of phenyl azide photolysis is known to be sensitive to the substituents of the phenyl azide, three photoaffinity labels were designed. The first, 3, would be predicted by the SAR to provide the highest potency in the in vitro assay. The second, 4, would consist of a simple phenyl azide commonly employed in the biochemical literature. The third molecule, 5, would flank the azido group with fluorines, a modification known to give a longer-lived singlet nitrene that can more effectively yield genuine insertion products upon photolysis.

Compounds 3, 4 and 5 were synthesized from 6 and the desired azido-containing benzaldehyde (4-azidobenzaldehyde (25), 4-azido-2-fluorobenzaldehdye (26), and 4-azido-2,3,5,6-tetra-fluorobenzaldehyde (27)), in the usual manner. Compound 25 could be obtained from the ethylene acetal of 4-nitrobenzaldehyde via catalytic hydrogenation and diazotization followed by reaction with sodium azide. In this study we chose to perform an Ullmann-type coupling with 4-iodobenzyl alcohol (23) and sodium azide followed by oxidation to the aldehyde (Scheme 4). This protocol was convenient on the milligram scale and provided access to the previously undescribed 26 from 4-bromo-2-fluoro-benzyl alcohol, 24. Compound 27 was synthesized according to a known procedure via an $S_NAr$ reaction of sodium azide with pentafluorobenzaldehyde.

Scheme 4. Synthesis and bioactivity of photoaffinity probes 3 and 4.

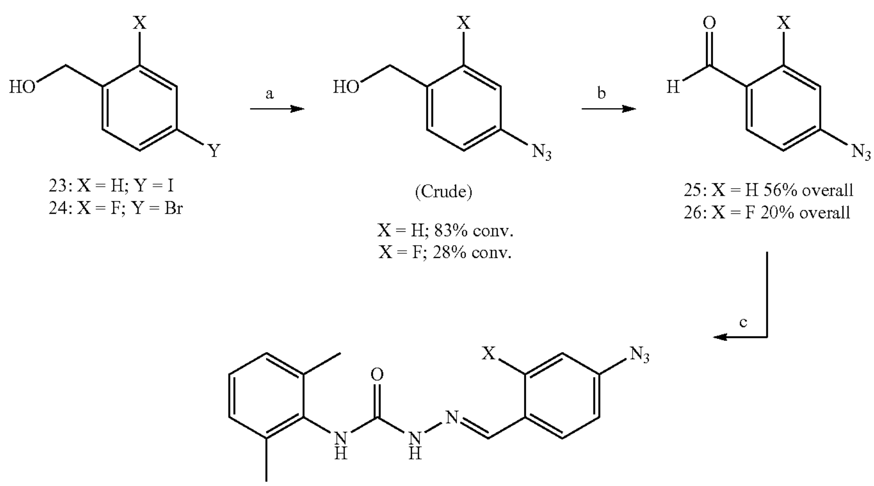

23: X = H; Y = I
24: X = F; Y = Br

25: X = H 56% overall
26: X = F 20% overall

3: X = F; $IC_{50}$: 2.2 ± 0.5 μM
4: X = H; $IC_{50}$: 2.8 ± 0.6 μM

Reagents and conditions: (a) $NaN_3$, CuI, $MeHNCH_2CH_2NHMe$, Na ascorbate, DMSO/$H_2O$; (b) PCC, DCM; (c) 5, EtOH, HOAc, reflux.

As predicted, 3 and 4 were inhibitors of LT membrane trafficking with 4 having an $IC_{50}$ of 2.8 μM and 3 giving an even more potent $IC_{50}$ of 2.2 μM, while 5 was only weakly protective against LT, beginning to show a biological effect at 25 μM. The reversibility of inhibition by 3-5 was confirmed by incubating cells with inhibitor-containing media and then exchanging it for fresh media prior to intoxication with LT. As expected, the arylsemicarbazones could be 'washed-out' and there was no cell viability in these experiments upon exposure to LT (FIG. 9). Irradiating the cell cultures incubated with 4 and 5 with 5 min of ultraviolet (UVB) light prior to media exchange conferred significant protection on cells against LT. Compound 3 did not offer statistically significant protection after UVB photolysis and media exchange. The irreversible protection provided to cells upon the irradiation of 4 and 5 implies that these compounds form covalent linkages with the target protein upon exposure to UVB light.

A common strategy for identifying proteins bound by photoaffinity probes is to incorporate an alkynyl moiety into the photoaffinity probe that can be conjugated with an azido-containing fluorescent dye following cell lysis. Given the low activity of 17 and the limited potential for making modifications in the $N^4$-phenyl ring, it is not apparent how such a 'clickable' linker could be included into a bioactive photoaffinity version of 1. Nevertheless, the convenience of this approach led us to synthesize compound 28, an $N^2$-propargyl analogue of 4 (Table 8). This compound did not offer any protection to cells at any concentration tested. Accordingly, radiolabelled versions of 5 are being considered as a means of identifying the bound proteins.

In conclusion, we have conducted a structure-activity relationship study that has examined how modifications in the struc-ture of 1 affect the cellular entry of LT. The data indicate a tight and relatively flat SAR, with many of the original structural fea-tures of 1 being preferred for bioactivity. Inclusion of a fluorine in the 2-position of the $N^1$-benzylidene portion appears to be a general strategy for increasing the potency of these arylsemicarbazones and, in the case of 2, improved potency to mid-nanomolar levels. The photoaffinity probes 3, 4 and 5 were synthesized from azido-containing benzaldehydes. Photolysis of 4 and 5 in the presence of RAW 264.7 cells conferred irreversible resistance to LT and implies that covalent bonds with the cellular target were generated. We are in the process of designing and preparing radiolabelled versions of these compounds to facilitate target identification.

M. References

1. Knodler L A, et al. (2001) Nature reviews. Molecular cell biology 2(8):578-588, 2. Sandvig K & van Deurs B (2005) Gene therapy 12(11):865-872, 3. Saenz J B, et al. (2007) Infection and immunity 75(9):4552-4561, 4. Wahome P G, et al. (2010) Toxicon: official journal of the International Society on Toxinology 56(3):313-323, 5. Stechmann B, et al. (2010) Cell 141(2):231-242, 6. Duesbery N S, et al. (1998) Science 280(5364):734-737, 7. Vitale G, et al. (1999) J Appl Microbiol 87(2):288, 8. Moayeri M & Leppla S H (2009) Molecular aspects of medicine 30(6):439-455, 9. Beall F A, et al. (1962) J Bacteriol 83:1274-1280, 10. Milne J C, et al. (1994) J Biol Chem 269(32):20607-20612, 11. Mogridge J, et al. (2002)

Proc Natl Acad Sci USA 99(10):7045-7048, 12. Kintzer A F, et al. (2009) J Mol Biol 392(3):614-629, 13. Bradley K A, et al. (2001) Nature 414(6860):225-229, 14. Scobie H M, et al. (2003) Proc Natl Acad Sci USA 100(9):5170-5174, 15. Bradley K A, et al. (2003) J Biol Chem 278(49):49342-49347, 16. Go M Y, et al. (2009) Infection and immunity 77(1):52-59, 17. Garlick K M & Mogridge J (2009) Biochemistry 48(44):10577-10581, 18. Abrami L, et al. (2006) J Cell Biol 172(2):309-320, 19. Abrami L, et al. (2003) J Cell Biol 160(3):321-328, 20. Abrami L, et al. (2010) PLoS pathogens 6(3):e1000792, 21. Lu Q, et al. (2004) Proc Natl Acad Sci USA 101(49):17246-17251, 22. Koehler T M & Collier R J (1991) Mol Microbiol 5(6):1501-1506, 23. Akai Y, et al. (2000) Rinsho Byori 48(9):867-871, 24. McCabe E S & Beall S T (1955) Am Pract Dig Treat 6(9):1310-1312, 25. Milne J C & Collier R J (1993) Mol Microbiol 10(3):647-653, 26. Miller C J, et al. (1999) Biochemistry 38(32):10432-10441, 27. Abrami L, et al. (2004) J Cell Biol 166(5):645-651, 28. Terra J K, et al. (2010) J Immunol 184(1):17-20, 29. Sanchez A M, et al. (2007) Antimicrob Agents Chemother 51(7):2403-2411, 30. Averette K M, et al. (2009) PLoS One 4(11):e7913, 31. Thomas D, et al. (2012) PLoS One 7(4):e34611, 32. Boyden E D & Dietrich W F (2006) Nat Genet 38(2):240-244, 33. Wickliffe K E, et al. (2008) Cellular microbiology 10(2):332-343, 34. Squires R C, et al. (2007) J Biol Chem 282(47):34260-34267, 35. Friedlander A M (1986) J Biol Chem 261(16):7123-7126, 36. Jurgeit A, et al. (2012) PLoS Pathog 8(10):e1002976, 37. Sigismund S, et al. (2008) Dev Cell 15(2):209-219, 38. Carpenter G & Cohen S (1976) J Cell Biol 71(1):159-171, 39. Stoscheck C M & Carpenter G (1984) J Cell Biol 98(3):1048-1053, 40. Chong A, et al. (2008) Infect Immun 76(12):5488-5499, 41. Chong A, et al. (2012) Autophagy 8(9):1342-1356, 42. Schlierf B, et al. (2000) Exp Cell Res 259(1):257-265, 43. Ullrich O, et al. (1996) J Cell Biol 135(4):913-924, 44. Collier R J (2001) Toxicon 39(11):1793-1803, 45. Iglewski B H & Kabat D (1975) Proc Natl Acad Sci USA 72(6):2284-2288, 46. Sandvig K & Olsnes S (1984) Acta histochemica. Supplement band 29:79-94, 47. Sandvig K & Olsnes S (1980) J Cell Biol 87(3 Pt 1):828-832, 48. Sandvig K & Olsnes S (1981) J Biol Chem 256(17):9068-9076, 49. FitzGerald D, et al. (1980) Cell 21(3):867-873, 50. FitzGerald D, et al. (1983) Rev Infect Dis 5 Suppl 5:S985-991, 51. Draper R K & Simon M I (1980) J Cell Biol 87(3 Pt 1):849-854, 52. Sandvig K & Olsnes S (1982) J Biol Chem 257(13):7504-7513, 53. Melby E L, et al. (1991) Journal of cellular biochemistry 47(3):251-260, 54. Gargi A, et al. (2012) Front Cell Infect Microbiol 2:124, 55. Lara-Tejero M & Galan J E (2000) Science 290(5490):354-357, 56. Lara-Tejero M (2001) Scientific World Journal 1:190-191, 57. Lara-Tejero M & Galan J E (2002) Trends Microbiol 10(3):147-152, 58. Guerra L, et al. (2005) Cellular microbiology 7(7):921-934, 59. Guerra L, et al. (2011) Toxins (Basel) 3(3): 172-190, 60. Eshraghi A, et al. (2010) J Biol Chem 285(24):18199-18207, 61. Carette J E, et al. (2011) Nat Biotechnol 29(6):542-546, 62. Gargi A, et al. (2013) Cellular interactions of the cytolethal distending toxins from *Escherichia coli* and *Haemophilus ducreyi*. J Biol Chem, 63. White J, et al. (1981) J Cell Biol 89(3):674-679, 64. White J, et al. (1982) Embo J 1(2):217-222, 65. Lenard J & Miller D K (1982) Cell 28(1):5-6, 66. Matlin K S, et al. (1981) J Cell Biol 91(3 Pt 1):601-613, 67. Matlin K S, et al. (1982) J Mol Biol 156(3):609-631, 68. Borrow P & Oldstone M B (1994) Virology 198(1):1-9, 69. Di Simone C, et al. (1994) Virology 198(2):455-465, 70. Di Simone C & Buchmeier M J (1995) Virology 209(1):3-9, 71. Rojek J M & Kunz S (2008) Cell Microbiol 10(4):828-835, 72. Beer C, et al. (2005) J Virol 79(16):10776-10787, 73. McClure M O, et al. (1990) J Gen Virol 71 (Pt 4):767-773, 74. Lee A M, et al. (2011) Virology 411(2):163-169, 75. Pasquato A, et al. (2012) Expert Rev Anti Infect Ther 10(11):1297-1309, 76. Service R F (1997) Science 275(5301):756-757, 77. Gessner A & Lother H (1989) J Virol 63(4):1827-1832, 78. Moreno H, et al. (2011) J Virol 85(14):7246-7255, 79. Oxford J S (1975) J Antimicrob Chemother 1(1):7-23, 80. Sidwell R W, et al. (1972) Science 177(4050):705-706, 81. Liu Y, et al. (2012) Ther Deliv 3(2):181-194, 82. Paliwal S R, et al. (2012) Crit Rev Ther Drug Carrier Syst 29(5):421-446, 83. Meng H, et al. (2013) Codelivery of an Optimal Drug/siRNA Combination Using Mesoporous Silica Nanoparticles To Overcome Drug Resistance in Breast Cancer in Vitro and in Vivo. ACS Nano, 84. Lu J, et al. (2012) Nanomedicine 8(2):212-220, 85. Li Z, et al. (2012) Chem Soc Rev 41(7):2590-2605, 86. Clemens D L, et al. (2012) Antimicrob Agents Chemother 56(5): 2535-2545, 87. Hom C, et al. (2010) Small 6(11):1185-1190, 88. Xia T, et al. (2009) ACS Nano 3(10):3273-3286, 89. Ezzell J W, et al. (1984) Infect Immun 45(3):761-767, 90. Newman Z L, et al. (2010) PLoS pathogens 6(5): e1000906, 91. Kheirabadi B S, et al. (2010) The Journal of trauma 69(5):1062-1072; discussion 1072-1063, 92. Macia E, et al. (2006) Dev Cell 10(6):839-850, 93. von Kleist L, et al. (2011) Cell 146(3):471-484, 94. Klausner R D, et al. (1992) J Cell Biol 116(5):1071-1080, 95. Cortese K, et al. (2013) Mol Biol Cell 24(2):129-144, 96. Engel S, et al. (2011) J Virol 85(9):4198-4211, 97. Moayeri M, et al. (2006) Infection and immunity 74(7):3707-3714, 98. Stenmark H, et al. (1994) Embo J 13(6):1287-1296, 99. Yogeeswari P, et al. (2005) J Med Chem 48(20):6202-6211, 100. Smith H & Keppie J (1954) Nature 173(4410):869-870, 101. Smith H, et al. (1954) Lancet 267(6836):474-476, 102. Shoop W L, et al. (2005) Proc Natl Acad Sci USA 102(22):7958-7963, 103. Panchal R G, et al. (2004) Nat Struct Mol Biol 11(1):67-72, 104. Schepetkin I A, et al. (2006) J Med Chem 49(17):5232-5244, 105. Turk B E, et al. (2004) Nat Struct Mol Biol 11(1):60-66, 106. Lee L V, et al. (2004) J Am Chem Soc 126(15):4774-4775, 107. Dell'Aica I, et al. (2004) EMBO Rep 5(4):418-422, 108. Bannwarth L, et al. (2012) Chem Biol 19(7):875-882, 109. Min D H, et al. (2004) Nat Biotechnol 22(6):717-723, 110. Scobie H M, et al. (2005) J Infect Dis 192(6):1047-1051, 111. Basha S, et al. (2006) Proc Natl Acad Sci USA 103(36):13509-13513, 112. Sarac M S, et al. (2004) Infect Immun 72(1):602-605, 113. Opal S M, et al. (2005) Infect Immun 73(8):5101-5105, 114. Komiyama T, et al. (2009) J Biol Chem 284(23):15729-15738, 115. Komiyama T, Swanson J A, & Fuller R S (2005) Antimicrob Agents Chemother 49(9):3875-3882, 116. Sellman B R, et al. (2001) J Biol Chem 276(11):8371-8376, 117. Joshi A, et al. (2011) 12(3):791-796, 118. Jiao G S, et al. (2006) Bioorg Med Chem Lett 16(6):1527-1531, 119. Backer M V, et al. (2007) Antimicrob Agents Chemother 51(1):245-251, 120. Shiryaev S A, et al. (2007) J Biol Chem 282(29): 20847-20853, 121. Kacprzak M M, et al. (2004) J Biol Chem 279(35):36788-36794, 122. Maddry J A, et al. (2011) J Biomol Screen 16(1):73-81, 123. Severson W E, et al. (2008) High-throughput screening of a 100,000-compound library for inhibitors of influenza A virus (H3N2). J Biomol Screen 13(9):879-887, 124. Noah J W, et al. (2007) Antiviral Res 73(1):50-59, 25. Bottini A, et al. (2012) Chem Med Chem 7(12):2227-2235, 126. Ortigoza M B, et al. (2012) PLoS Pathog 8(4):e1002668, 127. Lee A M, et al. (2008) J Biol Chem 283(27):18734-18742, 128. Radoshitzky S R, et al. (2012) Expert Opin Drug Discov 7(7):613-632. 129. Rao, P. D.; Dhanalekshmi, S.; Littler, B. J.; Lindsey, J. S. J. Org. Chem. 2000, 65, 7323. 130 Rosen, B. R.; Ruble, J. C.; Beauchamp, T. J.; Navarro, A. Org. Lett. 2011, 13, 2564. 131 Keana, J. F. W.; Cai, S. X. J. Org. Chem. 1990, 55, 3640. 132. Gillespie, E. J.; Ho, C.-L. C.; Balaji, K.; Clemens, D. L.; Deng, G.; Wang, Y. E.; Elsaesser, H. J.; Tamilselvam, B.; Gargi, A.; Dixon, S. D.; France, B.; Chamberlain, B. T.; Blanke, S. R.; Cheng, G.; de, l. T. J. C.; Brooks, D. G.; Jung, M. E.; Colicelli, J.; Damoiseaux, R.; Bradley, K. A. Proc Natl Acad Sci USA 2013, 110, E4904. 133. Yogeeswari, P.; Sriram, D.; Thirumurugan, R.; Raghavendran, J. V.; Sudhan, K.; Pavana, R. K.; Stables, J. J. Med. Chem. 2005, 48, 6202. 134. Rasmussen, C. R.; Villani, F. J., Jr.; Weaner, L. E.; Reynolds, B. E.; Hood, A. R.; Hecker, L. R.; Nortey, S. O.; Hanslin, A.; Costanzo, M. J.; et, a. Synthesis 1988, 456. 135. Andersen, J.; Madsen, U.; Bjorkling, F.; Liang, X. Synlett 2005, 2209. 136. Walton, R.; Lahti, P. M. Synth. Commun. 1998, 28, 1087. 137. Di Simone, C.; et al. *Virology* 1994, 198, 455-465. 138. Knodler, L. A.; et al. *Nat. Rev. Mol. Cell Biol.* 2001, 2, 578-588. 139. White, J.; et al. *J. Cell Biol.* 1981, 89, 674-679. 140. Gillespie, E. J.; et al. Proc. *Natl. Acad. Sci. U.S.A.*, Early Edition, 2013, (Nov. 4, 2013), 1-9. 141. Adkison, K. K et al. *Bioorg. Med. Chem. Lett.* 2006, 16, 978-983. 142. Leban, J.; et al. *Bioorg. Med. Chem.* 2008, 16, 4579-4588. 143. Yogeeswari, P.; et al. *J. Med. Chem.* 2005, 48, 6202-6211. 144. Sarojini, B. K.; et al. *Acta Crystallogr., Sect. E: Struct. Rep. Online* 2007, E63, o2946. 145. Naik, D. V.; et al. *Acta Crystallogr., Sect. B* 1974, 30B, 2396-2401. 146. Basuli, F.; et al. *Inorg. Chem.* 2001, 40, 1126-1133. 147. Casas, J. S.; Garcia-Tasende, M. S.; et al. *Coord. Chem. Rev.* 2000, 209, 197-261. 148. Lin, L et al. *New J. Chem.* 2012, 36, 2562-2567. 149. Tripathi, L.; et al. *Eur. J. Med. Chem.* 2012, 47, 153-166. 150. Rasmussen, C. R.; et al. *Synthesis* 1988, 456-459. 151. Gritsan, N. P.; et al. *Chem. Rev.* 2006, 106, 3844-3867. 152. Li, Y. Z.; et al. *J. Am. Chem. Soc.* 1988, 110, 8092-8098. 153. Kotzyba-Hibert, F.; et al. *Angew. Chem., Int. Ed. Engl.* 1995, 34, 1296-1312. 154. Keana, J. F. W.; et al. *J. Org. Chem.* 1990, 55, 3640-3647. 155. Schnapp, K. A.; et al. *Bioconjugate Chem.* 1993, 4, 172-177. 156. Walton, R.; et al. *Synth. Commun.* 1998, 28, 1087-1092. 157. Andersen, J.; et al. *Synlett* 2005, 2209-2213. 158. Lapinsky, D. *J. Bioorg. Med. Chem.* 2012, 20, 6237-6247.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting anthrax caused by exposure to *Bacillus anthracis* in a subject in need thereof, said method comprising administering an effective amount of a compound, or pharmaceutically acceptable salt thereof, to the subject, wherein the compound has the formula:

(IV)

(V)

wherein $R^1$ is independently hydrogen, halogen, $—CX^3_3$, $—OCX^3_3$, $—CN$, $—C(O)OH$, $—CONH_2$, $—NO_2$, $—SO_2Cl$, $—SO_2NH_2$, $—NHNH_2$, $—NHSO_2CH_3$, $—N_3$, $—NR^{11C}R^{12C}$, $—OR^{13C}$, $—SR^{14C}$, substituted alkyl, substituted heteroalkyl, substituted or unsubstituted cycloalkyl, substituted or unsubstituted heterocycloalkyl, substituted or unsubstituted aryl or substituted or unsubstituted heteroaryl;

$R^2$ is independently hydrogen, halogen, $—CX^3_3$, $—OCX^3_3$, $—CN$, $—C(O)OH$, $—CONH_2$, $—NO_2$, $—SO_2Cl$, $—SO_2NH_2$, $—NHNH_2$, $—NR^{11C}R^{12C}$, $—OR^{13C}$, $—SR^{14C}$, substituted or unsubstituted alkyl, unsubstituted heteroalkyl, substituted or unsubstituted cycloalkyl, substituted or unsubstituted heterocycloalkyl, substituted or unsubstituted aryl or substituted or unsubstituted heteroaryl;

$R^3$ is independently hydrogen, halogen, $—CX^3_3$, $—OCX^3_3$, $—CN$, $—C(O)OH$, $—CONH_2$, $—NO_2$, $—SO_2Cl$, $—SO_2NH_2$, $—NHNH_2$, $—NHSO_2CH_3$, $—N_3$, $—NR^{11C}R^{12C}$, $—OR^{13C}$, $—SR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

each $R^4$ is independently hydrogen, halogen, $—CX^3_3$, $—OCX^3_3$, $—CN$, $—C(O)OH$, $—CONH_2$, $—NO_2$, $—SO_2Cl$, $—SO_2NH_2$, $—NHNH_2$, $—NHSO_2CH_3$, $—N_3$, $—NR^{11C}R^{12C}$, $—OR^{13C}$, $—SR^{14C}$, substituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

$R^5$ is independently hydrogen, $—Cl$, $—Br$, $—I$, $—OCX^3_3$, $—CN$, $—C(O)OH$, $—CONH_2$, $—NO_2$, $—SO_2Cl$, $—SO_2NH_2$, $—NHNH_2$, $—NHSO_2CH_3$, $—N_3$, $—NR^{11C}R^{12C}$, $—OR^{13C}$, $—SR^{14C}$, unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;

wherein (i) at least one of $R^1$, $R^2$, $R^3$, $R^4$, or $R^5$ of Formula IV is not hydrogen; and (ii) at least one of $R^2$, $R^3$, or $R^4$ of Formula V is not hydrogen;

R⁶ is hydrogen or unsubstituted alkyl;
R⁷ is O, S, or NH;
each R⁸ is independently halogen, —CX₃, —OCX₃, —CN, —C(O)OH, —CONH₂, —NO₂, —SO₂Cl, —SO₂NH₂, —NHNH₂, —NHSO₂CH₃, —N₃, —NR¹¹R¹², —OR¹³, —SR¹⁴, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R⁹ is hydrogen;
each R¹¹, R¹², R¹³, and R¹⁴ is independently a hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R¹⁰ is hydrogen, halogen, —C(X²)₃, —OC(X²)₃, —CN, —C(O)OH, —CONH₂, —NO₂, —SO₂Cl, —SO₂NH₂, —NHNH₂, —NHSO₂CH₃, —N₃, —NR¹¹ᴮR¹²ᴮ, —OR¹³ᴮ, —SR¹⁴ᴮ, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R¹¹ᴬ, R¹²ᴬ, R¹³ᴬ, R¹⁴ᴬ, R¹¹ᴮ, R¹²ᴮ, R¹³ᴮ, R¹⁴ᴮ, R¹¹ᶜ, R¹²ᶜ, R¹³ᶜ, and R¹⁴ᶜ are independently a hydrogen, substituted or unsubstituted alkyl, unsubstituted heteroalkyl, substituted or unsubstituted cycloalkyl, substituted or unsubstituted heterocycloalkyl, substituted or unsubstituted aryl or substituted or unsubstituted heteroaryl;
L¹ is —S—;
each X is independently a halogen;
X¹, X² and X³ are independently a halogen; and
wherein the compound is not any of

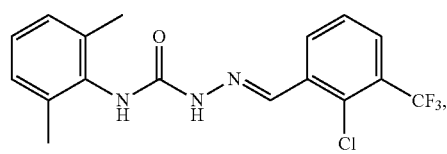

13b

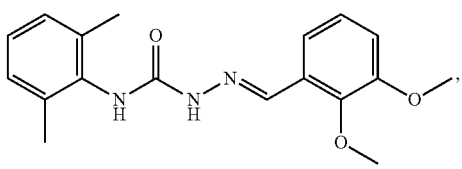

13g

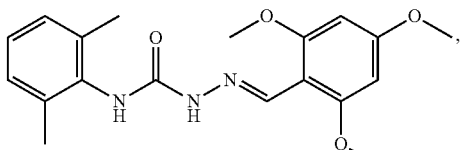

13h

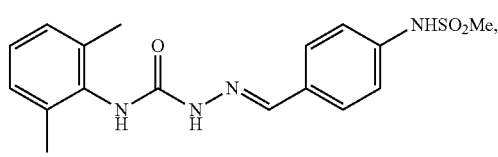

13p

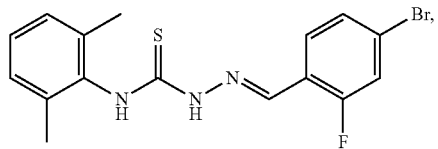

19b

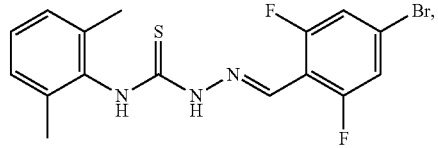

19c

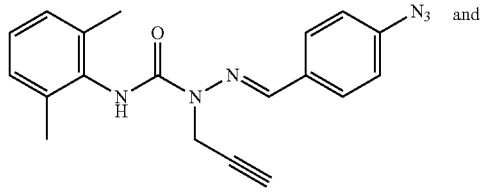

28 and

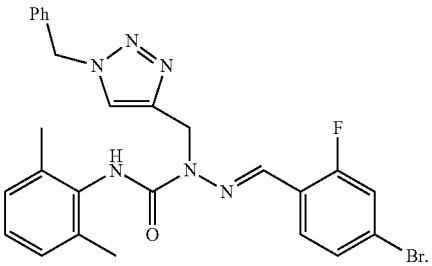 [SMILES: Cc1cccc(C)c1NC(=O)N(Cc1cn(Cc2ccccc2)nn1)/N=C/c1ccc(Br)cc1F]

2. The method of claim 1, wherein;
R¹ and R⁴ are independently hydrogen, halogen, —OR¹³ᶜ, substituted alkyl, substituted heteroalkyl, substituted or unsubstituted cycloalkyl, substituted or unsubstituted heterocycloalkyl, substituted or unsubstituted aryl or substituted or unsubstituted heteroaryl;
R² is independently hydrogen, halogen, —CX³₃, —CN, —NHSO₂CH₃, —N₃, —OR¹³ᶜ, substituted or unsubstituted alkyl, unsubstituted heteroalkyl, substituted or unsubstituted cycloalkyl, substituted or unsubstituted heterocycloalkyl, substituted or unsubstituted aryl or substituted or unsubstituted heteroaryl;
R³ and R⁵ are independently hydrogen, halogen, —CX³₃, —OR¹³ᶜ, unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
each R⁸ is independently substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl;
R¹⁰ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl; and
each R¹³ᶜ is independently a hydrogen or a substituted or unsubstituted alkyl.

3. The compound, of claim 1, wherein;
R¹ is independently hydrogen, halogen, or —OR¹³ᶜ;

$R^2$ is independently hydrogen, halogen, —$CX^3{}_3$, —CN, —$N_3$, —$OR^{13C}$, or unsubstituted alkyl;

$R^3$ is independently hydrogen, halogen, —$CX^3{}_3$, —$OR^{13C}$, or unsubstituted alkyl;

$R^4$ is independently hydrogen, halogen, —$OR^{13C}$, or unsubstituted alkyl;

$R^5$ is independently hydrogen, halogen, —$OR^{13C}$, or unsubstituted alkyl;

$R^6$ is independently hydrogen or unsubstituted alkyl;

each $R^8$ is independently an unsubstituted alkyl;

$R^9$ is independently hydrogen;

$R^{10}$ is independently hydrogen or unsubstituted alkyl;

each $R^{13C}$ is independently an unsubstituted alkyl; and $X^3$ is —F.

4. The method of claim 1, wherein the compound is:

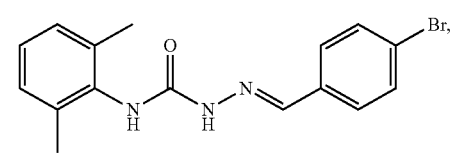
1

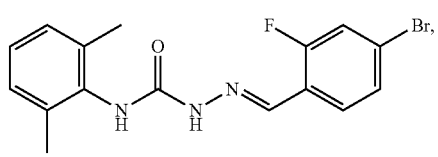
2

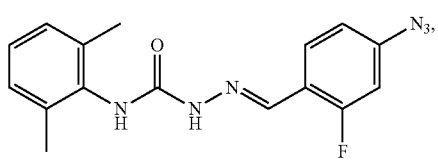
3

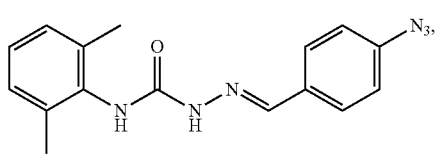
4

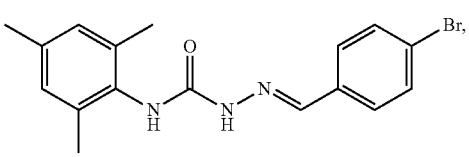
9b

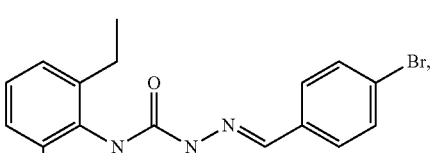
9c

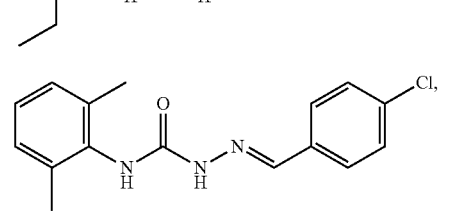
13a

-continued

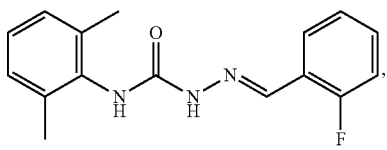
13c

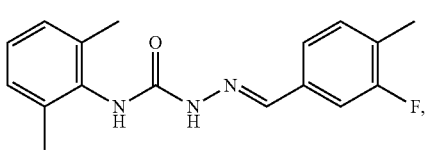
13d

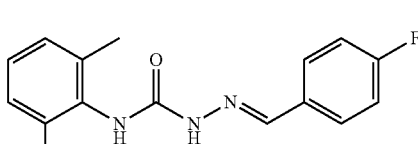
13e

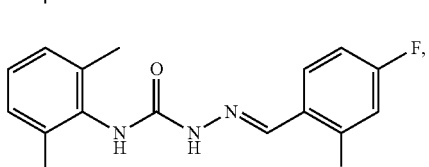
13f

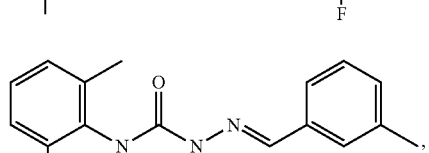
13j

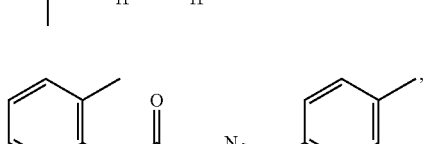
13k

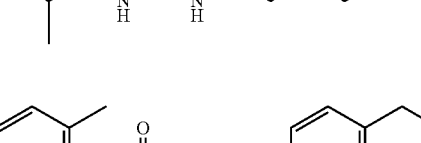
13l

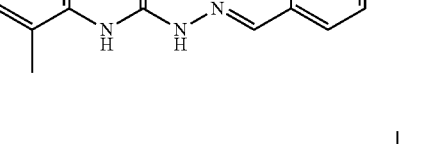
13m

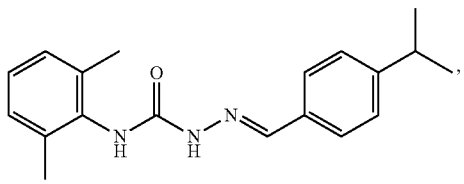
13n

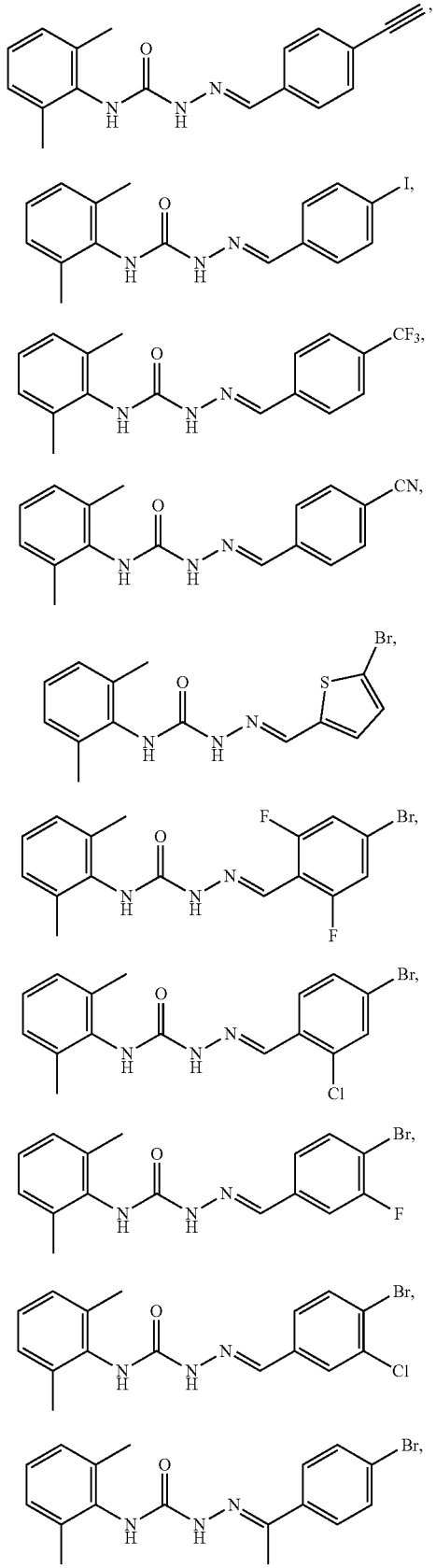
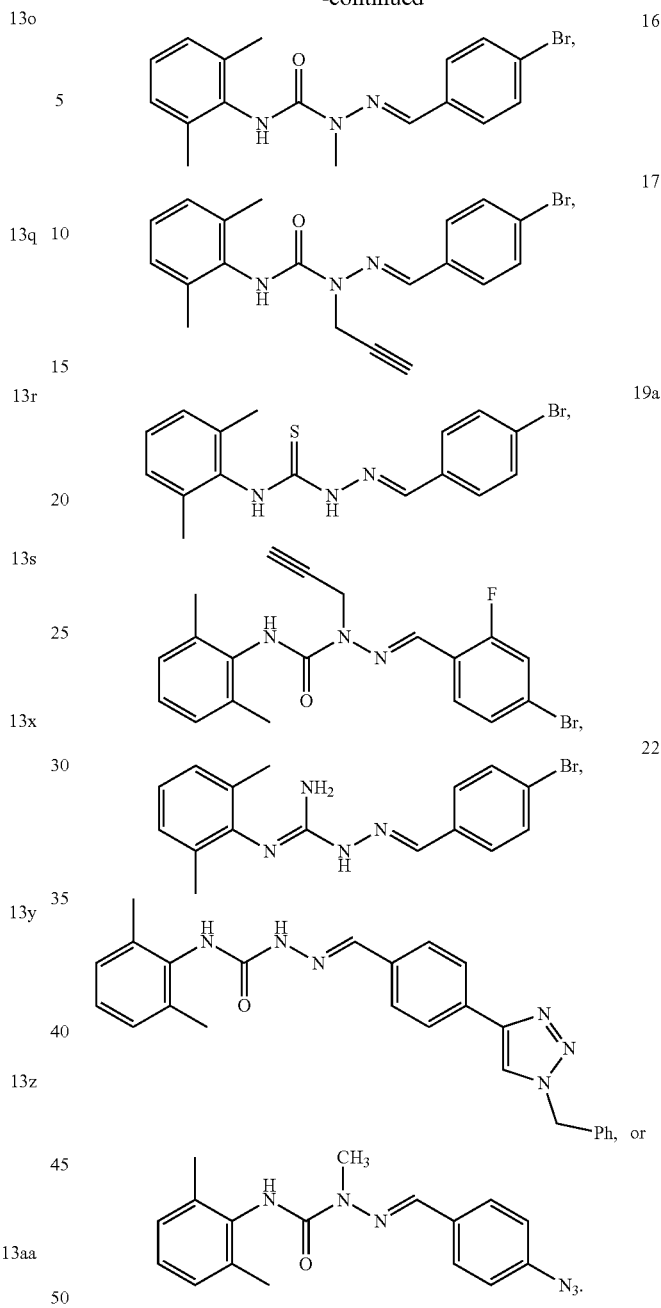

5. The method of claim 1, wherein the compound is co-administered with an antibiotic.

6. The method of claim 1, wherein the compound is co-administered with an doxycycline and/or ciprofloxacin.

7. The method of claim 4, wherein the compound is co-administered with an antibiotic.

8. The method of claim 4, wherein the compound is co-administered with an doxycycline and/or ciprofloxacin.

9. The method of claim 1, wherein $R^2$ is independently halogen, —$CX^3{}_3$, —$OCX^3{}_3$, —CN, —C(O)OH, —$CONH_2$, —$NO_2$, —$SO_2Cl$, —$SO_2NH_2$, —$NHNH_2$, —$NR^{11C}R^{12C}$, —$OR^{13C}$, —$SR^{14C}$, substituted or unsubstituted alkyl, unsubstituted heteroalkyl, substituted or unsubstituted cycloalkyl, substituted or unsubstituted heterocycloalkyl, substituted or unsubstituted aryl or substituted or unsubstituted heteroaryl.

10. The method of claim 1, wherein $R^2$ is independently halogen, $-CX^3{}_3$, $-CN$, $-NHSO_2CH_3$, $-N_3$, $-OR^{13C}$, substituted or unsubstituted alkyl, unsubstituted heteroalkyl, substituted or unsubstituted cycloalkyl, substituted or unsubstituted heterocycloalkyl, substituted or unsubstituted aryl or substituted or unsubstituted heteroaryl.

11. The method of claim 1, wherein $R^2$ is independently halogen, $-CX^3{}_3$, $-CN$, $-N_3$, $-OR^{13C}$, or unsubstituted alkyl.

* * * * *